US008716560B2

(12) United States Patent
Meyer

(10) Patent No.: US 8,716,560 B2
(45) Date of Patent: *May 6, 2014

(54) COMPOSITIONS AND METHODS FOR ALTERING ALPHA- AND BETA-TOCOTRIENOL CONTENT

(75) Inventor: Knut Meyer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/517,739

(22) Filed: Jun. 14, 2012

(65) Prior Publication Data

US 2012/0270323 A1    Oct. 25, 2012

Related U.S. Application Data

(63) Continuation of application No. 13/367,811, filed on Feb. 7, 2012, which is a continuation of application No. 11/559,024, filed on Nov. 13, 2006, now abandoned.

(60) Provisional application No. 60/736,600, filed on Nov. 14, 2005.

(51) Int. Cl.
*C12N 15/29* (2006.01)
*C12N 15/82* (2006.01)
*A01H 1/00* (2006.01)
*C07H 21/04* (2006.01)
*C07K 14/415* (2006.01)

(52) U.S. Cl.
USPC ............ 800/296; 435/6.1; 435/69.1; 435/468; 435/419; 435/320.1; 435/183; 530/370; 536/23.2; 536/23.6; 800/278

(58) Field of Classification Search
USPC ........... 435/6.1, 69.1, 468, 419, 252.3, 320.1, 435/183; 530/370; 536/23.2, 23.6; 800/278, 800/295, 296
See application file for complete search history.

(56) References Cited

U.S. PATENT DOCUMENTS

| 2003/0154513 | A1 | 8/2003 | Eenennaam et al. |
| 2004/0034886 | A1 | 2/2004 | Cahoon et al. |
| 2004/0266862 | A1 | 12/2004 | Wolf et al. |
| 2005/0002358 | A1 | 1/2005 | Miyoshi et al. |

FOREIGN PATENT DOCUMENTS

| WO | WO99/04622 | A1 | 2/1999 |
| WO | WO00/32757 | A2 | 6/2000 |
| WO | WO00/72862 | A1 | 12/2000 |
| WO | WO03016482 | A2 | 2/2003 |
| WO | WO03/082899 | A2 | 10/2003 |

OTHER PUBLICATIONS

Jorgen Soll et al., Tocopherol and Plastoquinone Synthesis in Spinach Chloroplasts Subfractions, Archives of Biochemistry and Biophysics, vol. 204(2):544-550, 1980.
Lester Packer et al., Molecular Aspects of Alpha-Tocotrienol Antioxidant Action and Cell Signaling, The Journal of Nutrition, pp. 369S-373S, vol. 131, 2001.
Andre Theriault et al., Tocotrienol: A Review of its Therapeutic Potential, Clinical Biochemistry, vol. 32(5):309-319, 1999.
Asaf A. Qureshi et al., The Structure of an Inhibitor of Cholesterol Biosynthesis Isolated From Barley*, The Journal of Biological Chemistry, vol. 261(23):10544-10550, 1986.
National Center for Biotechnology Information General Identifier No. 66732623, Accession No. AAY52459, May 31, 2005, Y. Hu et al., Cloning of Gamma Tocopherol Methyltransferase Gene in Lotus Corniculatus Var. Japonicus (*Lotus japonicus*).
National Center for Biotechnology Information General Identifier No. 62126056, Accession On: AY960126, Apr. 6, 2005, Y. Hu et al., Cloning Gamma-Tocopherol Methyltransferase Gene in Glycine Max.
National Center for Biotechnology Information General Identifier No. 50911846, Accession No. XM_467331, Nov. 9, 2004, The NCBI Genome Assembly Consortium.
The National Center for Biotechnology Information General Identifier No. 27448217, Accession No. AF381248, Jan. 1, 2003, Q. Ouyang et al., Gamma-Tocopherol Methyltransferase (TMT) MRNA.
National Center for Biotechnology Information General Identifier No. 17224291, Accession No. AF213481, Dec. 2, 2001, K.-H. Kim et al., Cloning of Perilla Gamma-Tocopherol Methyltransferase.
National Center for Biotechnology Information General Identifier No. 4106537, Accession No: AF104220, Jan. 26, 2006, D. Shintani et al., Elevating the Vitamin E Content of Plants Through Metabolic Engineering.
National Center for Biotechnology Information General Identifier No. 62115030, Accession No. AY962639, Apr. 5, 2005, Y. Hu et al., Cloning Gamma-Tocopherol Methyltransferase Gene in *Medicago truncaluta*.
National Center for Biotechnology Information General Identifier No. 61657537, Accession No. AJ884948, Apr. 15, 2005, G. Galvez-Valdivieso et al., Cloning and Characterization of Gamme-Tocopherol Methyltrasferase from the Unicellular Alga *Chlamydomonas reinhardtii*.
National Center for Biotechnology Information General Identifier No. 16331764, Accession No. NP_442492, Jul. 25, 2006, T. Kaneko et al., Sequence Analysis of the Genome of the Unicellular *Cyanobacterium synechocystis* SP. Strain PCC6803. II. Sequence Determination of the Entire Genome and Assignment of Potential Protein-Coding Regions.
National Center for Biotechnology Information General Identifier No. 17130893, Accession No. BAB73502, Oct. 22, 2004, T. Kaneko et al., Complete Genomic Sequence of the Filamentous Nitrogen-Fixing *Cyanobacterium anabaena* SP. Strain PCC7120.

(Continued)

*Primary Examiner* — Phuong Bui

(57) ABSTRACT

Preparation and use of isolated nucleic acids useful in altering the oil phenotype in plants. Isolated nucleic acids and their encoded polypeptides that alter alpha- and beta-tocotrienol content in seeds and oil obtained from the seeds. Expression cassettes, host cells and transformed plants containing the foregoing nucleic acids.

3 Claims, 2 Drawing Sheets

(56) References Cited

OTHER PUBLICATIONS

National Center for Biotechnology Information General Identifier No. 37522659, Accession No. NP_926036, Dec. 3, 2005, Y. Nakamura et al., Complete Genome Structure of *Gloeobacter violaceus* PCC 7421, A Cyanobacterium That Lacks Thylakoids (Supplement).

Chikako Kiyose et al., Distribution and Metabolism of Tocopherols and Tocotrienols in Vivo, J. Clin. Biochem Nutr., vol. 35:47-52, 2004.

Balasulojini Karunanandaa et al., Metabolically Engineered Oilseed Crops With Enhanced Seed Tocopherol, Metabolic Engineering, vol. 7:384-400, 2005.

Edgar B. Cahoon et al., Metabolic Redesign of Vitamin E Biosynthesis in Plants for Tocotrienol Production and Increased Antioxidant Content, Nature Biotechnology, vol. 21(9):1082-1087, 2003.

C. Bertoli et al., Characterization of Chilean Hazelnut (*Gevuina avellana* Mol) Seed Oil, JAOCS, vol. 75(8):1037-1040, 1998.

Henry E. Valentin et al.: "Biotechnological Production and Appln of Vit. E: Current State and Prospects", Applied Microbiology and Biotechnology, vol. 68, No. 4, 2005, pp. 436-444.

Eva Collakova et al.: "Homogentisate Phytyltransferase Activity is Limiting for Tocopherol Biosynthesis in *Arabidopsis*", Plant Physiology, vol. 131, No. 2, 2003, pp. 632-642.

```
                      SEQUENCE LISTING

<160> NUMBER OF SEQ ID NOS: 52

<210> SEQ ID NO 1
<211> LENGTH: 1457
<212> TYPE: DNA
<213> ORGANISM: Hordeum vulgare
<220> FEATURE:
<221> NAME/KEY: misc_feature
<222> LOCATION: (1410)..(1410)
<223> OTHER INFORMATION: n is a, c, g, or t
<220> FEATURE:
<221> NAME/KEY: misc_feature
<222> LOCATION: (1421)..(1421)
<223> OTHER INFORMATION: n is a, c, g, or t

<400> SEQUENCE: 1 ccoctcottt acacagatcc gcgggttaac ttcctcctcc ggaggccgcc cggccggcga      60
ggatgcaagc cgtcacggcg gcggccgcgg cggggcagct gctaacagat acgaggagag     120
ggcccagatg tagggctcgg ctgggaacga cgagattatc ctggacaggt cgatttgcag     180
tggaagcttt tgcaggccag tgccaaagtg ctactactgt aatgcataaa ttcagtgcca     240
tttctcaagc tgctaggcct agaagaaaca caaagagaca gtgcagcgat gattatccag     300
ccctccaagc tggatgcagc gaggttaatt gggatcaaaa cggttccaac gccaatcggc     360
ttgaggaaat caggggagat gttttgaaga aattgcgctc tttctatgaa ttttgcaggc     420
cacacacaat ttttggcact ataataggta taacttcagt gtctctcctg ccaatgaaga     480
```

```
gcatagatga ttttactgtc acggtactac gaggatatct cgaggctttg actgctgctt    540
tatgtatgaa catttatgtg gtcgggctga atcagctata tgacattcag attgacaaga    600
tcaacaagcc aggtcttcca ttggcatctg gggaattttc agtagcaact ggagttttct    660
tagtactcgc attcctgatc atgagcttta gcataggaat acgttccgga tcggcgccac    720
tgatgtgtgc tttaattgtc agcttccttc ttggaagtgc gtactccatt gaggctccgt    780
tcctccggtg gaaacggcac gcgctcctcg ctgcatcatg tatcctattt gtgagggcta    840
tcttggtcca gttggctttc tttgcacata tgcagcaaca tgttctgaaa aggccattgg    900
cagcaaccaa atcgctggtg tttgcaacat tgtttatgtg ttgcttctct gccgtcatag    960
cactattcaa ggatattcca gatgttgatg gagatcgaga ctttggtatc caatccttga   1020
gtgtgagatt ggggcctcaa agagtgtatc agctctgcat aagcatattg ttgacagcct   1080
atggcgctgc cactctagta ggagcttcat ccacaaacct atttcaaaag atcatcactg   1140
tgtctggtca tggcctgctt gctttgacac tttggcagag agcgcagcac tttgaggttg   1200
aaaaccaagc gcgtgtcaca tcattttaca tgttcatttg gaagctattc tatgcagagt   1260
atttccttat accatttgtg cagtgaaatt tgtacaaggg ccagcagatg tgaactatat   1320
atacatgtaa aacaaattat attactgatg atactcaatc caatgcttgg attttgcttg   1380
tactgtgcta tctgtaattt catgatctan agaagagca natgttggat gtgtaaaaaa   1440
aaaaaaaaaa aaaaaaa                                                  1457

<210> SEQ ID NO 2
<211> LENGTH: 407
<212> TYPE: PRT
<213> ORGANISM: Hordeum vulgare

<400> SEQUENCE: 2

Met Gln Ala Val Thr Ala Ala Ala Ala Gly Gln Leu Leu Thr Asp
1               5                   10                  15

Thr Arg Arg Gly Pro Arg Cys Arg Ala Arg Leu Gly Thr Thr Arg Leu
                20                  25                  30

Ser Trp Thr Gly Arg Phe Ala Val Glu Ala Phe Ala Gly Gln Cys Gln
            35                  40                  45

Ser Ala Thr Thr Val Met His Lys Phe Ser Ala Ile Ser Gln Ala Ala
        50                  55                  60

Arg Pro Arg Arg Asn Thr Lys Arg Gln Cys Ser Asp Asp Tyr Pro Ala
65                  70                  75                  80

Leu Gln Ala Gly Cys Ser Glu Val Asn Trp Asp Gln Asn Gly Ser Asn
                85                  90                  95

Ala Asn Arg Leu Glu Glu Ile Arg Gly Asp Val Leu Lys Lys Leu Arg
            100                 105                 110

Ser Phe Tyr Glu Phe Cys Arg Pro His Thr Ile Phe Gly Thr Ile Ile
        115                 120                 125

Gly Ile Thr Ser Val Ser Leu Leu Pro Met Lys Ser Ile Asp Asp Phe
    130                 135                 140

Thr Val Thr Val Leu Arg Gly Tyr Leu Glu Ala Leu Thr Ala Ala Leu
145                 150                 155                 160

Cys Met Asn Ile Tyr Val Val Gly Leu Asn Gln Leu Tyr Asp Ile Gln
                165                 170                 175

Ile Asp Lys Ile Asn Lys Pro Gly Leu Pro Leu Ala Ser Gly Glu Phe
            180                 185                 190

Ser Val Ala Thr Gly Val Phe Leu Val Leu Ala Phe Leu Ile Met Ser
        195                 200                 205
```

Phe Ser Ile Gly Ile Arg Ser Gly Ser Ala Pro Leu Met Cys Ala Leu
    210                 215                 220
Ile Val Ser Phe Leu Leu Gly Ser Ala Tyr Ser Ile Glu Ala Pro Phe
225                 230                 235                 240
Leu Arg Trp Lys Arg His Ala Leu Leu Ala Ala Ser Cys Ile Leu Phe
                245                 250                 255
Val Arg Ala Ile Leu Val Gln Leu Ala Phe Phe Ala His Met Gln Gln
            260                 265                 270
His Val Leu Lys Arg Pro Leu Ala Ala Thr Lys Ser Leu Val Phe Ala
        275                 280                 285
Thr Leu Phe Met Cys Cys Phe Ser Ala Val Ile Ala Leu Phe Lys Asp
    290                 295                 300
Ile Pro Asp Val Asp Gly Asp Arg Asp Phe Gly Ile Gln Ser Leu Ser
305                 310                 315                 320
Val Arg Leu Gly Pro Gln Arg Val Tyr Gln Leu Cys Ile Ser Ile Leu
                325                 330                 335
Leu Thr Ala Tyr Gly Ala Ala Thr Leu Val Gly Ala Ser Ser Thr Asn
            340                 345                 350
Leu Phe Gln Lys Ile Ile Thr Val Ser Gly His Gly Leu Leu Ala Leu
        355                 360                 365
Thr Leu Trp Gln Arg Ala Gln His Phe Glu Val Glu Asn Gln Ala Arg
    370                 375                 380
Val Thr Ser Phe Tyr Met Phe Ile Trp Lys Leu Phe Tyr Ala Glu Tyr
385                 390                 395                 400
Phe Leu Ile Pro Phe Val Gln
            405

<210> SEQ ID NO 3
<211> LENGTH: 1365
<212> TYPE: DNA
<213> ORGANISM: Triticum aestivum

<400> SEQUENCE: 3
ctttcacaca gatcccaggc cgcttttctc ctccggtggc cgcccggcga ggatgcaagc     60
caccacggcc gcggcggcgg cgcagctgct aacagatacg aggagagggc ccagatgtag    120
tagggctcgg ctgggagcga cgagattatc ctggccaggt cgatttgcag tggaagcttt    180
tgcaggccgg tgccaaagca gtgctactac tgtcacgcat agattcagtg ccatttctca    240
agctacaagc cctagaagaa aggcaaggag gcagtgcagc gatgatcagt cagccctcca    300
agctggatgc agcaaggtta atcgcgatca acatggttac gacgtgaact ggtttgagga    360
aatcagccaa gaagtttcga agaaattgcg cgctttctac cagttctgca gaccacacac    420
aatctttggc actatcatag cataacttc agtgtctctc ctgccaatga agagcataga    480
tgattttact gcaacggtac taaaagggta tctcgaggct ttggctgctg ctttatgtat    540
gaacatttat gtggtagggc tgaatcagct atatgacatt cagattgaca agatcaacaa    600
gccaggtctt ccattggcag ctggggaatt ttcagtagca actggggtat ttttagtagt    660
cacattcctg atcatgagct ttagcatcgg aatacattcc ggatcggtgc cactgatgta    720
tgctttagtt gtcagcttcc ttcttggaag tgcatactcc attgaggctc cgttgctccg    780
gtggaaacgg cacgcactcc tcgctgcatc ctgtatccta tttgtgaggg ctatcttggt    840
ccagttggct ttctttgcac atatgcagca acatgttctg aaaaggccct tggcagcaac    900
aaaatcactg gtgtttgcaa cattgttcat gtgttgcttc tctgccgtca tagctctatt    960

```
caaggatata cctgatgttg atggagaccg agattttggc atccaatcct tgagtgtgag   1020
attggggcca aaagagtgt atcagctctg cataagcata ctgttgacag cctatttggc   1080
tgccactgta gtaggagctt catccacaca cctacttcaa agataatca ctgtgtctgg   1140 tcatggcctg cttgcactaa cactttggca gagagcgcgg caccttgagg ttgaaaatca   1200
agcgcgtgtc acatcatttt acatgttcat ttggaagcta ttctatgcag agtatttcct   1260
tataccattt gtgcagtgaa atttgtacaa gggccagcag atgtgagcta tatatacatg   1320
taaaacaaat tatattactg atgatacct atccaatgct tggaa              1365
```

<210> SEQ ID NO 4
<211> LENGTH: 408
<212> TYPE: PRT
<213> ORGANISM: Triticum aestivum

<400> SEQUENCE: 4

```
Met Gln Ala Thr Thr Ala Ala Ala Ala Gln Leu Leu Thr Asp Thr
 1               5                  10                  15

Arg Arg Gly Pro Arg Cys Ser Arg Ala Arg Leu Gly Ala Thr Arg Leu
            20                  25                  30

Ser Trp Pro Gly Arg Phe Ala Val Glu Ala Phe Ala Gly Arg Cys Gln
        35                  40                  45

Ser Ser Ala Thr Thr Val Thr His Arg Phe Ser Ala Ile Ser Gln Ala
    50                  55                  60

Thr Ser Pro Arg Arg Lys Ala Arg Arg Gln Cys Ser Asp Asp Gln Ser
65                  70                  75                  80

Ala Leu Gln Ala Gly Cys Ser Lys Val Asn Arg Asp Gln His Gly Tyr
                85                  90                  95

Asp Val Asn Trp Phe Glu Glu Ile Ser Gln Glu Val Ser Lys Lys Leu
            100                 105                 110

Arg Ala Phe Tyr Gln Phe Cys Arg Pro His Thr Ile Phe Gly Thr Ile
        115                 120                 125

Ile Gly Ile Thr Ser Val Ser Leu Leu Pro Met Lys Ser Ile Asp Asp
    130                 135                 140

Phe Thr Ala Thr Val Leu Lys Gly Tyr Leu Glu Ala Leu Ala Ala Ala
145                 150                 155                 160

Leu Cys Met Asn Ile Tyr Val Val Gly Leu Asn Gln Leu Tyr Asp Ile
                165                 170                 175

Gln Ile Asp Lys Ile Asn Lys Pro Gly Leu Pro Leu Ala Ala Gly Glu
            180                 185                 190

Phe Ser Val Ala Thr Gly Val Phe Leu Val Val Thr Phe Leu Ile Met
        195                 200                 205

Ser Phe Ser Ile Gly Ile His Ser Gly Ser Val Pro Leu Met Tyr Ala
    210                 215                 220

Leu Val Val Ser Phe Leu Leu Gly Ser Ala Tyr Ser Ile Glu Ala Pro
225                 230                 235                 240

Leu Leu Arg Trp Lys Arg His Ala Leu Leu Ala Ala Ser Cys Ile Leu
                245                 250                 255

Phe Val Arg Ala Ile Leu Val Gln Leu Ala Phe Phe Ala His Met Gln
            260                 265                 270

Gln His Val Leu Lys Arg Pro Leu Ala Ala Thr Lys Ser Leu Val Phe
        275                 280                 285

Ala Thr Leu Phe Met Cys Cys Phe Ser Ala Val Ile Ala Leu Phe Lys
    290                 295                 300

Asp Ile Pro Asp Val Asp Gly Asp Arg Asp Phe Gly Ile Gln Ser Leu
```

```
                305                 310                 315                 320
Ser Val Arg Leu Gly Pro Gln Arg Val Tyr Gln Leu Cys Ile Ser Ile
                    325                 330                 335

Leu Leu Thr Ala Tyr Leu Ala Ala Thr Val Val Gly Ala Ser Ser Thr
                340                 345                 350

His Leu Gln Lys Ile Ile Thr Val Ser Gly His Gly Leu Leu Ala
        355                 360                 365

Leu Thr Leu Trp Gln Arg Ala Arg His Leu Glu Val Glu Asn Gln Ala
            370                 375                 380

Arg Val Thr Ser Phe Tyr Met Phe Ile Trp Lys Leu Phe Tyr Ala Glu
385                 390                 395                 400

Tyr Phe Leu Ile Pro Phe Val Gln
                405

<210> SEQ ID NO 5
<211> LENGTH: 1242
<212> TYPE: DNA
<213> ORGANISM: Oryza sativa

<400> SEQUENCE: 5
agacgatgca agcctcatcg gcggcggcgg cggcggcgtg ctcggctatc aagccggcgg      60
cgcatcagca caccgtgcaa gtccaggaag ataagagggg atcggaattc agggctcggt     120
ttggaacgag gaaactgtcc tggggaggta aattgtcggt ggaaaattct gctctacacc     180
agtgtcaaag tctcacaaga agcataagga ggcaaaaaag acaacattct ccagtcctcc     240
aagtgagatg ctatgccatt gctggtgatc agcacgaatc catcgccact gagtttgaag     300
aaatttgcaa agaagttccc cagaaactgg gagcttttta tcggttttgc cgaccccaca     360 caattttttgg cactataata ggaatcactt cagtttctct cctgccaatg aggagcctag     420
atgattttac tatgaaagca ttatggggat tcttgaggc tttatcctct tctttatgta     480
tgaatatcta tgttgtaggc ctgaatcaac tatatgacat ccagattgat aaggtcaata     540
agcccagcct tccgttggcg tcaggagaat tttcagtggc aactggagca gtgttagtac     600
tcacgtcctt gatcatgagc attgccattg gaatcagatc caaatcagct cctttgttat     660
gtgctttgtt tatcagtttc tttcttggaa gtgcatactc tgttgatgct ccgttactcc     720
ggtggaaaag gaacgcgttt ctcgctgcat cttgtatact atttgtaaga gctgtcttag     780
ttcagctagc tttctttgca catatgcagc aacatgttct gaagaggccc ttggcaccaa     840
caaagtcggt ggttttcgca acattattca tgtgttgctt ttcttcagtt atagctttat     900
tcaaggatat tccagatatt gatggtgaca gacattttgg cgtcgaatcc ctgagcgtac     960
gtttgggtcc agaaagagtg tattggctct gcataaacat actattaaca gcatatgggg    1020
ctgccatttt ggctggagca tcatctacaa atctatgtca aatgattatc accgttttcg    1080
gccatggcct gcttgccttt gcactttggc agagagcaca gcactgtgac gttgaaaaca    1140
aggcgtggat cacatcattt tacatgttca tttggaagtt gttctacgct gagtatttcc    1200
ttataccatt tgtgcagtga gcactatata cacaagggca ag                      1242

<210> SEQ ID NO 6
<211> LENGTH: 404
<212> TYPE: PRT
<213> ORGANISM: Oryza sativa

<400> SEQUENCE: 6

Met Gln Ala Ser Ser Ala Ala Ala Ala Ala Cys Ser Ala Ile Lys
1               5                   10                  15
```

Pro Ala Ala His Gln His Thr Val Gln Val Gln Glu Asp Lys Arg Gly
           20                  25                  30

Ser Glu Phe Arg Ala Arg Phe Gly Thr Arg Lys Leu Ser Trp Gly Gly
            35                  40                  45

Lys Leu Ser Val Glu Asn Ser Ala Leu His Gln Cys Gln Ser Leu Thr
 50                  55                  60

Arg Ser Ile Arg Arg Gln Lys Arg Gln His Ser Pro Val Leu Gln Val
 65                  70                  75                  80

Arg Cys Tyr Ala Ile Ala Gly Asp Gln His Glu Ser Ile Ala Thr Glu
                 85                  90                  95

Phe Glu Glu Ile Cys Lys Glu Val Pro Gln Lys Leu Gly Ala Phe Tyr
            100                 105                 110

Arg Phe Cys Arg Pro His Thr Ile Phe Gly Thr Ile Ile Gly Ile Thr
            115                 120                 125

Ser Val Ser Leu Leu Pro Met Arg Ser Leu Asp Asp Phe Thr Met Lys
130                 135                 140

Ala Leu Trp Gly Phe Leu Glu Ala Leu Ser Ser Ser Leu Cys Met Asn
145                 150                 155                 160

Ile Tyr Val Val Gly Leu Asn Gln Leu Tyr Asp Ile Gln Ile Asp Lys
                165                 170                 175

Val Asn Lys Pro Ser Leu Pro Leu Ala Ser Gly Glu Phe Ser Val Ala
            180                 185                 190

Thr Gly Ala Val Leu Val Leu Thr Ser Leu Ile Met Ser Ile Ala Ile
            195                 200                 205

Gly Ile Arg Ser Lys Ser Ala Pro Leu Leu Cys Ala Leu Phe Ile Ser
210                 215                 220

Phe Phe Leu Gly Ser Ala Tyr Ser Val Asp Ala Pro Leu Leu Arg Trp
225                 230                 235                 240

Lys Arg Asn Ala Phe Leu Ala Ala Ser Cys Ile Leu Phe Val Arg Ala
                245                 250                 255

Val Leu Val Gln Leu Ala Phe Phe Ala His Met Gln Gln His Val Leu
            260                 265                 270

Lys Arg Pro Leu Ala Pro Thr Lys Ser Val Val Phe Ala Thr Leu Phe
            275                 280                 285

Met Cys Cys Phe Ser Ser Val Ile Ala Leu Phe Lys Asp Ile Pro Asp
290                 295                 300

Ile Asp Gly Asp Arg His Phe Gly Val Glu Ser Leu Ser Val Arg Leu
305                 310                 315                 320

Gly Pro Glu Arg Val Tyr Trp Leu Cys Ile Asn Ile Leu Leu Thr Ala
                325                 330                 335

Tyr Gly Ala Ala Ile Leu Ala Gly Ala Ser Ser Thr Asn Leu Cys Gln
            340                 345                 350

Met Ile Ile Thr Val Phe Gly His Gly Leu Leu Ala Phe Ala Leu Trp
            355                 360                 365

Gln Arg Ala Gln His Cys Asp Val Glu Asn Lys Ala Trp Ile Thr Ser
370                 375                 380

Phe Tyr Met Phe Ile Trp Lys Leu Phe Tyr Ala Glu Tyr Phe Leu Ile
385                 390                 395                 400

Pro Phe Val Gln

<210> SEQ ID NO 7
<211> LENGTH: 1730
<212> TYPE: DNA
<213> ORGANISM: Zea mays

<400> SEQUENCE: 7

```
ccttgagccg ttccgctgcc attcgaccac caccgccacg gcggcgccga tgccgactac    60
aaccactcgc agagactacc gcctccagcc ccgccgcttc tcatctccac gcagccgtcc   120
gatggccaag cggctcgccg gtgccgacaa agaggtgctc gtcgaggtgg tgaggttcac   180
gcataagagc ggactgaggg gctgtgacgg cggctggaag gatttcctgg cccagaacga   240
caggaagttt ggcgcgtcgg tgagcgaccc gaggaagcgc tccagggacg tgctgttcgc   300
cttcctgcag accttcccca aggatttcca agaaaacac ttgatgccac tagtccgacg    360
agagccaccg gaagacaacg caggcattcc tcagtcccca aagtgagctg ctgggcagct   420
gctcatcacc aacacaattc taaccccag cagtttcagg cgattggcat acgaatcgca    480
aagacgctgc atgccttcta tcagttctgc cgaccacaca caatatttgg aaccataata   540
ggcattactt cggtgtctat cctgccagtg aagagcctgg acgattttac gttgatagct   600
atatggggat ttctcgaggc tttggccgcc gcattatgta tgaacgttta tgtagtaggg   660
ctgaacaagg tcaataagcc aaccctccca ttatcgttcg agagttttc aatgccaact    720
gcagtattgt tagtagtggc attcttggtc atgagcatta gcatcggaat aagatcaaag   780
tctgctccat tgatgtgtgc tttgcttgtt tgcttccttc ttggaagcgc atacccatt    840
gacgtcccat tactccggtg aagcgacat gcttttctag ctgcattctg cataatcttt    900
gtgaggcctg tagtggtcca gttagctttc tttgcacaca tgcagcaaca tgttctgaag   960
aggcccttgg cacctacaag gtcggtggtc tttgcaacat gtttcatgtg ttgcttcgct  1020
gcagtaatag cgctattcaa ggatattcct gatgtcgatg gagatagaga tttcggcatt  1080
cagtccatga ctgtacgatt aggccaacag gagtgcata ggctctgcat taatattctc   1140
atgacagcat acgcagccgc aattttggta ggcgcgtcat ctacgaacct gtatcagaag  1200
attgtcattg tgtctggtca tggcttgctt gcctccacac tctggcaaag agcacaacaa  1260
tttgacattg agaataagga ttgtatcaca caattttata tgttcatttg gaagttattc  1320
tacgccgagt attttcttat accattgtg tagtaaagaa tcatgcgaag aacaacaccc   1380
ctgctataga catgtgaagg tttattgcta atgttactct accccctgct atagacatgt  1440
gaaggtttat tgctaatgtt actctaccga atggtctgaa tgtctatgcg tcatttgaat  1500
gtaatatgac tatttgttgt atcagggtaa caactggagc aaatgtacca tgtatattaa  1560
gcattaattt aactgcatca tttgtaccat gtatattatg actatgtatg agatattgtc  1620
tcttattagt actggatgtg atgtgtctta ttatgactat ggatgagact tttgtgatgt  1680
aattgatgag actatggttt taaatattgt tatgtgattg tgtgtgagat             1730
```

<210> SEQ ID NO 8
<211> LENGTH: 380
<212> TYPE: PRT
<213> ORGANISM: Zea mays

<400> SEQUENCE: 8

```
Arg Leu Glu Gly Phe Pro Gly Pro Glu Arg Gln Glu Val Trp Arg Val
1               5                   10                  15

Gly Glu Arg Pro Glu Glu Ala Leu Gln Gly Arg Ala Val Arg Leu Pro
            20                  25                  30

Ala Asp Leu Pro Gln Gly Phe Pro Glu Glu Thr Leu Asp Ala Thr Ser
        35                  40                  45

Pro Thr Arg Ala Thr Gly Arg Gln Arg Arg His Ser Ser Val Pro Lys
    50                  55                  60
```

Val Ser Cys Trp Ala Ala His His Gln His Asn Ser Asn Pro Gln
65                  70                  75                  80

Gln Phe Gln Ala Ile Gly Ile Arg Ile Ala Lys Thr Leu His Ala Phe
            85                  90                  95

Tyr Gln Phe Cys Arg Pro His Thr Ile Phe Gly Thr Ile Ile Gly Ile
        100                 105                 110

Thr Ser Val Ser Ile Leu Pro Val Lys Ser Leu Asp Asp Phe Thr Leu
        115                 120                 125

Ile Ala Ile Trp Gly Phe Leu Glu Ala Leu Ala Ala Leu Cys Met
130                 135                 140

Asn Val Tyr Val Val Gly Leu Asn Lys Val Asn Lys Pro Thr Leu Pro
145                 150                 155                 160

Leu Ser Phe Gly Glu Phe Ser Met Pro Thr Ala Val Leu Leu Val Val
            165                 170                 175

Ala Phe Leu Val Met Ser Ile Ser Ile Gly Ile Arg Ser Lys Ser Ala
        180                 185                 190

Pro Leu Met Cys Ala Leu Leu Val Cys Phe Leu Leu Gly Ser Ala Tyr
        195                 200                 205

Pro Ile Asp Val Pro Leu Leu Arg Trp Lys Arg His Ala Phe Leu Ala
210                 215                 220

Ala Phe Cys Ile Ile Phe Val Arg Pro Val Val Gln Leu Ala Phe
225                 230                 235                 240

Phe Ala His Met Gln Gln His Val Leu Lys Arg Pro Leu Ala Pro Thr
            245                 250                 255

Arg Ser Val Val Phe Ala Thr Cys Phe Met Cys Cys Phe Ala Ala Val
        260                 265                 270

Ile Ala Leu Phe Lys Asp Ile Pro Asp Val Asp Gly Asp Arg Asp Phe
        275                 280                 285

Gly Ile Gln Ser Met Thr Val Arg Leu Gly Gln Gln Arg Val His Arg
290                 295                 300

Leu Cys Ile Asn Ile Leu Met Thr Ala Tyr Ala Ala Ile Leu Val
305                 310                 315                 320

Gly Ala Ser Ser Thr Asn Leu Tyr Gln Lys Ile Val Ile Val Ser Gly
            325                 330                 335

His Gly Leu Leu Ala Ser Thr Leu Trp Gln Arg Ala Gln Gln Phe Asp
        340                 345                 350

Ile Glu Asn Lys Asp Cys Ile Thr Gln Phe Tyr Met Phe Ile Trp Lys
        355                 360                 365

Leu Phe Tyr Ala Glu Tyr Phe Leu Ile Pro Phe Val
370                 375                 380

<210> SEQ ID NO 9
<211> LENGTH: 1769
<212> TYPE: DNA
<213> ORGANISM: Zea mays
<220> FEATURE:
<221> NAME/KEY: misc_feature
<222> LOCATION: (1206)..(1207)
<223> OTHER INFORMATION: n is a, c, g, or t

<400> SEQUENCE: 9
ccacgcgtcc gcgaccacca ccaccacggt gccgccgacg ccgaccacaa ccactcgtag    60
agactaccgt ctccgccccc gctgcttctc gtctccacgc agccgtccga tggccaagcg   120
gctcgccggc gccaacaaag aggtagggga cggcatgcca acaaagcagc ccacccggac   180
tcggcaggcc gcctcgtttc gctaacccat ttgatctgcg ccgggtgctc gtcgaggtgg   240

```
tgaggttcac gcagaagagc ggactgaggg gctgtgacgg tggctggaag gatttcctgg    300
cccggaacga caggaagttt ggagcgtcgg tgagcgacca gaggaagcgc tctagggacg    360
tgttgttcgc cttcctacag accttcccca aggatttcca gaagaaacac ttgatgccac    420
tagtccgacg agagccactg gaaggcaaca caggcattcc tcagtcccca aagtgagctg    480
ctgggcagct gctcatcacc aacacaattc taacccccag cagtttcagg cgattggcat    540
acgaatcgca aagacgctgc atgccttta tcagttctgc cgaccacaca caatatttgg    600
aaccataata ggcattactt cggtgtctct cctgccagtg aagagcctgg acgattttac    660
gttgatagct atatggggat ttctcgaggc tttggccgcc gcattatgta tgaacgttta    720
tgtagtaggg ctgaaccagc tatttgacat tgagattgac aaggtcaata agccaaccct    780
cccattagcg tccggagagt tttcagtgcc aactgcagta ttgttagtag tggcattctt    840
ggtcatgagc attagcatcg gaataagatc aaagtgtgcg ccattgatgt gtgctttgct    900
tgttagcttc cttcttggaa gcgcatactc cattgacgtt ccattactcc gatggaagcg    960
acatgctttt ctagctgcat tctgcataat ctttgtgagg gctgtagtgg tccggttagc   1020
tttctttgca cacatgcagc aacatgttct gaagaggccc ttggcaccta caaggtcggt   1080
ggtctttgca acatgtttca tgtgttgctt cgctgcagta atagcgctat tcaaggatat   1140
tcctgatgtc gatggagata gagattttcgg cattcagtcc atgactgtac gattaggcca   1200
acaganngag ctctgcatta atattctcat gacagcatac gcagtcacaa ttttggtagg   1260
agcgttgtct acgaacctgt atcagaagat tgtcattgtg tctggtcatg gcttgcttgc   1320
ctccacactc tggcaaagag cacaacaatt tgacattgag aataaggatt gtatcacaca   1380
attttatatg ttcatttgga agttattcta tgccgagtat tttcttatac catttgtgta   1440
gtaaagaatc atgcgaagaa catcacccct gctatagaca tgtgaaggtt cattgctaat   1500
gttactctac cgaatggtct gaatgtctat gcgtcatttg tatgtaatat gactttgttg   1560
tatcagggta caactggag caaatgtacc atgtatatta agcattaatt tagctgtgtc    1620
atttgtacca tgtatattat gactatgtat gagatattgt ctcttattag tactagatgt   1680
gatgtgtctt attatgacta tggatgaaac ttttgtgatg taattgatga gactatggat   1740
ttaaatattg ttaaaaaaaa aaaaaaaaa                                     1769
```

<210> SEQ ID NO 10
<211> LENGTH: 361
<212> TYPE: PRT
<213> ORGANISM: Zea mays
<220> FEATURE:
<221> NAME/KEY: misc_feature
<222> LOCATION: (284)..(284)
<223> OTHER INFORMATION: Xaa can be any naturally occurring amino acid

<400> SEQUENCE: 10

Gly Arg Val Val Arg Leu Pro Thr Asp Leu Pro Gln Gly Phe Pro Glu
1               5                   10                  15

Glu Thr Leu Asp Ala Thr Ser Pro Thr Arg Ala Thr Gly Arg Gln His
            20                  25                  30

Arg His Ser Ser Val Pro Lys Val Ser Cys Trp Ala Ala Ala His His
        35                  40                  45

Gln His Asn Ser Asn Pro Gln Gln Phe Gln Ala Ile Gly Ile Arg Ile
    50                  55                  60

Ala Lys Thr Leu His Ala Phe Tyr Gln Phe Cys Arg Pro His Thr Ile
65                  70                  75                  80

```
Phe Gly Thr Ile Ile Gly Ile Thr Ser Val Ser Leu Leu Pro Val Lys
                85                  90                  95
Ser Leu Asp Asp Phe Thr Leu Ile Ala Ile Trp Gly Phe Leu Glu Ala
            100                 105                 110
Leu Ala Ala Leu Cys Met Asn Val Tyr Val Val Gly Leu Asn Gln
        115                 120                 125
Leu Phe Asp Ile Glu Ile Asp Lys Val Asn Lys Pro Thr Leu Pro Leu
    130                 135                 140
Ala Ser Gly Glu Phe Ser Val Pro Thr Ala Val Leu Leu Val Val Ala
145                 150                 155                 160
Phe Leu Val Met Ser Ile Ser Ile Gly Ile Arg Ser Lys Cys Ala Pro
                165                 170                 175
Leu Met Cys Ala Leu Leu Val Ser Phe Leu Leu Gly Ser Ala Tyr Ser
            180                 185                 190
Ile Asp Val Pro Leu Leu Arg Trp Lys Arg His Ala Phe Leu Ala Ala
        195                 200                 205
Phe Cys Ile Ile Phe Val Arg Ala Val Val Val Arg Leu Ala Phe Phe
    210                 215                 220
Ala His Met Gln Gln His Val Leu Lys Arg Pro Leu Ala Pro Thr Arg
225                 230                 235                 240
Ser Val Val Phe Ala Thr Cys Phe Met Cys Cys Phe Ala Ala Val Ile
                245                 250                 255
Ala Leu Phe Lys Asp Ile Pro Asp Val Asp Gly Asp Arg Asp Phe Gly
            260                 265                 270
Ile Gln Ser Met Thr Val Arg Leu Gly Gln Gln Xaa Glu Leu Cys Ile
        275                 280                 285
Asn Ile Leu Met Thr Ala Tyr Ala Val Thr Ile Leu Val Gly Ala Leu
    290                 295                 300
Ser Thr Asn Leu Tyr Gln Lys Ile Val Ile Ser Gly His Gly Leu
305                 310                 315                 320
Leu Ala Ser Thr Leu Trp Gln Arg Ala Gln Gln Phe Asp Ile Glu Asn
                325                 330                 335
Lys Asp Cys Ile Thr Gln Phe Tyr Met Phe Ile Trp Lys Leu Phe Tyr
            340                 345                 350
Ala Glu Tyr Phe Leu Ile Pro Phe Val
        355                 360

<210> SEQ ID NO 11
<211> LENGTH: 1053
<212> TYPE: DNA
<213> ORGANISM: Glycine max

<400> SEQUENCE: 11
atggccaccg tggtgaggat cccaacaatc tcatgcatcc acatccacac gttccgttcc      60
caatcccctc gcactttcgc cagaatccgg gtcggaccca gtcgtgggc tcctattcgg     120 gcatcggcag cgagctcgga gagggggag atagtattgg agcagaagcc aagaaggat     180 gacaagaaga agctgcagaa gggaatcgca gagttttacg acgagtcgtc tggcttatgg     240
gagaacattt ggggcgacca catgcaccat ggcttttatg actcggattc cactgtttcg     300
ctttcggatc atcgtgctgc tcagatccga atgatccaag agtctcttcg ctttgcctct     360
gtttctgagg agcgtagtaa atggcccaag agtatagttg atgttgggtg tggcataggt     420
ggcagctcta gataccctggc caagaaattt ggagcaacca gtgtaggcat cactctgagt     480
cctgttcaag ctcaaagagc aaatgctctt gctgctgctc aaggattggc tgataaggtt     540
```

-continued

```
tcctttcagg ttgctgacgc tctacagcaa ccattctctg acggccagtt tgatctggtg    600
tggtccatgg agagtggaga gcatatgcct gacaaagcta agtttgttgg agagttagct    660
cgggtagcag caccaggtgc cattataata atagtaacat ggtgccacag ggatcttggc    720
cctgacgaac aatccttaca tccatgggag caagatctct taagaagat ttgcgatgca     780 tattacctcc ctgcctggtg ctcaacttct gattatgtta agttgctcca atccctgtca    840
cttcaggaca tcaagtcaga agattggtct cgctttgttg ctccattttg gccagcagtg    900
atacgctcag ccttcacatg gaagggtcta tcttcactct gagcagtgg acaaaaaacg     960 ataaaaggag ctttggctat gccattgatg atagagggat acaagaaaga tctaattaag   1020
tttgccatca ttacatgtcg aaaacctgaa taa                                1053
```

<210> SEQ ID NO 12
<211> LENGTH: 350
<212> TYPE: PRT
<213> ORGANISM: Glycine max

<400> SEQUENCE: 12

```
Met Ala Thr Val Val Arg Ile Pro Thr Ile Ser Cys Ile His Ile His
1               5                   10                  15

Thr Phe Arg Ser Gln Ser Pro Arg Thr Phe Ala Arg Ile Arg Val Gly
            20                  25                  30

Pro Arg Ser Trp Ala Pro Ile Arg Ala Ser Ala Ala Ser Ser Glu Arg
        35                  40                  45

Gly Glu Ile Val Leu Glu Gln Lys Pro Lys Lys Asp Asp Lys Lys Lys
    50                  55                  60

Leu Gln Lys Gly Ile Ala Glu Phe Tyr Asp Glu Ser Ser Gly Leu Trp
65                  70                  75                  80

Glu Asn Ile Trp Gly Asp His Met His His Gly Phe Tyr Asp Ser Asp
                85                  90                  95

Ser Thr Val Ser Leu Ser Asp His Arg Ala Ala Gln Ile Arg Met Ile
            100                 105                 110

Gln Glu Ser Leu Arg Phe Ala Ser Val Ser Glu Glu Arg Ser Lys Trp
        115                 120                 125

Pro Lys Ser Ile Val Asp Val Gly Cys Gly Ile Gly Gly Ser Ser Arg
    130                 135                 140

Tyr Leu Ala Lys Lys Phe Gly Ala Thr Ser Val Gly Ile Thr Leu Ser
145                 150                 155                 160

Pro Val Gln Ala Gln Arg Ala Asn Ala Leu Ala Ala Ala Gln Gly Leu
                165                 170                 175

Ala Asp Lys Val Ser Phe Gln Val Ala Asp Ala Leu Gln Gln Pro Phe
            180                 185                 190

Ser Asp Gly Gln Phe Asp Leu Val Trp Ser Met Glu Ser Gly Glu His
        195                 200                 205

Met Pro Asp Lys Ala Lys Phe Val Gly Glu Leu Ala Arg Val Ala Ala
    210                 215                 220

Pro Gly Ala Ile Ile Ile Ile Val Thr Trp Cys His Arg Asp Leu Gly
225                 230                 235                 240

Pro Asp Glu Gln Ser Leu His Pro Trp Glu Gln Asp Leu Leu Lys Lys
                245                 250                 255

Ile Cys Asp Ala Tyr Tyr Leu Pro Ala Trp Cys Ser Thr Ser Asp Tyr
            260                 265                 270

Val Lys Leu Leu Gln Ser Leu Ser Leu Gln Asp Ile Lys Ser Glu Asp
        275                 280                 285
```

```
Trp Ser Arg Phe Val Ala Pro Phe Trp Pro Ala Val Ile Arg Ser Ala
        290                 295                 300

Phe Thr Trp Lys Gly Leu Ser Ser Leu Leu Ser Ser Gly Gln Lys Thr
305                 310                 315                 320

Ile Lys Gly Ala Leu Ala Met Pro Leu Met Ile Glu Gly Tyr Lys Lys
                325                 330                 335

Asp Leu Ile Lys Phe Ala Ile Ile Thr Cys Arg Lys Pro Glu
                340                 345                 350

<210> SEQ ID NO 13
<211> LENGTH: 1331
<212> TYPE: DNA
<213> ORGANISM: Glycine max

<400> SEQUENCE: 13
gtgacatggc caccgtggtg aggatcccaa caatctcatg catccacatc cacacgttcc     60
gttcccaatc ccctcgcact ttcgccagaa tccgggtcgg acccaggtcg tgggctccta    120
ttcgggcatc ggcagcgagc tcggagagag gggagatagt attggagcag aagccgaaga    180
aggatgacaa gaagaagctg cagaagggaa tcgcagagtt ttacgacgag tcgtctggct    240
tatgggagaa catttggggc gaccacatgc accatggctt ttatgactcg gattccactg    300
tttcgctttc ggatcatcgt gctgctcaga tccgaatgat ccaagagtct cttcgctttg    360
cctctgtttc tgaggagcgt agtaaatggc ccaagagtat agttgatgtt gggtgtggca    420
taggtggcag ctctagatac ctggccaaga aatttggagc aaccagtgta ggcatcactc    480
tgagtcctgt tcaagctcaa agagcaaatg ctcttgctgc tgctcaagga ttggctgata    540
aggtttcctt tcaggttgct gacgctctac agcaaccatt ctctgacggc cagtttgatc    600
tggtgtggtc catggagagt ggagagcata tgcctgacaa agctaagttt gttggagagt    660
tagctcgggt agcagcacca ggtgccatta taataatagt aacatggtgc cacagggatc    720
ttggccctga cgaacaatcc ttacatccat gggagcaaga tctcttaaag aagatttgcg    780
atgcatatta cctccctgcc tggtgctcaa cttctgatta tgttaagttg ctccaatccc    840
tgtcacttca ggacatcaag tcagaagatt ggtctcgctt gttgctcca ttttggccag    900 cagtgatacg ctcagccttc acatggaagg gtctatcttc actcttgagc agtggtaagc    960
ttggaattta tattgcattt caaaaacaaa ccccccccatc ttctattgca acttgcaagt   1020
cttatgtcac tgatcattat ttccacacta gataacccctt tacaactaag aacgtagtct   1080
tcatgttcag cgaaatagat aaaaatatgc aacagagtca gagacagggt gcatgatatt   1140
tacaagaaaa tatctttat atatataaat gattcaatca aattacttga tgaggattat   1200
gagtgaaaat gagaggacag tcatagaaac tttatcctac attccttcta tttccacttc   1260
tgtcaaatat tcctttcatc ttagctatgc tacttgactt gagtaaaaaa aaaaaaaaaa   1320 aaaaaaaaa a                                                          1331

<210> SEQ ID NO 14
<211> LENGTH: 349
<212> TYPE: PRT
<213> ORGANISM: Glycine max

<400> SEQUENCE: 14

Met Ala Thr Val Val Arg Ile Pro Thr Ile Ser Cys Ile His Ile His
1               5                   10                  15

Thr Phe Arg Ser Gln Ser Pro Thr Phe Ala Arg Ile Arg Val Gly
            20                  25                  30
```

```
Pro Arg Ser Trp Ala Pro Ile Arg Ala Ser Ala Ser Glu Arg
         35                  40                  45

Gly Glu Ile Val Leu Glu Gln Lys Pro Lys Asp Lys Lys
 50                  55                  60

Leu Gln Lys Gly Ile Ala Glu Phe Tyr Asp Glu Ser Ser Gly Leu Trp
 65                  70                  75                  80

Glu Asn Ile Trp Gly Asp His Met His Gly Phe Tyr Asp Ser Asp
                 85                  90                  95

Ser Thr Val Ser Leu Ser Asp His Arg Ala Ala Gln Ile Arg Met Ile
                100                 105                 110

Gln Glu Ser Leu Arg Phe Ala Ser Val Ser Glu Arg Ser Lys Trp
            115                 120                 125

Pro Lys Ser Ile Val Asp Val Gly Cys Gly Ile Gly Gly Ser Ser Arg
130                 135                 140

Tyr Leu Ala Lys Lys Phe Gly Ala Thr Ser Val Gly Ile Thr Leu Ser
145                 150                 155                 160

Pro Val Gln Ala Gln Arg Ala Asn Ala Leu Ala Ala Gln Gly Leu
                165                 170                 175

Ala Asp Lys Val Ser Phe Gln Val Ala Asp Ala Leu Gln Gln Pro Phe
            180                 185                 190

Ser Asp Gly Gln Phe Asp Leu Val Trp Ser Met Glu Ser Gly Glu His
            195                 200                 205

Met Pro Asp Lys Ala Lys Phe Val Gly Glu Leu Ala Arg Val Ala Ala
210                 215                 220

Pro Gly Ala Ile Ile Ile Ile Val Thr Trp Cys His Arg Asp Leu Gly
225                 230                 235                 240

Pro Asp Glu Gln Ser Leu His Pro Trp Glu Gln Asp Leu Leu Lys Lys
                245                 250                 255

Ile Cys Asp Ala Tyr Tyr Leu Pro Ala Trp Cys Ser Thr Ser Asp Tyr
                260                 265                 270

Val Lys Leu Leu Gln Ser Leu Ser Leu Gln Asp Ile Lys Ser Glu Asp
            275                 280                 285

Trp Ser Arg Phe Val Ala Pro Phe Trp Pro Ala Val Ile Arg Ser Ala
290                 295                 300

Phe Thr Trp Lys Gly Leu Ser Ser Leu Ser Ser Gly Lys Leu Gly
305                 310                 315                 320

Ile Tyr Ile Ala Phe Gln Lys Gln Thr Pro Pro Ser Ser Ile Ala Thr
                325                 330                 335

Cys Lys Ser Tyr Val Thr Asp His Tyr Phe His Thr Arg
            340                 345

<210> SEQ ID NO 15
<211> LENGTH: 1301
<212> TYPE: DNA
<213> ORGANISM: Zea mays

<400> SEQUENCE: 15
ccacgcgtcc gcctcggcct cttttaaata tcgcgcatcc cggcgccgca aatggctcac      60
gcggcgctgc tccattgctc ccagtcctcc aggagcctcg cagcctgccg ccgcggcagc     120
cactaccgcg ccccttcgca cgtcccgcgc cactcccgcc gtctccgacg cgccgtcgtc     180
agcctgcgtc cgatggcctc gtcgacggct caggcccccg cgacggcgcc gccgggtctg     240
aaggagggca tcgcggggct gtacgacgag tcgtcggggc tgtgggagaa catctggggc     300
gaccacatgc accacggctt ctacgactcg agcgaggccg cctccatggc cgatcaccgc     360
```

```
cgcgcccaga tccgcatgat cgaggaggcg ctcgccttcg ccggtgtccc agcctcagat       420
gatccagaga agacaccaaa aacaatagtc gatgtcggat gtggcattgg tggtagctca       480
aggtacttgg cgaagaaata cggagcgcag tgcactggga tcacgttgag ccctgttcaa       540
gccgagagag gaaatgctct cgctgcagcg caggggttgt cggatcaggt tactctgcaa       600
gttgctgatg ctctggagca accgtttcct gacgggcagt tcgatctggt gtggtccatg       660
gagagtggcg agcacatgcc ggacaagaga aagtttgtta gtgagctagc acgcgtggcg       720
gctcctggag ggacaataat catcgtgaca tggtgccata ggaacctgga tccatccgaa       780
acctcgctaa agcccgatga actgagcctc ctgaggagga tatgcgacgc gtactacctc       840
ccggactggt gctcaccttc agactatgtg acattgcca agtcactgtc tctcgaggat        900
atcaagacag ctgactggtc ggagaacgtg gccccgtttt ggcccgccgt gataaaatca       960
gcgctaacat ggaagggctt cacctctctg ctgacgaccg gatggaagac gatcagaggc      1020
gcgatggtga tgccgctaat gatccagggc tacaagaagg gcctcatcaa attcaccatc      1080
atcacctgtc gcaagcctgg agccgcgtag gaggaggcca aggagcacaa gttactggca      1140
caggcacagg agtgtcatgt gcaataatgt agattcgtgg ccccatcgcc gtctactcat      1200
ctgtactgca ccaaaatcaa cattctccta ggtgttaaat aatttctgc cactcgtcga      1260 gatatttcaa attcactgtt ccacaaaaaa aaaaaaaaaa g                         1301
```

<210> SEQ ID NO 16
<211> LENGTH: 352
<212> TYPE: PRT
<213> ORGANISM: Zea mays

<400> SEQUENCE: 16

```
Met Ala His Ala Ala Leu Leu His Cys Ser Gln Ser Ser Arg Ser Leu
1               5                   10                  15

Ala Ala Cys Arg Arg Gly Ser His Tyr Arg Ala Pro Ser His Val Pro
            20                  25                  30

Arg His Ser Arg Arg Leu Arg Arg Ala Val Val Ser Leu Arg Pro Met
        35                  40                  45

Ala Ser Ser Thr Ala Gln Ala Pro Ala Thr Ala Pro Pro Gly Leu Lys
    50                  55                  60

Glu Gly Ile Ala Gly Leu Tyr Asp Glu Ser Ser Gly Leu Trp Glu Asn
65                  70                  75                  80

Ile Trp Gly Asp His Met His His Gly Phe Tyr Asp Ser Ser Glu Ala
                85                  90                  95

Ala Ser Met Ala Asp His Arg Arg Ala Gln Ile Arg Met Ile Glu Glu
            100                 105                 110

Ala Leu Ala Phe Ala Gly Val Pro Ala Ser Asp Asp Pro Glu Lys Thr
        115                 120                 125

Pro Lys Thr Ile Val Asp Val Gly Cys Gly Ile Gly Gly Ser Ser Arg
    130                 135                 140

Tyr Leu Ala Lys Lys Tyr Gly Ala Gln Cys Thr Gly Ile Thr Leu Ser
145                 150                 155                 160

Pro Val Gln Ala Glu Arg Gly Asn Ala Leu Ala Ala Gln Gly Leu
            165                 170                 175

Ser Asp Gln Val Thr Leu Gln Val Ala Asp Ala Leu Glu Gln Pro Phe
            180                 185                 190

Pro Asp Gly Gln Phe Asp Leu Val Trp Ser Met Glu Ser Gly Glu His
        195                 200                 205

Met Pro Asp Lys Arg Lys Phe Val Ser Glu Leu Ala Arg Val Ala Ala
```

```
                210                 215                 220
Pro Gly Gly Thr Ile Ile Val Thr Trp Cys His Arg Asn Leu Asp
225                 230                 235                 240

Pro Ser Glu Thr Ser Leu Lys Pro Asp Glu Leu Ser Leu Leu Arg Arg
                245                 250                 255

Ile Cys Asp Ala Tyr Tyr Leu Pro Asp Trp Cys Ser Pro Ser Asp Tyr
                260                 265                 270

Val Asp Ile Ala Lys Ser Leu Ser Leu Glu Asp Ile Lys Thr Ala Asp
                275                 280                 285

Trp Ser Glu Asn Val Ala Pro Phe Trp Pro Ala Val Ile Lys Ser Ala
                290                 295                 300

Leu Thr Trp Lys Gly Phe Thr Ser Leu Leu Thr Thr Gly Trp Lys Thr
305                 310                 315                 320

Ile Arg Gly Ala Met Val Met Pro Leu Met Ile Gln Gly Tyr Lys Lys
                325                 330                 335

Gly Leu Ile Lys Phe Thr Ile Ile Thr Cys Arg Lys Pro Gly Ala Ala
                340                 345                 350

<210> SEQ ID NO 17
<211> LENGTH: 1257
<212> TYPE: DNA
<213> ORGANISM: Triticum aestivum
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t

<400> SEQUENCE: 17
gaggctccaa atacaaaatg gcaaactccg nccgccctgc tccactcact cctctccacc      60
gcctggacgc cgcgccgccg cctcgaccga gcctcggcca cgcggctcgc cccgtccccc     120
ggcctgtcct gccgctcctc ccggccagac ngctccgtgc gcccgatggc gtcgtcgacg     180
accgcggccc gggcgacgcg cgcgccgccg ggctgaagga gggcatcgcg gggctctacg     240
acgagtcgtc cggcctgtgg gagagcatct ggggcgagca catgcaccac ggcttctacg     300
actccggcga ggccgcctcc atgtccgacc accgccgcgc ccagatccgc atgatcgagg     360
aggccctcgc cttcgccgcc gtccccgacg atccgacaaa caaacccaaa acgattgttg     420
atgttggatg cggaatcggt ggtagctcaa gatacctggc gaacaaatat ggagcacaat     480
gctctgggat cacattgagc ccagtgcaag ctgagagagg aaatgccctc gcggcagcgc     540
aggggttgtc ggacaaggct tctttccaag ttgctgatgc tctggagcaa ccatttcctg     600
atgggcagtt tgatcttgtc tggtctatgg agagtggtga gcacatgccg aacaaacaga     660
agtttgtaag cgagctggca cgcgtcgcag ctccaggagc aactatcatc atcgtgacct     720
ggtgccatag gaacctcgcg ccgtcggagg actcactgaa acctgacgag ctgaatcttt     780
tgaaaaagat ttgtgatgca tattacctcc cggattggtg ctcgccctcg gattatgtca     840
agattgccga gtcattgtct cttgaggata tcaaaacggc cgactggtca gaaaacgtgg     900
ccccgttctg gcctgctgtc atccaatcag cactgacatg gaaaggcctc acttctctac     960
taaggagtgg atggaagacg ataaagggag cactggtgat gcctctcatg atccaaggct    1020
acaagaaagg cctcattaag ttcagcatca tcacctgccg caaacccaag gcagccatag    1080
aaggagaacc tgaggccgca tcgcccagtg tagaatagaa cccatgtgat tggaatagac    1140
```

-continued

```
tcggcttgct gtcgcctcgt agctgaataa ttttgtgtta ccgtgcctct ctatctgcaa    1200
ctggaagtgg cataggaaag tggttcctaa agcaaaaaaa aaaaaaaaaa aaaaaaa       1257
```

<210> SEQ ID NO 18
<211> LENGTH: 366
<212> TYPE: PRT
<213> ORGANISM: Triticum aestivum
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 18

```
Met Ala Asn Ser Xaa Arg Pro Ala Pro Leu Thr Pro Leu His Arg Leu
1               5                   10                  15

Asp Ala Ala Pro Pro Arg Pro Ser Leu Gly His Ala Ala Arg Pro
            20                  25                  30

Val Pro Arg Pro Val Leu Pro Leu Pro Ala Arg Xaa Leu Arg Ala
        35                  40                  45

Pro Asp Gly Val Val Asp Arg Gly Pro Gly Asp Ala Ala Pro Pro
    50                  55                  60

Gly Leu Lys Glu Gly Ile Ala Gly Leu Tyr Asp Glu Ser Gly Leu
65                  70                  75                  80

Trp Glu Ser Ile Trp Gly Glu His Met His Gly Phe Tyr Asp Ser
                85                  90                  95

Gly Glu Ala Ala Ser Met Ser Asp His Arg Arg Ala Gln Ile Arg Met
            100                 105                 110

Ile Glu Glu Ala Leu Ala Phe Ala Ala Val Pro Asp Asp Pro Thr Asn
        115                 120                 125

Lys Pro Lys Thr Ile Val Asp Val Gly Cys Gly Ile Gly Gly Ser Ser
    130                 135                 140

Arg Tyr Leu Ala Asn Lys Tyr Gly Ala Gln Cys Ser Gly Ile Thr Leu
145                 150                 155                 160

Ser Pro Val Gln Ala Glu Arg Gly Asn Ala Leu Ala Ala Gln Gly
                165                 170                 175

Leu Ser Asp Lys Ala Ser Phe Gln Val Ala Asp Ala Leu Glu Gln Pro
            180                 185                 190

Phe Pro Asp Gly Gln Phe Asp Leu Val Trp Ser Met Glu Ser Gly Glu
        195                 200                 205

His Met Pro Asn Lys Gln Lys Phe Val Ser Glu Leu Ala Arg Val Ala
    210                 215                 220

Ala Pro Gly Ala Thr Ile Ile Ile Val Thr Trp Cys His Arg Asn Leu
225                 230                 235                 240

Ala Pro Ser Glu Asp Ser Leu Lys Pro Asp Glu Leu Asn Leu Lys
                245                 250                 255

Lys Ile Cys Asp Ala Tyr Tyr Leu Pro Asp Trp Cys Ser Pro Ser Asp
            260                 265                 270

Tyr Val Lys Ile Ala Glu Ser Leu Ser Leu Glu Asp Ile Lys Thr Ala
        275                 280                 285

Asp Trp Ser Glu Asn Val Ala Pro Phe Trp Pro Ala Val Ile Gln Ser
    290                 295                 300

Ala Leu Thr Trp Lys Gly Leu Thr Ser Leu Leu Arg Ser Gly Trp Lys
305                 310                 315                 320
```

Thr Ile Lys Gly Ala Leu Val Met Pro Leu Met Ile Gln Gly Tyr Lys
            325                 330                 335

Lys Gly Leu Ile Lys Phe Ser Ile Ile Thr Cys Arg Lys Pro Gln Ala
            340                 345                 350

Ala Ile Glu Gly Glu Pro Glu Ala Ala Ser Pro Ser Val Glu
            355                 360                 365

<210> SEQ ID NO 19
<211> LENGTH: 1077
<212> TYPE: DNA
<213> ORGANISM: Lotus corniculatus

<400> SEQUENCE: 19
atggccacga tgatgatgtc aattttttcca ccaccaccaa gcgtggcttc attatttata     60
ctatcacact gcactcacac aattcgtgta caatcaacaa cgcagttcac aggttttttct    120
ataagaacca gaacacgtga ttgtagtaga attctgttaa cagaagaacg agaaatggcg    180
gtgatggagg agaagaagct tttgcagacc ggaatcgctg agttctacga cgagtcgtcc    240
gggttatggg aagacatgtg gggagaccac atgcatcacg gttttacga gcaggatgtc    300
accgtctctg tttcagacca ccgtgttgct cagatccgaa tgattgaaga gtctcttcgt    360
tttgctgcac tttctgagga tccagctaaa aagccagaga gtatagtgga tgttgggtgc    420
ggcataggag gcagttctag gtacctagct aagaaatttc aggcaaagag cgttggtatc    480
actctgagtc ctgttcaagc tcagagagca atgctcttg ctgcttctca aggcttagct    540
gacaaggttt cctttcaagt tgctgatgct ctagagcaac cattccctga tggtcagttt    600
gatctggtgt ggtccatgga gagtggagag catatgcctg acaaacctaa gtttgttggc    660
gagttagctc gggtggcagc accaggtggg accataataa ttgtaacatg gtgccaccgg    720
gatcttggac cagctgaaga atccctgcag ccatgggagc agaatctctt gaagaggata    780
tgcgatgcat tttaccttcc agcatggtgc tcaactgctg attatgtcaa attgctggaa    840
tcccattcac ttcaggacat caaatcagca gattggtctc cctttgttgc tccatttttgg    900
ccagctgtga tacgctcagc atttacatgg aagggtctca cttcactgtt gcgcagtgga    960
atgaaaacca taaaaggagc tttggctatg ccattgatga tagaaggatt caagaagggt   1020
gtcatcaagt tgccattgt tacatgtaga aagcctgaaa atgtggagat agaataa      1077

<210> SEQ ID NO 20
<211> LENGTH: 358
<212> TYPE: PRT
<213> ORGANISM: Lotus corniculatus

<400> SEQUENCE: 20

Met Ala Thr Met Met Met Ser Ile Phe Pro Pro Pro Ser Val Ala
1               5                   10                  15

Ser Leu Phe Ile Leu Ser His Cys Thr His Thr Ile Arg Val Gln Ser
            20                  25                  30

Thr Thr Gln Phe Thr Gly Phe Ser Ile Arg Thr Arg Thr Arg Asp Cys
        35                  40                  45

Ser Arg Ile Leu Leu Thr Glu Glu Arg Glu Met Ala Val Met Glu Glu
    50                  55                  60

Lys Lys Leu Leu Gln Thr Gly Ile Ala Glu Phe Tyr Asp Glu Ser Ser
65                  70                  75                  80

Gly Leu Trp Glu Asp Met Trp Gly Asp His Met His His Gly Phe Tyr
                85                  90                  95

Glu Gln Asp Val Thr Val Ser Val Ser Asp His Arg Val Ala Gln Ile

```
              100                 105                 110
Arg Met Ile Glu Glu Ser Leu Arg Phe Ala Ala Leu Ser Glu Asp Pro
            115                 120                 125

Ala Lys Lys Pro Glu Ser Ile Val Asp Val Gly Cys Gly Ile Gly Gly
            130                 135                 140

Ser Ser Arg Tyr Leu Ala Lys Lys Phe Gln Ala Lys Ser Val Gly Ile
145                 150                 155                 160

Thr Leu Ser Pro Val Gln Ala Gln Arg Ala Asn Ala Leu Ala Ala Ser
                165                 170                 175

Gln Gly Leu Ala Asp Lys Val Ser Phe Gln Val Ala Asp Ala Leu Glu
            180                 185                 190

Gln Pro Phe Pro Asp Gly Gln Phe Asp Leu Val Trp Ser Met Glu Ser
            195                 200                 205

Gly Glu His Met Pro Asp Lys Pro Lys Phe Val Gly Glu Leu Ala Arg
            210                 215                 220

Val Ala Ala Pro Gly Gly Thr Ile Ile Ile Val Thr Trp Cys His Arg
225                 230                 235                 240

Asp Leu Gly Pro Ala Glu Glu Ser Leu Gln Pro Trp Glu Gln Asn Leu
                245                 250                 255

Leu Lys Arg Ile Cys Asp Ala Phe Tyr Leu Pro Ala Trp Cys Ser Thr
            260                 265                 270

Ala Asp Tyr Val Lys Leu Leu Glu Ser His Ser Leu Gln Asp Ile Lys
            275                 280                 285

Ser Ala Asp Trp Ser Pro Phe Val Ala Pro Phe Trp Pro Ala Val Ile
            290                 295                 300

Arg Ser Ala Phe Thr Trp Lys Gly Leu Thr Ser Leu Leu Arg Ser Gly
305                 310                 315                 320

Met Lys Thr Ile Lys Gly Ala Leu Ala Met Pro Leu Met Ile Glu Gly
                325                 330                 335

Phe Lys Lys Gly Val Ile Lys Phe Ala Ile Val Thr Cys Arg Lys Pro
            340                 345                 350

Glu Asn Val Glu Ile Glu
            355

<210> SEQ ID NO 21
<211> LENGTH: 1292
<212> TYPE: DNA
<213> ORGANISM: Glycine max

<400> SEQUENCE: 21
agcctttatt agtaattgac tattgaaggt tgggcacccg tgagtgacat ggccaccgtg      60
gtgaggatcc caacaatctc atgcatccac atccacacgt tccgttccca atcccctcgc     120
actttcgcca gaatccgggt cggacccagg tcgtgggctc ctattcgggc atcggcagcg     180
agctcggaga gagggagat agtattggag cagaagccga agaaggatga caagaagaag     240
ctgcagaagg gaatcgcaga gttttacgac gagtcttctg gcttatggga gaacatttgg     300
ggcgaccaca tgcaccatgg cttttatgac tcggattcca ctgtttcgct ttcggatcat     360
cgtgctgctc agatccgaat gatccaagag tctcttcgct ttgcctctgt ttctgaggag     420
cgtagtaaat ggcccaagag tatagttgat gttgggtgtg cataggtgg cagctctaga     480 tacctggcca agaaatttgg agcaaccagt gtaggcatca ctctgagtcc tgttcaagct     540
caaagagcaa atgctcttgc tgctgctcaa ggattggctg ataaggtttc ctttcaggtt     600
gctgacgctc tacagcaacc attctctgac ggccagtttg atctggtgtg gtccatggag     660
```

-continued

```
agtggagagc atatgcctga caaagctaag tttgttggag agttagctcg ggtagcagca      720
ccaggtgcca ctataataat agtaacatgg tgccacaggg atcttggccc tgacgaacaa      780
tccttacatc catgggagca agatctctta aagaagattt gcgatgcata ttacctccct      840
gcctggtgct caacttctga ttatgttaag ttgctccaat ccctgtcact tcaggacatc      900
aagtcagaag attggtctcg ctttgttgct ccattttggc cagcagtgat acgctcagcc      960
ttcacatgga agggtctaac ttcactcttg agcagtggac aaaaaacgat aaaaggagct     1020
ttggctatgc cattgatgat agagggatac aagaaagatc taattaagtt tgccatcatt     1080
acatgtcgaa aacctgaata aatggagagg caggattact tttatagaat gaaccaagtt     1140
tccaacaggt cgtttatttc gatagttgag aaacaagaga aaaataaat gaaggggtt      1200 gttcgatttt tattttagtt ttctacatat gcaatatctc ctatgattgg cgaaaatata     1260
ttatctactt aaataaaaaa aaaaaaaaaa aa                                   1292
```

<210> SEQ ID NO 22
<211> LENGTH: 350
<212> TYPE: PRT
<213> ORGANISM: Glycine max

<400> SEQUENCE: 22

```
Met Ala Thr Val Val Arg Ile Pro Thr Ile Ser Cys Ile His Ile His
1               5                   10                  15

Thr Phe Arg Ser Gln Ser Pro Arg Thr Phe Ala Arg Ile Arg Val Gly
            20                  25                  30

Pro Arg Ser Trp Ala Pro Ile Arg Ala Ser Ala Ala Ser Ser Glu Arg
        35                  40                  45

Gly Glu Ile Val Leu Glu Gln Lys Pro Lys Lys Asp Lys Lys Lys
    50                  55                  60

Leu Gln Lys Gly Ile Ala Glu Phe Tyr Asp Glu Ser Ser Gly Leu Trp
65                  70                  75                  80

Glu Asn Ile Trp Gly Asp His Met His His Gly Phe Tyr Asp Ser Asp
                85                  90                  95

Ser Thr Val Ser Leu Ser Asp His Arg Ala Ala Gln Ile Arg Met Ile
            100                 105                 110

Gln Glu Ser Leu Arg Phe Ala Ser Val Ser Glu Glu Arg Ser Lys Trp
        115                 120                 125

Pro Lys Ser Ile Val Asp Val Gly Cys Gly Ile Gly Gly Ser Ser Arg
    130                 135                 140

Tyr Leu Ala Lys Lys Phe Gly Ala Thr Ser Val Gly Ile Thr Leu Ser
145                 150                 155                 160

Pro Val Gln Ala Gln Arg Ala Asn Ala Leu Ala Ala Ala Gln Gly Leu
                165                 170                 175

Ala Asp Lys Val Ser Phe Gln Val Ala Asp Ala Leu Gln Gln Pro Phe
            180                 185                 190

Ser Asp Gly Gln Phe Asp Leu Val Trp Ser Met Glu Ser Gly Glu His
        195                 200                 205

Met Pro Asp Lys Ala Lys Phe Val Gly Glu Leu Ala Arg Val Ala Ala
    210                 215                 220

Pro Gly Ala Thr Ile Ile Ile Val Thr Trp Cys His Arg Asp Leu Gly
225                 230                 235                 240

Pro Asp Glu Gln Ser Leu His Pro Trp Glu Gln Asp Leu Leu Lys Lys
                245                 250                 255

Ile Cys Asp Ala Tyr Tyr Leu Pro Ala Trp Cys Ser Thr Ser Asp Tyr
            260                 265                 270
```

Val Lys Leu Leu Gln Ser Leu Ser Leu Gln Asp Ile Lys Ser Glu Asp
            275                 280                 285

Trp Ser Arg Phe Val Ala Pro Phe Trp Pro Ala Val Ile Arg Ser Ala
        290                 295                 300

Phe Thr Trp Lys Gly Leu Thr Ser Leu Leu Ser Gly Gln Lys Thr
305                 310                 315                 320

Ile Lys Gly Ala Leu Ala Met Pro Leu Met Ile Glu Gly Tyr Lys Lys
                325                 330                 335

Asp Leu Ile Lys Phe Ala Ile Ile Thr Cys Arg Lys Pro Glu
                340                 345                 350

<210> SEQ ID NO 23
<211> LENGTH: 1301
<212> TYPE: DNA
<213> ORGANISM: Oryza sativa

<400> SEQUENCE: 23

| | |
|---|---|
| agacgccaga gcgctacaaa atggcccacg ccgccgcggc cacgggcgca ctggcaccgc | 60 |
| tgcatccact gctccgctgc acgagccgtc atctctgcgc ctcggcttcc cctcgcgccg | 120 |
| gcctctgcct ccaccaccac cgccgccgcc gccgcagcag ccggaggacg aaactcgccg | 180 |
| tgcgcgcgat ggcaccgacg ttgtcctcgt cgtcgacggc ggcggcagct ccccggggc | 240 |
| tgaaggaggg catcgcgggg ctctacgacg agtcgtccgg cgtgtgggag agcatctggg | 300 |
| gcgagcacat gcaccacggc ttctacgacg ccggcgaggc cgcctccatg tccgaccacc | 360 |
| gccgcgccca gatccgcatg atcgaggaat ccctcgcctt cgccgccgtc cccgatgatg | 420 |
| cggagaagaa acccaaaagt gtagttgatg ttggctgtgg cattggtggt agctcaagat | 480 |
| acttggcgaa caaatacgga gcgcaatgct acggcatcac gttgagtccg gtgcaggctg | 540 |
| aaagaggaaa tgccctcgcg gcagagcaag ggttatcaga caaggtctcc tttcaagttg | 600 |
| gtgatgcatt ggagcagcct tttcctgatg ggcagtttga tcttgtctgg tccatggaga | 660 |
| gtggcgagca catgccagac aaacggcagt ttgtaagcga gctggcacgc gtcgcagctc | 720 |
| ctggggcgag aataatcatt gtgacctggt gccataggaa cctcgagcca tccgaagagt | 780 |
| ccctgaaacc tgatgagctg aatctcctga aaaggatatg cgatgcatat tatctcccag | 840 |
| actggtgctc tccttctgat tatgtcaaaa ttgccgagtc actgtctctt gaggatataa | 900 |
| ggacagctga ttggtcagag aacgtcgccc cattctggcc tgcggttata aaatcagcat | 960 |
| tgacatggaa aggtttaact tctctgctaa gaagtgggtg gaagacgata gagagtgcaa | 1020 |
| tggtgatgcc tctgatgatc gaaggataca agaaagggct catcaaattc accatcatca | 1080 |
| cctgtcgcaa gcccgaaaca acgcagtagt accctagtag tgaaattacg ctcctgctat | 1140 |
| cttctccatc acgaataatg caaattctga cgagttagca cctactgatg gcgatttgtt | 1200 |
| gatttgggga acagccagtg cactgttacc acgtcattga tttttgtactc gtcagactta | 1260 |
| aaaaaaaat atccatgaat gtgcactcca aatacgtcaa g | 1301 |

<210> SEQ ID NO 24
<211> LENGTH: 362
<212> TYPE: PRT
<213> ORGANISM: Oryza sativa

<400> SEQUENCE: 24

Met Ala His Ala Ala Ala Ala Thr Gly Ala Leu Ala Pro Leu His Pro
1               5                   10                  15

Leu Leu Arg Cys Thr Ser Arg His Leu Cys Ala Ser Ala Ser Pro Arg

|  |  | 20 |  |  |  | 25 |  |  |  | 30 |  |  |
|---|---|---|---|---|---|---|---|---|---|---|---|---|

Ala Gly Leu Cys Leu His His His Arg Arg Arg Arg Ser Ser Arg
            35                  40                  45

Arg Thr Lys Leu Ala Val Arg Ala Met Ala Pro Thr Leu Ser Ser Ser
50                  55                  60

Ser Thr Ala Ala Ala Pro Pro Gly Leu Lys Glu Gly Ile Ala Gly
65                  70                  75                  80

Leu Tyr Asp Glu Ser Ser Gly Val Trp Glu Ser Ile Trp Gly Glu His
                85                  90                  95

Met His His Gly Phe Tyr Asp Ala Gly Glu Ala Ala Ser Met Ser Asp
            100                 105                 110

His Arg Arg Ala Gln Ile Arg Met Ile Glu Glu Ser Leu Ala Phe Ala
        115                 120                 125

Ala Val Pro Asp Asp Ala Glu Lys Lys Pro Lys Ser Val Val Asp Val
    130                 135                 140

Gly Cys Gly Ile Gly Gly Ser Ser Arg Tyr Leu Ala Asn Lys Tyr Gly
145                 150                 155                 160

Ala Gln Cys Tyr Gly Ile Thr Leu Ser Pro Val Gln Ala Glu Arg Gly
                165                 170                 175

Asn Ala Leu Ala Ala Glu Gln Gly Leu Ser Asp Lys Val Ser Phe Gln
            180                 185                 190

Val Gly Asp Ala Leu Glu Gln Pro Phe Pro Asp Gly Gln Phe Asp Leu
        195                 200                 205

Val Trp Ser Met Glu Ser Gly Glu His Met Pro Asp Lys Arg Gln Phe
    210                 215                 220

Val Ser Glu Leu Ala Arg Val Ala Ala Pro Gly Ala Arg Ile Ile Ile
225                 230                 235                 240

Val Thr Trp Cys His Arg Asn Leu Glu Pro Ser Glu Ser Leu Lys
                245                 250                 255

Pro Asp Glu Leu Asn Leu Leu Lys Arg Ile Cys Asp Ala Tyr Tyr Leu
            260                 265                 270

Pro Asp Trp Cys Ser Pro Ser Asp Tyr Val Lys Ile Ala Glu Ser Leu
        275                 280                 285

Ser Leu Glu Asp Ile Arg Thr Ala Asp Trp Ser Glu Asn Val Ala Pro
    290                 295                 300

Phe Trp Pro Ala Val Ile Lys Ser Ala Leu Thr Trp Lys Gly Leu Thr
305                 310                 315                 320

Ser Leu Leu Arg Ser Gly Trp Lys Thr Ile Arg Gly Ala Met Val Met
                325                 330                 335

Pro Leu Met Ile Glu Gly Tyr Lys Lys Gly Leu Ile Lys Phe Thr Ile
            340                 345                 350

Ile Thr Cys Arg Lys Pro Glu Thr Thr Gln
        355                 360

<210> SEQ ID NO 25
<211> LENGTH: 1265
<212> TYPE: DNA
<213> ORGANISM: Brassica sp.

<400> SEQUENCE: 25
tttctccaac caacctctca ttataaatga aagcgactct cgcaccaccc tcctctctca     60
taagcctccc caggcacaaa gtatcttctc tccgttcacc gtcgcttctc cttcagtccc    120
agcggccatc ctcagcctta atgacaacga cggcaacacg tggaagcgta gctgtgacgg    180
ctgctgctac ctcctccgct gaggcgctgc gagaaggaat agcggaattc tacaacgaga    240

```
cgtcgggatt atgggaggag atttggggag atcatatgca tcacggcttc tacgatcccg    300
attcctctgt tcaactttca gattccggtc accgggaagc tcagatccgg atgattgaag    360
agtctctacg tttcgccggc gttactgaag aggagaaaaa gataaagaga gtggtggatg    420
ttgggtgtgg gatcggagga agctcaaggt atattgcctc taaatttggt gccgaatgca    480
ttggcatcac actcagtccc gttcaagcca agagagccaa tgatctcgcc gccgctcaat    540
cactctctca taaggtttcc ttccaagttg cagatgcatt ggaccaacca tttgaagatg    600
gtattttcga tcttgtttgg tcaatggaaa gcggtgagca tatgcctgac aaggccaagt    660
tcgtgaagga attggtacgt gtgacggctc caggaggaag gataataata gtgacatggt    720
gccacagaaa tctatcccaa ggggaagaat ctttgcagcc atgggagcag aacctcttgg    780
acagaatctg caaacattt tatctcccgg cctggtgctc cacctctgat tatgtcgagt    840
tgcttcaatc cctctcgctc caggatatta gtgtgcaga ttggtcagag aacgtagctc    900
ctttctggcc ggcggttata cgaaccgcat taacgtggaa gggccttgtg tctctgcttc    960
gtagtggtat gaagagtata aaggagcat tgacaatgcc attgatgatt gaagggtaca    1020
agaaaggtgt cattaaattt ggcatcatcg cttgccagaa gcctctctaa gttcaatcta    1080
aacaataaaa ttgtcgtact tttcagcgaa ttgatttcta tctatgatat aggagattga    1140
ataagagtca cgtgagaaat gtggatgcat gaaatccctt aaacgtcatt aatgttcgtt    1200
catggctacg ttgtctattt tagataaata tacaagttga aggtgtcaa aaaaaaaaaa    1260 aaaaa                                                                1265
```

<210> SEQ ID NO 26
<211> LENGTH: 347
<212> TYPE: PRT
<213> ORGANISM: Brassica sp.

<400> SEQUENCE: 26

```
Met Lys Ala Thr Leu Ala Pro Pro Ser Ser Leu Ile Ser Leu Pro Arg
1               5                   10                  15

His Lys Val Ser Ser Leu Arg Ser Pro Ser Leu Leu Gln Ser Gln
            20                  25                  30

Arg Pro Ser Ser Ala Leu Met Thr Thr Thr Ala Thr Arg Gly Ser Val
        35                  40                  45

Ala Val Thr Ala Ala Ala Thr Ser Ser Ala Glu Ala Leu Arg Glu Gly
    50                  55                  60

Ile Ala Glu Phe Tyr Asn Glu Thr Ser Gly Leu Trp Glu Glu Ile Trp
65                  70                  75                  80

Gly Asp His Met His His Gly Phe Tyr Asp Pro Asp Ser Ser Val Gln
                85                  90                  95

Leu Ser Asp Ser Gly His Arg Glu Ala Gln Ile Arg Met Ile Glu Glu
            100                 105                 110

Ser Leu Arg Phe Ala Gly Val Thr Glu Glu Lys Lys Ile Lys Arg
        115                 120                 125

Val Val Asp Val Gly Cys Gly Ile Gly Gly Ser Arg Tyr Ile Ala
    130                 135                 140

Ser Lys Phe Gly Ala Glu Cys Ile Gly Ile Thr Leu Ser Pro Val Gln
145                 150                 155                 160

Ala Lys Arg Ala Asn Asp Leu Ala Ala Ala Gln Ser Leu Ser His Lys
                165                 170                 175

Val Ser Phe Gln Val Ala Asp Ala Leu Asp Gln Pro Phe Glu Asp Gly
            180                 185                 190
```

```
Ile Phe Asp Leu Val Trp Ser Met Glu Ser Gly Glu His Met Pro Asp
        195                 200                 205

Lys Ala Lys Phe Val Lys Glu Leu Val Arg Val Thr Ala Pro Gly Gly
    210                 215                 220

Arg Ile Ile Ile Val Thr Trp Cys His Arg Asn Leu Ser Gln Gly Glu
225                 230                 235                 240

Glu Ser Leu Gln Pro Trp Glu Gln Asn Leu Leu Asp Arg Ile Cys Lys
                245                 250                 255

Thr Phe Tyr Leu Pro Ala Trp Cys Ser Thr Ser Asp Tyr Val Glu Leu
            260                 265                 270

Leu Gln Ser Leu Ser Leu Gln Asp Ile Lys Cys Ala Asp Trp Ser Glu
        275                 280                 285

Asn Val Ala Pro Phe Trp Pro Ala Val Ile Arg Thr Ala Leu Thr Trp
    290                 295                 300

Lys Gly Leu Val Ser Leu Leu Arg Ser Gly Met Lys Ser Ile Lys Gly
305                 310                 315                 320

Ala Leu Thr Met Pro Leu Met Ile Glu Gly Tyr Lys Lys Gly Val Ile
                325                 330                 335

Lys Phe Gly Ile Ile Ala Cys Gln Lys Pro Leu
            340                 345
```

<210> SEQ ID NO 27
<211> LENGTH: 1369
<212> TYPE: DNA
<213> ORGANISM: Perilla frutescens

<400> SEQUENCE: 27

```
gtcaaaatca ccaattacct atttccttca atatccgcaa tttccacatg cactgcacat      60
atctttaatt aaataaccgc aaagctcaat ggccgaggcg gtcacgccag gtatctgcac     120
caccgggtgg cgccgcggtg gggtccacgc tcccacttat aatatttcta taaagccagc     180
gacagcgttg ctggttggct gcaccaccaa aaccaaaagc attacttctt tttccacaga     240
ctccctcagg acacgtggca gagcacgtcg cccgacgatg agcctgaacg ccgctgcggc     300
ggagatggag acggagatgg agaccttgcg taaagggatt gcggagttct acgacgagtc     360
gtcggggggt gggagaaaca tatggggaga ccacatgcac cacggctttt acgagccggc     420
cgccgacgtc tccatctccg accatcgcgc cgcccagatc cgcatgattg aggagtccct     480
ccgattcgct tccttctctc cgataactac gacggagaaa ccgaagaata tagttgatgt     540
gggatgtggt ataggaggca gttctaggta tctggcaaga aaatatgggg ctaaattgtc     600
tagggctatt actctcttcca gccctgtgca agcgcagaga gctcaacagc ttgctgatgc     660
tcaaggatta aatggcaagg tttcctttga agttgctgat gcgttgaacc aaccatttcc     720
tgaagggaag tttgatctgg tttggtcgat ggagagtgga gaacacatgc ctgataagaa     780
aaagtttgta aatgagctgg tgcgtgtggc tgctcctggt ggaagaataa tcatcgttac     840
atggtgccac agggacctat caccttctga agaatctctt cgccaagagg agaaagattt     900
gctaaacaaa atatgtagtg cttattatct tccagcatgg tgctctactg ctgactatgt     960
caaattactc gactccctct caatggagga cattaagtct gcagactggt ctgaccatgt    1020
cgctccattt tggccggcag ttataaagtc ggcattgaca tggaagggca taccctcact    1080
gctaaggagc ggatggaaga ctataagagg agcaatggtg atgccattga tgatcgaagg    1140
atataagaag ggcgtgatca aatttgccat cattacatgc cgaaaacctg catcttaata    1200
aatagggcct aacaaatcat tgatggatat agatatagtg ttgcttctgg tattttcaca    1260
```

```
tttgatggcc cttatattgt taggtataac gtacttgtca tttctttat ccgtttataa    1320 attataatga aagaagcttt ccttcaattc acaaaaaaaa aaaaaaaaa               1369
```

<210> SEQ ID NO 28
<211> LENGTH: 369
<212> TYPE: PRT
<213> ORGANISM: Perilla frutescens

<400> SEQUENCE: 28

```
Met Ala Glu Ala Val Thr Pro Gly Ile Cys Thr Thr Gly Trp Arg Arg
1               5                   10                  15

Gly Gly Val His Ala Pro Thr Tyr Asn Ile Ser Ile Lys Pro Ala Thr
            20                  25                  30

Ala Leu Leu Val Gly Cys Thr Thr Lys Thr Lys Ser Ile Thr Ser Phe
        35                  40                  45

Ser Thr Asp Ser Leu Arg Thr Arg Gly Arg Ala Arg Arg Pro Thr Met
    50                  55                  60

Ser Leu Asn Ala Ala Ala Ala Glu Met Glu Thr Glu Met Glu Thr Leu
65                  70                  75                  80

Arg Lys Gly Ile Ala Glu Phe Tyr Asp Glu Ser Ser Gly Val Trp Glu
                85                  90                  95

Asn Ile Trp Gly Asp His Met His His Gly Phe Tyr Glu Pro Ala Ala
            100                 105                 110

Asp Val Ser Ile Ser Asp His Arg Ala Ala Gln Ile Arg Met Ile Glu
        115                 120                 125

Glu Ser Leu Arg Phe Ala Ser Phe Ser Pro Ile Thr Thr Thr Glu Lys
    130                 135                 140

Pro Lys Asn Ile Val Asp Val Gly Cys Gly Ile Gly Gly Ser Ser Arg
145                 150                 155                 160

Tyr Leu Ala Arg Lys Tyr Gly Ala Lys Leu Ser Arg Ala Ile Thr Leu
                165                 170                 175

Ser Ser Pro Val Gln Ala Gln Arg Ala Gln Gln Leu Ala Asp Ala Gln
            180                 185                 190

Gly Leu Asn Gly Lys Val Ser Phe Glu Val Ala Asp Ala Leu Asn Gln
        195                 200                 205

Pro Phe Pro Glu Gly Lys Phe Asp Leu Val Trp Ser Met Glu Ser Gly
    210                 215                 220

Glu His Met Pro Asp Lys Lys Phe Val Asn Glu Leu Val Arg Val
225                 230                 235                 240

Ala Ala Pro Gly Gly Arg Ile Ile Ile Val Thr Trp Cys His Arg Asp
                245                 250                 255

Leu Ser Pro Ser Glu Glu Ser Leu Arg Gln Glu Lys Asp Leu Leu
            260                 265                 270

Asn Lys Ile Cys Ser Ala Tyr Tyr Leu Pro Ala Trp Cys Ser Thr Ala
        275                 280                 285

Asp Tyr Val Lys Leu Leu Asp Ser Leu Ser Met Glu Asp Ile Lys Ser
    290                 295                 300

Ala Asp Trp Ser Asp His Val Ala Pro Phe Trp Pro Ala Val Ile Lys
305                 310                 315                 320

Ser Ala Leu Thr Trp Lys Gly Ile Thr Ser Leu Leu Arg Ser Gly Trp
                325                 330                 335

Lys Thr Ile Arg Gly Ala Met Val Met Pro Leu Met Ile Glu Gly Tyr
            340                 345                 350

Lys Lys Gly Val Ile Lys Phe Ala Ile Ile Thr Cys Arg Lys Pro Ala
```

```
            355                 360                 365
Ser

<210> SEQ ID NO 29
<211> LENGTH: 1350
<212> TYPE: DNA
<213> ORGANISM: Arabidopsis thaliana

<400> SEQUENCE: 29
ccacgcgtcc gcaaataatc cctgacttcg tcacgtttct ttgtatctcc aacgtccaat      60
aaatgaaagc aactctagca gcaccctctt ctctcacaag cctcccttat cgaaccaact     120
cttctttcgg ctcaaagtca tcgcttctct ttcggtctcc atcctcctcc tcctcagtct     180
ctatgacgac aacgcgtgga aacgtggctg tggcggctgc tgctacatcc actgaggcgc     240
taagaaaagg aatagcggag ttctacaatg aaacttcggg tttgtgggaa gagatttggg     300
gagatcatat gcatcatggc ttttatgacc ctgattcttc tgttcaactt tctgattctg     360
gtcacaagga agctcagatc cgtatgattg aagagtctct ccgtttcgcc ggtgttactg     420
atgaagagga ggagaaaaag ataaagaaag tagtggatgt tgggtgtggg attggaggaa     480
gctcaagata tcttgcctct aaatttggag ctgaatgcat tggcattact ctcagccctg     540
ttcaggccaa gagagccaat gatctcgcgg ctgctcaatc actctctcat aaggcttcct     600
tccaagttgc ggatgcgttg gatcagccat tcgaagatgg aaaattcgat ctagtgtggt     660
cgatggagag tggtgagcat atgcctgaca aggccaagtt tgtaaaagag ttggtacgtg     720
tggcggctcc aggaggtagg ataataatag tgacatggtg ccatagaaat ctatctgcgg     780
gggaggaagc tttgcagccg tgggagcaaa acatcttgga caaaatctgt aagacgttct     840
atctcccggc ttggtgctcc accgatgatt atgtcaactt gcttcaatcc cattctctcc     900
aggatattaa gtgtgcggat tggtcagaga acgtagctcc tttctggcct gcggttatac     960
ggactgcatt aacatggaag ggccttgtgt ctctgcttcg tagtggtatg aaaagtatta    1020
aaggagcatt gacaatgcca ttgatgattg aaggttacaa gaaaggtgtc attaagtttg    1080
gtatcatcac ttgccagaag ccactctaag tctaaagcta tactaggaga ttcaataaga    1140
ctataagagt agtgtctcat gtgaaagcat gaaattcctt aaaaacgtca atgttaagcc    1200
tatgcttcgt tatttgtttt agataagtat catttcactc ttgtctaagg tagttttctat    1260 aaacaataaa taccatgaat tagctcatgt tatctggtaa attctcggaa gtgattgtca    1320
tggattaact caaaaaaaaa aaaaaaaaaa                                      1350

<210> SEQ ID NO 30
<211> LENGTH: 348
<212> TYPE: PRT
<213> ORGANISM: Arabidopsis thaliana

<400> SEQUENCE: 30

Met Lys Ala Thr Leu Ala Ala Pro Ser Ser Leu Thr Ser Leu Pro Tyr
1               5                   10                  15

Arg Thr Asn Ser Ser Phe Gly Ser Lys Ser Ser Leu Leu Phe Arg Ser
            20                  25                  30

Pro Ser Ser Ser Ser Val Ser Met Thr Thr Thr Arg Gly Asn Val
        35                  40                  45

Ala Val Ala Ala Ala Thr Ser Thr Glu Ala Leu Arg Lys Gly Ile
    50                  55                  60

Ala Glu Phe Tyr Asn Glu Thr Ser Gly Leu Trp Glu Glu Ile Trp Gly
65                  70                  75                  80
```

```
Asp His Met His His Gly Phe Tyr Asp Pro Asp Ser Ser Val Gln Leu
                85                  90                  95

Ser Asp Ser Gly His Lys Glu Ala Gln Ile Arg Met Ile Glu Glu Ser
            100                 105                 110

Leu Arg Phe Ala Gly Val Thr Asp Glu Glu Glu Lys Lys Ile Lys
            115                 120                 125

Lys Val Val Asp Val Gly Cys Gly Ile Gly Gly Ser Ser Arg Tyr Leu
130                 135                 140

Ala Ser Lys Phe Gly Ala Glu Cys Ile Gly Ile Thr Leu Ser Pro Val
145                 150                 155                 160

Gln Ala Lys Arg Ala Asn Asp Leu Ala Ala Ala Gln Ser Leu Ser His
                165                 170                 175

Lys Ala Ser Phe Gln Val Ala Asp Ala Leu Asp Gln Pro Phe Glu Asp
            180                 185                 190

Gly Lys Phe Asp Leu Val Trp Ser Met Glu Ser Gly Glu His Met Pro
        195                 200                 205

Asp Lys Ala Lys Phe Val Lys Glu Leu Val Arg Val Ala Ala Pro Gly
    210                 215                 220

Gly Arg Ile Ile Ile Val Thr Trp Cys His Arg Asn Leu Ser Ala Gly
225                 230                 235                 240

Glu Glu Ala Leu Gln Pro Trp Glu Gln Asn Ile Leu Asp Lys Ile Cys
                245                 250                 255

Lys Thr Phe Tyr Leu Pro Ala Trp Cys Ser Thr Asp Tyr Val Asn
            260                 265                 270

Leu Leu Gln Ser His Ser Leu Gln Asp Ile Lys Cys Ala Asp Trp Ser
        275                 280                 285

Glu Asn Val Ala Pro Phe Trp Pro Ala Val Ile Arg Thr Ala Leu Thr
    290                 295                 300

Trp Lys Gly Leu Val Ser Leu Leu Arg Ser Gly Met Lys Ser Ile Lys
305                 310                 315                 320

Gly Ala Leu Thr Met Pro Leu Met Ile Glu Gly Tyr Lys Lys Gly Val
                325                 330                 335

Ile Lys Phe Gly Ile Ile Thr Cys Gln Lys Pro Leu
            340                 345
```

<210> SEQ ID NO 31
<211> LENGTH: 1330
<212> TYPE: DNA
<213> ORGANISM: Medicago truncatula
<220> FEATURE:
<221> NAME/KEY: misc_feature
<222> LOCATION: (1306)..(1306)
<223> OTHER INFORMATION: n is a, c, g, or t
<220> FEATURE:
<221> NAME/KEY: misc_feature
<222> LOCATION: (1310)..(1310)
<223> OTHER INFORMATION: n is a, c, g, or t
<220> FEATURE:
<221> NAME/KEY: misc_feature
<222> LOCATION: (1320)..(1320)
<223> OTHER INFORMATION: n is a, c, g, or t

<400> SEQUENCE: 31 aatattttt  atgattgaaa  atgaagtaag  atctgtggag  catgatctta  tcatttagtc      60
aggtcaatta  tgaaaataac  aattcatcac  catacgtaca  tgtcttgtag  caacaaaaga    120
aatcccattt  tggtagtagt  agtttcgtgc  gtacctaaat  tacggtttaa  tagtaacagc    180
aaaaattgtg  ccttgttttt  tgttgtatt  gcgcggtgta  ccgttgcaag  tgataacaca    240

-continued

| | |
|---|---|
| caacacaaca taaccatggt tgttacaaca acgagaatct cttcattatt acactgcaca | 300 |
| cacacatttc ctcagcacca cagagacact atcattacta ctacaacaac aacactcaac | 360 |
| agtagaagaa gaaaaggttc attgcgtgta tcaatggcgg cggtgaaaga agtgatggtg | 420 |
| gtaatggaag aagaagagaa gaagaaactt cagttagagg atcaatcaaa atggccaaag | 480 |
| agtgtagttg atgttgggtg tggcataggg ggcagttcaa ggtacctggc caagaaattt | 540 |
| ggggcaaact gtgtaggcat cactctcagc cctgttcaag ctgaaagagc taatgctcta | 600 |
| gctgctgctc aaggattagc cgataaggtt tcctttcaag ttgctgacgc tctacaacaa | 660 |
| ccattccctg atggccagtt tgatctagtg tggtcaatgg agagcggaga gcatatgcct | 720 |
| aacaaaccaa gtttgttgg agagttagct cgggtagcag caccgggtgg caccataata | 780 |
| atagtaacat ggtgtcatag ggatcttcgc ccggatgaag aatccctaca acaatgggag | 840 |
| aaggatctct tgaagaagat atgtgattca ttttatcttc cggagtggtg ctcaactgct | 900 |
| gattatgtca aattacttga aaccatgtcc cttcaggaca tcaaatcagc agattggtct | 960 |
| cccttttgttg ctccattttg gccagcagtg atacgttcag cattaacatg aagggtttc | 1020 |
| acctcaatct tgcggagtgg actaaaaact ataaaaggag ctttggctat gccattgatg | 1080 |
| atagaaggat ttaggaaggg tgtgattaag tttgccatta tcacatgtcg aaagcctgaa | 1140 |
| aacgcagatg gtcaatgatt ttatatgatg aaacagaatt cctacatgtc atttatttg | 1200 |
| atagttcaca caaaacaaat aagaaataaa gaatacgtgt ttctgccatg tcagatccaa | 1260 |
| ctgtgattga ataattgaag gaaagatgta agctagttcc tgttgngtan cctccaatcn | 1320 |
| aaaaaaaaaa | 1330 |

<210> SEQ ID NO 32
<211> LENGTH: 362
<212> TYPE: PRT
<213> ORGANISM: Medicago truncatula

<400> SEQUENCE: 32

Met Lys Ile Thr Ile His His Thr Tyr Met Ser Cys Ser Asn Lys
1               5                   10                  15

Arg Asn Pro Ile Leu Val Val Val Ser Cys Val Pro Lys Leu Arg
                20                  25                  30

Phe Asn Ser Asn Ser Lys Asn Cys Ala Leu Phe Phe Cys Cys Ile Ala
            35                  40                  45

Arg Cys Thr Val Ala Ser Asp Asn Thr Gln His Asn Ile Thr Met Val
        50                  55                  60

Val Thr Thr Thr Arg Ile Ser Ser Leu Leu His Cys Thr His Thr Phe
65                  70                  75                  80

Pro Gln His His Arg Asp Thr Ile Ile Thr Thr Thr Thr Thr Leu
                85                  90                  95

Asn Ser Arg Arg Arg Lys Gly Ser Leu Arg Val Ser Met Ala Ala Val
            100                 105                 110

Lys Glu Val Met Val Val Met Glu Glu Glu Lys Lys Lys Leu Gln
        115                 120                 125

Leu Glu Asp Gln Ser Lys Trp Pro Lys Ser Val Val Asp Val Gly Cys
    130                 135                 140

Gly Ile Gly Gly Ser Ser Arg Tyr Leu Ala Lys Lys Phe Gly Ala Asn
145                 150                 155                 160

Cys Val Gly Ile Thr Leu Ser Pro Val Gln Ala Glu Arg Ala Asn Ala
                165                 170                 175

Leu Ala Ala Ala Gln Gly Leu Ala Asp Lys Val Ser Phe Gln Val Ala

```
                    180                 185                 190
Asp Ala Leu Gln Gln Pro Phe Pro Asp Gly Gln Phe Asp Leu Val Trp
        195                 200                 205

Ser Met Glu Ser Gly Glu His Met Pro Asn Lys Pro Lys Phe Val Gly
210                 215                 220

Glu Leu Ala Arg Val Ala Ala Pro Gly Gly Thr Ile Ile Val Thr
225                 230                 235                 240

Trp Cys His Arg Asp Leu Arg Pro Asp Glu Glu Ser Leu Gln Gln Trp
                245                 250                 255

Glu Lys Asp Leu Leu Lys Lys Ile Cys Asp Ser Phe Tyr Leu Pro Glu
            260                 265                 270

Trp Cys Ser Thr Ala Asp Tyr Val Lys Leu Leu Glu Thr Met Ser Leu
        275                 280                 285

Gln Asp Ile Lys Ser Ala Asp Trp Ser Pro Phe Val Ala Pro Phe Trp
    290                 295                 300

Pro Ala Val Ile Arg Ser Ala Leu Thr Trp Lys Gly Phe Thr Ser Ile
305                 310                 315                 320

Leu Arg Ser Gly Leu Lys Thr Ile Lys Gly Ala Leu Ala Met Pro Leu
                325                 330                 335

Met Ile Glu Gly Phe Arg Lys Gly Val Ile Lys Phe Ala Ile Ile Thr
            340                 345                 350

Cys Arg Lys Pro Glu Asn Ala Asp Gly Gln
        355                 360

<210> SEQ ID NO 33
<211> LENGTH: 1573
<212> TYPE: DNA
<213> ORGANISM: Chlamydomonas sp.

<400> SEQUENCE: 33
agattaaaac aaaaccgctg agaagtttgc caagatgccc agcactgcgc tgcaagggca      60
cacgctgccc tcaagctctg catgcctagg tagagctaca cgccatgtat gcagagtgtc     120
cacacggagc cggcgcgctg tgacggttcg cgcgggaccg ctggagacgc tcgtgaagcc     180
gctcacgacg ctgggaaagg tcagcgacct caaagtcggc atcgccaact tctatgacga     240
gtcttcggag ctgtggggaga acatgtgggg ggagcacatg catcacggct actatcccaa     300
gggtgccccc gtcaagagca accagcaggc acagatcgat atgattgagg agacgctcaa     360
ggtggctggt gtgacacaag ccaagaagat ggtggacgtg ggctgcggca tcggcggcag     420
ctcgcgctac atcagccgca agttcggctg cacctccaac ggcatcacgc tcagccccaa     480
gcaggctgct cgcgccaatg cgctgagcaa ggagcagggc tttggcgaca gctgcagtt     540
ccaggtgggc gacgcgctgg cgcagccgtt cgaggccggc gccttcgacc tggtgtggtc     600
catggagagc ggcgagcaca tgcccgacaa gaagaagttt gtgtcggagc tggcgcgcgt     660
gtgtgcgccc ggcggcaccg tgattgtggt gacgtggtgc caccgcgtgt gggtccgggg     720
cgaggcgggc ttgcgcgagg acgagaaggc gctgctggac cgcatcaacg aggcctacta     780
cctgcccgac tggtgctccg tggcagacta ccagaaactg ttcgaggcac aaggcctgac     840
tgacatccag acccgcgact ggagccagga ggtgtcgccc ttctggggcg ccgtgatcgc     900
cacggccctg accagcgagg gtctggcggg tctggccaag gcgggctgga ccaccatcaa     960
gggcgccctg gtgatgccgc tcatggccga gggcttcaga gcggcctca tcaagttcaa    1020
cctcatcagc ggccgcaagc tgcagcagta gtagcagtgc ggcggcaatg cggctgtagc    1080
agcagtggta gtggtagcag ggggccagcg gggctgcaga ctatggaggg agcgcccaat    1140
```

```
cgccgcggag ctcttgcttg tgtttgtcgt tgtgatgagg tcagtggcgc gatggcgcaa      1200
gaagccaggg acggaccggc tcgcgaggag tggtggcaac tgcattcatg gtgggtgtga      1260
ccgcgtgggc gtgagcgcgt gagggtcagg tgagaacgaa cgggccaggc aagaggacat      1320
ggattgcggg gctgcaggat gggggactgt catcgtatcg ctgtgagctg gtgacagagc      1380
tggtgaccgg acaagcagct gtgaggaccc ggcgcggcat agcgtcgccg gtgtgaccgc      1440
cgtttctctt tgggcaacgc aaaccaggtg actcagggggg cacccccttt cttgtcttcg      1500
ggctgcatca cgcatggtgc cacgcatgtc atgtgcacct gaggctattg caagttggct      1560
ggttgggcat gtc                                                         1573
```

<210> SEQ ID NO 34
<211> LENGTH: 338
<212> TYPE: PRT
<213> ORGANISM: Chlamydomonas sp.

<400> SEQUENCE: 34

```
Met Pro Ser Thr Ala Leu Gln Gly His Thr Leu Pro Ser Ser Ser Ala
1               5                   10                  15

Cys Leu Gly Arg Ala Thr Arg His Val Cys Arg Val Ser Thr Arg Ser
            20                  25                  30

Arg Arg Ala Val Thr Val Arg Ala Gly Pro Leu Glu Thr Leu Val Lys
        35                  40                  45

Pro Leu Thr Thr Leu Gly Lys Val Ser Asp Leu Lys Val Gly Ile Ala
    50                  55                  60

Asn Phe Tyr Asp Glu Ser Ser Glu Leu Trp Glu Asn Met Trp Gly Glu
65                  70                  75                  80

His Met His His Gly Tyr Tyr Pro Lys Gly Ala Pro Val Lys Ser Asn
                85                  90                  95

Gln Gln Ala Gln Ile Asp Met Ile Glu Glu Thr Leu Lys Val Ala Gly
            100                 105                 110

Val Thr Gln Ala Lys Lys Met Val Asp Val Gly Cys Gly Ile Gly Gly
        115                 120                 125

Ser Ser Arg Tyr Ile Ser Arg Lys Phe Gly Cys Thr Ser Asn Gly Ile
    130                 135                 140

Thr Leu Ser Pro Lys Gln Ala Ala Arg Ala Asn Ala Leu Ser Lys Glu
145                 150                 155                 160

Gln Gly Phe Gly Asp Lys Leu Gln Phe Gln Val Gly Asp Ala Leu Ala
                165                 170                 175

Gln Pro Phe Glu Ala Gly Ala Phe Asp Leu Val Trp Ser Met Glu Ser
            180                 185                 190

Gly Glu His Met Pro Asp Lys Lys Lys Phe Val Ser Glu Leu Ala Arg
        195                 200                 205

Val Cys Ala Pro Gly Gly Thr Val Ile Val Thr Trp Cys His Arg
    210                 215                 220

Val Leu Gly Pro Gly Glu Ala Gly Leu Arg Glu Asp Glu Lys Ala Leu
225                 230                 235                 240

Leu Asp Arg Ile Asn Glu Ala Tyr Tyr Leu Pro Asp Trp Cys Ser Val
                245                 250                 255

Ala Asp Tyr Gln Lys Leu Phe Glu Ala Gln Gly Leu Thr Asp Ile Gln
            260                 265                 270

Thr Arg Asp Trp Ser Gln Glu Val Ser Pro Phe Trp Gly Ala Val Ile
        275                 280                 285

Ala Thr Ala Leu Thr Ser Glu Gly Leu Ala Gly Leu Ala Lys Ala Gly
```

```
            290                 295                 300
Trp Thr Thr Ile Lys Gly Ala Leu Val Met Pro Leu Met Ala Glu Gly
305                 310                 315                 320

Phe Arg Arg Gly Leu Ile Lys Phe Asn Leu Ile Ser Gly Arg Lys Leu
                325                 330                 335

Gln Gln

<210> SEQ ID NO 35
<211> LENGTH: 954
<212> TYPE: DNA
<213> ORGANISM: Synechocystis sp.

<400> SEQUENCE: 35
atggtttacc atgttaggcc taagcacgcc ctgttcttag cattctattg ttatttctct     60
ttgcttacca tggccagcgc caccattgcc agtgcagacc tctacgaaaa aattaaaaat    120
ttctacgacg actccagcgg tctctgggaa gacgtttggg gtgagcatat gcaccacggc    180
tactacggtc cccacggcac ctatcggatc gatcgccgcc aggctcaaat tgatctgatc    240
aaagaactat tggcctgggc agtgcccaa atagcgcca aaccacgaaa aattctcgat    300
ttaggctgtg gcattggcgg cagtagtttg tacttggccc agcaacacca gcagaagtg    360 atggggcta gtctttcccc agtgcaggtg gaacgggcgg gggaagggc cagggccctg    420 gggttgggct caacctgcca gtttcaggtg gccaatgcct tggatttgcc ctttgcttcc    480
gattcctttg actgggtttg gtcgttggaa agtggggagc acatgcccaa caaagctcag    540
tttttacaag aagcttggcg ggtacttaaa ccaggtggcc gtctgatttt agcgacctgg    600
tgtcatcgtc ccattgatcc cggcaatggc cccctgactg ccgatgaacg tcgccatctc    660
caagccatct atgacgttta ctgtttgccc tatgtggttt ccctgccgga ctacgaggcg    720
atcgccaggg aatgtgggtt tggggaaatt aagactgccg attggtcagt ggcggtggca    780 ccttttttggg accgggtgat tgagtctgcg ttcgatcccc gggtgttgtg ggccttgggg    840 caagcgggc caaaaattat caatgccgcc ctgtgtttac gattaatgaa atggggctat    900
gaacggggat tagtgcgttt tggcttatta acggggataa agccttaagt tga          954

<210> SEQ ID NO 36
<211> LENGTH: 317
<212> TYPE: PRT
<213> ORGANISM: Synechocystis sp.

<400> SEQUENCE: 36

Met Val Tyr His Val Arg Pro Lys His Ala Leu Phe Leu Ala Phe Tyr
1               5                   10                  15

Cys Tyr Phe Ser Leu Leu Thr Met Ala Ser Ala Thr Ile Ala Ser Ala
                20                  25                  30

Asp Leu Tyr Glu Lys Ile Lys Asn Phe Tyr Asp Asp Ser Ser Gly Leu
            35                  40                  45

Trp Glu Asp Val Trp Gly Glu His Met His His Gly Tyr Tyr Gly Pro
        50                  55                  60

His Gly Thr Tyr Arg Ile Asp Arg Arg Gln Ala Gln Ile Asp Leu Ile
65                  70                  75                  80

Lys Glu Leu Leu Ala Trp Ala Val Pro Gln Asn Ser Ala Lys Pro Arg
                85                  90                  95

Lys Ile Leu Asp Leu Gly Cys Gly Ile Gly Gly Ser Ser Leu Tyr Leu
            100                 105                 110

Ala Gln Gln His Gln Ala Glu Val Met Gly Ala Ser Leu Ser Pro Val
```

```
                 115                 120                 125
Gln Val Glu Arg Ala Gly Glu Arg Ala Arg Ala Leu Gly Leu Gly Ser
        130                 135                 140

Thr Cys Gln Phe Gln Val Ala Asn Ala Leu Asp Leu Pro Phe Ala Ser
145                 150                 155                 160

Asp Ser Phe Asp Trp Val Trp Ser Leu Glu Ser Gly Glu His Met Pro
                165                 170                 175

Asn Lys Ala Gln Phe Leu Gln Glu Ala Trp Arg Val Leu Lys Pro Gly
            180                 185                 190

Gly Arg Leu Ile Leu Ala Thr Trp Cys His Arg Pro Ile Asp Pro Gly
        195                 200                 205

Asn Gly Pro Leu Thr Ala Asp Glu Arg Arg His Leu Gln Ala Ile Tyr
    210                 215                 220

Asp Val Tyr Cys Leu Pro Tyr Val Val Ser Leu Pro Asp Tyr Glu Ala
225                 230                 235                 240

Ile Ala Arg Glu Cys Gly Phe Gly Glu Ile Lys Thr Ala Asp Trp Ser
                245                 250                 255

Val Ala Val Ala Pro Phe Trp Asp Arg Val Ile Glu Ser Ala Phe Asp
            260                 265                 270

Pro Arg Val Leu Trp Ala Leu Gly Gln Ala Gly Pro Lys Ile Ile Asn
        275                 280                 285

Ala Ala Leu Cys Leu Arg Leu Met Lys Trp Gly Tyr Glu Arg Gly Leu
    290                 295                 300

Val Arg Phe Gly Leu Leu Thr Gly Ile Lys Pro Leu Val
305                 310                 315

<210> SEQ ID NO 37
<211> LENGTH: 843
<212> TYPE: DNA
<213> ORGANISM: Anabaena sp.

<400> SEQUENCE: 37
atgagtgcaa cactttacca acaaattcag caattttacg atgcttcctc tgggctgtgg      60
gaagagattt ggggcgaaca tatgcaccac ggctattatg gtgcagacgg tactgaacaa     120 aaaaccgcc gtcaggcgca aattgattta attgaagaat tactcacttg gcaggagta     180 caaacagcag aaaatatact agatgtgggt tgtggtattg gtggtagttc tctgtatttg     240
gcaggaaagt tgaatgctaa agctacagga attaccctga gtccagtgca agccgctaga     300
gccacagaaa gagccaagga agctggttta agtggtagaa gtcagttttt agtggcaaat     360
gcccaagcaa tgcctttga tgataattct tttgacttgg tgtggtcgct agaaagtggc     420
gaacatatgc cagataaaac caagttttttg caagagtgtt atcgagtctt gaaaccgggc     480
ggtaagttaa tcatggtgac atggtgtcat cgtcccactg ataaaacacc actgacggct     540
gatgaaaaaa acacctaga agatatttat cgggtgtatt gtttgcctta tgtaatttcg     600
ttgccggagt atgaagcgat cgcacgtcaa ctaccattaa ataatatccg caccgccgac     660
tggtcgcaat ccgtcgccca attttggaac atagtcatcg attccgcctt tacccccaa     720 gcaatattcg gcttactccg cgcaggttgg actaccatcc aaggagcctt atcactaggc     780
ttaatgcgtc gcggctatga gcgcgggtta attcggtttg ggttgctttg tggggataag     840
tga                                                                    843

<210> SEQ ID NO 38
<211> LENGTH: 280
<212> TYPE: PRT
```

<213> ORGANISM: Anabaena sp.

<400> SEQUENCE: 38

```
Met Ser Ala Thr Leu Tyr Gln Gln Ile Gln Gln Phe Tyr Asp Ala Ser
1               5                   10                  15
Ser Gly Leu Trp Glu Glu Ile Trp Gly Glu His Met His His Gly Tyr
            20                  25                  30
Tyr Gly Ala Asp Gly Thr Glu Gln Lys Asn Arg Arg Gln Ala Gln Ile
        35                  40                  45
Asp Leu Ile Glu Glu Leu Leu Thr Trp Ala Gly Val Gln Thr Ala Glu
    50                  55                  60
Asn Ile Leu Asp Val Gly Cys Gly Ile Gly Gly Ser Ser Leu Tyr Leu
65                  70                  75                  80
Ala Gly Lys Leu Asn Ala Lys Ala Thr Gly Ile Thr Leu Ser Pro Val
                85                  90                  95
Gln Ala Ala Arg Ala Thr Glu Arg Ala Lys Glu Ala Gly Leu Ser Gly
            100                 105                 110
Arg Ser Gln Phe Leu Val Ala Asn Ala Gln Ala Met Pro Phe Asp Asp
        115                 120                 125
Asn Ser Phe Asp Leu Val Trp Ser Leu Glu Ser Gly Glu His Met Pro
130                 135                 140
Asp Lys Thr Lys Phe Leu Gln Glu Cys Tyr Arg Val Leu Lys Pro Gly
145                 150                 155                 160
Gly Lys Leu Ile Met Val Thr Trp Cys His Arg Pro Thr Asp Lys Thr
                165                 170                 175
Pro Leu Thr Ala Asp Glu Lys Lys His Leu Glu Asp Ile Tyr Arg Val
            180                 185                 190
Tyr Cys Leu Pro Tyr Val Ile Ser Leu Pro Glu Tyr Glu Ala Ile Ala
        195                 200                 205
Arg Gln Leu Pro Leu Asn Asn Ile Arg Thr Ala Asp Trp Ser Gln Ser
    210                 215                 220
Val Ala Gln Phe Trp Asn Ile Val Ile Asp Ser Ala Phe Thr Pro Gln
225                 230                 235                 240
Ala Ile Phe Gly Leu Leu Arg Ala Gly Trp Thr Thr Ile Gln Gly Ala
                245                 250                 255
Leu Ser Leu Gly Leu Met Arg Arg Gly Tyr Glu Arg Gly Leu Ile Arg
            260                 265                 270
Phe Gly Leu Leu Cys Gly Asp Lys
        275                 280
```

<210> SEQ ID NO 39
<211> LENGTH: 846
<212> TYPE: DNA
<213> ORGANISM: Gloeobacter violaceus

<400> SEQUENCE: 39

```
atgggcgagc gaacggttct caacgaaaat atccggcggt tctacgacgc gtcctccggg      60
ttgtggagg aggtctgggg cgagcacatg caccacggcc actgggaagt gggggaagcg     120
gacaaagatc gccgcgtcgc ccaggtggat ttggtcgtca ggctcctcga ctgggcgggg     180
atcgaccggg ccgagtcgat cgtcgatgtc ggctgcggca tcggcggcag cagtctgttt     240
ctggcggagc gcttcggcgc ccgggtggag ggatcaccc tcagcccgt gcagtgtaag     300
cgcgccgccg agcgcgcccg cgagcaccat ctggacgggc gcgcgcactt tcaggtggcc     360
gacgcccacc ggatgcccct cgccgacggc cggttcgacc tggtctggtc gctcgaaagc     420
```

```
ggtgagcaca tggccgacaa ggcccaattt ttgcgcgaat gccaccgggt gctcaggccc    480
ggcggccgct tcgtgtttgt gacttggtgc tgtcgccacg gcgccttgga cgcgcgggat    540
caaaaatggc tcggggcgat ctaccggatc taccacctgc cctacatcct ctcgatcgag    600
agctacacgc agttgcttgg tgagacgggg ttctcgggca ttcggaccac cgactggtcc    660
gatcgggtgg cccgcttctg gtcgctggtc atcgattcgg ccctcgaacc ggcggtgctg    720
tggaaggtga tcgcccaggg accgacggta atcaaaggcg cgctcgccat gcagttgatg    780
cggcgcagct acgcgcgggg gctggtgcgc ttcggcgtgt cgcggcccaa aaaggcggag    840
ggataa                                                              846
```

<210> SEQ ID NO 40
<211> LENGTH: 281
<212> TYPE: PRT
<213> ORGANISM: Gloeobacter violaceus

<400> SEQUENCE: 40

```
Met Gly Glu Arg Thr Val Leu Asn Glu Asn Ile Arg Arg Phe Tyr Asp
 1               5                  10                  15

Ala Ser Ser Gly Leu Trp Glu Val Trp Gly Glu His Met His His
            20                  25                  30

Gly His Trp Glu Val Gly Glu Ala Asp Lys Asp Arg Arg Val Ala Gln
        35                  40                  45

Val Asp Leu Val Val Arg Leu Leu Asp Trp Ala Gly Ile Asp Arg Ala
    50                  55                  60

Glu Ser Ile Val Asp Val Gly Cys Gly Ile Gly Gly Ser Ser Leu Phe
65                  70                  75                  80

Leu Ala Glu Arg Phe Gly Ala Arg Val Glu Gly Ile Thr Leu Ser Pro
                85                  90                  95

Val Gln Cys Lys Arg Ala Ala Glu Arg Ala Arg Glu His His Leu Asp
            100                 105                 110

Gly Arg Ala His Phe Gln Val Ala Asp Ala His Arg Met Pro Phe Ala
        115                 120                 125

Asp Gly Arg Phe Asp Leu Val Trp Ser Leu Glu Ser Gly Glu His Met
    130                 135                 140

Ala Asp Lys Ala Gln Phe Leu Arg Glu Cys His Arg Val Leu Arg Pro
145                 150                 155                 160

Gly Gly Arg Phe Val Phe Val Thr Trp Cys Cys Arg His Gly Ala Leu
                165                 170                 175

Asp Ala Arg Asp Gln Lys Trp Leu Gly Ala Ile Tyr Arg Ile Tyr His
            180                 185                 190

Leu Pro Tyr Ile Leu Ser Ile Glu Ser Tyr Thr Gln Leu Leu Gly Glu
        195                 200                 205

Thr Gly Phe Ser Gly Ile Arg Thr Thr Asp Trp Ser Asp Arg Val Ala
    210                 215                 220

Arg Phe Trp Ser Leu Val Ile Asp Ser Ala Leu Glu Pro Ala Val Leu
225                 230                 235                 240

Trp Lys Val Ile Ala Gln Gly Pro Thr Val Ile Lys Gly Ala Leu Ala
                245                 250                 255

Met Gln Leu Met Arg Arg Ser Tyr Ala Arg Gly Leu Val Arg Phe Gly
            260                 265                 270

Val Phe Ala Ala Gln Lys Ala Glu Gly
        275                 280
```

<210> SEQ ID NO 41

```
<211> LENGTH: 8615
<212> TYPE: DNA
<213> ORGANISM: Artificial Sequence
<220> FEATURE:
<223> OTHER INFORMATION: plasmid KS308
<220> FEATURE:
<221> NAME/KEY: misc_feature
<222> LOCATION: (6642)..(6642)
<223> OTHER INFORMATION: n is a, c, g, or t

<400> SEQUENCE: 41
ggccgcgaca caagtgtgag agtactaaat aaatgctttg gttgtacgaa atcattacac      60
taaataaaat aatcaaagct tatatatgcc ttccgctaag gccgaatgca aagaaattgg     120
ttctttctcg ttatcttttg ccacttttac tagtacgtat taattactac ttaatcatct     180
ttgtttacgg ctcattatat ccgtcgacgg cgcgcccgat catccggata tagttcctcc     240
tttcagcaaa aaacccctca agacccgttt agaggcccca aggggttatg ctagttattg     300
ctcagcggtg gcagcagcca actcagcttc ctttcgggct ttgttagcag ccggatcgat     360
ccaagctgta cctcactatt cctttgccct cggacgagtg ctggggcgtc ggtttccact     420
atcggcgagt acttctacac agccatcggt ccagacggcc gcgcttctgc gggcgatttg     480
tgtacgcccg acagtcccgg ctccggatcg gacgattgcg tcgcatcgac cctgcgccca     540
agctgcatca tcgaaattgc cgtcaaccaa gctctgatag agttggtcaa gaccaatgcg     600
gagcatatac gcccggagcc gcggcgatcc tgcaagctcc ggatgcctcc gctcgaagta     660
gcgcgtctgc tgctccatac aagccaacca cggcctccag aagaagatgt tggcgacctc     720
gtattgggaa tccccgaaca tcgcctcgct ccagtcaatg accgctgtta tgcggccatt     780
gtccgtcagg acattgttgg agccgaaatc cgcgtgcacg aggtgccgga cttcggggca     840
gtcctcggcc caaagcatca gctcatcgag agcctgcgcg acggacgcac tgacggtgtc     900
gtccatcaca gtttgccagt gatacacatg gggatcagca atcgcgcata tgaaatcacg     960
ccatgtagtg tattgaccga ttccttgcgg tccgaatggg ccgaacccgc tcgtctggct    1020
aagatcggcc gcagcgatcg catccatagc ctccgcgacc ggctgcagaa cagcgggcag    1080
ttcggtttca ggcaggtctt gcaacgtgac accctgtgca cggcgggaga tgcaataggt    1140
caggctctcg ctgaattccc caatgtcaag cacttccgga atcgggagcg cggccgatgc    1200
aaagtgccga taaacataac gatctttgta gaaaccatcg gcgcagctat ttacccgcag    1260
gacatatcca cgccctccta catcgaagct gaaagcacga gattcttcgc cctccgagag    1320
ctgcatcagg tcggagacgc tgtcgaactt ttcgatcaga aacttctcga cagcgtcgc    1380
ggtgagttca ggctttttcca tgggtatatc tccttcttaa agttaaacaa aattatttct    1440
agagggaaac cgttgtggtc tccctatagt gagtcgtatt aatttcgcgg gatcgagatc    1500
gatccaattc caatcccaca aaaatctgag cttaacagca cagttgctcc tctcagagca    1560
gaatcgggta ttcaacaccc tcatatcaac tactacgttg tgtataacgg tccacatgcc    1620
ggtatatacg atgactgggg ttgtacaaag gcggcaacaa acggcgttcc cggagttgca    1680
cacaagaaat ttgccactat tacagaggca agagcagcag ctgacgcgta cacaacaagt    1740
cagcaaacag acaggttgaa cttcatcccc aaaggagaag ctcaactcaa gcccaagagc    1800
tttgctaagg ccctaacaag cccaccaaag caaaaagccc actggctcac gctaggaacc    1860
aaaaggccca gcagtgatcc agccccaaaa gagatctcct tgccccggga gattacaatg    1920
gacgatttcc tctatcttta cgatctagga aggaagttcg aaggtgaagg tgacgacact    1980
atgttcacca ctgataatga aaggttagc ctcttcaatt tcagaaagaa tgctgaccca    2040
```

```
cagatggtta gagaggccta cgcagcaggt ctcatcaaga cgatctaccc gagtaacaat    2100
ctccaggaga tcaaatacct tcccaagaag gttaaagatg cagtcaaaag attcaggact    2160
aattgcatca agaacacaga gaaagacata tttctcaaga tcagaagtac tattccagta    2220
tggacgattc aaggcttgct tcataaacca aggcaagtaa tagagattgg agtctctaaa    2280
aaggtagttc ctactgaatc taaggccatg catggagtct aagattcaaa tcgaggatct    2340
aacagaactc gccgtgaaga ctggcgaaca gttcatacag agtcttttac gactcaatga    2400
caagaagaaa atcttcgtca acatggtgga gcacgacact ctggtctact ccaaaaatgt    2460
caaagataca gtctcagaag accaaagggc tattgagact tttcaacaaa ggataatttc    2520
gggaaacctc ctcggattcc attgcccagc tatctgtcac ttcatcgaaa ggacagtaga    2580
aaaggaaggt ggctcctaca aatgccatca ttgcgataaa ggaaaggcta tcattcaaga    2640
tgcctctgcc gacagtggtc ccaaagatgg acccccaccc acgaggagca tcgtggaaaa    2700
agaagacgtt ccaaccacgt cttcaaagca agtggattga tgtgacatct ccactgacgt    2760
aagggatgac gcacaatccc actatccttc gcaagaccct tcctctatat aaggaagttc    2820
atttcatttg gagaggacac gctcgagctc atttctctat tacttcagcc ataacaaaag    2880
aactcttttc tcttcttatt aaaccatgaa aaagcctgaa ctcaccgcga cgtctgtcga    2940
gaagtttctg atcgaaaagt tcgacagcgt ctccgacctg atgcagctct cggagggcga    3000
agaatctcgt gctttcagct tcgatgtagg agggcgtgga tatgtcctgc gggtaaatag    3060
ctgcgccgat ggtttctaca agatcgtta tgtttatcgg cactttgcat cggccgcgct    3120
cccgattccg gaagtgcttg acattgggga attcagcgag agcctgacct attgcatctc    3180
ccgccgtgca cagggtgtca cgttgcaaga cctgcctgaa accgaactgc ccgctgttct    3240
gcagccggtc gcggaggcca tggatgcgat cgctgcggcc gatcttagcc agacgagcgg    3300
gttcggccca ttcggaccgc aaggaatcgg tcaatacact acatggcgtg atttcatatg    3360
cgcgattgct gatccccatg tgtatcactg gcaaactgtg atggacgaca ccgtcagtgc    3420
gtccgtcgcg caggctctcg atgagctgat gctttgggcc gaggactgcc ccgaagtccg    3480
gcacctcgtg cacgcggatt tcggctccaa caatgtcctg acggacaatg gccgcataac    3540
agcggtcatt gactggagcg aggcgatgtt cggggattcc caatacgagg tcgccaacat    3600
cttcttctgg aggccgtggt tggcttgtat ggagcagcag acgcgctact cgagcggag    3660 gcatccggag cttgcaggat cgccgcggct ccgggcgtat atgctccgca ttggtcttga    3720
ccaactctat cagagcttgg ttgacggcaa tttcgatgat gcagcttggg cgcagggtcg    3780
atgcgacgca atcgtccgat ccggagccgg gactgtcggg cgtacacaaa tcgcccgcag    3840
aagcgcggcc gtctggaccg atggctgtgt agaagtactc gccgatagtg aaaccgacg    3900 ccccagcact cgtccgaggg caaaggaata gtgaggtacc taaagaagga gtgcgtcgaa    3960
gcagatcgtt caaacatttg gcaataaagt ttcttaagat tgaatcctgt tgccggtctt    4020
gcgatgatta tcatataatt tctgttgaat tacgttaagc atgtaataat taacatgtaa    4080
tgcatgacgt tatttatgag atgggttttt atgattagag tcccgcaatt atacatttaa    4140
tacgcgatag aaaacaaaat atagcgcgca aactaggata aattatcgcg cgcggtgtca    4200
tctatgttac tagatcgatg tcgaatctga tcaacctgca ttaatgaatc ggccaacgcg    4260
cggggagagg cggtttgcgt attgggcgct cttccgcttc ctcgctcact gactcgctgc    4320
gctcggtcgt tcggctgcgg cgagcggtat cagctcactc aaaggcggta atacggttat    4380
ccacagaatc aggggataac gcaggaaaga acatgtgagc aaaaggccag caaaaggcca    4440
```

```
ggaaccgtaa aaaggccgcg ttgctggcgt ttttccatag gctccgcccc cctgacgagc   4500
atcacaaaaa tcgacgctca agtcagaggt ggcgaaaccc gacaggacta taaagatacc   4560
aggcgtttcc ccctggaagc tccctcgtgc gctctcctgt tccgaccctg ccgcttaccg   4620
gatacctgtc cgccttttct ccttcgggaa gcgtggcgct ttctcaatgc tcacgctgta   4680
ggtatctcag ttcggtgtag gtcgttcgct ccaagctggg ctgtgtgcac gaaccccccg   4740
ttcagcccga ccgctgcgcc ttatccggta actatcgtct tgagtccaac ccggtaagac   4800
acgacttatc gccactggca gcagccactg gtaacaggat tagcagagcg aggtatgtag   4860
gcggtgctac agagttcttg aagtggtggc ctaactacgg ctacactaga aggacagtat   4920
ttggtatctg cgctctgctg aagccagtta ccttcggaaa aagagttggt agctcttgat   4980
ccggcaaaca aaccaccgct ggtagcggtg gtttttttgt ttgcaagcag cagattacgc   5040
gcagaaaaaa aggatctcaa gaagatcctt tgatcttttc tacggggtct gacgctcagt   5100
ggaacgaaaa ctcacgttaa gggattttgg tcatgacatt aacctataaa aataggcgta   5160
tcacgaggcc ctttcgtctc gcgcgtttcg gtgatgacgg tgaaaacctc tgacacatgc   5220
agctcccgga gacggtcaca gcttgtctgt aagcggatgc cgggagcaga caagcccgtc   5280
agggcgcgtc agcgggtgtt ggcgggtgtc ggggctggct taactatgcg gcatcagagc   5340
agattgtact gagagtgcac catatggaca tattgtcgtt agaacgcggc tacaattaat   5400
acataacctt atgtatcata cacatacgat ttaggtgaca ctatagaacg gcgcgccaag   5460
cttggatcct cgaagagaag ggttaataac acactttttt aacatttta acacaaattt   5520 tagttatta aaaatttatt aaaaaattta aaataagaag aggaactctt taaataaatc   5580
taacttacaa aatttatgat ttttaataag ttttcaccaa taaaaatgt cataaaaata   5640 tgttaaaaag tatattatca atattctctt tatgataaat aaaaagaaaa aaaaaataaa   5700
agttaagtga aaatgagatt gaagtgactt taggtgtgta taaatatatc aaccccgcca   5760
acaatttatt taatccaaat atattgaagt atattattcc atagccttta tttatttata   5820
tatttattat ataaaagctt tatttgttct aggttgttca tgaaatattt ttttggtttt   5880
atctccgttg taagaaaatc atgtgctttg tgtcgccact cactattgca gcttttcat   5940 gcattggtca gattgacggt tgattgtatt tttgttttt atggttttgt gttatgactt   6000
aagtcttcat ctctttatct cttcatcagg tttgatggtt acctaatatg gtccatgggt   6060
acatgcatgg ttaaattagg tggccaactt tgttgtgaac gatagaattt ttttatatt   6120 aagtaaacta ttttatatt atgaaataat aataaaaaaa atattttatc attattaaca   6180
aaatcatatt agttaatttg ttaactctat aataaaagaa atactgtaac attcacatta   6240
catggtaaca tctttccacc cttttcattg ttttttgttt gatgactttt ttcttgttt   6300 aaatttattt cccttctttt aaatttggaa tacattatca tcatatataa actaaaatac   6360
taaaaacagg attacacaaa tgataaataa taacacaaat atttataaat ctagctgcaa   6420
tatatttaaa ctagctatat cgatattgta aaataaaact agctgcattg atactgataa   6480
aaaaatatca tgtgctttct ggactgatga tgcagtatac ttttgacatt gcctttattt   6540
tatttttcag aaaagctttc ttagttctgg gttcttcatt atttgtttcc catctccatt   6600
gtgaattgaa tcatttgctt cgtgtcacaa atacaattta gntaggtaca tgcattggtc   6660
agattcacgg tttattatgt catgacttaa gttcatggta gtacattacc tgccacgcat   6720
gcattatatt ggttagattt gataggcaaa tttggttgtc aacaatataa atataaataa   6780
tgtttttata ttacgaaata acagtgatca aaacaaacag ttttatcttt attaacaaga   6840
```

| | |
|---|---|
| ttttgttttt gtttgatgac gttttttaat gtttacgctt tccccttct tttgaattta | 6900 |
| gaacacttta tcatcataaa atcaaatact aaaaaaatta catatttcat aaataataac | 6960 |
| acaaatattt ttaaaaaatc tgaaataata atgaacaata ttacatatta tcacgaaaat | 7020 |
| tcattaataa aaatattata taaataaaat gtaatagtag ttatatgtag gaaaaaagta | 7080 |
| ctgcacgcat aatatataca aaagattaa aatgaactat tataaataat aacactaaat | 7140 |
| taatggtgaa tcatatcaaa ataatgaaaa agtaaataaa atttgtaatt aacttctata | 7200 |
| tgtattacac acacaaataa taaataatag taaaaaaaat tatgataaat atttaccatc | 7260 |
| tcataagata tttaaaataa tgataaaaat atagattatt ttttatgcaa ctagctagcc | 7320 |
| aaaaagagaa cacgggtata tataaaaaga gtacctttaa attctactgt acttccttta | 7380 |
| ttcctgacgt ttttatatca agtggacata cgtgaagatt ttaattatca gtctaaatat | 7440 |
| ttcattagca cttaatactt ttctgtttta ttcctatcct ataagtagtc ccgattctcc | 7500 |
| caacattgct tattcacaca actaactaag aaagtcttcc atagcccccc aagcggccgc | 7560 |
| atggccaccg tggtgaggat cccaacaatc tcatgcatcc acatccacac gttccgttcc | 7620 |
| caatcccctc gcactttcgc cagaatccgg gtcggaccca ggtcgtgggc tcctattcgg | 7680 |
| gcatcggcag cgagctcgga gagaggggag atagtattgg agcagaagcc gaagaaggat | 7740 |
| gacaagaaga agctgcagaa gggaatcgca gagttttacg acgagtcgtc tggcttatgg | 7800 |
| gagaacattt ggggcgacca catgcaccat ggcttttatg actcggattc cactgtttcg | 7860 |
| ctttcggatc atcgtgctgc tcagatccga atgatccaag agtctcttcg ctttgcctct | 7920 |
| gtttctgagg agcgtagtaa atggcccaag agtatagttg atgttgggtg tggcataggt | 7980 |
| ggcagctcta gatacctggc caagaaattt ggagcaacca gtgtaggcat cactctgagt | 8040 |
| cctgttcaag ctcaaagagc aaatgctctt gctgctgctc aaggattggc tgataaggtt | 8100 |
| tcctttcagg ttgctgacgc tctacagcaa ccattctctg acggccagtt tgatctggtg | 8160 |
| tggtccatgg agagtggaga gcatatgcct gacaaagcta agtttgttgg agagttagct | 8220 |
| cgggtagcag caccaggtgc cattataata atagtaacat ggtgccacag ggatcttggc | 8280 |
| cctgacgaac aatccttaca tccatgggag caagatctct taaagaagat ttgcgatgca | 8340 |
| tattacctcc ctgcctggtg ctcaacttct gattatgtta agttgctcca atccctgtca | 8400 |
| cttcaggaca tcaagtcaga agattggtct cgctttgttg ctccattttg gccagcagtg | 8460 |
| atacgctcag ccttcacatg gaagggtcta tcttcactct tgagcagtgg acaaaaaacg | 8520 |
| ataaaggag ctttggctat gccattgatg atagagggat acaagaaaga tctaattaag | 8580 |
| tttgccatca ttacatgtcg aaaacctgaa taagc | 8615 |

<210> SEQ ID NO 42
<211> LENGTH: 9571
<212> TYPE: DNA
<213> ORGANISM: Artificial Sequence
<220> FEATURE:
<223> OTHER INFORMATION: plasmid KS270

<400> SEQUENCE: 42

| | |
|---|---|
| taatatctta aaaataatga ttaatattta acccaaaata attagtatga ttggtaagga | 60 |
| agatatccat gttatgtttg gatgtgagtt tgatctagag caaagcttac tagagtcgac | 120 |
| cgatccgtcg acggcgcgcc cgatcatccg gatatagttc ctccttttcag caaaaaaccc | 180 |
| ctcaagaccc gtttagaggc cccaaggggt tatgctagtt attgctcagc ggtggcagca | 240 |
| gccaactcag cttcctttcg ggctttgtta gcagccggat cgatccaagc tgtacctcac | 300 |

```
tattcctttg ccctcggacg agtgctgggg cgtcggtttc cactatcggc gagtacttct    360
acacagccat cggtccagac ggccgcgctt ctgcgggcga tttgtgtacg cccgacagtc    420
ccggctccgg atcggacgat tgcgtcgcat cgaccctgcg cccaagctgc atcatcgaaa    480
ttgccgtcaa ccaagctctg atagagttgg tcaagaccaa tgcggagcat atacgcccgg    540
agccgcggcg atcctgcaag ctccggatgc ctccgctcga agtagcgcgt ctgctgctcc    600
atacaagcca accacggcct ccagaagaag atgttggcga cctcgtattg ggaatccccg    660
aacatcgcct cgctccagtc aatgaccgct gttatgcggc cattgtccgt caggacattg    720
ttggagccga atccgcgtg cacgaggtgc cggacttcgg ggcagtcctc ggcccaaagc    780
atcagctcat cgagagcctg cgcgacggac gcactgacgg tgtcgtccat cacagtttgc    840
cagtgataca catggggatc agcaatcgcg catatgaaat cacgccatgt agtgtattga    900
ccgattcctt gcggtccgaa tgggccgaac ccgctcgtct ggctaagatc ggccgcagcg    960
atcgcatcca tagcctccgc gaccggctgc agaacagcgg gcagttcggt ttcaggcagg   1020
tcttgcaacg tgacaccctg tgcacggcgg gagatgcaat aggtcaggct ctcgctgaat   1080
tccccaatgt caagcacttc cggaatcggg agcgcggccg atgcaaagtg ccgataaaca   1140
taacgatctt tgtagaaacc atcggcgcag ctatttaccc gcaggacata tccacgccct   1200
cctacatcga agctgaaagc acgagattct tcgccctccg agagctgcat caggtcggag   1260
acgctgtcga acttttcgat cagaaacttc tcgacagacg tcgcggtgag ttcaggcttt   1320
tccatgggta tatctccttc ttaaagttaa acaaaattat ttctagaggg aaaccgttgt   1380
ggtctcccta tagtgagtcg tattaatttc gcgggatcga gatctgatca acctgcatta   1440
atgaatcggc caacgcgcgg ggagaggcgg tttgcgtatt gggcgctctt ccgcttcctc   1500
gctcactgac tcgctgcgct cggtcgttcg gctgcggcga gcggtatcag ctcactcaaa   1560
ggcggtaata cggttatcca cagaatcagg ggataacgca ggaaagaaca tgtgagcaaa   1620
aggccagcaa aaggccagga accgtaaaaa ggccgcgttg ctggcgtttt tccataggct   1680
ccgcccccct gacgagcatc acaaaaatcg acgctcaagt cagaggtggc gaaacccgac   1740
aggactataa agataccagg cgtttccccc tggaagctcc ctcgtgcgct ctcctgttcc   1800
gaccctgccg cttaccggat acctgtccgc ctttctccct tcgggaagcg tggcgctttc   1860
tcaatgctca cgctgtaggt atctcagttc ggtgtaggtc gttcgctcca agctgggctg   1920
tgtgcacgaa ccccccgttc agcccgaccg ctgcgcctta tccggtaact atcgtcttga   1980
gtccaacccg gtaagacacg acttatcgcc actggcagca gccactggta acaggattag   2040
cagagcgagg tatgtaggcg gtgctacaga gttcttgaag tggtggccta actacggcta   2100
cactagaagg acagtatttg gtatctgcgc tctgctgaag ccagttacct tcggaaaaag   2160
agttggtagc tcttgatccg gcaaacaaac caccgctggt agcggtggtt ttttgtttg    2220 caagcagcag attacgcgca gaaaaaaagg atctcaagaa gatcctttga tcttttctac   2280
ggggtctgac gctcagtgga acgaaaactc acgttaaggg attttggtca tgacattaac   2340
ctataaaaat aggcgtatca cgaggccctt tcgtctcgcg cgtttcggtg atgacggtga   2400
aaacctctga cacatgcagc tcccggagac ggtcacagct tgtctgtaag cggatgccgg   2460
gagcagacaa gcccgtcagg gcgcgtcagc gggtgttggc gggtgtcggg gctggcttaa   2520
ctatgcggca tcagagcaga ttgtactgag agtgcaccat atggacatat tgtcgttaga   2580
acgcggctac aattaataca taaccttatg tatcatacac atacgattta ggtgacacta   2640
tagaacggcg cgccaagctt ggatcctaga actagaaacg tgatgccact tgttattgaa   2700
```

```
gtcgattaca gcatctattc tgttttacta tttataactt tgccatttct gacttttgaa      2760
aactatctct ggatttcggt atcgctttgt gaagatcgag caaaagagac gttttgtgga      2820
cgcaatggtc caaatccgtt ctacatgaac aaattggtca caatttccac taaaagtaaa      2880
taaatggcaa gttaaaaaag gaatatgcat tttactgatt gcctaggtga gctccaagag      2940
aagttgaatc tacacgtcta ccaaccgcta aaaaagaaa acattgata tgtaacctga       3000 ttccattagc ttttgacttc ttcaacagat tctctactta gatttctaac agaaatatta     3060
ttactagcac atcattttca gtctcactac agcaaaaaat ccaacggcac aatacagaca     3120
acaggagata tcagactaca gagatagata gatgctactg catgtagtaa gttaaataaa     3180
aggaaaataa aatgtcttgc taccaaaact actacagact atgatgctca ccacaggcca     3240
aatcctgcaa ctaggacagc attatcttat atatattgta caaacaagc atcaaggaac      3300 atttggtcta ggcaatcagt acctcgttct accatcaccc tcagttatca catccttgaa     3360
ggatccatta ctgggaatca tcggcaacac atgctcctga tggggcacaa tgacatcaag     3420
aaggtagggg ccaggggtgt ccaacattct ctgaattgcc gctctaagct cttccttctt    3480
cgtcactcgc gctgccggta tcccacaagc atcagcaaac ttgagcatgt ttgggaatat    3540
ctcgctctcg ctagacggat ctccaagata ggtgtgagct ctattggact tgtagaacct    3600
atcctccaac tgaaccacca tacccaaatg ctgattgttc aacaacaata tcttaactgg   3660
gagattctcc actcttatag tggccaactc ctgaacattc atgatgaaac taccatcccc  3720
atcaatgtca accacaacag ccccaggggtt agcaacagca gcaccaatag ccgcaggcaa  3780
tccaaaaccc atggctccaa gaccccctga ggtcaaccac tgcctcggtc tcttgtactt  3840
gtaaaactgc gcagcccaca tttgatgctg cccaaccccca gtactaacaa tagcatctcc  3900
attagtcaac tcatcaagaa cctcgatagc atgctgcgga gaaatcgcgt cctggaatgt  3960
cttgtaaccc aatggaaact tgtgtttctg cacattaatc tcttctctcc aacctccaag   4020
atcaaactta ccctccactc ctttctcctc caaaatcata ttaattccct tcaaggccaa    4080
cttcaaatcc gcgcaaaccg acacgtgcgc ctgcttgttc ttcccaatct cggcagaatc    4140
aatatcaatg tgaacaatct tagccctact agcaaaagcc tcaagcttcc cagtaacacg   4200
gtcatcaaac cttaccccaa aggcaagcaa caaatcacta ttgtcaacag catagttagc    4260
ataaacagta ccatgcatac ccagcatctg aagggaatat tcatcaccaa taggaaaagt   4320
tccaagaccc attaaagtgc tagcaacggg aataccagtg agttcaacaa agcgcctcaa   4380
ttcagcactg gaattcaaac tgccaccgcc gacgtagaga acgggctttt gggcctccat   4440
gatgagtctg acaatgtgtt ccaattgggc ctcggcgggg ggcctgggca gcctggcgag  4500
gtaaccgggg aggttaacgg gctcgtccca attaggcacg gcgagttgct gctgaacgtc   4560
tttgggaatg tcgatgagga ccggaccggg gcggccggag gtggcgacga agaaagcctc   4620
ggcgacgacg cggggatgt cgtcgacgtc gaggatgagg tagttgtgct tcgtgatgga   4680
tctgctcacc tccacgatcg gggtttcttg gaaggcgtcg gtgccgatca tccggcgggc   4740
gacctggccg gtgatggcga cgactgggac gctgtccatt aaagcgtcgg cgaggccgct   4800
cacgaggttg gtggcgccgg ggccggaggt ggcaatgcag acgccgggga ggccggagga   4860
acgcgcgtag ccttcggcgg cgaagacgcc gccctgctcg tggcgcggga gcacgttgcg   4920
gatggcggcg gagcgcgtga gcgcctggtg gatctccatc gacgcaccgc cggggtacgc   4980
gaacaccgtc gtcacgccct gcctctccag cgcctccaca aggatgtccg cgcccttgcg   5040
aggttcgccg gaggcgaacc gtgacacgaa gggctccgtg gtcggcgctt ccttggtgaa   5100
```

```
gggcgccgcc gtgggggagtt tggagatgga acatttgatt ttgagagcgt ggttgggttt    5160
ggtgagggtt tgatgagaga gagggagggt ggatctagta atgcgtttgg ggaaggtggg    5220
gtgtgaagag gaagaagaga atcgggtggt tctggaagcg gtggccgcca ttgtgttgtg    5280
tggcatggtt atacttcaaa aactgcacaa caagcctaga gttagtacct aaacagtaaa    5340
tttacaacag agagcaaaga cacatgcaaa aatttcagcc ataaaaaaag ttataataga    5400
atttaaagca aaagtttcat tttttaaaca tatatacaaa caaactggat ttgaaggaag    5460
ggattaattc ccctgctcaa agtttgaatt cctattgtga cctatactcg aataaaattg    5520
aagcctaagg aatgtatgag aaacaagaaa acaaaacaaa actacagaca aacaagtaca    5580
attacaaaat tcgctaaaat tctgtaatca ccaaacccca tctcagtcag cacaaggccc    5640
aaggtttatt ttgaaataaa aaaaaagtga ttttatttct cataagctaa aagaaagaaa    5700
ggcaattatg aaatgatttc gactagatct gaaagtccaa cgcgtattcc gcagatatta    5760
aagaaagagt agagtttcac atggatccta gatggaccca gttgaggaaa aagcaaggca    5820
aagcaaacca gaagtgcaag atccgaaatt gaaccacgga atctaggatt tggtagaggg    5880
agaagaaaag taccttgaga ggtagaagag aagagaagag cagagagata tatgaacgag    5940
tgtgtcttgg tctcaactct gaagcgatac gagtttagag gggagcattg agttccaatt    6000
tatagggaaa ccgggtggca ggggtgagtt aatgacggaa aagccctaa gtaacgagat    6060
tggattgtgg gttagattca accgtttgca tccgcggctt agattgggga agtcagagtg    6120
aatctcaacc gttgactgag ttgaaaattg aatgtagcaa ccaattgagc caaccccagc    6180
ctttgcccctt tgatttttgat ttgtttgttg catactttttt atttgtcttc tggttctgac    6240
tctcttttctc tcgtttcaat gccaggttgc ctactcccac accactcaca agaagattct    6300
actgttagta ttaaatattt tttaatgtat taaatgatga atgcttttgt aaacagaaca    6360
agactatgtc taataagtgt cttgcaacat ttttttaagaa attaaaaaaa atatatttat    6420
tatcaaaatc aaatgtatga aaaatcatga ataatataat tttatacatt ttttttaaaaa    6480
atctttttaat ttcttacgcg ccaagctttt gatccatgcc cttcatttgc cgcttattaa    6540
ttaattttggt aacagtccgt actaatcagt tacttatcct tcccccatca taattaatct    6600
tggtagtctc gaatgccaca acactgacta gtctcttgga tcataagaaa agccaagga    6660
acaaaagaag acaaaacaca atgagagtat cctttgcata gcaatgtcta agttcataaa    6720
attcaaacaa aaacgcaatc acacacagtg gacatcactt atccactagc tgatcaggat    6780
cgccgcgtca agaaaaaaaa actggacccc aaaagccatg cacaacaaca cgtactcaca    6840
aaggtgtcaa tcgagcagcc caaaacattc accaactcaa cccatcatga gccctcacat    6900
ttgttgtttc taacccaacc tcaaactcgt attctcttcc gccacctcat ttttgtttat    6960
ttcaacaccc gtcaaactgc atgccacccc gtggccaaat gtccatgcat gttaacaaga    7020
cctatgacta taaatagctg caatctcggc ccaggttttc atcatcaaga accagttcaa    7080
tatcctagta caccgtatta aagaatttaa gatatactgc ggccgcagga tgcaagccgt    7140
cacgcggcg gccgcggcgg ggcagctgct aacagatacg aggagagggc ccagatgtag    7200
ggctcggctg gaacgacga gattatcctg gacaggtcga tttgcagtgg aagcttttgc    7260
aggccagtgc caaagtgcta ctactgtaat gcataaattc agtgccattt ctcaagctgc    7320
taggcctaga gaaacacaaa agagacagtg cagcgatgat tatccagccc tccaagctgg    7380
atgcagcgag gttaattggg atcaaaacgg ttccaacgcc aatcggcttg aggaaatcag    7440
gggagatgtt ttgaagaaat tgcgctcttt ctatgaattt tgcaggccac acacaatttt    7500
```

```
tggcactata ataggtataa cttcagtgtc tctcctgcca atgaagagca tagatgattt    7560
tactgtcacg gtactacgag gatatctcga ggctttgact gctgctttat gtatgaacat    7620
ttatgtggtc gggctgaatc agctatatga cattcagatt gacaagatca acaagccagg    7680
tcttccattg gcatctgggg aattttcagt agcaactgga gttttcttag tactcgcatt    7740
cctgatcatg agctttagca taggaatacg ttccggatcg gcgccactga tgtgtgcttt    7800
aattgtcagc ttccttcttg gaagtgcgta ctccattgag gctccgttcc tccggtggaa    7860
acggcacgcg ctcctcgctg catcatgtat cctatttgtg agggctatct tggtccagtt    7920
ggctttcttt gcacatatgc agcaacatgt tctgaaaagg ccattggcag caaccaaatc    7980
gctggtgttt gcaacattgt ttatgtgttg cttctctgcc gtcatagcac tattcaagga    8040
tattccagat gttgatggag atcgagactt tggtatccaa tccttgagtg tgagattggg    8100
gcctcaaaga gtgtatcagc tctgcataag catattgttg acagcctatg gcgctgccac    8160
tctagtagga gcttcatcca caaacctatt tcaaaagatc atcactgtgt ctggtcatgg    8220
cctgcttgct ttgacacttt ggcagagagc gcagcacttt gaggttgaaa accaagcgcg    8280
tgtcacatca ttttacatgt tcatttggaa gctattctat gcagagtatt tccttatacc    8340
atttgtgcag tgaaatttgt acaagggcca gcagatgtga agcggccgca agtatgaact    8400
aaaatgcatg taggtgtaag agctcatgga gagcatggaa tattgtatcc gaccatgtaa    8460
cagtataata actgagctcc atctcacttc ttctatgaat aaacaaagga tgttatgata    8520
tattaacact ctatctatgc accttattgt tctatgataa atttcctctt attattataa    8580
atcatctgaa tcgtgacggc ttatggaatg cttcaaatag tacaaaaaca aatgtgtact    8640
ataagacttt ctaaacaatt ctaaccttag cattgtgaac gagacataag tgttaagaag    8700
acataacaat tataatggaa gaagtttgtc tccattata tattatata tacccactta    8760
tgtattatat taggatgtta aggagacata acaattataa agagagaagt ttgtatccat    8820
ttatatatta tatactaccc atttatatat tatacttatc cacttattta atgtctttat    8880
aaggtttgat ccatgatatt tctaatattt tagttgatat gtatatgaaa gggtactatt    8940
tgaactctct tactctgtat aaaggttgga tcatccttaa agtgggtcta tttaatttta    9000
ttgcttctta cagataaaaa aaaaattatg agttggtttg ataaaatatt gaaggattta    9060
aaataataat aaataacata taatatatgt atataaattt attataatat aacatttatc    9120
tataaaaaag taaatattgt cataaatcta tacaatcgtt tagccttgct ggacgaatct    9180
caattattta aacgagagta aacatatttg acttttggt tatttaacaa attattattt    9240
aacactatat gaatttttt tttttatcag caaagaataa aattaaatta agaaggacaa    9300
tggtgtccca atcctatac aaccaacttc cacaagaaag tcaagtcaga gacaacaaaa    9360
aaacaagcaa aggaaatttt ttaatttgag ttgtcttgtt tgctgcataa tttatgcagt    9420
aaaacactac acataacccct tttagcagta gagcaatggt tgaccgtgtg cttagcttct    9480
tttatttat tttttatca gcaaagaata aataaaataa aatgagacac ttcagggatg    9540
tttcaacaag cttggatccg tcgacggcgc g                                  9571
```

<210> SEQ ID NO 43
<211> LENGTH: 9522
<212> TYPE: DNA
<213> ORGANISM: Artificial Sequence
<220> FEATURE:
<223> OTHER INFORMATION: plasmid KS319
<220> FEATURE:
<221> NAME/KEY: misc_feature
<222> LOCATION: (1257)..(1257)

<223> OTHER INFORMATION: n is a, c, g, or t

<400> SEQUENCE: 43

```
aattacaacg gtatatatcc tgccgtcgac ggtatcgata agcttgatat cgaattcctg    60
cagccccgcg ccaagcttgg atcctcgaag agaagggtta ataacacact tttttaacat   120
ttttaacaca aattttagtt atttaaaaat ttattaaaaa atttaaaata agaagaggaa   180
ctctttaaat aaatctaact tacaaaattt atgattttta ataagttttc accaataaaa   240
aatgtcataa aaatatgtta aaagtatat tatcaatatt ctctttatga taaataaaaa    300
gaaaaaaaa ataaaagtta agtgaaaatg agattgaagt gactttaggt gtgtataaat    360
atatcaaccc cgccaacaat ttatttaatc caaatatatt gaagtatatt attccatagc   420
ctttatttat ttatatattt attatataaa agctttattt gttctaggtt gttcatgaaa   480
tatttttttg gttttatctc cgttgtaaga aaatcatgtg ctttgtgtcg ccactcacta   540
ttgcagcttt ttcatgcatt ggtcagattg acgttgatt gtatttttgt tttttatggt    600
tttgtgttat gacttaagtc ttcatctctt tatctcttca tcaggtttga tggttaccta   660
atatggtcca tgggtacatg catggttaaa ttaggtggcc aactttgttg tgaacgatag   720
aatttttttt atattaagta aactattttt atattatgaa ataataataa aaaaaatatt   780
ttatcattat taacaaaatc atattagtta atttgttaac tctataataa aagaaatact   840
gtaacattca cattacatgg taacatcttt ccacccttc atttgttttt tgtttgatga    900
cttttttct tgtttaaatt tatttcctt cttttaaatt tggaatacat tatcatcata     960
tataaactaa aatactaaaa acaggattac acaaatgata aataataaca caaatattta  1020
taaatctagc tgcaatatat ttaaactagc tatatcgata ttgtaaaata aaactagctg  1080
cattgatact gataaaaaaa tatcatgtgc tttctggact gatgatgcag tatacttttg  1140
acattgcctt tattttattt ttcagaaaag cttttcttagt tctgggttct tcattatttg  1200
tttcccatct ccattgtgaa ttgaatcatt tgcttcgtgt cacaaataca atttagntag  1260
gtacatgcat tggtcagatt cacggtttat tatgtcatga cttaagttca tggtagtaca  1320
ttacctgcca cgcatgcatt atattggtta gatttgatag gcaaatttgg ttgtcaacaa  1380
tataaatata aataatgttt ttatattacg aaataacagt gatcaaaaca aacagttta    1440
tctttattaa caagattttg ttttttgtttg atgacgtttt ttaatgttta cgcttttcccc  1500
cttcttttga atttagaaca ctttatcatc ataaaatcaa atactaaaaa aattacatat  1560
ttcataaata ataacacaaa tattttttaaa aaatctgaaa taataatgaa caatattaca  1620
tattatcacg aaaattcatt aataaaaata ttatataaat aaaatgtaat agtagttata  1680
tgtaggaaaa aagtactgca cgcataatat atacaaaaag attaaaatga actattataa  1740
ataataacac taaattaatg gtgaatcata tcaaaataat gaaaaagtaa ataaaatttg  1800
taattaactt ctatatgtat tacacacaca aataataaat aatagtaaaa aaaattatga  1860
taaatattta ccatctcata agatattaa aataatgata aaaatataga ttatttttta   1920
tgcaactagc tagccaaaaa gagaacacgg gtatatataa aaagagtacc tttaaattct  1980
actgtacttc ctttattcct gacgttttta tatcaagtgg acatacgtga agattttaat  2040
tatcagtcta aatatttcat tagcacttaa tacttttctg ttttattcct atcctataag  2100
tagtcccgat tctcccaaca ttgcttattc acacaactaa ctaagaaagt cttccatagc  2160
ccccccagcg gccgcatggc caccgtggtg aggatcccaa caatctcatg catccacatc  2220
cacacgttcc gttcccaatc ccctcgcact ttcgccagaa tccgggtcgg acccaggtcg  2280
```

-continued

```
tgggctccta ttcgggcatc ggcagcgagc tcggagagag gggagatagt attggagcag    2340
aagccgaaga aggatgacaa gaagaagctg cagaagggaa tcgcagagtt ttacgacgag    2400
tcgtctggct tatgggagaa catttggggc gaccacatgc accatggctt ttatgactcg    2460
gattccactg tttcgctttc ggatcatcgt gctgctcaga tccgaatgat ccaagagtct    2520
cttcgctttg cctctgtttc tgaggagcgt agtaaatggc caagagtat agttgatgtt     2580 gggtgtggca taggtggcag ctctagatac ctggccaaga aatttggagc aaccagtgta    2640
ggcatcactc tgagtcctgt tcaagctcaa agagcaaatg ctcttgctgc tgctcaagga    2700
ttggctgata aggtttcctt tcaggttgct gacgctctac agcaaccatt ctctgacggc    2760
cagtttgatc tggtgtggtc catggagagt ggagagcata tgcctgacaa agctaagttt    2820
gttggagagt tagctcgggt agcagcacca ggtgccatta ataatagt aacatggtgc      2880 cacagggatc ttggccctga cgaacaatcc ttacatccat gggagcaaga tctcttaaag    2940
aagatttgcg atgcatatta cctccctgcc tggtgctcaa cttctgatta tgttaagttg    3000
ctccaatccc tgtcacttca ggacatcaag tcagaagatt ggtctcgctt tgttgctcca    3060
ttttggccag cagtgatacg ctcagccttc acatggaagg gtctatcttc actcttgagc    3120
agtggacaaa aaacgataaa aggagctttg gctatgccat tgatgataga gggatacaag    3180
aaagatctaa ttaagtttgc catcattaca tgtcgaaaac ctgaataagc ggccgcgaca    3240
caagtgtgag agtactaaat aaatgctttg gttgtacgaa atcattacac taaataaaat    3300
aatcaaagct tatatatgcc ttccgctaag gccgaatgca agaaattgg ttctttctcg     3360 ttatcttttg ccacttttac tagtacgatc caagcttgtt gaaacatccc tgaagtgtct    3420
cattttattt tatttattct ttgctgataa aaaaataaaa taaagaagc taagcacacg     3480 gtcaaccatt gctctactgc taaaagggtt atgtgtagtg ttttactgca taaattatgc    3540
agcaaacaag acaactcaaa ttaaaaaatt cctttgcttt gttttttttgt tgtctctgac   3600 ttgactttct tgtggaagtt ggttgtataa ggattgggac accattgtcc ttcttaattt    3660
aattttattc tttgctgata aaaaaaaaaa tttcatatag tgttaaataa taatttgtta    3720
aataaccaaa aagtcaaata tgtttactct cgtttaaata attgagattc gtccagcaag    3780
gctaaacgat tgtatagatt tatgacaata tttactttt tatagataaa tgttatatta    3840
taataaattt atatacatat attatatgtt atttattat attttaaatc cttcaatatt    3900
ttatcaaacc aactcataat ttttttttta tctgtaagaa gcaataaaat taaatagacc    3960
cactttaagg atgatccaac ctttatacag agtaagagag ttcaaatagt acccttcat    4020 atacatatca actaaaatat tagaaatatc atggatcaaa ccttataag acattaaata   4080 agtggataag tataatatat aaatgggtag tatataatat ataaatggat acaaacttct   4140
ctctttataa ttgttatgtc tccttaacat cctaatataa tacataagtg ggtaatatat    4200
aatatataaa tggagacaaa cttcttccat tataattgtt atgtcttctt aacacttatg    4260
tctcgttcac aatgctaagg ttagaattgt ttagaaagtc ttatagtaca catttgtttt    4320
tgtactattt gaagcattcc ataagccgtc acgattcaga tgatttataa taataagagg    4380
aaatttatca tagaacaata aggtgcatag atagagtgtt aatatatcat aacatccttt    4440
gtttattcat agaagaagtg agatggagct cagttattat actgttacat ggtcggatac    4500
aatattccat gctctccatg agctcttaca cctacatgca ttttagttca tacttgcggc    4560
cgcttcacat ctgctggccc ttgtacaaat ttcactgcac aaatggtata aggaaatact    4620
ctgcatagaa tagcttccaa atgaacatgt aaaatgatgt gacacgcgct tggttttcaa    4680
```

```
cctcaaagtg ctgcgctctc tgccaaagtg tcaaagcaag caggccatga ccagacacag   4740
tgatgatctt ttgaaatagg tttgtggatg aagctcctac tagagtggca gcgccatagg   4800
ctgtcaacaa tatgcttatg cagagctgat acactctttg aggccccaat ctcacactca   4860
aggattggat accaaagtct cgatctccat caacatctgg aatatccttg aatagtgcta   4920
tgacggcaga gaagcaacac ataaacaatg ttgcaaacac cagcgatttg gttgctgcca   4980
atggcctttt cagaacatgt tgctgcatat gtgcaaagaa agccaactgg accaagatag   5040
ccctcacaaa taggatacat gatgcagcga ggagcgcgtg ccgtttccac cggaggaacg   5100
gagcctcaat ggagtacgca cttccaagaa ggaagctgac aattaaagca cacatcagtg   5160
gcgccgatcc ggaacgtatt cctatgctaa agctcatgat caggaatgcg agtactaaga   5220
aaactccagt tgctactgaa aattccccag atgccaatgg aagacctggc ttgttgatct   5280
tgtcaatctg aatgtcatat agctgattca gcccgaccac ataaatgttc atacataaag   5340
cagcagtcaa agcctcgaga tatcctcgta gtaccgtgac agtaaaatca tctatgctct   5400
tcattggcag agagacact  gaagttatac ctattatagt gccaaaaatt gtgtgtggcc   5460
tgcaaaattc atagaaagag cgcaatttct caaaacatc  tcccctgatt tcctcaagcc   5520
gattggcgtt ggaaccgttt tgatcccaat taacctcgct gcatccagct tggagggctg   5580
gataatcatc gctgcactgt ctctttgtgt ttcttctagg cctagcagct tgagaaatgg   5640
cactgaattt atgcattaca gtagtagcac tttggcactg gcctgcaaaa gcttccactg   5700
caaatcgacc tgtccaggat aatctcgtcg ttcccagccg agcccacat  ctgggccctc   5760 tcctcgtatc tgttagcagc tgccccgccg cggccgccgc cgtgacggct tgcatcctgc   5820
ggccgcagta tatcttaaat tctttaatac ggtgtactag gatattgaac tggttcttga   5880
tgatgaaaac ctgggccgag attgcagcta tttatagtca taggtcttgt taacatgcat   5940
ggacatttgg ccacggggtg gcatgcagtt tgacgggtgt tgaaataaac aaaaatgagg   6000
tggcggaaga gaatacgagt ttgaggttgg gttagaaaca acaaatgtga gggctcatga   6060
tgggttgagt tggtgaatgt tttgggctgc tcgattgaca cctttgtgag tacgtgttgt   6120
tgtgcatggc ttttggggtc cagtttttttt ttcttgacgc ggcgatcctg atcagctagt   6180
ggataagtga tgtccactgt gtgtgattgc gtttttgttt gaattttatg aacttagaca   6240
ttgctatgca aaggatactc tcattgtgtt ttgtcttctt tgttccttg  gcttttctt    6300 atgatccaag agactagtca gtgttgtggc attcgagact accaagatta attatgatgg   6360
gggaaggata agtaactgat tagtacggac tgttaccaaa ttagtattaa ttactactta   6420
atcatctttg tttacggctc attatatccg tcgactctag aggatccccg ggtaccgagc   6480
tcgaattcac tggccgtcgt tttacaacgt cgtgactggg aaaaccctgg cgttacccaa   6540
cttaatcgcc ttgcagcaca tccccctttc gccagctggc gtaatagcga agaggcccgc   6600
accgatcgcc cttcccaaca gttgcgcagc ctgaatggcg aatggatcga tccgtcgatc   6660
gaccaaagcg gccatcgtgc ctccccactc ctgcagttcg ggggcatgga tgcgcggata   6720
gccgctgctg gttcctggg  tgccgacgga tttgcactgc cggtagaact ccgcgaggtc   6780
gtccagcctc aggcagcagc tgaaccaact cgcgagggga tcgagcccct gctgagcctc   6840
gacatgttgt cgcaaaattc gccctggacc cgccaacga  tttgtcgtca ctgtcaaggt   6900
ttgacctgca cttcatttgg ggcccacata caccaaaaaa atgctgcata attctcgggg   6960
cagcaagtcg gttacccggc cgccgtgctg gaccgggttg aatggtgccc gtaactttcg   7020
gtagagcgga cggccaatac tcaacttcaa ggaatctcac ccatgcgcgc cggcggggaa   7080
```

```
ccggagttcc cttcagtgaa cgttattagt tcgccgctcg gtgtgtcgta gatactagcc    7140 cctgggcct  tttgaaattt gaataagatt tatgtaatca gtcttttagg tttgaccggt    7200
tctgccgctt ttttaaaat  tggatttgta ataataaaac gcaattgttt gttattgtgg    7260
cgctctatca tagatgtcgc tataaaccta ttcagcacaa tatattgttt tcattttaat    7320
attgtacata taagtagtag ggtacaatca gtaaattgaa cggagaatat tattcataaa    7380
aatacgatag taacgggtga tatattcatt agaatgaacc gaaaccggcg gtaaggatct    7440
gagctacaca tgctcaggtt ttttacaacg tgcacaacag aattgaaagc aaatatcatg    7500
cgatcatagg cgtctcgcat atctcattaa gcagggggt  gggcgaagaa ctccagcatg    7560
agatccccgc gctggaggat catccagccg gcgtcccgga aaacgattcc gaagcccaac    7620
ctttcataga aggcggcggt ggaatcgaaa tctcgtgatg gcaggttggg cgtcgcttgg    7680
tcggtcattt cgaaccccag agtcccgctc agaagaactc gtcaagaagg cgatagaagg    7740
cgatgcgctg cgaatcggga gcggcgatac cgtaaagcac gaggaagcgg tcagcccatt    7800
cgccgccaag ctcttcagca atatcacggg tagccaacgc tatgtcctga tagcggtccg    7860
ccacacccag ccggccacag tcgatgaatc cagaaaagcg gccatttccc accatgatat    7920
tcggcaagca ggcatcgcca tgggtcacga cgagatcctc gccgtcgggc atgcgcgcct    7980
tgagcctggc gaacagttcg gctggcgcga gcccctgatg ctcttcgtcc agatcatcct    8040
gatcgacaag accggcttcc atccgagtac gtgctcgctc gatgcgatgt ttcgcttggt    8100
ggtcgaatgg gcaggtagcc ggatcaagcg tatgcagccg ccgcattgca tcagccatga    8160
tggatacttt ctcggcagga gcaaggtgag atgacaggag atcctgcccc ggcacttcgc    8220
ccaatagcag ccagtccctt cccgcttcag tgacaacgtc gagcacagct gcgcaaggaa    8280
cgcccgtcgt ggccagccac gatagccgcg ctgcctcgtc ctgcagttca ttcagggcac    8340
cggacaggtc ggtcttgaca aaaagaaccg ggcgcccctg cgctgacagc cggaacacgg    8400
cggcatcaga gcagccgatt gtctgttgtg cccagtcata gccgaatagc ctctccaccc    8460
aagcggccgg agaacctgcg tgcaatccat cttgttcaat catgcgaaac gatccccgca    8520
agcttggaga ctggtgattt cagcgtgtcc tctccaaatg aaatgaactt ccttatatag    8580
aggaagggtc ttgcgaagga tagtgggatt gtgcgtcatc ccttacgtca gtggagatat    8640
cacatcaatc cacttgcttt gaagacgtgg ttggaacgtc ttcttttttcc acgatgctcc    8700 tcgtgggtgg gggtccatct ttgggaccac tgtcggcaga ggcatcttca acgatggcct    8760
ttcctttatc gcaatgatgg catttgtagg agccaccttc cttttccact atcttcacaa    8820
taaagtgaca gatagctggg caatggaatc cgaggaggtt tccggatatt acccttttgtt   8880 gaaaagtctc aattgcccctt tggtcttctg agactgtatc tttgatattt ttggagtaga   8940
caagcgtgtc gtgctccacc atgttgacga agattttctt cttgtcattg agtcgtaaga   9000
gactctgtat gaactgttcg ccagtcttta cggcgagttc tgttaggtcc tctatttgaa   9060
tctttgactc catggccttt gattcagtgg gaactacctt tttagagact ccaatctcta   9120
ttacttgcct tggtttgtga agcaagcctt gaatcgtcca tactgaaata gtacttctga   9180
tcttgagaaa tatatctttc tctgtgttct tgatgcagtt agtcctgaat cttttgactg   9240
catctttaac cttcttggga aggtatttga tctcctggag attattgctc gggtagatcg   9300
tcttgatgag acctgctgcg taagcctctc taaccatctg tgggttagca ttcttttctga  9360 aattgaaaag gctaatcttc tcattatcag tggtgaacat ggtatcgtca ccttctccgt   9420
cgaacttcct gactagatcg tagagataga ggaagtcgtc cattgtgatc tctggggcaa   9480
```

| aggagatctg aattatcatt tacaattgaa tatatcctgc ca | 9522 |

```
<210> SEQ ID NO 44
<211> LENGTH: 35
<212> TYPE: DNA
<213> ORGANISM: Artificial Sequence
<220> FEATURE:
<223> OTHER INFORMATION: primer

<400> SEQUENCE: 44
```

| agcgcggccg catggccacc gtggtgagga tccca | 35 |

```
<210> SEQ ID NO 45
<211> LENGTH: 39
<212> TYPE: DNA
<213> ORGANISM: Artificial Sequence
<220> FEATURE:
<223> OTHER INFORMATION: primer

<400> SEQUENCE: 45
```

| agcgcggccg cttattcagg ttttcgacat gtaatgatg | 39 |

```
<210> SEQ ID NO 46
<211> LENGTH: 1224
<212> TYPE: DNA
<213> ORGANISM: Artificial
<220> FEATURE:
<223> OTHER INFORMATION: open reading frame from barley HGGT cDNA
      (SEQ ID NO:1)

<400> SEQUENCE: 46
```

| atgcaagccg tcacggcggc ggccgcggcg gggcagctgc taacagatac gaggagaggg | 60 |
| cccagatgta gggctcggct gggaacgacg agattatcct ggacaggtcg atttgcagtg | 120 |
| gaagcttttg caggccagtg ccaaagtgct actactgtaa tgcataaatt cagtgccatt | 180 |
| tctcaagctc ctaggcctag aagaaacaca aagagacagt gcagcgatga ttatccagcc | 240 |
| ctccaagctg gatgcagcga ggttaattgg gatcaaaacg gttccaacgc caatcggctt | 300 |
| gaggaaatca ggggagatgt tttgaagaaa ttgcgctctt tctatgaatt ttgcaggcca | 360 |
| cacacaattt ttggcactat aataggtata acttcagtgt ctctcctgcc aatgaagagc | 420 |
| atagatgatt ttactgtcac ggtactacga ggatatctcg aggctttgac tgctgcttta | 480 |
| tgtatgaaca tttatgtggt cgggctgaat cagctatatg acattcagat tgacaagatc | 540 |
| aacaagccag tcttccatt ggcatctggg gaattttcag tagcaactgg agttttctta | 600 |
| gtactcgcat tcctgatcat gagctttagc ataggaatac gttccggatc ggcgccactg | 660 |
| atgtgtgctt taattgtcag cttccttctt ggaagtgcgt actccattga ggctccgttc | 720 |
| ctccggtgga acggcacgc gctcctcgct gcatcatgta tcctatttgt gagggctatc | 780 |
| ttggtccagt tggctttctt tgcacatatg cagcaacatg ttctgaaaag gccattggca | 840 |
| gcaaccaaat cgctggtgtt tgcaacattg tttatgtgtt gcttctctgc cgtcatagca | 900 |
| ctattcaagg atattccaga tgttgatgga gatcgagact tggtatcca atccttgagt | 960 |
| gtgagattgg ggcctcaaag agtgtatcag ctctgcataa gcatattgtt gacagcctat | 1020 |
| ggcgctgcca ctctagtagg agcttcatcc acaaacctat tcaaaagat catcactgtg | 1080 |
| tctggtcatg gcctgcttgc tttgacactt tggcagagag cgcagcactt tgaggttgaa | 1140 |
| aaccaagcgc gtgtcacatc atttacatg ttcatttgga agctattcta tgcagagtat | 1200 |
| ttccttatac catttgtgca gtga | 1224 |

```
<210> SEQ ID NO 47
<211> LENGTH: 38
<212> TYPE: DNA
<213> ORGANISM: Artificial Sequence
<220> FEATURE:
<223> OTHER INFORMATION: primer

<400> SEQUENCE: 47
ttgcggccgc aggatgcaag ccgtcacggc ggcagccg                              38

<210> SEQ ID NO 48
<211> LENGTH: 33
<212> TYPE: DNA
<213> ORGANISM: Artificial Sequence
<220> FEATURE:
<223> OTHER INFORMATION: primer

<400> SEQUENCE: 48
ttgcggccgc ttcacatctg ctggcccttg tac                                  33

<210> SEQ ID NO 49
<211> LENGTH: 8312
<212> TYPE: DNA
<213> ORGANISM: Artificial Sequence
<220> FEATURE:
<223> OTHER INFORMATION: plasmid SC38

<400> SEQUENCE: 49
ggccgcaagt atgaactaaa atgcatgtag gtgtaagagc tcatggagag catggaatat     60
tgtatccgac catgtaacag tataataact gagctccatc tcacttcttc tatgaataaa    120
caaaggatgt tatgatatat taacactcta tctatgcacc ttattgttct atgataaatt    180
tcctcttatt attataaatc atctgaatcg tgacggctta tggaatgctt caaatagtac    240
aaaaacaaat gtgtactata agactttcta aacaattcta accttagcat tgtgaacgag    300
acataagtgt taagaagaca taacaattat aatggaagaa gtttgtctcc atttatatat    360
tatatattac ccacttatgt attatattag gatgttaagg agacataaca attataaaga    420
gagaagtttg tatccatttta tatattatat actacccatt tatatattat acttatccac    480
ttatttaatg tctttataag gtttgatcca tgatatttct aatattttag ttgatatgta    540
tatgaaaggg tactatttga actctcttac tctgtataaa ggttggatca tcctaaagt     600 gggtctattt aatttttattg cttcttacag ataaaaaaaa aattatgagt tggtttgata    660
aaatattgaa ggatttaaaa taataataaa taacatataa tatatgtata taaatttatt    720
ataatataac atttatctat aaaaaagtaa atattgtcat aaatctatac aatcgtttag    780
ccttgctgga cgaatctcaa ttatttaaac gagagtaaac atatttgact ttttggttat    840
ttaacaaatt attatttaac actatatgaa atttttttt tatcagcaa agaataaaat       900 taaattaaga aggacaatgg tgtcccaatc cttatacaac caacttccac aagaaagtca    960
agtcagagac aacaaaaaaa caagcaaagg aaattttta atttgagttg tcttgtttgc    1020
tgcataattt atgcagtaaa acactacaca taacccttttt agcagtagag caatggttga    1080
ccgtgtgctt agcttctttt attttattttt tttatcagca aagaataaat aaaataaaat    1140
gagacacttc agggatgttt caacaagctt ggatccgtcg acggcgcgcc cgatcatccg    1200
gatatagttc ctcctttcag caaaaaaccc ctcaagaccc gtttagaggc cccaagggg     1260 tatgctagtt attgctcagc ggtggcagca gccaactcag cttcctttcg ggctttgtta    1320
gcagccggat cgatccaagc tgtacctcac tattcctttg cctcggacg agtgctgggg    1380 cgtcggtttc cactatcggc gagtacttct acacagccat cggtccagac ggccgcgctt    1440
```

```
ctgcgggcga tttgtgtacg cccgacagtc ccggctccgg atcggacgat tgcgtcgcat   1500
cgaccctgcg cccaagctgc atcatcgaaa ttgccgtcaa ccaagctctg atagagttgg   1560
tcaagaccaa tgcggagcat atacgcccgg agccgcggcg atcctgcaag ctccggatgc   1620
ctccgctcga agtagcgcgt ctgctgctcc atacaagcca accacggcct ccagaagaag   1680
atgttggcga cctcgtattg ggaatcccccg aacatcgcct cgctccagtc aatgaccgct   1740
gttatgcggc cattgtccgt caggacattg ttggagccga atccgcgtg cacgaggtgc    1800 cggacttcgg ggcagtcctc ggcccaaagc atcagctcat cgagagcctg cgcgacggac   1860
gcactgacgg tgtcgtccat cacagtttgc cagtgataca catggggatc agcaatcgcg   1920
catatgaaat cacgccatgt agtgtattga ccgattcctt gcggtccgaa tgggccgaac   1980
ccgctcgtct ggctaagatc ggccgcagcg atcgcatcca tagcctccgc gaccggctgc   2040
agaacagcgg gcagttcggt ttcaggcagg tcttgcaacg tgacaccctg tgcacggcgg   2100
gagatgcaat aggtcaggct ctcgctgaat tccccaatgt caagcacttc cggaatcggg   2160
agcgcggccg atgcaaagtg ccgataaaca taacgatctt tgtagaaacc atcggcgcag   2220
ctatttaccc gcaggacata tccacgccct cctacatcga agctgaaagc acgagattct   2280
tcgccctccg agagctgcat caggtcggag acgctgtcga acttttcgat cagaaacttc   2340
tcgacagacg tcgcggtgag ttcaggcttt tccatgggta tatctccttc ttaaagttaa   2400
acaaaattat ttctagaggg aaaccgttgt ggtctcccta tagtgagtcg tattaatttc   2460
gcgggatcga gatcgatcca attccaatcc cacaaaaatc tgagcttaac agcacagttg   2520
ctcctctcag agcagaatcg ggtattcaac accctcatat caactactac gttgtgtata   2580
acggtccaca tgccggtata tacgatgact ggggttgtac aaaggcggca acaaacggcg   2640
ttcccggagt tgcacacaag aaatttgcca ctattacaga ggcaagagca gcagctgacg   2700
cgtacacaac aagtcagcaa acagacaggt tgaacttcat ccccaaagga gaagctcaac   2760
tcaagcccaa gagctttgct aaggccctaa caagcccacc aaagcaaaaa gcccactggc   2820
tcacgctagg aaccaaaagg cccagcagtg atccagcccc aaaagagatc tccttttgccc   2880 cggagattac aatggacgat ttcctctatc tttacgatct aggaaggaag ttcgaaggtg   2940
aaggtgacga cactatgttc accactgata atgagaaggt tagcctcttc aatttcagaa   3000
agaatgctga cccacagatg gttagagagg cctacgcagc aggtctcatc aagacgatct   3060
acccgagtaa caatctccag gagatcaaat accttcccaa gaaggttaaa gatgcagtca   3120
aaagattcag gactaattgc atcaagaaca cagagaaaga catatttctc aagatcagaa   3180
gtactattcc agtatggacg attcaaggct tgcttcataa accaaggcaa gtaatagaga   3240
ttggagtctc taaaaaggta gttcctactg aatctaaggc catgcatgga gtctaagatt   3300
caaatcgagg atctaacaga actcgccgtg aagactggcg aacagttcat acagagtctt   3360
ttacgactca atgacaagaa gaaaatcttc gtcaacatgg tggagcacga cactctggtc   3420
tactccaaaa atgtcaaaga tacagtctca gaagaccaaa gggctattga acttttcaa    3480 caaaggataa tttcgggaaa cctcctcgga ttccattgcc cagctatctg tcacttcatc   3540
gaaaggacag tagaaaagga aggtggctcc tacaaatgcc atcattgcga taaaggaaag   3600
gctatcattc aagatgcctc tgccgacagt ggtcccaaag atggacccc acccacgagg    3660 agcatcgtgg aaaaagaaga cgttccaacc acgtcttcaa agcaagtgga ttgatgtgac   3720
atctccactg acgtaaggga tgacgcacaa tcccactatc cttcgcaaga cccttcctct   3780
atataaggaa gttcatttca tttggagagg acacgctcga gctcatttct ctattacttc   3840
```

```
agccataaca aaagaactct tttctcttct tattaaacca tgaaaaagcc tgaactcacc    3900
gcgacgtctg tcgagaagtt tctgatcgaa aagttcgaca gcgtctccga cctgatgcag    3960
ctctcggagg gcgaagaatc tcgtgctttc agcttcgatg taggagggcg tggatatgtc    4020
ctgcgggtaa atagctgcgc cgatggtttc tacaaagatc gttatgttta tcggcacttt    4080
gcatcggccg cgctcccgat tccggaagtg cttgacattg gggaattcag cgagagcctg    4140
acctattgca tctcccgccg tgcacagggt gtcacgttgc aagacctgcc tgaaaccgaa    4200
ctgcccgctg ttctgcagcc ggtcgcggag gccatgatg cgatcgctgc ggccgatctt    4260
agccagacga gcgggttcgg cccattcgga ccgcaaggaa tcggtcaata cactacatgg    4320
cgtgatttca tatgcgcgat tgctgatccc catgtgtatc actggcaaac tgtgatggac    4380
gacaccgtca gtgcgtccgt cgcgcaggct ctcgatgagc tgatgctttg ggccgaggac    4440
tgccccgaag tccggcacct cgtgcacgcg gatttcggct ccaacaatgt cctgacggac    4500
aatggccgca taacagcggt cattgactgg agcgaggcga tgttcgggga ttcccaatac    4560
gaggtcgcca acatcttctt ctggaggccg tggttggctt gtatggagca gcagacgcgc    4620
tacttcgagc ggaggcatcc ggagcttgca ggatcgccgc ggctccgggc gtatatgctc    4680
cgcattggtc ttgaccaact ctatcagagc ttggttgacg gcaatttcga tgatgcagct    4740
tgggcgcagg gtcgatgcga cgcaatcgtc cgatccggag ccgggactgt cgggcgtaca    4800
caaatcgccc gcagaagcgc ggccgtctgg accgatggct gtgtagaagt actcgccgat    4860
agtggaaacc gacgcccag cactcgtccg agggcaaagg aatagtgagg tacctaaaga    4920
aggagtgcgt cgaagcagat cgttcaaaca tttggcaata aagtttctta agattgaatc    4980
ctgttgccgg tcttgcgatg attatcatat aatttctgtt gaattacgtt aagcatgtaa    5040
taattaacat gtaatgcatg acgttattta tgagatgggt ttttatgatt agagtcccgc    5100
aattatacat ttaatacgcg atagaaaaca aaatatagcg cgcaaactag gataaattat    5160
cgcgcgcggt gtcatctatg ttactagatc gatgtcgaat ctgatcaacc tgcattaatg    5220
aatcggccaa cgcgcgggga gaggcggttt gcgtattggg cgctcttccg cttcctcgct    5280
cactgactcg ctgcgctcgg tcgttcggct gcggcgagcg gtatcagctc actcaaaggc    5340
ggtaatacgg ttatccacag aatcagggga taacgcagga aagaacatgt gagcaaaagg    5400
ccagcaaaag gccaggaacc gtaaaaaggc cgcgttgctg gcgttttcc ataggctccg    5460 cccccctgac gagcatcaca aaaatcgacg ctcaagtcag aggtggcgaa acccgacagg    5520
actataaaga taccaggcgt ttccccctgg aagctccctc gtgcgctctc ctgttccgac    5580
cctgccgctt accggatacc tgtccgcctt tctcccttcg ggaagcgtgg cgctttctca    5640
atgctcacgc tgtaggtatc tcagttcggt gtaggtcgtt cgctccaagc tgggctgtgt    5700
gcacgaaccc cccgttcagc ccgaccgctg cgccttatcc ggtaactatc gtcttgagtc    5760
caacccggta agacacgact tatcgccact ggcagcagcc actggtaaca ggattagcag    5820
agcgaggtat gtaggcggtg ctacagagtt cttgaagtgg tggcctaact acggctacac    5880
tagaaggaca gtatttggta tctgcgctct gctgaagcca gttaccttcg gaaaaagagt    5940
tggtagctct tgatccggca aacaaaccac cgctggtagc ggtggttttt tgtttgcaa    6000 gcagcagatt acgcgcagaa aaaaaggatc tcaagaagat cctttgatct tttctacggg    6060
gtctgacgct cagtggaacg aaaactcacg ttaagggatt ttggtcatga cattaaccta    6120
taaaaatagg cgtatcacga ggccctttcg tctcgcgcgt ttcggtgatg acggtgaaaa    6180
cctctgacac atgcagctcc cggagacggt cacagcttgt ctgtaagcgg atgccgggag    6240
```

```
cagacaagcc cgtcagggcg cgtcagcggg tgttggcggg tgtcgggct ggcttaacta    6300 tgcggcatca gagcagattg tactgagagt gcaccatatg gacatattgt cgttagaacg    6360
cggctacaat taatacataa ccttatgtat catacacata cgatttaggt gacactatag    6420
aacggcgcgc caagcttttg atccatgccc ttcatttgcc gcttattaat taatttggta    6480
acagtccgta ctaatcagtt acttatcctt cccccatcat aattaatctt ggtagtctcg    6540
aatgccacaa cactgactag tctcttggat cataagaaaa agccaaggaa caaagaaga     6600 caaaacacaa tgagagtatc ctttgcatag caatgtctaa gttcataaaa ttcaaacaaa    6660
aacgcaatca cacacagtgg acatcactta tccactagct gatcaggatc gccgcgtcaa    6720
gaaaaaaaaa ctggacccca aaagccatgc acaacaacac gtactcacaa aggtgtcaat    6780
cgagcagccc aaaacattca ccaactcaac ccatcatgag ccctcacatt tgttgtttct    6840
aacccaacct caaactcgta ttctcttccg ccacctcatt tttgtttatt tcaacacccg    6900
tcaaactgca tgccaccccg tggccaaatg tccatgcatg ttaacaagac ctatgactat    6960
aaatagctgc aatctcggcc caggttttca tcatcaagaa ccagttcaat atcctagtac    7020
accgtattaa agaatttaag atatactgcg gccgcaggat gcaagccgtc acggcggcgg    7080
ccgcggcggg gcagctgcta acagatacga ggagagggcc cagatgtagg gctcggctgg    7140
gaacgacgag attatcctgg acaggtcgat ttgcagtgga agcttttgca ggccagtgcc    7200
aaagtgctac tactgtaatg cataaattca gtgccatttc tcaagctgct aggcctagaa    7260
gaaacacaaa gagacagtgc agcgatgatt atccagccct ccaagctgga tgcagcgagg    7320
ttaattggga tcaaaacggt tccaacgcca atcggcttga ggaaatcagg ggagatgttt    7380
tgaagaaatt gcgctctttc tatgaatttt gcaggccaca cacaatttttt ggcactataa    7440 taggtataac ttcagtgtct ctcctgccaa tgaagagcat agatgatttt actgtcacgg    7500
tactacgagg atatctcgag gctttgactg ctgctttatg tatgaacatt tatgtggtcg    7560
ggctgaatca gctatatgac attcagattg acaagatcaa caagccaggt cttccattgg    7620
catctgggga attttcagta gcaactggag ttttcttagt actcgcattc ctgatcatga    7680
gctttagcat aggaatacgt tccggatcgg cgccactgat gtgtgcttta attgtcagct    7740
tccttcttgg aagtgcgtac tccattgagg ctccgttcct ccggtggaaa cggcacgcgc    7800
tcctcgctgc atcatgtatc ctatttgtga gggctatctt ggtccagttg gctttctttg    7860
cacatatgca gcaacatgtt ctgaaaaggc cattggcagc aaccaaatcg ctggtgtttg    7920
caacattgtt tatgtgttgc ttctctgccg tcatagcact attcaaggat attccagatg    7980
ttgatggaga tcgagacttt ggtatccaat ccttgagtgt gagattgggg cctcaaagag    8040
tgtatcagct ctgcataagc atattgttga cagcctatgg cgctgccact ctagtaggag    8100
cttcatccac aaacctattt caaaagatca tcactgtgtc tggtcatggc ctgcttgctt    8160
tgacactttg gcagagagcg cagcactttg aggttgaaaa ccaagcgcgt gtcacatcat    8220
tttacatgtt catttggaag ctattctatg cagagtattt cttataccca tttgtgcagt    8280
gaaatttgta caagggccag cagatgtgaa gc                                  8312
```

<210> SEQ ID NO 50
<211> LENGTH: 8137
<212> TYPE: DNA
<213> ORGANISM: Artificial
<220> FEATURE:
<223> OTHER INFORMATION: plasmid SC1

<400> SEQUENCE: 50

```
cgcgtacaca acaagtcagc aaacagacag gttgaacttc atccccaaag gagaagctca      60
actcaagccc aagagctttg ctaaggccct aacaagccca ccaaagcaaa aagcccactg     120
gctcacgcta ggaaccaaaa ggcccagcag tgatccagcc ccaaaagaga tctcctttgc     180
cccggagatt acaatggacg atttcctcta tctttacgat ctaggaagga agttcgaagg     240
tgaaggtgac gacactatgt tcaccactga taatgagaag gttagcctct tcaatttcag     300
aaagaatgct gacccacaga tggttagaga ggcctacgca gcaggtctca tcaagacgat     360
ctacccgagt aacaatctcc aggagatcaa ataccttccc aagaaggtta agatgcagt      420 caaaagattc aggactaatt gcatcaagaa cacagagaaa gacatatttc tcaagatcag     480
aagtactatt ccagtatgga cgattcaagg cttgcttcat aaaccaaggc aagtaataga     540
gattggagtc tctaaaaagg tagttcctac tgaatctaag gccatgcatg gagtctaaga     600
ttcaaatcga ggatctaaca gaactcgccg tgaagactgg cgaacagttc atacagagtc     660
ttttacgact caatgacaag aagaaaatct tcgtcaacat ggtggagcac gacactctgg     720
tctactccaa aaatgtcaaa gatacagtct cagaagacca aagggctatt gagacttttc     780
aacaaaggat aatttcggga aacctcctcg gattccattg cccagctatc tgtcacttca     840
tcgaaaggac agtagaaaag gaaggtggct cctacaaatg ccatcattgc gataaggaa      900 aggctatcat tcaagatgcc tctgccgaca gtggtcccaa agatggaccc ccacccacga     960
ggagcatcgt ggaaaaagaa gacgttccaa ccacgtcttc aaagcaagtg gattgatgtg    1020
acatctccac tgacgtaagg gatgacgcac aatcccacta tccttcgcaa gacccttcct    1080
ctatataagg aagttcattt catttggaga ggacacgctc gagctcattt ctctattact    1140
tcagccataa caaagaact cttttctctt cttattaaac catgaaaaag cctgaactca     1200
ccgcgacgtc tgtcgagaag tttctgatcg aaaagttcga cagcgtctcc gacctgatgc    1260
agctctcgga gggcgaagaa tctcgtgctt tcagcttcga tgtaggaggg cgtggatatg    1320
tcctgcgggt aaatagctgc gccgatggtt tctacaaaga tcgttatgtt tatcggcact    1380
ttgcatcggc cgcgctcccg attccggaag tgcttgacat tggggaattc agcgagagcc    1440
tgacctattg catctcccgc cgtgcacagg gtgtcacgtt gcaagacctg cctgaaaccg    1500
aactgcccgc tgttctgcag ccggtcgcgg aggccatgga tgcgatcgct gcggccgatc    1560
ttagccagac gagcgggttc ggcccattcg gaccgcaagg aatcggtcaa tacactacat    1620
ggcgtgattt catatgcgcg attgctgatc cccatgtgta tcactggcaa actgtgatgg    1680
acgacaccgt cagtgcgtcc gtcgcgcagg ctctcgatga gctgatgctt tgggccgagg    1740
actgccccga gtccggcac ctcgtgcacg cggatttcgg ctccaacaat gtcctgacgg     1800
acaatggccg cataacagcg gtcattgact ggagcgaggc gatgttcggg gattcccaat    1860
acgaggtcgc caacatcttc ttctggaggc cgtggttggc ttgtatggag cagcagacgc    1920
gctacttcga gcggaggcat ccggagcttg caggatcgcc gcggctccgg gcgtatatgc    1980
tccgcattgg tcttgaccaa ctctatcaga gcttggttga cggcaatttc gatgatgcag    2040
cttgggcgca gggtcgatgc gacgcaatcg tccgatccgg agccgggact gtcgggcgta    2100
cacaaatcgc ccgcagaagc gcggccgtct ggaccgatgg ctgtgtagaa gtactcgccg    2160
atagtggaaa ccgacgcccc agcactcgtc cgagggcaaa ggaatagtga ggtacctaaa    2220
gaaggagtgc gtcgaagcag atcgttcaaa catttggcaa taaagtttct taagattgaa    2280
tcctgttgcc ggtcttgcga tgattatcat ataatttctg ttgaattacg ttaagcatgt    2340
aataattaac atgtaatgca tgacgttatt tatgagatgg gtttttatga ttagagtccc    2400
```

```
gcaattatac atttaatacg cgatagaaaa caaaatatag cgcgcaaact aggataaatt    2460
atcgcgcgcg gtgtcatcta tgttactaga tcgatgtcga cgatcatccg gatatagttc    2520
ctcctttcag caaaaaaccc ctcaagaccc gtttagaggc cccaaggggt tatgctagtt    2580
attgctcagc ggtggcagca gccaactcag cttcctttcg ggctttgtta gcagccggat    2640
cgatccaagc tgtacctcac tattcctttg ccctcggacg agtgctgggg cgtcggtttc    2700
cactatcggc gagtacttct acacagccat cggtccagac ggccgcgctt ctgcgggcga    2760
tttgtgtacg cccgacagtc ccggctccgg atcggacgat tgcgtcgcat cgaccctgcg    2820
cccaagctgc atcatcgaaa ttgccgtcaa ccaagctctg atagagttgg tcaagaccaa    2880
tgcggagcat atacgcccgg agccgcggcg atcctgcaag ctccggatgc ctccgctcga    2940
agtagcgcgt ctgctgctcc atacaagcca accacggcct ccagaagaag atgttggcga    3000
cctcgtattg ggaatcccg aacatcgcct cgctccagtc aatgaccgct gttatgcggc    3060
cattgtccgt caggacattg ttggagccga atccgcgtg cacgaggtgc cggacttcgg    3120
ggcagtcctc ggcccaaagc atcagctcat cgagagcctg cgcgacggac gcactgacgg    3180
tgtcgtccat cacagtttgc cagtgataca catggggat agcaatcgcg catatgaaat    3240
cacgccatgt agtgtattga ccgattcctt gcggtccgaa tgggccgaac ccgctcgtct    3300
ggctaagatc ggccgcagcg atcgcatcca tagcctccgc gaccggctgc agaacagcgg    3360
gcagttcggt ttcaggcagg tcttgcaacg tgacaccctg tgcacggcgg gagatgcaat    3420
aggtcaggct ctcgctgaat tccccaatgt caagcacttc cggaatcggg agcgcggccg    3480
atgcaaagtg ccgataaaca taacgatctt tgtagaaacc atcggcgcag ctatttaccc    3540
gcaggacata tccacgccct cctacatcga agctgaaagc acgagattct cgcccctccg    3600
agagctgcat caggtcggag acgctgtcga acttttcgat cagaaacttc tcgacagacg    3660
tcgcggtgag ttcaggcttt tccatgggta tatctccttc ttaaagttaa acaaaattat    3720
ttctagaggg aaaccgttgt ggtctcccta tagtgagtcg tattaatttc gcgggatcga    3780
gatctgatca acctgcatta atgaatcggc caacgcgcgg ggagaggcgg tttgcgtatt    3840
gggcgctctt ccgcttcctc gctcactgac tcgctgcgct cggtcgttcg gctgcggcga    3900
gcggtatcag ctcactcaaa ggcggtaata cggttatcca cagaatcagg ggataacgca    3960
ggaaagaaca tgtgagcaaa aggccagcaa aaggccagga accgtaaaaa ggccgcgttg    4020
ctggcgtttt tccataggct ccgcccccct gacgagcatc acaaaaatcg acgctcaagt    4080
cagaggtggc gaaacccgac aggactataa agataccagg cgtttccccc tggaagctcc    4140
ctcgtgcgct ctcctgttcc gaccctgccg cttaccggat acctgtccgc ctttctccct    4200
tcgggaagcg tggcgctttc tcaatgctca cgctgtaggt atctcagttc ggtgtaggtc    4260
gttcgctcca agctgggctg tgtgcacgaa ccccccgttc agcccgaccg ctgcgcctta    4320
tccggtaact atcgtcttga gtccaacccg gtaagacacg acttatcgcc actggcagca    4380
gccactggta acaggattag cagagcgagg tatgtaggcg gtgctacaga gttcttgaag    4440
tggtggccta actacggcta cactagaagg acagtatttg gtatctgcgc tctgctgaag    4500
ccagttacct tcggaaaaag agttggtagc tcttgatccg gcaaacaaac caccgctggt    4560
agcggtggtt ttttgtttg caagcagcag attacgcgca gaaaaaagg atctcaagaa    4620 gatcctttga tcttttctac ggggtctgac gctcagtgga acgaaaactc acgttaaggg    4680
attttggtca tgacattaac ctataaaaat aggcgtatca cgaggccctt tcgtctcgcg    4740
cgtttcggtg atgacggtga aaacctctga cacatgcagc tcccggagac ggtcacagct    4800
```

```
tgtctgtaag cggatgccgg gagcagacaa gcccgtcagg gcgcgtcagc gggtgttggc    4860
gggtgtcggg gctggcttaa ctatgcggca tcagagcaga ttgtactgag agtgcaccat    4920
atggacatat tgtcgttaga acgcggctac aattaataca taaccttatg tatcatacac    4980
atacgattta ggtgacacta tagaactcga gcagctgaag cttgatccat gcccttcatt    5040
tgccgctatt aattaatttg gtaacagtag tccgtactaa tcagttactt atccttcctc    5100
catcataatt aatcttggta gtctcgaatg ccacaacact gactagtctc ttggatcata    5160
agaaaaagcc aaggaacaaa agaagacaaa acacaatgag agtatccttt gcatagcaat    5220
gtctaagttc ataaaattca acaaaaacg caatcacaca cagtggacat cacttatcca     5280
ctagctgaat caggatcgcc gcgtcaagaa aaaaaactg gaccccaaaa gccatgcaca     5340
acaacacgta ctcacaaagg tgtcaatcga gcagcccaaa acattcacca actcaaccca    5400
tcatgagccc tcacatttgt tgtttctaac ccaacctcaa actcgtattc tcttccgcca    5460 cctcatttt gtttatttca acaccccgtca aactgcatgc caccccgtgg ccaaatgtcc     5520
atgcatgtta acaagaccta tgactataaa tatctgcaat ctcggcccag gttttcatca    5580
tcaagaacca gttcaatatc ctagtacacc gtattaaaga atttaagata tactaacagc    5640
ggccgcatgg ccaccgtggt gaggatccca acaatctcat gcatccacat ccacacgttc    5700
cgttcccaat cccctcgcac tttcgccaga atccgggtcg gacccaggtc gtgggctcct    5760
attcgggcat cggcagcgag ctcggagaga ggggagatag tattggagca gaagccgaag    5820
aaggatgaca agaagaagct gcagaaggga atcgcagagt tttacgacga gtcgtctggc    5880
ttatgggaga acatttgggg cgaccacatg caccatggct tttatgactc ggattccact    5940
gtttcgcttt cggatcatcg tgctgctcag atccgaatga tccaagagtc tcttcgcttt    6000
gcctctgttt ctgaggagcg tagtaaatgg cccaagagta tagttgatgt tgggtgtggc    6060
ataggtggca gctctagata cctggccaag aaatttggag caaccagtgt aggcatcact    6120
ctgagtcctg ttcaagctca aagagcaaat gctcttgctg ctgctcaagg attggctgat    6180
aaggtttcct ttcaggttgc tgacgctcta cagcaaccat tctctgacgg ccagtttgat    6240
ctggtgtggt ccatggagag tggagagcat atgcctgaca aagctaagtt tgttggagag    6300
ttagctcggg tagcagcacc aggtgccatt ataataatag taacatggtg ccacagggat    6360
cttggccctg acgaacaatc cttacatcca tgggagcaag atctcttaaa gaagatttgc    6420
gatgcatatt acctccctgc ctggtgctca acttctgatt atgttaagtt gctccaatcc    6480
ctgtcacttc aggacatcaa gtcagaagat tggtctcgct ttgttgctcc attttggcca    6540
gcagtgatac gctcagcctt cacatggaag ggtctatctt cactcttgag cagtggacaa    6600
aaaacgataa aaggagcttt ggctatgcca ttgatgatag agggatacaa gaaagatcta    6660
attaagtttg ccatcattac atgtcgaaaa cctgaataag cggccgctac atggccacgt    6720
gcatgaagta tgaactaaaa tgcatgtagg tgtaagagct catggagagc atggaatatt    6780
gtatccgacc atgtaacagt ataataactg agctccatct cacttcttct atgaataaac    6840
aaaggatgtt atgatatatt aacactctat ctatgcacct tattgttcta tgataaattt    6900
cctcttatta ttataaatca tctgaatcgt gacggcttat ggaatgcttc aaatagtaca    6960
aaaacaaatg tgtactataa gactttctaa acaattctaa ctttagcatt gtgaacgaga    7020
cataagtgtt aagaagacat aacaattata atggaagaag tttgtctcca tttatatatt    7080
atatattacc cacttatgta ttatattagg atgttaagga gacataacaa ttataaagag    7140
agaagtttgt atccatttat atattatata ctacccattt atatattata cttatccact    7200
```

```
tatttaatgt ctttataagg tttgatccat gatatttcta atattttagt tgatatgtat    7260
atgaaagggt actatttgaa ctctcttact ctgtataaag gttggatcat ccttaaagtg    7320
ggtctattta atttattgc ttcttacaga taaaaaaaaa attatgagtt ggtttgataa    7380
aatattgaag gatttaaaat aataataaat aataaataac atataatata tgtatataaa    7440
tttattataa tataacattt atctataaaa aagtaaatat tgtcataaat ctatacaatc    7500
gtttagcctt gctggacgac tctcaattat ttaaacgaga gtaaacatat ttgactttt    7560 ggttatttaa caaattatta tttaacacta tatgaaattt ttttttttta tcagcaaaga    7620
aataaaatta aattaagaag gacaatggtg tgtcccaatc cttatacaac caacttccac    7680
aagaaagtca agtcagagac aacaaaaaaa caagcaaagg aaatttttta atttgagttg    7740
tcttgtttgc tgcataattt atgcagtaaa acactacaca taacccttt agcagtagag    7800 caatggttga ccgtgtgctt agcttcttt attttattt tttatcagca aagaataaat    7860
aaaataaaat gagacacttc agggatgttt caacaagctt cccgggtcta gaggatccaa    7920
ttccaatccc acaaaaatct gagcttaaca gcacagttgc tcctctcaga gcagaatcgg    7980
gtattcaaca ccctcatatc aactactacg ttgtgtataa cggtccacat gccggtatat    8040
acgatgactg gggttgtaca aaggcggcaa caaacggcgt tcccggagtt gcacacaaga    8100
aatttgccac tattacagag gcaagagcag cagctga                             8137

<210> SEQ ID NO 51
<211> LENGTH: 11934
<212> TYPE: DNA
<213> ORGANISM: Artificial Sequence
<220> FEATURE:
<223> OTHER INFORMATION: sequence of plasmid KS325
<220> FEATURE:
<221> NAME/KEY: misc_feature
<222> LOCATION: (10748)..(10748)
<223> OTHER INFORMATION: n is a, c, g, or t

<400> SEQUENCE: 51
cgcgccaagc ttttgatcca tgcccttcat ttgccgctta ttaattaatt tggtaacagt      60
ccgtactaat cagttactta tccttccccc atcataatta atcttggtag tctcgaatgc     120
cacaacactg actagtctct tggatcataa gaaaaagcca aggaacaaaa gaagacaaaa     180
cacaatgaga gtatcctttg catagcaatg tctaagttca taaaattcaa acaaaaacgc     240
aatcacacac agtggacatc acttatccac tagctgatca ggatcgccgc gtcaagaaaa     300
aaaaactgga ccccaaaagc catgcacaac aacacgtact cacaaaggtg tcaatcgagc     360
agcccaaaac attcaccaac tcaacccatc atgagccctc acatttgttg tttctaaccc     420
aacctcaaac tcgtattctc ttccgccacc tcatttttgt ttatttcaac acccgtcaaa     480
ctgcatgcca ccccgtggcc aaatgtccat gcatgttaac aagacctatg actataaata     540
gctgcaatct cggcccaggt tttcatcatc aagaaccagt tcaatatcct agtacaccgt     600
attaaagaat ttaagatata ctgcggccgc aggatgcaag ccgtcacggc ggcggccacg     660
gcggggcagc tgctaacaga tacgaggaga gggcccagat gtagggctcg gctgggaacg     720
acgagattat cctggacagg tcgatttgca gtggaagctt tgcaggcca gtgccaaagt     780 gctactactg taatgcataa attcagtgcc atttctcaag ctgctaggcc tagaagaaac     840
acaaagagac agtgcagcga tgattatcca gccctccaag ctggatgcag cgaggttaat     900
tgggatcaaa acggttccaa cgccaatcgg cttgaggaaa tcaggggaga tgttttgaag     960
aaattgcgct ctttctatga atttgcagg ccacacacaa ttttggcac tataataggt    1020
```

```
ataacttcag tgtctctcct gccaatgaag agcatagatg attttactgt cacggtacta   1080
cgaggatatc tcgaggcttt gactgctgct ttatgtatga acatttatgt ggtcgggctg   1140
aatcagctat atgacattca gattgacaag atcaacaagc caggtcttcc attggcatct   1200
ggggaatttt cagtagcaac tggagttttc ttagtactcg cattcctgat catgagcttt   1260
agcataggaa tacgttccgg atcggcgcca ctgatgtgtg ctttaattgt cagcttcctt   1320
cttggaagtg cgtactccat tgaggctccg ttcctccggt ggaaacggca cgcgctcctc   1380
gctgcatcat gtatcctatt tgtgagggct atcttggtcc agttggcttt ctttgcacat   1440
atgcagcaac atgttctgaa aaggccattg gcagcaacca atcgctggt gtttgcaaca   1500 ttgtttatgt gttgcttctc tgccgtcata gcactattca aggatattcc agatgttgat   1560
ggagatcgag actttggtat ccaatccttg agtgtgagat tggggcctca aagagtgtat   1620
cagctctgca taagcatatt gttgacagcc tatggcgctg ccactctagt aggagcttca   1680
tccacaaacc tatttcaaaa gatcatcact gtgtctggtc atggcctgct tgctttgaca   1740
ctttggcaga gagcgcagca ctttgaggtt gaaaaccaag cgcgtgtcac atcattttac   1800
atgttcattt ggaagctatt ctatgcagag tatttcctta taccatttgt gcagtgaaat   1860
ttgtacaagg ccagcagat gtgaagcggc cgcaagtatg aactaaaatg catgtaggtg   1920
taagagctca tggagagcat ggaatattgt atccgaccat gtaacagtat aataactgag   1980
ctccatctca cttcttctat gaataaacaa aggatgttat gatatattaa cactctatct   2040 atgcaccttta ttgttctatg ataaatttcc tcttattatt ataaatcatc tgaatcgtga   2100
cggcttatgg aatgcttcaa atagtacaaa acaaatgtg tactataaga ctttctaaac   2160
aattctaacc ttagcattgt gaacgagaca taagtgttaa aagacataa caattataat   2220 ggaagaagtt tgtctccatt tatatattat atattaccca cttatgtatt atattaggat   2280
gttaaggaga cataacaatt ataaagagag aagtttgtat ccatttatat attatatact   2340
acccatttat atattatact tatccactta tttaatgtct ttataaggtt tgatccatga   2400
tatttctaat attttagttg atatgtatat gaaagggtac tatttgaact ctcttactct   2460
gtataaaggt tggatcatcc ttaaagtggg tctatttaat tttattgctt cttacagata   2520
aaaaaaaaat tatgagttgg tttgataaaa tattgaagga tttaaaataa taataaataa   2580
catataatat atgtatataa atttattata atataacatt tatctataaa aaagtaaata   2640
ttgtcataaa tctatacaat cgtttagcct tgctggacga atctcaatta tttaaacgag   2700
agtaaacata tttgactttt tggttattta acaaattatt atttaacact atatgaaatt   2760 tttttttta tcagcaaaga ataaaattaa attaagaagg acaatggtgt cccaatcctt   2820
atacaaccaa cttccacaag aaagtcaagt cagagacaac aaaaaaacaa gcaaaggaaa   2880
ttttttaatt tgagttgtct tgtttgctgc ataatttatg cagtaaaaca ctacacataa   2940 ccccttttagc agtagagcaa tggttgaccg tgtgcttagc ttcttttatt ttatttttt   3000 atcagcaaag aataaataaa ataaaatgag acacttcagg gatgtttcaa caagcttgga   3060
tccgtcgacg gcgcgcccga tcatccggat atagttcctc ctttcagcaa aaaccccctc   3120
aagacccgtt tagaggcccc aaggggttat gctagttatt gctcagcggt ggcagcagcc   3180
aactcagctt cctttcgggc tttgttagca gccggatcga tccaagctgt acctcactat   3240
tcctttgccc tcggacgagt gctggggcgt cggtttccac tatcggcgag tacttctaca   3300
cagccatcgg tccagacggc cgcgcttctg cgggcgattt gtgtacgccc gacagtcccg   3360
gctccggatc ggacgattgc gtcgcatcga ccctgcgccc aagctgcatc atcgaaattg   3420
```

```
ccgtcaacca agctctgata gagttggtca agaccaatgc ggagcatata cgcccggagc   3480
cgcggcgatc ctgcaagctc cggatgcctc cgctcgaagt agcgcgtctg ctgctccata   3540
caagccaacc acggcctcca gaagaagatg ttggcgacct cgtattggga atccccgaac   3600
atcgcctcgc tccagtcaat daccgctgtt atgcggccat tgtccgtcag dacattgttg   3660
gagccgaaat ccgcgtgcac gaggtgccgg acttcggggc agtcctcggc ccaaagcatc   3720
agctcatcga gagcctgcgc gacggacgca ctgacggtgt cgtccatcac agtttgccag   3780
tgatacacat ggggatcagc aatcgcgcat atgaaatcac gccatgtagt gtattgaccg   3840
attccttgcg gtccgaatgg gccgaacccg ctcgtctggc taagatcggc cgcagcgatc   3900
gcatccatag cctccgcgac cggctgcaga acagcgggca gttcggtttc aggcaggtct   3960
tgcaacgtga caccctgtgc acggcgggag atgcaatagg tcaggctctc gctgaattcc   4020
ccaatgtcaa gcacttccgg aatcgggagc gcggccgatg caaagtgccg ataaacataa   4080
cgatctttgt agaaaccatc ggcgcagcta tttacccgca ggacatatcc acgccctcct   4140
acatcgaagc tgaaagcacg agattcttcg ccctccgaga gctgcatcag gtcggagacg   4200
ctgtcgaact tttcgatcag aaacttcctg acagacgtcg cggtgagttc aggcttttcc   4260
atgggtatat ctccttctta aagttaaaca aaattatttc tagagggaaa ccgttgtggt   4320
ctccctatag tgagtcgtat taatttcgcg ggatcgagat cgatccaatt ccaatcccac   4380
aaaaatctga gcttaacagc acagttgctc ctctcagagc agaatcgggt attcaacacc   4440
ctcatatcaa ctactacgtt gtgtataacg gtccacatgc cggtatatac gatgactggg   4500
gttgtacaaa ggcggcaaca acggcgttc ccggagttgc acacaagaaa tttgccacta   4560
ttacagaggc aagagcagca gctgacgcgt acacaacaag tcagcaaaca gacaggttga   4620
acttcatccc caaggagaa gctcaactca gcccaagag ctttgctaag gccctaacaa   4680
gcccaccaaa gcaaaagcc cactggctca cgctaggaac caaaggccc agcagtgatc   4740 cagccccaaa agagatctcc tttgccccgg agattacaat ggacgatttc ctctatcttt   4800
acgatctagg aaggaagttc gaaggtgaag gtgacgacac tatgttcacc actgataatg   4860
agaaggttag cctcttcaat ttcagaaaga atgctgaccc acagatggtt agagaggcct   4920
acgcagcagg tctcatcaag acgatctacc cgagtaacaa tctccaggag atcaaatacc   4980
ttcccaagaa ggttaaagat gcagtcaaaa gattcaggac taattgcatc aagaacacag   5040
agaaagacat atttctcaag atcagaagta ctattccagt atggacgatt caaggcttgc   5100
ttcataaacc aaggcaagta atagagattg gagtctctaa aaaggtagtt cctactgaat   5160
ctaaggccat gcatggagtc taagattcaa atcgaggatc taacagaact cgccgtgaag   5220
actggcgaac agttcataca gagtctttta cgactcaatg acaagaagaa aatcttcgtc   5280
aacatggtgg agcacgacac tctggtctac tccaaaaatg tcaaagatac agtctcagaa   5340
gaccaaaggg ctattgagac ttttcaacaa aggataattt cgggaaacct cctcggattc   5400
cattgcccag ctatctgtca cttcatcgaa aggacagtag aaaaggaagg tggctcctac   5460
aaatgccatc attgcgataa aggaaaggct atcattcaag atgcctctgc cgacagtggt   5520
cccaaagatg gacccccacc cacgaggagc atcgtggaaa aagaagacgt tccaaccacg   5580
tcttcaaagc aagtggattg atgtgacatc tccactgacg taagggatga cgcacaatcc   5640
cactatcctt cgcaagaccc ttcctctata taaggaagtt catttcattt ggagaggaca   5700
cgctcgagct catttctcta ttacttcagc cataacaaaa gaactctttt ctcttcttat   5760
taaaccatga aaaagcctga actcaccgcg acgtctgtcg agaagtttct gatcgaaaag   5820
```

```
ttcgacagcg tctccgacct gatgcagctc tcggagggcg aagaatctcg tgctttcagc   5880
ttcgatgtag gagggcgtgg atatgtcctg cgggtaaata gctgcgccga tggtttctac   5940
aaagatcgtt atgtttatcg gcactttgca tcggccgcgc tcccgattcc ggaagtgctt   6000
gacattgggg aattcagcga gagcctgacc tattgcatct cccgccgtgc acagggtgtc   6060
acgttgcaag acctgcctga aaccgaactg cccgctgttc tgcagccggt cgcggaggcc   6120
atggatgcga tcgctgcggc cgatcttagc cagacgagcg ggttcggccc attcggaccg   6180
caaggaatcg gtcaatacac tacatggcgt gatttcatat gcgcgattgc tgatccccat   6240
gtgtatcact ggcaaactgt gatggacgac accgtcagtc cgtccgtcgc gcaggctctc   6300
gatgagctga tgcttttgggc cgaggactgc cccgaagtcc ggcacctcgt gcacgcggat   6360
ttcggctcca acaatgtcct gacggacaat ggccgcataa cagcggtcat tgactggagc   6420
gaggcgatgt tcggggattc ccaatacgag gtcgccaaca tcttcttctg gaggccgtgg   6480
ttggcttgta tggagcagca gacgcgctac ttcgagcgga ggcatccgga gcttgcagga   6540
tcgccgcggc tccgggcgta tatgctccgc attggtcttg accaactcta tcagagcttg   6600
gttgacggca atttcgatga tgcagcttgg gcgcagggtc gatgcgacgc aatcgtccga   6660
tccggagccg ggactgtcgg gcgtacacaa atcgcccgca gaagcgcggc cgtctggacc   6720
gatggctgtg tagaagtact cgccgatagt ggaaaccgac gccccagcac tcgtccgagg   6780
gcaaaggaat agtgaggtac ctaaagaagg agtgcgtcga agcagatcgt tcaaacattt   6840
ggcaataaag tttcttaaga ttgaatcctg ttgccggtct tgcgatgatt atcatataat   6900
ttctgttgaa ttacgttaag catgtaataa ttaacatgta atgcatgacg ttatttatga   6960
gatgggtttt tatgattaga gtcccgcaat tatacattta atacgcgata gaaaacaaaa   7020
tatagcgcgc aaactaggat aaattatcgc gcgcggtgtc atctatgtta ctagatcgat   7080
gtcgaatctg atcaacctgc attaatgaat cggccaacgc gcggggagag gcggtttgcg   7140
tattgggcgc tcttccgctt cctcgctcac tgactcgctg cgctcggtcg ttcggctgcg   7200
gcgagcggta tcagctcact caaaggcggt aatacggtta tccacagaat caggggataa   7260
cgcaggaaag aacatgtgag caaaaggcca gcaaaggcca ggaaccgta aaaaggccgc   7320 gttgctggcg ttttccata ggctccgccc ccctgacgag catcacaaaa atcgacgctc   7380
aagtcagagg tggcgaaacc cgacaggact ataaagatac caggcgtttc ccctggaag   7440 ctccctcgtg cgctctcctg ttccgaccct gccgcttacc ggatacctgt ccgcctttct   7500
cccttcggga agcgtggcgc tttctcaatg ctcacgctgt aggtatctca gttcggtgta   7560
ggtcgttcgc tccaagctgg gctgtgtgca cgaaccccc gttcagcccg accgctgcgc   7620
cttatccggt aactatcgtc ttgagtccaa cccggtaaga cacgacttat cgccactggc   7680
agcagccact ggtaacagga ttagcagagc gaggtatgta ggcggtgcta cagagttctt   7740
gaagtggtgg cctaactacg gctacactag aaggacagta tttggtatct gcgctctgct   7800
gaagccagtt accttcggaa aaagagttgg tagctcttga tccggcaaac aaaccaccgc   7860
tggtagcggt ggttttttg tttgcaagca gcagattacg cgcagaaaaa aaggatctca   7920
agaagatcct ttgatctttt ctacggggtc tgacgctcag tggaacgaaa actcacgtta   7980
agggattttg gtcatgacat taacctataa aaataggcgt atcacgaggc cctttcgtct   8040
cgcgcgtttc ggtgatgacg gtgaaaacct ctgacacatg cagctcccgg agacggtcac   8100
agcttgtctg taagcggatg ccgggagcag acaagcccgt cagggcgcgt cagcgggtgt   8160
tggcgggtgt cggggctggc ttaactatgc ggcatcagag cagattgtac tgagagtgca   8220
```

```
ccatatggac atattgtcgt tagaacgcgg ctacaattaa tacataacct tatgtatcat   8280
acacatacga tttaggtgac actatagaac ggcgcgccgt cgacggatat aatgagccgt   8340
aaacaaagat gattaagtag taattaatac gtactagtaa aagtggcaaa agataacgag   8400
aaagaaccaa tttctttgca ttcggcctta gcggaaggca tatataagct ttgattattt   8460
tatttagtgt aatgatttcg tacaaccaaa gcatttattt agtactctca cacttgtgtc   8520
gcggccgtaa gcttggatcc tctagagcgg ccgcccttt ttttttttt ttgtggaaca    8580
gtgaatttga aatatctcga cgagtggcag aaaattattt aacacctagg agaatgttga   8640
ttttggtgca gtacagatga gtagacggcg atggggccac gaatctacat tattgcacat   8700
gacactcctg tgcctgtgcc agtaacttgt gctccttggc ctcctcctac gcggctccag   8760
gcttgcgaca ggtgatgatg gtgaatttga tgaggcccctt cttgtagccc tggatcatta   8820
gcggcatcac catcgcgcct ctgatcgtct tccatccggt cgtcagcaga gaggtgaagc   8880
ccttccatgt tagcgctgat tttatcacgg cgggccaaaa cggggccacg ttctccgacc   8940
agtcagctgt cttgatatcc tcgagagaca gtgacttggc aatgtccaca tagtctgaag   9000
gtgagcacca gtccgggagg tagtacgcgt cgcatatcct cctcaggagg ctcagttcat   9060
cgggctttag cgaggtttcg gatggatcca ggttcctatg gcaccatgtc acgatgatta   9120
ttgtccctcc aggagccgcc acgcgtgcta gctcactaac aaactttctc ttgtccggca   9180
tgtgctcgcc actctccatg gaccacacca gatcgaactg cccgtcagga aacggttgct   9240
ccagagcatc agcaacttgc agagtaacct gatccgacaa cccctgcgct gcagcgagag   9300
catttcctct ctcggcttga acagggctca acgtgatccc agtgcactgc gctccgtatt   9360
tcttcgccaa gtaccttgag ctaccaccaa tgccacatcc gacatcgact attgtttttg   9420
gtgtcttctc tggatcatct gaggctggga caccggcgaa ggcgagcgcc tcctcgatca   9480
tgcggatctg ggcgcggcgg tgatcggcca tggaggcggc ctcgctcgag tcgtagaagc   9540
cgtggtgcat gtggtcgccc cagatgttct cccacagccc cgacgactcg tcgtacagcc   9600
ccgcgatgcc ctccttcaga cccggcgcg ccgtcgcggg ggcctgagcc gtcgacgagg   9660
ccatcggacg caggctgacg acggcgcgtc ggagacggcg ggagtggcgc gggacgtgcg   9720
aaggggcgcg gtagtggctg ccgcggcggc aggctgcgag gctcctggag gactgggagc   9780
aatggagcag cgccgcgtga gccatttgcg gcgccgggat gcgcgatatt tggccgcttg   9840
gggggctatg gaagactttc ttagttagtt gtgtgaataa gcaatgttgg gagaatcggg   9900
actacttata ggataggaat aaaacagaaa agtattaagt gctaatgaaa tatttagact   9960
gataattaaa atcttcacgt atgtccactt gatataaaaa cgtcaggaat aaaggaagta  10020
cagtagaatt taaaggtact ctttttatat atacccgtgt tctcttttttg gctagctagt  10080
tgcataaaaa ataatctata tttttatcat tatttttaaat atcttatgag atggtaaata  10140
tttatcataa ttttttttac tattatttat tatttgtgtg tgtaatacat atagaagtta  10200
attacaaatt ttatttactt tttcattatt ttgatatgat tcaccattaa tttagtgtta  10260
ttatttataa tagttcattt taatcttttt gtatatatta tgcgtgcagt acttttttcc  10320
tacatataac tactattaca ttttatttat ataatatttt tattaatgaa ttttcgtgat  10380
aatatgtaat attgttcatt attatttcag attttttaaa aatatttgtg ttattattta  10440
tgaaatatgt aattttttta gtatttgatt ttatgatgat aaagtgttct aaattcaaaa  10500
gaagggggaa agcgtaaaca ttaaaaaacg tcatcaaaca aaaacaaaat cttgttaata  10560
aagataaaac tgtttgtttt gatcactgtt atttcgtaat ataaaaacat tatttatatt  10620
```

| | | |
|---|---|---|
| tatattgttg acaaccaaat ttgcctatca aatctaacca atataatgca tgcgtggcag | 10680 |
| gtaatgtact accatgaact taagtcatga cataataaac cgtgaatctg accaatgcat | 10740 |
| gtacctanct aaattgtatt tgtgacacga agcaaatgat tcaattcaca atggagatgg | 10800 |
| gaaacaaata atgaagaacc cagaactaag aaagcttttc tgaaaaataa aataaaggca | 10860 |
| atgtcaaaag tatactgcat catcagtcca gaaagcacat gatatttttt tatcagtatc | 10920 |
| aatgcagcta gttttatttt acaatatcga tatagctagt ttaaatatat tgcagctaga | 10980 |
| tttataaata tttgtgttat tatttatcat ttgtgtaatc ctgttttag tattttagtt | 11040 |
| tatatatgat gataatgtat tccaaattta aagaaggga aataaattta aacaagaaaa | 11100 |
| aaagtcatca aacaaaaaac aaatgaaagg gtggaaagat gttaccatgt aatgtgaatg | 11160 |
| ttacagtatt tcttttatta tagagttaac aaattaacta atatgatttt gttaataatg | 11220 |
| ataaatatt ttttttatta ttatttcata atataaaat agtttactta atataaaaaa | 11280 |
| aattctatcg ttcacaacaa agttggccac ctaatttaac catgcatgta cccatggacc | 11340 |
| atattaggta accatcaaac ctgatgaaga gataaagaga tgaagactta agtcataaca | 11400 |
| caaaccata aaaaacaaaa atacaatcaa ccgtcaatct gaccaatgca tgaaaaagct | 11460 |
| gcaatagtga gtggcgacac aaagcacatg attttcttac aacggagata aaaccaaaaa | 11520 |
| aatatttcat gaacaaccta gaacaaataa agcttttata taataaatat ataaataaat | 11580 |
| aaaggctatg gaataatata cttcaatata tttggattaa ataaattgtt ggcggggttg | 11640 |
| atatatttat acacacctaa agtcacttca atctcatttt cacttaactt ttattttttt | 11700 |
| tttcttttta tttatcataa agagaatatt gataatatac ttttttaacat atttttatga | 11760 |
| catttttat tggtgaaaac ttattaaaaa tcataaattt tgtaagttag atttatttaa | 11820 |
| agagttcctc ttcttatttt aaattttta ataaattttt aaataactaa aatttgtgtt | 11880 |
| aaaaatgtta aaaagtgtg ttattaaccc ttctcttcga ggatccaagc ttgg | 11934 |

<210> SEQ ID NO 52
<211> LENGTH: 9779
<212> TYPE: DNA
<213> ORGANISM: Artificial Sequence
<220> FEATURE:
<223> OTHER INFORMATION: sequence of the T-DNA of the plant
      transformation vector pZBL120xKS325xSC38
<220> FEATURE:
<221> NAME/KEY: misc_feature
<222> LOCATION: (4282)..(4282)
<223> OTHER INFORMATION: n is a, c, g, or t

<400> SEQUENCE: 52

| | | |
|---|---|---|
| aattacaacg gtatatatcc tgccgcgtcg acggatccaa gcttgttgaa acatccctga | 60 |
| agtgtctcat tttattttat ttattctttg ctgataaaaa aataaaataa aagaagctaa | 120 |
| gcacacggtc aaccattgct ctactgctaa aagggttatg tgtagtgttt tactgcataa | 180 |
| attatgcagc aaacaagaca actcaaatta aaaaatttcc tttgcttgtt ttttgttgt | 240 |
| ctctgacttg actttcttgt ggaagttggt tgtataagga ttgggacacc attgtccttc | 300 |
| ttaatttaat tttattcttt gctgataaaa aaaaaattt catatagtgt taaataataa | 360 |
| tttgttaaat aaccaaaaag tcaaatatgt ttactctcgt ttaaataatt gagattcgtc | 420 |
| cagcaaggct aaacgattgt atagatttat gacaatattt acttttttat agataaatgt | 480 |
| tatattataa taaatttata tacatatatt atatgttatt tattattatt ttaaatcctt | 540 |
| caatatttta tcaaaccaac tcataatttt tttttatct gtaagaagca ataaaattaa | 600 |

```
atagacccac tttaaggatg atccaacctt tatacagagt aagagagttc aaatagtacc      660
ctttcatata catatcaact aaaatattag aaatatcatg gatcaaacct tataaagaca      720
ttaaataagt ggataagtat aatatataaa tgggtagtat ataatatata aatggataca      780
aacttctctc tttataattg ttatgtctcc ttaacatcct aatataatac ataagtgggt      840
aatatataat atataaatgg agacaaactt cttccattat aattgttatg tcttcttaac      900
acttatgtct cgttcacaat gctaaggtta gaattgttta gaaagtctta tagtacacat      960
ttgtttttgt actatttgaa gcattccata agccgtcacg attcagatga tttataataa     1020
taagaggaaa tttatcatag aacaataagg tgcatagata gagtgttaat atatcataac     1080
atcctttgtt tattcataga agaagtgaga tggagctcag ttattatact gttacatggt     1140
cggatacaat attccatgct ctccatgagc tcttacacct acatgcattt tagttcatac     1200
ttgcggccgc ttcacatctg ctggcccttg tacaaatttc actgcacaaa tggtataagg     1260
aaatactctg catagaatag cttccaaatg aacatgtaaa atgatgtgac acgcgcttgg     1320
ttttcaacct caaagtgctg cgctctctgc caaagtgtca aagcaagcag gccatgacca     1380
gacacagtga tgatcttttg aaataggttt gtggatgaag ctcctactag agtggcagcg     1440
ccataggctg tcaacaatat gcttatgcag agctgataca ctctttgagg ccccaatctc     1500
acactcaagg attggatacc aaagtctcga tctccatcaa catctggaat atccttgaat     1560
agtgctatga cggcagagaa gcaacacata aacaatgttg caaacaccag cgatttggtt     1620
gctgccaatg gccttttcag aacatgttgc tgcatatgtg caagaaagc caactggacc     1680 aagatagccc tcacaaatag gatacatgat gcagcgagga gcgcgtgccg tttccaccgg     1740
aggaacggag cctcaatgga gtacgcactt ccaagaagga agctgacaat taaagcacac     1800
atcagtggcg ccgatccgga acgtattcct atgctaaagc tcatgatcag gaatgcgagt     1860
actaagaaaa ctccagttgc tactgaaaat tccccagatg ccaatggaag acctggcttg     1920
ttgatcttgt caatctgaat gtcatatagc tgattcagcc cgaccacata aatgttcata     1980
cataaagcag cagtcaaagc ctcgagatat cctcgtagta ccgtgacagt aaaatcatct     2040
atgctcttca ttggcaggag agacactgaa gttataccta ttatagtgcc aaaaattgtg     2100
tgtggcctgc aaaattcata gaaagagcgc aatttcttca aaacatctcc cctgatttcc     2160
tcaagccgat tggcgttgga accgttttga tcccaattaa cctcgctgca tccagcttgg     2220
agggctggat aatcatcgct gcactgtctc tttgtgtttc ttctaggcct agcagcttga     2280
gaaatggcac tgaatttatg cattacagta gtagcacttt ggcactggcc tgcaaaagct     2340
tccactgcaa atcgacctgt ccaggataat ctcgtcgttc ccagccgagc cctacatctg     2400
ggccctctcc tcgtatctgt tagcagctgc cccgccgtgg ccgccgccgt gacggcttgc     2460
atcctgcggc cgcagtatat cttaaattct ttaatacggt gtactaggat attgaactgg     2520
ttcttgatga tgaaaacctg ggccgagatt gcagctattt atagtcatag gtcttgttaa     2580
catgcatgga catttggcca cggggtggca tgcagtttga cgggtgttga aataaacaaa     2640
aatgaggtgg cggaagagaa tacgagtttg aggttgggtt agaaacaaca aatgtgaggg     2700
ctcatgatgg gttgagttgg tgaatgtttt gggctgctcg attgacacct tgtgagtac     2760 gtgttgttgt gcatggcttt tggggtccag tttttttttc ttgacgcggc gatcctgatc     2820
agctagtgga taagtgatgt ccactgtgtg tgattgcgtt tttgtttgaa ttttatgaac     2880
ttagacattg ctatgcaaag gatactctca ttgtgttttg tcttcttttg ttccttggct     2940 tttttcttatg atccaagaga ctagtcagtg ttgtggcatt cgagactacc aagattaatt     3000
```

-continued

```
atgatggggg aaggataagt aactgattag tacggactgt taccaaatta attaataagc   3060
ggcaaatgaa gggcatggat caaaagcttg gcgcgccaag cttggatcct cgaagagaag   3120
ggttaataac acactttttt aacattttta acacaaattt tagttattta aaaatttatt   3180
aaaaaattta aaataagaag aggaactctt taaataaatc taacttacaa aatttatgat   3240
ttttaataag ttttcaccaa taaaaaatgt cataaaaata tgttaaaaag tatattatca   3300
atattctctt tatgataaat aaaaagaaaa aaaaaataaa agttaagtga aaatgagatt   3360
gaagtgactt taggtgtgta taaatatatc aaccccgcca acaatttatt taatccaaat   3420
atattgaagt atattattcc atagccttta tttatttata tatttattat ataaaagctt   3480
tatttgttct aggttgttca tgaaatattt ttttggtttt atctccgttg taagaaaatc   3540
atgtgctttg tgtcgccact cactattgca gcttttttcat gcattggtca gattgacggt   3600
tgattgtatt tttgttttttt atggttttgt gttatgactt aagtcttcat ctctttatct   3660
cttcatcagg tttgatggtt acctaatatg gtccatgggt acatgcatgg ttaaattagg   3720
tggccaactt tgttgtgaac gatagaattt tttttatatt aagtaaacta tttttatatt   3780
atgaaataat aataaaaaaa atattttatc attattaaca aaatcatatt agttaatttg   3840
ttaactctat aataaaagaa atactgtaac attcacatta catggtaaca tctttccacc   3900 cttttcatttg ttttttttgttt gatgactttt tttcttgttt aaatttattt cccttctttt   3960
aaatttggaa tacattatca tcatatataa actaaaatac taaaaacagg attacacaaa   4020
tgataaataa taacacaaat atttataaat ctagctgcaa tatatttaaa ctagctatat   4080
cgatattgta aaataaaact agctgcattg atactgataa aaaaatatca tgtgctttct   4140
ggactgatga tgcagtatac ttttgacatt gcctttattt tatttttcag aaaagctttc   4200
ttagttctgg gttcttcatt atttgtttcc catctccatt gtgaattgaa tcatttgctt   4260
cgtgtcacaa atacaattta gntaggtaca tgcattggtc agattcacgg tttattatgt   4320
catgacttaa gttcatggta gtacattacc tgccacgcat gcattatatt ggttagattt   4380
gataggcaaa tttggttgtc aacaatataa atataaataa tgtttttata ttacgaaata   4440
acagtgatca aaacaaacag ttttatcttt attaacaaga ttttgttttt gtttgatgac   4500
gttttttaat gtttacgctt tccccctttct tttgaattta gaacacttta tcatcataaa   4560
atcaaatact aaaaaaatta catatttcat aaataataac acaaatattt ttaaaaaatc   4620
tgaaataata atgaacaata ttacatatta tcacgaaaat tcattaataa aaatattata   4680
taaataaaat gtaatagtag ttatatgtag gaaaaaagta ctgcacgcat aatatataca   4740 aaagattaa aatgaactat tataaataat aacactaaat taatggtgaa tcatatcaaa   4800
ataatgaaaa agtaaataaa atttgtaatt aacttctata tgtattacac acacaaataa   4860
taaataatag taaaaaaaat tatgataaat atttaccatc tcataagata tttaaaataa   4920
tgataaaaat atagattatt ttttatgcaa ctagctagcc aaaaagagaa cacgggtata   4980
tataaaaaga gtacctttaa attctactgt acttccttta ttcctgacgt ttttatatca   5040
agtggacata cgtgaagatt ttaattatca gtctaaatat ttcattagca cttaatactt   5100
ttctgtttta ttcctatcct ataagtagtc ccgattctcc caacattgct tattcacaca   5160
actaactaag aaagtcttcc atagccccccc aagcggccaa atatcgcgca tcccggcgcc   5220
gcaaatggct cacgcggcgc tgctccattg ctcccagtcc tccaggagcc tcgcagcctg   5280
ccgccgcggc agccactacc gcgcccctte gcacgtcccg cgccactccc gccgtctccg   5340
acgcgccgtc gtcagcctgc gtccgatggc ctcgtcgacg gctcaggccc ccgcgacggc   5400
```

-continued

```
gccgccgggt ctgaaggagg gcatcgcggg gctgtacgac gagtcgtcgg ggctgtggga      5460
gaacatctgg ggcgaccaca tgcaccacgg cttctacgac tcgagcgagg ccgcctccat      5520
ggccgatcac cgccgcgccc agatccgcat gatcgaggag gcgctcgcct tcgccggtgt      5580
cccagcctca gatgatccag agaagacacc aaaaacaata gtcgatgtcg gatgtggcat      5640
tggtggtagc tcaaggtact tggcgaagaa atacggagcg cagtgcactg ggatcacgtt      5700
gagccctgtt caagccgaga gaggaaatgc tctcgctgca gcgcaggggt tgtcggatca      5760
ggttactctg caagttgctg atgctctgga gcaaccgttt cctgacgggc agttcgatct      5820
ggtgtggtcc atggagagtg gcgagcacat gccggacaag agaaagtttg ttagtgagct      5880
agcacgcgtg gcggctcctg gagggacaat aatcatcgtg acatggtgcc ataggaacct      5940
ggatccatcc gaaacctcgc taaagcccga tgaactgagc ctcctgagga ggatatgcga      6000
cgcgtactac ctcccggact ggtgctcacc ttcagactat gtggacattg ccaagtcact      6060
gtctctcgag gatatcaaga cagctgactg gtcggagaac gtggcccccgt tttggccccgc    6120 cgtgataaaa tcagcgctaa catggaaggg cttcacctct ctgctgacga ccggatggaa      6180
gacgatcaga ggcgcgatgg tgatgccgct aatgatccag ggctacaaga agggcctcat      6240
caaattcacc atcatcacct gtcgcaagcc tggagccgcg taggaggagg ccaaggagca      6300
caagttactg gcacaggcac aggagtgtca tgtgcaataa tgtagattcg tggccccatc      6360
gccgtctact catctgtact gcaccaaaat caacattctc ctaggtgtta aataatttc      6420 tgccactcgt cgagatattt caaattcact gttccacaaa aaaaaaaaaa aagggcggc     6480 cgctctagag gatccaagct tacggccgcg acacaagtgt gagagtacta aataaatgct    6540
ttggttgtac gaaatcatta cactaaataa aataatcaaa gcttatatat gccttccgct    6600
aaggccgaat gcaaagaaat tggttctttc tcgttatctt ttgccacttt tactagtacg    6660
tattaattac tacttaatca tctttgttta cggctcatta tatccgtcga ctctagagga    6720
tccccgggta ccgagctcga attcactggc cgtcgtttta caacgtcgtg actgggaaaa    6780
ccctggcgtt acccaactta atcgccttgc agcacatccc cctttcgcca gctggcgtaa    6840
tagcgaagag gcccgcaccg atcgcccttc ccaacagttg cgcagcctga atggcgaatg    6900
gatcgatccg tcgatcgacc aaagcggcca tcgtgcctcc ccactcctgc agttcggggg    6960
catggatgcg cggatagccg ctgctggttt cctggatgcc gacggatttg cactgccggt    7020
agaactccgc gaggtcgtcc agcctcaggc agcagctgaa ccaactcgcg aggggatcga    7080 gccccctgctg agcctcgaca tgttgtcgca aaattcgccc tggacccgcc caacgatttg    7140
tcgtcactgt caaggtttga cctgcacttc atttggggcc cacatacacc aaaaaaatgc    7200
tgcataattc tcggggcagc aagtcggtta cccggccgcc gtgctggacc gggttgaatg    7260
gtgcccgtaa ctttcggtag agcggacggc caatactcaa cttcaaggaa tctcacccat    7320
gcgcgccggc ggggaaccgg agttcccttc agtgaacgtt attagttcgc cgctcggtgt    7380
gtcgtagata ctagcccctg ggccttttg aaatttgaat aagatttatg taatcagtct    7440
tttaggtttg accggttctg ccgcttttt taaaattgga tttgtaataa taaaacgcaa    7500
ttgtttgtta ttgtggcgct ctatcataga tgtcgctata aacctattca gcacaatata    7560
ttgttttcat tttaatattg tacatataag tagtagggta caatcagtaa attgaacgga    7620
gaatattatt cataaaaata cgatagtaac gggtgatata ttcattagaa tgaaccgaaa    7680
ccggcggtaa ggatctgagc tacacatgct caggtttttt acaacgtgca caacagaatt    7740
gaaagcaaat atcatgcgat cataggcgtc tcgcatatct cattaaagca ggggtgggc     7800
```

```
gaagaactcc agcatgagat ccccgcgctg gaggatcatc cagccggcgt cccggaaaac   7860
gattccgaag cccaaccttt catagaaggc ggcggtggaa tcgaaatctc gtgatggcag   7920
gttgggcgtc gcttggtcgg tcatttcgaa ccccagagtc ccgctcagaa gaactcgtca   7980
agaaggcgat agaaggcgat gcgctgcgaa tcgggagcgg cgataccgta aagcacgagg   8040
aagcggtcag cccattcgcc gccaagctct tcagcaatat cacgggtagc caacgctatg   8100
tcctgatagc ggtccgccac acccagccgg ccacagtcga tgaatccaga aaagcggcca   8160
ttttccacca tgatattcgg caagcaggca tcgccatggg tcacgacgag atcctcgccg   8220
tcggcatgc gcgccttgag cctggcgaac agttcggctg gcgcgagccc ctgatgctct   8280
tcgtccagat catcctgatc gacaagaccg gcttccatcc gagtacgtgc tcgctcgatg   8340
cgatgtttcg cttggtggtc gaatgggcag gtagccggat caagcgtatg cagccgccgc   8400
attgcatcag ccatgatgga tactttctcg gcaggagcaa ggtgagatga caggagatcc   8460
tgccccggca cttcgcccaa tagcagccag tcccttcccg cttcagtgac aacgtcgagc   8520
acagctgcgc aaggaacgcc cgtcgtggcc agccacgata gccgcgctgc ctcgtcctgc   8580
agttcattca gggcaccgga caggtcggtc ttgacaaaaa gaaccgggcg ccctgcgct   8640
gacagccgga acacggcggc atcagagcag ccgattgtct gttgtgccca gtcatagccg   8700
aatagcctct ccacccaagc ggccggagaa cctgcgtgca atccatcttg ttcaatcatg   8760
cgaaacgatc cccgcaagct tggagactgg tgatttcagc gtgtcctctc caaatgaaat   8820
gaacttcctt atatagagga agggtcttgc gaaggatagt gggattgtgc gtcatccctt   8880
acgtcagtgg agatatcaca tcaatccact tgctttgaag acgtggttgg aacgtcttct   8940
ttttccacga tgctcctcgt gggtgggggt ccatctttgg gaccactgtc ggcagaggca   9000
tcttcaacga tggcctttcc tttatcgcaa tgatggcatt tgtaggagcc accttcctt   9060
tccactatct tcacaataaa gtgacagata gctgggcaat ggaatccgag gaggtttccg   9120
gatattaccc tttgttgaaa agtctcaatt gcccttttggt cttctgagac tgtatctttg   9180
atattttgg agtagacaag cgtgtcgtgc tccaccatgt tgacgaagat tttcttcttg   9240
tcattgagtc gtaagagact ctgtatgaac tgttcgccag tctttacggc gagttctgtt   9300
aggtcctcta tttgaatctt tgactccatg gcctttgatt cagtgggaac taccttttta   9360
gagactccaa tctctattac ttgccttggt ttgtgaagca agccttgaat cgtccatact   9420
ggaatagtac ttctgatctt gagaaatata tctttctctg tgttcttgat gcagttagtc   9480
ctgaatctttt tgactgcatc tttaaccttc ttgggaaggt atttgatctc ctggagatta   9540
ttgctcgggt agatcgtctt gatgagacct gctgcgtaag cctctctaac catctgtggg   9600
ttagcattct ttctgaaatt gaaaaggcta atcttctcat tatcagtggt gaacatggta   9660
tcgtcacctt ctccgtcgaa cttcctgact agatcgtaga gatagaggaa gtcgtccatt   9720
gtgatctctg gggcaaagga gatctgaatt atcatttaca attgaatata tcctgccat   9779
```

COMPOSITIONS AND METHODS FOR ALTERING ALPHA- AND BETA-TOCOTRIENOL CONTENT

This application is a continuation application of U.S. application Ser. No. 13/367,811, filed Feb. 7, 2012, which is a continuation application of U.S. application Ser. No. 11/559,024, filed Nov. 13, 2006 and now abandoned, which claims the benefit of U.S. Provisional Application No. 60/736,600, filed Nov. 14, 2005, the entire content of which is herein incorporated by reference.

FIELD OF INVENTION

The field of the invention relates to plant breeding and molecular biology, and particularly to alteration of oil phenotype in plants through the use of nucleic acid fragments encoding homogentisate geranylgeranyl transferase and gamma-tocopherol methyltransferase.

BACKGROUND

Tocotrienols are vitamin E-related compounds whose occurrence in plants is limited primarily to the seeds and fruits of most monocot species (e.g., palm, wheat, rice and barley). Tocotrienols are structurally similar to tocopherols, including α-tocopherol or vitamin E, which occur ubiquitously in the plant kingdom as well as in photosynthetic microbes such as *Synechocystis*.

Tocotrienols and tocopherols both contain a chromanol head group that is linked to a hydrocarbon side chain. The only structural difference between these molecules is the presence of three double bonds in the hydrocarbon side chain of tocotrienols. This difference is related to the biosynthetic origins of the side chains. Tocopherol side chains are derived from phytyl-pyrophosphate (PP), and the tocotrienol side chains are believed to be derived from geranylgeranyl-PP, see FIG. 1 and FIG. 2, respectively (Soil et al. (1980) *Arch. Biochem. Biophys.* 204:544-550).

At least four forms or molecular species of tocopherols and tocotrienols occur in nature: alpha, beta, gamma and delta (α, β, γ and δ, respectively). These molecular species contain different numbers of methyl groups that are bound to the aromatic portion of the chromanol head. Like tocopherols, tocotrienols are potent lipid-soluble antioxidants and therefore have considerable nutritive value in human and animal diets (Packer et al. (2001) *J. Nutr.* 131:369 S-373S). In addition, tocotrienols are believed to have therapeutic properties including a demonstrated ability to down regulate cholesterol biosynthesis (Theriault et al. (1999) *Clin. Biochem.* 32:309-319; Qureshii et al. (1986) *J. Biol. Chem.* 261:10544-10550).

The first committed step in the tocopherol biosynthetic pathway is the prenylation of homogentisic acid with phytyl-diphosphate to form 2-methyl-6-phytylbenzoquinol (MPBQ). Two distinct methyltransferase enzymes catalyze methylations of the aromatic moiety of tocopherols (VTE3 and VTE4). 2-methyl-6-phytylbenzoquinol methyltransferase (VTE3) acts on the tocopherol intermediate MPBQ prior to cyclization. Cyclization of the product of the first methylation reaction (2,3-dimethyl-5-phytylbenzoquinol) with tocopherol cyclase (VTE1) provides gamma-tocopherol. Gamma-tocopherol is further methylated to alpha-tocopherol by the second methyltransferase enzyme of tocopherol biosynthesis, gamma-tocopherol methyltransferase (VTE4). The same enzyme methylates delta-tocopherol thereby generating beta-tocopherol.

It has been speculated that the first committed step in the biosynthesis of tocotrienols involves the condensation of geranylgeranyl-PP and homogentisate to form 2-methyl-6-geranylgeranylbenzoquinol (Soil et al. (1980) *Arch. Biochem. Biophys.* 204:544-550). The enzyme that catalyzes this reaction can thus be functionally described as a homogentisate geranylgeranyl transferase (HGGT). After cyclization and an initial methylation, the last step of tocotrienol production would require the methylation of gamma-tocotrienol to alpha-tocotrienol or delta-tocotrienol to beta-tocotrienol.

Functional identification of genes or cDNAs encoding homogentisate geranylgeranyl transferase (HGGT) and gamma-tocopherol methyltransferase polypeptides has been reported. However, the use of these nucleic acids in combination to manipulate the biosynthesis of the nutritionally important tocotrienols, such as alpha- and beta-tocotrienol, in plants, seeds and microbial hosts has not yet been reported.

SUMMARY OF THE INVENTION

Compositions and methods for the alteration of the alpha- and beta-tocotrienol content and composition of plants are provided. The compositions comprise nucleotide molecules comprising nucleotide sequences for HGGT and gamma-tocopherol methyltransferase. The compositions can be used to transform plants to manipulate the synthetic pathway for tocol compounds.

Transformed plants, plant cells, plant tissues, seed and grain are provided. Transformed plants of the invention find use in methods for improving grain or seed characteristics including, but not limited to, antioxidant level or activity.

Seeds obtained from such plants and oil obtained from these seeds constitute another aspect of the present invention.

Expression cassettes comprising sequences of the invention are provided. Isolated polypeptides encoded by the nucleotide sequences of the invention are also provided.

BRIEF DESCRIPTION OF THE DRAWINGS AND SEQUENCE LISTING

The invention can be more fully understood from the following detailed description and the accompanying drawings and Sequence Listing which form a part of this application.

DETAILED DESCRIPTION

Figure 1:
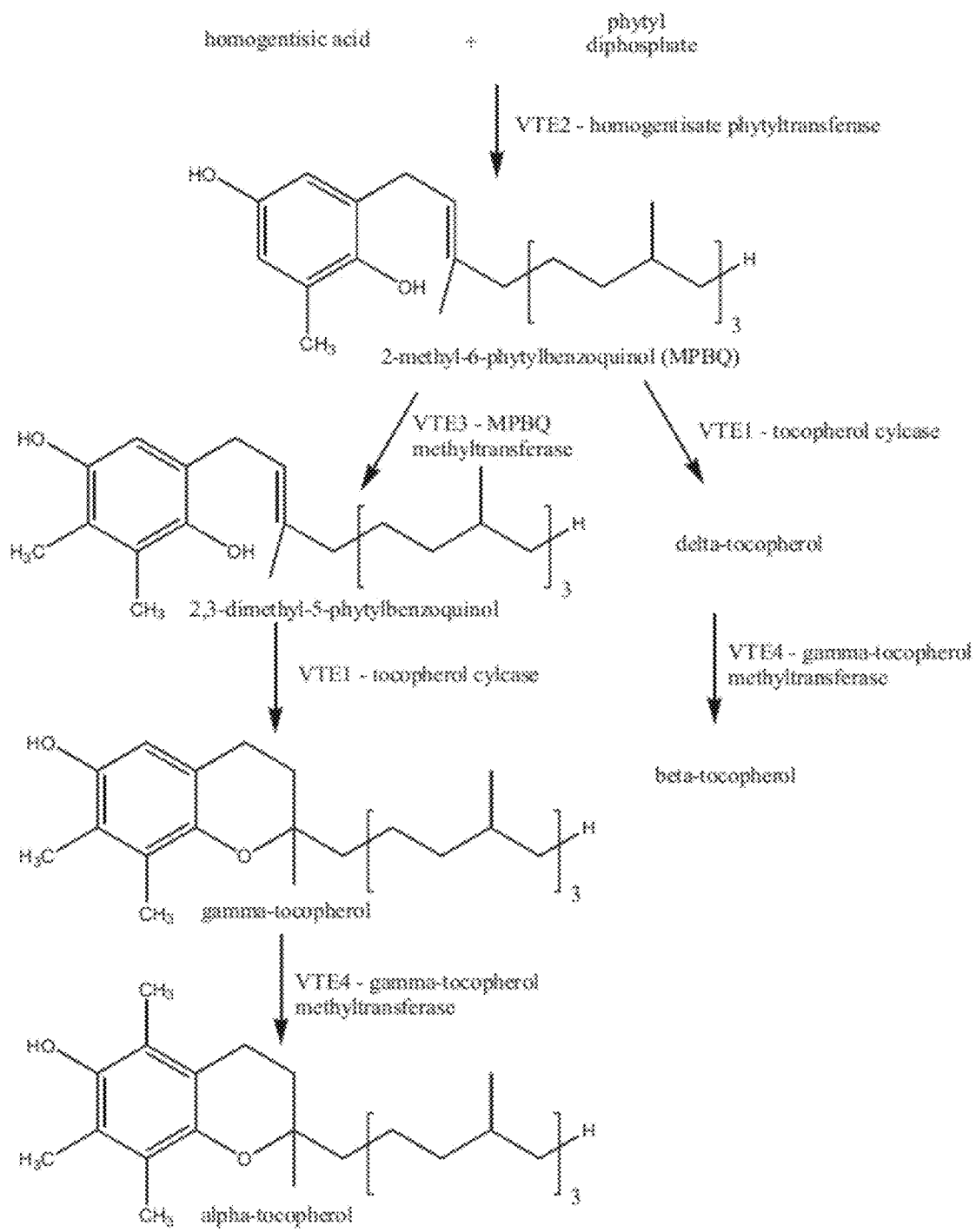
FIG. 1 is a schematic depiction of the tocopherol biosynthetic pathway.
Figure 2:
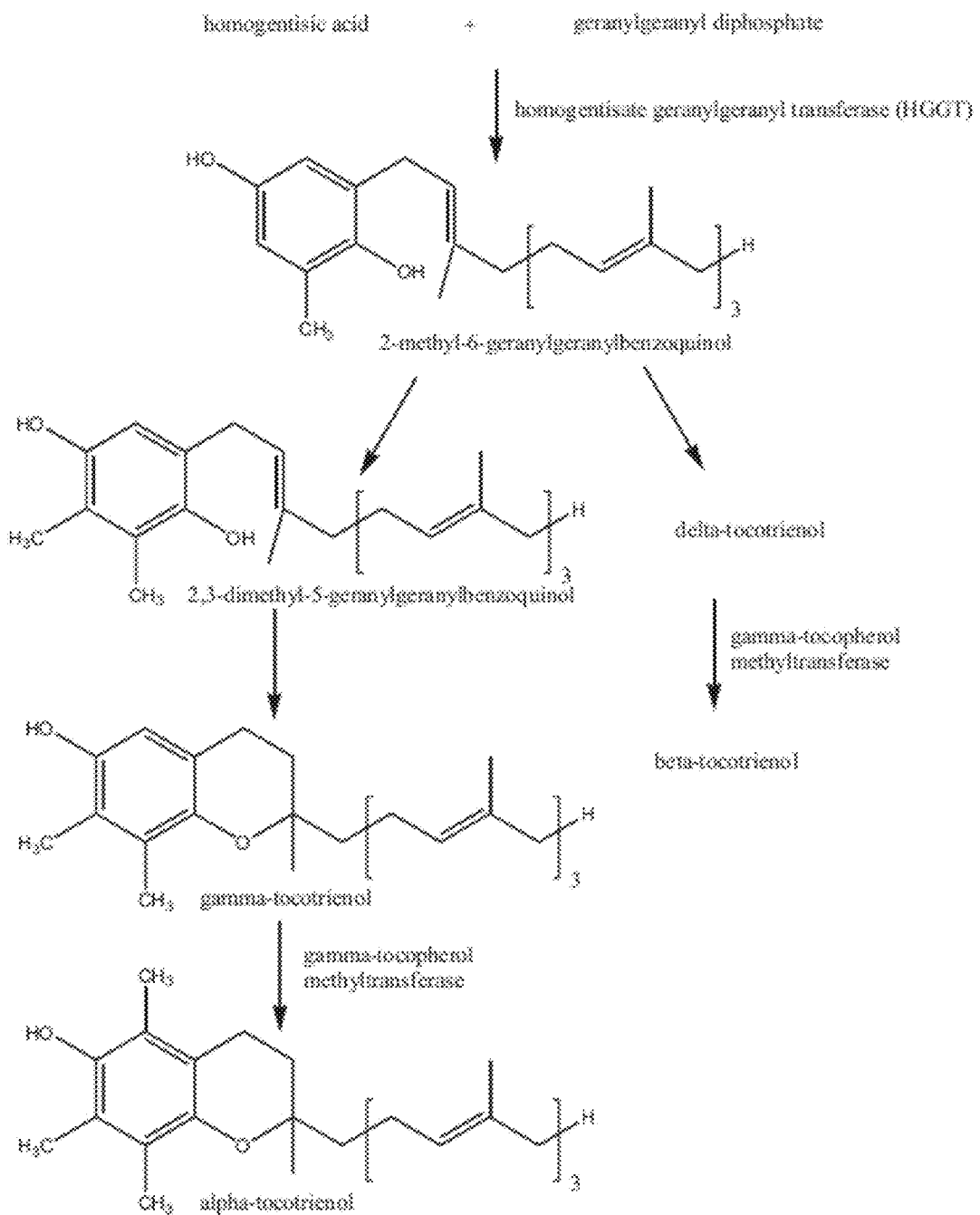
FIG. 2 is a schematic depiction of the tocotrienol biosynthetic pathway.

The combination of HGGT and gamma-tocopherol methyltransferase polynucleotides may be used in plant cells and photosynthetic microbes to alter the tocols, such as tocotrienols, produced in the cells. More specifically, the instant invention shows, inter alia, that the combination of HGGT and gamma-tocopherol methyltransferase polynucleotides may be used to significantly increase the content of vitamin E-related antioxidants, specifically alpha- and beta-tocotrienol, in edible tissues of vegetable, fruit, and agronomic crop plants, including grains such as maize and soybean seed and the oil obtained from these seeds.

The invention includes compositions and methods for altering tocols. The compositions and methods find use in improving the antioxidant quality of grain for use as food for humans and feed for livestock. Furthermore, the tocols can be extracted, purified or further altered via processing.

As used herein, "grain" means the mature seed produced by commercial growers for purposes other than reproducing the species and/or immature seed as an integral part of whole plant maize harvested for silage. As used herein, grain includes plant parts commonly categorized as a fruit, nut or vegetable.

As used herein, "wild-type" refers to untransformed organisms and descendants of untransformed organisms.

The term "tocol" refers generally to any of the tocopherol and tocotrienol molecular species (e.g., α-, β-, γ-, and δ-) that are known to occur in biological systems. The term "tocol content" refers to the total amount of tocopherol and tocotrienol in a whole plant, tissue, or cell or in a microbial host. The term "tocol composition" refers both to the ratio of the various tocols produced in any given biological system and to characteristics, such as antioxidant activity, of any one tocol compound. When the alteration of tocols is taught or claimed herein, such alteration can be to tocol content and/or tocol composition. When an increase of tocols is taught or claimed herein, such increase refers to an increase of tocol content and/or an increase of tocol activity.

The term "tocotrienol" refers generally to any of the tocotrienol molecular species (e.g., α, β, γ, and δ) that are known to occur in biological systems. The term "tocotrienol content" refers to the total amount of tocotrienol in a whole plant, tissue, or cell or in a microbial host. The term "tocotrienol composition" refers both to the ratio of the various tocotrienols produced in any given biological system and to characteristics, such as antioxidant activity, of any one tocotrienol compound. When the alteration of a tocotrienol is taught or claimed herein, such alteration can be to tocotrienol content and/or tocotrienol composition. When an increase of tocotrienols is taught or claimed herein, such increase refers to an increase of tocotrienol content and/or an increase of tocotrienol activity.

The term "homogentisate phytyltransferase" or "HPT" refers to the enzyme that catalyzes the condensation of homogentisate (or homogentisic acid) and phytyl pyrophosphate (or phytyl diphosphate). This reaction is believed to be the committed step in tocopherol biosynthesis. Other names that have been used to refer to this enzyme include "homogentisate phytyl pyrophosphate prenyltransferase" and "homogentisate phytyl diphosphate prenyltransferase". The shortened version phytyl/prenyl transferase is also used.

The term "homogentisate geranylgeranyl transferase" or "HGGT" refers to the enzyme that catalyzes the condensation of homogentisate (or homogentisic acid) and geranylgeranyl pyrophosphate (or geranylgeranyl diphosphate). This reaction is an important step in tocotrienol biosynthesis and can result in the alteration of the tocol content and/or composition. HGGT enzymes may include, but are not limited to, those shown in Table 1.

TABLE 1

Homogentisate Geranylgeranyl Transferase Enzymes

| | | SEQ ID NO: | |
|---|---|---|---|
| Protein | Clone Designation | (Nucleotide) | (Amino Acid) |
| barley homogentisate geranylgeranyl transferase | bdl2c.pk006.o2 | 1 | 2 |
| wheat homogentisate geranylgeranyl transferase | wdk2c.pk012.f2:cgs | 3 | 4 |
| rice homogentisate geranylgeranyl transferase | rds1c.pk007.m9 | 5 | 6 |

TABLE 1-continued

Homogentisate Geranylgeranyl Transferase Enzymes

| | | SEQ ID NO: | |
|---|---|---|---|
| Protein | Clone Designation | (Nucleotide) | (Amino Acid) |
| maize homogentisate geranylgeranyl transferase | cco1n.pk087.l17:cgs | 7 | 8 |
| maize homogentisate geranylgeranyl transferase | p0058.chpbj67r:fis | 9 | 10 |

The term "gamma-tocopherol methyltransferase" or "γ-TMT" or "GTMT" (all which may be used interchangeably) refers to the enzyme that catalyzes the methylation of gamma- and delta-tocopherol to alpha- and beta-tocopherol, respectively, and to the methylation of gamma- and delta-tocotrienol to alpha- and beta-tocotrienol, respectively. This reaction is an important step in tocotrienol biosynthesis and can result in the alteration of the tocol content and/or composition. gamma-tocopherol methyltransferase enzymes may include, but are not limited to, those shown in Table 2.

TABLE 2 gamma-Tocopherol Methyltransferase Enzymes

| | | SEQ ID NO: | |
|---|---|---|---|
| Protein | Clone Designation or GenBank Accession No. | (Nucleotide) | (Amino Acid) |
| Soybean gamma-tocopherol Methyltransferase | sah1c.pk004.g2 | 11 | 12 |
| Soybean gamma-tocopherol Methyltransferase | sah1c.pk001.k8:fis | 13 | 14 |
| maize gamma-tocopherol methyltransferase | p0060.coran49r:fis | 15 | 16 |
| wheat gamma-tocopherol methyltransferase | wr1.pk0077.f1:fis | 17 | 18 |
| lotus corniculatus gamma-tocopherol methyltransferase | GenBank Accession No. DQ13360 | 19 | 20 |
| soybean gamma-tocopherol methyltransferase | GenBank Accession No. AY960126 | 21 | 22 |
| rice gamma-tocopherol methyltransferase | GenBank Accession No. XM467331 | 23 | 24 |
| Brassica gamma-tocopherol Methyltransferase | GenBank Accession No. AF381248 | 25 | 26 |
| Perilla frutescens gamma-tocopherol methyltransferase | GenBank Accession No. AF213481 | 27 | 28 |
| Arabidopsis thaliana gamma-tocopherol methyltransferase | GenBank Accession No. AF104220 | 29 | 30 |
| Medicago truncatula gamma-tocopherol Methyltransferase | GenBank Accession No. AY962639 | 31 | 32 |
| Chlamydomonas gamma-tocopherol methyltransferase | GenBank Accession No. AJ884948 | 33 | 34 |
| Synechocystis gamma-tocopherol methyltransferase | GenBank Accession No. NP_442492 | 35 | 36 |
| Anabaena gamma-tocopherol Methyltransferase | GenBank Accession No. BAB73502 | 37 | 38 |
| Gloeobacter violaceus gamma-tocopherol methyltransferase | GenBank Accession No. NP_926036 | 39 | 40 |

Limited information regarding enzymes catalyzing methylations of gamma- and delta-tocotrienol is available. U.S. Application No. 2003154513 discloses sequences derived from cotton, maize and the cyanobacteria *Anabaena*. These sequences show similarity to gamma-tocopherol methyltransferase genes from *Arabidopsis* (PCT Publication No. WO 99/04622) and soybean (PCT Publication No. WO 00/032757). The heterologously expressed enzyme from maize, a moncotyledoneous plant, showed almost equal activity with tocopherol and tocotrienol substrates. On the other hand, gamma-tocopherol methyltransferase orthologs from the dicotyledoneous plant cotton or blue-green algae showed only trace activities with tocotrienol substrates.

The invention provides isolated nucleotide molecules comprising the combination of nucleotide sequences encoding HGGT and gamma-tocopherol methyltransferase. Also provided are isolated polypeptides encoded by such nucleotide sequences. The nucleotide sequences find use in methods for altering alpha- and beta-tocotrienols in a biological system such as a plant. The methods include improving the antioxidant activity of grain, altering tocotrienols in a plant or part thereof, and improving tocols in a host. The methods comprise transforming a plant or host with at least one nucleotide construct comprising at least a portion of at least one nucleotide sequence encoding HGGT and at least a portion of at least one nucleotide sequence encoding gamma-tocopherol methyltransferase. If desired, the nucleotide construct may additionally comprise at least one operably linked regulatory sequence that drives expression in the plant of interest. Such a nucleotide construct can be used to increase the expression of HGGT and/or gamma-tocopherol methyltransferase.

Also provided are novel compositions of seed and extracted oils. Seed and extracted oils are provided that have unexpectantly high levels of alpha- and beta-tocotrienol. Seed or oil with high levels of alpha-tocotrienol have better bioavailabilty of alpha-tocotrienol as compared to other tocotrienol species (Kiyose et al. (2004) *J. Clin. Biochem. Nutr.* 35(1):47-52, entitiled—Distribution and metabolism of tocopherols and tocotrienols in vivo).

Among the many applications of improved tocols, tocotrienols and antioxidant activity are improved storage of grain, improved stability of oil extracted from grain, benefits to humans consuming the grain, improved meat quality from animals consuming the grain, and the production of novel tocols or tocotrienols for cosmetic, industrial and/or nutraceutical use (U.S. Application No. 2004266862; Karunanandaa et al. (2005) *Metab. Eng.* 7:384-400). It is also known that the presence of tocols in plant vegetative green tissue such as leaf tissue is necessary to protect the plant from the photo-oxidative damage induced directly and indirectly by the production of free oxygen radicals in the chloroplast during oxygenic photosynthesis. It is therefore likely that ectopic expression of tocotrienols in green plant tissue, such as leaf tissue, in addition to the normal tocopherol content of the leaf will lead to an increase ability to withstand such photo-oxidative damage, and thus lead to an increase in the photosynthetic capacity of the plant. This would translate to an increase in harvestable yield for the plant over the entire growing season.

The nucleotide construct of the invention may additionally comprise at least one regulatory sequence that drives expression in a host or plant. Optional regulatory sequences include, for maize, an embryo preferred promoter such as promoters for the 16 kDa and 18 kDa oleosin genes, an endosperm preferred promoter, such as the promoter for the 10 kDa zein gene, and a vegetative promoter such as promoters for ubiquitin genes.

If desired, two or more of such nucleotide sequences may be linked or joined together to form one polynucleotide molecule, and such a polynucleotide may be used to transform a plant. For example, a nucleotide construct comprising a nucleotide sequence encoding an HGGT can be linked with another nucleotide sequence encoding the same or another HGGT. Nucleotide sequences encoding both HGGT and gamma-tocopherol methyltransferase may also be linked in a nucleotide construct. Similarly, the two nucleotide sequences can be provided on different nucleotide constructs, and each of the separate nucleotide sequences can be operably linked to at least one regulatory sequence that drives expression in a plant. For example, a construct may be used that increases total HGGT activity and decreases total HPT activity, thereby resulting in shunting the pathway towards the production of tocotrienols and decreased production of tocopherols.

An alternative strategy may also be used. If separate nucleotide constructs are employed for an HGGT nucleotide sequence and a gamma-tocopherol methyltransferase nucleotide sequence, two individual plants may be transformed with the nucleotide constructs, and the plants may then be crossed to produce progeny having the desired genotype of both the HGGT and gamma-tocopherol methyltransferase nucleotide sequences (i.e., also referred to as genetic stacks).

Additionally, a construct to down-regulate the geranylgeranyl reductase responsible for producing phytol pyrophosphate, one of the precursors for tocopherol biosynthesis, may be linked in cis with a construct to express HGGT. The result of this manipulation would be an increased pool size of geranylgeranyl-pyrophosphate and a corresponding increase of flux into the tocotrienol biosynthetic pathway. Flux into tocotrienols can also be increased by increasing flux of carbon into the shikimate pathway and non-mevalonate pathway of isoprenoid biosynthesis. Specifically, this flux can be accomplished through chloroplast-targeted expression of genes such as bifunctional chorismate mutase-prephenate dehydrogenase (TYRA) (from bacteria) and p-hydroxyphenylpyruvate dioxygenase (HPPD) genes from plants (Karunanandaa et al. (2005) *Metab. Eng.* 7:384-400).

Nucleic acid molecules of the present invention are preferably recombinant nucleic acid molecules (or may also be referred to as recombinant DNA constructs).

As used herein, "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

As used herein, "recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The methods of the present invention can be employed to alter tocols or tocotrienols in any plant or part thereof, and antioxidant activity may thereby be altered. Plants that may be used in the invention include, but are not limited to, field crops (e.g., alfalfa, barley, bean, maize, cotton, flax, pea, rape, rice, rye, safflower, sorghum, oats, millet, soybean, sunflower, tobacco, and wheat); vegetable crops (e.g., asparagus, beet, broccoli, cabbage, carrot, cauliflower, celery, cucumber, eggplant, lettuce, onion, pepper, potato, pumpkin, radish, spinach, squash, taro, tomato, and zucchini); and fruit and nut crops (e.g., almond, apple, apricot, banana, blackberry, blueberry, cacao, cherry, coconut, cranberry, date, fajoa, filbert, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon) and *Arabidopsis*. Some methods of the invention involve altering the antioxidant levels in grain and other parts of a plant that may be subjected to post-harvest processing. With post-harvest processing, the tocols or tocotrienols so produced can be a valuable source of recovery for millers and other processors.

Grain or vegetable oil derived from transgenic plants containing elevated levels of alpha- and beta-tocotrienol may be fed to livestock and poultry to improve the oxidative stability of meat products. Examples of improvements with practical benefit include increased color stability of fresh beef during retail display and enhanced flavor stability of precooked meat products stored under refrigeration. These and other quality-related improvements may be expected because tocotrienols function as chain-breaking free radical scavengers in muscle tissue, and thus reduce oxidative reactions that degrade meat quality and reduce shelf life.

For example, improved beef quality can be demonstrated by feeding cattle a diet formulated with at least about 300-ppm of total alpha- and beta-tocotrienol obtained from high-tocotrienol transgenic grain or vegetable oil for at least 100 days. For comparison, a group of cattle reared on a standard diet (no additional tocotrienol) under otherwise identical conditions can serve as the control treatment ("control group"). To assess fresh meat color stability, ribeye steaks harvested from each animal are individually packaged in foam trays with PVC overwrap and placed under simulated retail display for seven days. Fresh steak color is subjectively evaluated by trained panelists on a graded scale for visual color intensity and discoloration. Color is also evaluated instrumentally using a HunterLab MiniScan™ Spectrophotometer or similar device to assess the "a* value", which is a measure of the degree of redness. Results of these assays demonstrate that over time steaks from cattle fed a high tocotrienol diet, on average, exhibit better subjective visual scores and higher (i.e., better) a* instrumental values than ribeye steaks from the control group over time. The improvement in color stability extends retail display time and thus reduces the amount of fresh product discounted and discarded due to color deterioration. Other fresh beef products, including ground beef, will also exhibit improved color stability with and thus provide a similar benefit to retailers. (See also WO Publication No. 2005/002358, herein incorporated in its entirety by reference).

Methods for assessing tocopherol content and tocopherol composition (including tocopherol activity) are known in the art. Tocopherol content and composition may be measured by HPLC in combination with fluorescence detection. Such methods are described in numerous literature references (e.g., Kamal-Eldi A., Gorgen S., Pettersson J., Lampi A. M. (2000) *J. Chromatogr. A* 881:217-227; Bonvehi J. S., Coll F. V., Rius I. A. (2000) *J. AOAC Intl.* 83:627-634; Goffman F. D. and Böhme T. (2001) *J. Agric. Food Chem.* 49:4990-4994). Such methods typically involve the resolution of tocopherol molecular species contained in complex mixtures by use of a normal or reverse phase HPLC matrix. Eluted tocopherol molecular species are then detected by fluorescence of the chromanol head group with an excitation wavelength typically in the range of 290 to 295 nm and an emission wavelength typically in the range of 325 to 335 nm. Using this methodology, the composition of a tocopherol mixture can be determined by comparing the retention times of separated molecular species with those of known standards. The content of each tocopherol molecular species can be measured by the relative intensity of its fluorescence emission at the selected wavelength. The absolute amount of each tocopherol species can be determined by measuring the intensity of fluorescence emission relative to that of an internal standard, which is added in a known amount to the tocopherol mixture prior to HPLC analysis. A suitable internal standard can include a tocopherol analog that is not normally found in nature (e.g., 5,7-dimethyltocol) or a naturally occurring tocopherol molecular species that is not present in a given tocopherol mixture. The total tocopherol content of a complex mixture of compounds can be derived by summing the absolute amount of each of the component tocopherol molecular species as determined by HPLC analysis.

Methods for assessing tocotrienol content and tocotrienol composition (including tocotrienol activity) are known in the art. Tocotrienol content and composition may be measured by HPLC using methods described above for the analysis of tocopherol content and composition. Using HPLC techniques described in Example 3 and elsewhere (e.g., Podda M., Weber C., Traber M. G., Packer L. (1996) *J. Lipid Res.* 37:893-901), tocotrienol molecular species can be readily resolved from tocopherol molecular species in a complex mixture. The occurrence and structural identification of tocotrienols in a complex mixture can be determined by gas chromatography-mass spectrometry as described by Frega N., Mozzon M., and Bocci F. (1998) *J. Amer. Oil Chem. Soc.* 75:1723-1728.

In addition, lipophilic antioxidant activity may be measured by assays including the inhibition of the coupled auto-oxidation of linoleic acid and β-carotene and oxygen radical absorbance capacity (ORAC) as described elsewhere (Serbinova E. A. and Packer L. (1994) *Meth. Enzymol.* 234: 354-366; Emmons C. L., Peterson D. M., Paul G. L. (1999) *J. Agric. Food Chem.* 47:4894-4898); Huang D et al (2002) *J. Agric. Food Chem.*). Such methods typically involve measuring the ability of antioxidant compounds (i.e., tocols) in test materials to inhibit the decline of fluorescence of a model substrate (fluorescein, phycoerythrin) induced by a peroxyl radical generator (2',2'-azobis[20amidinopropane]dihydrochloride).

The invention encompasses isolated or substantially purified nucleic acid or polypeptide compositions. An "isolated" or "purified" nucleic acid molecule or polypeptide, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, 0.3 kb or 0.1 kb of nucleotide sequences that naturally flank the nucleic acid molecule in genomic DNA of the cell from which the nucleic acid is derived. A polypeptide that is substantially free of cellular material includes preparations of polypeptide having less than about 30%, 20%, 10%, 5%, (by dry weight) of contaminating polypeptide. When the polypeptide of the invention or biologically active portion thereof is recombinantly produced, preferably culture medium represents less than about 30%, 20%, 10%, 5%, 3% or 1% (by dry weight) of chemical precursors or non-polypeptide-of-interest chemicals.

Fragments and variants of the disclosed nucleotide sequences and polypeptides encoded thereby are also encompassed by the present invention. By "fragment" is intended a portion of the nucleotide sequence or a portion of the amino acid sequence. Functional fragments of a nucleotide sequence may encode polypeptide fragments that retain the biological activity of the native protein and hence HGGT activity and/or gamma-tocopherol methyltransferase activity. Alternatively, fragments of a nucleotide sequence that are useful as hybridization probes generally do not encode polypeptides retaining biological activity. Thus, fragments of a nucleotide sequence may range from at least about 20 nucleotides, about 30 nucleotides, about 50 nucleotides, about 70 nucleotides, about 100 nucleotides, about 150 nucleotides and up to the full-length nucleotide sequence encoding the polypeptides of the invention.

A fragment of a HGGT nucleotide sequence that encodes a biologically active portion of an HGGT polypeptide of the invention will encode at least 15, 25, 30, 50, 75, 100, or 125 contiguous amino acids, or up to the total number of amino acids present in a full-length HGGT polypeptide of the invention (for example, 407, 408, 404, 380 and 361 amino acids for SEQ ID NO:2, 4, 6, 8 and 10, respectively). Fragments of a HGGT nucleotide sequence that are useful as hybridization probes or PCR primers generally need not encode a biologically active portion of an HGGT polypeptide.

Thus, a fragment of an HGGT nucleotide sequence may encode a biologically active portion of an HGGT polypeptide, or it may be a fragment that can be used as a hybridization probe or PCR primer using methods disclosed below. A biologically active portion of an HGGT polypeptide can be prepared by isolating a portion of one of the HGGT nucleotide sequences of the invention, expressing the encoded portion of the HGGT polypeptide (e.g., by recombinant expression in vitro) and assessing the activity of the encoded portion of the HGGT polypeptide.

Nucleic acid molecules that are fragments of an HGGT nucleotide sequence comprise at least 16, 20, 50, 75, 100, 150, 200, 250, 300, 350, 400, 450, 500, 550, 600, 650, or 700 nucleotides, or up to the number of nucleotides present in a full-length HGGT nucleotide sequence disclosed herein (for example, 1457, 1365, 1242, 1730, and 1769 nucleotides for SEQ ID NO:1, 3, 5, 7 and 9, respectively).

Likewise, a fragment of a gamma-tocopherol methyltransferase nucleotide sequence that encodes a biologically active portion of a gamma-tocopherol methyltranferase polypeptide of the invention will encode at least 15, 25, 30, 50, 75, 100, or 125 contiguous amino acids, or up to the total number of amino acids present in a full-length gamma-tocopherol methyltranferase polypeptide of the invention. Fragments of a gamma-tocopherol methyltranferase nucleotide sequence that are useful as hybridization probes or PCR primers generally need not encode a biologically active portion of a gamma-tocopherol methyltransferase polypeptide.

Thus, a fragment of an gamma-tocopherol methyltranferase nucleotide sequence may encode a biologically active portion of an gamma-tocopherol methyltranferase polypeptide, or it may be a fragment that can be used as a hybridization probe or PCR primer using methods disclosed below. A biologically active portion of an gamma-tocopherol methyltranferase polypeptide can be prepared by isolating a portion of one of the gamma-tocopherol methyltranferase nucleotide sequences of the invention, expressing the encoded portion of the gamma-tocopherol methyltranferase polypeptide (e.g., by recombinant expression in vitro) and assessing the activity of the encoded portion of the gamma-tocopherol methyltranferase polypeptide.

Nucleic acid molecules that are fragments of an gamma-tocopherol methyltranferase nucleotide sequence comprise at least 16, 20, 50, 75, 100, 150, 200, 250, 300, 350, 400, 450, 500, 550, 600, 650, or 700 nucleotides, or up to the number of nucleotides present in a full-length gamma-tocopherol methyltranferase nucleotide sequence disclosed herein.

By "variants" is intended substantially similar sequences. For nucleotide sequences, conservative variants include those sequences that, because of the degeneracy of the genetic code, encode the amino acid sequence of one of the HGGT and/or gamma-tocopherol methyltransferase polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode an HGGT and/or gamma-tocopherol methyltransferase polypeptide of the invention. Generally, variants of a particular nucleotide sequence of the invention will have at least about 80% generally at least about 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" polypeptide is intended a polypeptide derived from the native polypeptide by deletion (so-called truncation) or addition of one or more amino acids to the N-terminal and/or C-terminal end of the native polypeptide; deletion or addition of one or more amino acids at one or more sites in the native polypeptide; or substitution of one or more amino acids at one or more sites in the native polypeptide. Variant polypeptides encompassed by the present invention are biologically active, that is they continue to possess the desired biological activity of the native polypeptide, that is, HGGT and/or gamma-tocopherol methyltransferase activity as described herein. Such variants may result from, for example, genetic polymorphism or from human manipulation. Biologically active variants of a native HGGT and/or gamma-tocopherol methyltransferase polypeptide of the invention will have at least about 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native polypeptide as determined by sequence alignment programs described elsewhere herein using default parameters. A biologically active variant of a polypeptide of the invention may differ from that polypeptide by as few as 1-15 amino acid residues, as few as 1-10, such as 6-10, as few as 5, as few as 4, 3, 2, or even 1 amino acid residue.

The polypeptides of the invention may be altered in various ways including amino acid substitutions, deletions, truncations, and insertions. Methods for such manipulations are generally known in the art. For example, amino acid sequence variants of the HGGT and/or gamma-tocopherol methyltransferase polypeptides can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the polypeptide of interest may be found in the model of Dayhoff et al. (1978) *Atlas of Protein*

*Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the polypeptides of the invention encompass both naturally occurring polypeptides as well as variations and modified forms thereof. Such variants will continue to possess the desired HGGT and/or gamma-tocopherol methyltransferase activity. Preferably, the mutations that will be made in the DNA encoding the variant will not place the sequence out of reading frame and preferably will not create complementary regions that could produce secondary mRNA structure. See, EP Patent Application Publication No. 75,444.

The deletions, insertions, and substitutions of the polypeptide sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays. That is, the activity can be evaluated by assays for HGGT and/or gamma-tocopherol methyltransferase activity.

Variant nucleotide sequences and polypeptides also encompass sequences and polypeptides derived from a mutagenic and recombinogenic procedure such as DNA shuffling. With such a procedure, one or more different HGGT and/or gamma-tocopherol methyltransferase coding sequences can be manipulated to create a new HGGT and/or gamma-tocopherol methyltransferase polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the HGGT polynucleotides of the invention and/or other HGGT genes to obtain a new gene coding for a polypeptide with an improved property of interest, such as an increased $K_m$ in the case of an enzyme. Likewise, using this approach, sequence motifs encoding a domain of interest may be shuffled between the gamma-tocopherol methyltransferase polynucleotides of the invention and/or other gamma-tocopherol methyltransferase genes to obtain a new gene coding for a polypeptide with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants, more particularly other monocots or dicots. In this manner, methods such as PCR, hybridization, and the like can be used to identify such sequences based on their sequence homology to the sequences set forth herein. Sequences isolated based on their sequence identity to the entire HGGT and/or gamma-tocopherol methyltransferase nucleotide sequences set forth herein or to fragments thereof are encompassed by the present invention. Such sequences include sequences that are orthologs of the disclosed sequences. By "orthologs" is intended polynucleotides derived from a common ancestral gene and which are found in different species as a result of speciation. Polynucleotides found in different species are considered orthologs when their nucleotide sequences and/or their encoded polypeptide sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

For clarification, "PCR" or "polymerase chain reaction" is a technique for the synthesis of large quantities of specific DNA segments, and consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the HGGT and/or gamma-tocopherol methyltransferase sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire HGGT and/or gamma-tocopherol methyltransferase sequence disclosed herein, or one or more portions thereof, may be used as a probe capable of specifically hybridizing to corresponding HGGT and/or gamma-tocopherol methyltransferase sequences and messenger RNAs. To achieve specific hybridization under a variety of conditions, such probes include sequences that are unique among HGGT and/or gamma-tocopherol methyltransferase sequences and are preferably at least about 10 nucleotides in length, and most preferably at least about 20 nucleotides in length. Such probes may be used to amplify corresponding HGGT and/or gamma-tocopherol methyltransferase sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Isolated sequences that encode for a HGGT and/or gamma-tocopherol methyltransferase polypeptide and which hybridize under stringent conditions to the HGGT and/or gamma-tocopherol methyltransferase sequences disclosed herein, or to fragments thereof, are encompassed by the present invention.

Nucleotides (usually found in their T-monophosphate form) are often referred to herein by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "W" for A or T, "H" for A or C or T, "D" for A or G or T, "M" for A or C, "S" for C or G, "V" for A or C or G, "B" for C or G or T "I" for inosine, and "N" for A, C, G, or T.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988), supra. A PAM120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990), supra. BLAST nucleotide searches can be performed with the BLASTN program, score=100, wordlength=12, to obtain nucleotide sequences homologous to a nucleotide sequence encoding a polypeptide of the invention. BLAST polypeptide searches can be performed with the BLASTX program, score=50, wordlength=3, to obtain amino acid sequences homologous to a polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for polypeptides) can be used. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for polypeptide sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

Alternatively, for purposes of the present invention, comparison of nucleotide or polypeptide sequences for determination of percent sequence identity to the HGGT or gamma-tocopherol methyltransferase sequences disclosed herein is preferably made using CLUSTAL with the following changes from the default parameters. For amino acid sequence comparisons a Gap Penalty of 10 and Gap Length Penalty of 10 was used for multiple alignments and a KTUPLE of 2, Gap Penalty of 3, Window of 5 and Diagonals Saved of 5 was used for pairwise alignments. For nucleotide sequence comparisons, a Gap Penalty of 10 and Gap Length Penalty of 10 was used for multiple alignments and a KTUPLE of 2, Gap Penalty of 5, Window of 4 and Diagonals Saved of 4 was used for pairwise alignments. Any equivalent program can also be used to determine percent sequence identity. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to polypeptides it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of polypeptides encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one polypeptide, or at least one RNA, such as, for example, an antisense RNA that is complementary to at least a portion of an mRNA. Typically such a nucleotide construct is comprised of a coding sequence for a polypeptide or an RNA operably linked to 5' and 3' transcriptional regulatory regions. Alternatively, it is also recognized that the methods of the invention may employ a nucleotide construct that is not capable of directing, in a transformed plant, the expression of a polypeptide or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, homologous recombination, chimeric vectors, chimeric mutational vectors, chimeric repair vectors, mixed-duplex oligonucleotides, self-complementary chimeric oligonucleotides, and recombinogenic oligonucleobases. See, U.S. Pat. Nos. 5,565, 350; 5,731,181; 5,756,325; 5,760,012; 5,795,972; and 5,871, 984; all of which are herein incorporated by reference. See also, PCT Publication No. WO 98/49350, PCT Publication No. WO 99/07865, PCT Publication No. WO 99/25821, PCT Publication No. WO03093428, Jeske et al. (2001) *EMBO* 20:6158-6167, and Beetham et al. (1999) *Proc. Natl. Acad. Sci. USA* 96:8774-8778; herein incorporated by reference.

The HGGT and gamma-tocopherol methyltransferase sequences of the invention are provided in expression cassettes for expression in the plant of interest. The cassette(s) will include at least one 5' and 3' regulatory sequences operably linked to a HGGT and/or gamma-tocopherol methyltransferase nucleotide sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two polypeptide coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the HGGT and/or gamma-tocopherol methyltransferase nucleotide sequence to be under the transcriptional regulation of the regulatory regions. The expression cassette may additionally contain selectable marker genes.

The expression cassette will include in the 5'-3' direction of transcription, a transcriptional and translational initiation region, a HGGT and/or gamma-tocopherol methyltransferase polynucleotide sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of HGGT and/or gamma-tocopherol methyltransferase in the plant, plant cell or other host. Thus, the phenotype of the plant, plant cell or other host is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, chemically regulated, tissue-preferred, or other promoters for expression in plants.

Such constitutive promoters include, for example, the core promoter of the Rsyn7 promoter and other constitutive promoters disclosed in PCT Publication No. WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Chemically regulated promoters can be used to modulate the expression of a gene in a plant through the application of an exogenous chemical regulator. Depending upon the objective, the promoter may be a chemical inducible promoter, where application of the chemical induces gene expression, or a chemical repressible promoter, where application of the chemical represses gene expression. Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemically regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991)

*Mol. Gen. Genet.* 227:229-237, and U.S. Pat. Nos. 5,814,618 and 5,789,156), herein incorporated by reference.

Tissue-preferred promoters can be utilized to target enhanced HGGT and/or gamma-tocopherol methyltransferase expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3): 337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2): 207-218 (soybean root-preferred glutamine synthetase gene); Keller and Baumgartner (1991) *Plant Cell* 3(10):1051-1061 (root-preferred control element in the GRP 1.8 gene of French bean); Sanger et al. (1990) *Plant Mol. Biol.* 14(3):433-443 (root-preferred promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-preferred promoters isolated from hemoglobin genes from the nitrogen-fixing non-legume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-preferred promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root preferred in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4): 681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also the promoters found in the following: End1 and End2 (WO 00/12733), Led (WO 2002/42424), Jip1 (WO 2002/42424), EAP1 (U.S. Patent Publication No. 2004/0210043), ODP2 (U.S. Patent Publication No. 2005/0223432); all of which are herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts or other plastids. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The HGGT and/or gamma-tocopherol methyltransferase polypeptides of the invention can be targeted to specific compartments within the plant cell. Methods for targeting polypeptides to a specific compartment are known in the art. Generally, such methods involve modifying the nucleotide sequence encoding the polypeptide in such a manner as to add or remove specific amino acids from the polypeptide encoded thereby. Such amino acids comprise targeting signals for targeting the polypeptide to a specific compartment such as, for example, a plastid, the nucleus, the endoplasmic reticulum, the vacuole, the mitochondrion, the peroxisome, the Golgi apparatus, and for secretion from the cell. Targeting sequences for targeting a polypeptide to a specific cellular compartment, or for secretion, are known to those of ordinary skill in the art. Chloroplast-targeting or plastid-targeting sequences are known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6): 789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36): 27447-27457); and the light harvesting chlorophyll a/b binding protein (LHBP) (Lamppa et al. (1988) *J. Biol. Chem.* 263:14996-14999). See also Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin B phosphotransferase, as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christopherson et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 49:603-612; Figge et al. (1988) Cell 52:713-722; Deuschle et al. (1989) Proc. Natl. Acad. Ad. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90:1917-1921; Labow et al. (1990) Mol. Cell. Biol. 10:3343-3356; Zambretti et al. (1992) Proc. Natl. Acad. Sci. USA 89:3952-3956; Baim et al. (1991) Proc. Natl. Acad. Sci. USA 88:5072-5076; Wyborski et al. (1991) Nucleic Acids Res. 19:4647-4653; Hillenand-Wissman (1989) Topics Mol. Struc. Biol. 10:143-162; Degenkolb et al. (1991) Antimicrob. Agents Chemother. 35:1591-1595; Kleinschnidt et al. (1988) Biochemistry 27:1094-1104; Bonin (1993) Ph.D. Thesis, University of Heidelberg; Gossen et al. (1992) Proc. Natl. Acad. Sci. USA 89:5547-5551; Oliva et al. (1992) Antimicrob. Agents Chemother. 36:913-919; Hlavka et al. (1985) Handbook of Experimental Pharmacology, Vol. 78 (Springer-Verlag, Berlin); Gill et al. (1988) Nature 334:721-724. Such disclosures are herein incorporated by reference.

Other genes that could serve as selectable or scorable markers in the recovery of transgenic events but that might not be required in the final product would include, but are not limited to: GUS (β-glucoronidase), Jefferson (1987) Plant Mol. Biol. Rep. 5:387); fluorescent proteins, such as, GFP (green florescence protein), YFP (yello florescence protein), RFP (red florescence protein) and CYP (cyan florescence protein), WO 00/34321, WO 00/34526, WO 00/34323, WO 00/34322, WO 00/34318, WO 00/34319, WO 00/34320, WO 00/34325, WO 00/34326, WO 00/34324, Chalfie et al. (1994) Science 263:802; luciferase, Teeri et al. (1989) EMBO J. 8:343; and the maize genes encoding for anthocyanin production, Ludwig et al. (1990) Science 247:449.

The above list of selectable marker genes is not meant to be limiting. Any selectable marker gene can be used in the present invention.

The invention involves transforming host cells with the nucleotide constructs of the invention. Generally, the nucleotide construct will comprise a HGGT nucleotide and/or gamma-tocopherol methyltransferase sequence of the invention, either a full length sequence or functional fragment thereof, operably linked to a promoter that drives expression in the host cell of interest. Host cells include, but are not limited to: plant cells; animal cells; fungal cells, particularly yeast cells; and bacterial cells.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320-334), electroporation (Riggs et al. (1986) Proc. Natl. Acad. Sci. USA 83:5602-5606, Agrobacterium-mediated transformation (Townsend et al., U.S. Pat. No. 5,563,055; Zhao et al., U.S. Pat. No. 5,981,840), direct gene transfer (Paszkowski et al. (1984) EMBO J. 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886, 244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); McCabe et al. (1988) Biotechnology 6:923-926); and Led transformation (PCT Publication No. 00/028058). Also see Weissinger et al. (1988) Ann. Rev. Genet. 22:421-477; Sanford et al. (1987) Particulate Science and Technology 5:27-37 (onion); Christou et al. (1988) Plant Physiol. 87:671-674 (soybean); McCabe et al. (1988) Bio/Technology 6:923-926 (soybean); Finer and McMullen (1991) In Vitro Cell Dev. Biol. 27P:175-182 (soybean); Singh et al. (1998) Theor. Appl. Genet. 96:319-324 (soybean); Datta et al. (1990) Biotechnology 8:736-740 (rice); Klein et al. (1988) Proc. Natl. Acad. Sci. USA 85:4305-4309 (maize); Klein et al. (1988) Biotechnology 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91:440-444 (maize); Fromm et al. (1990) Biotechnology 8:833-839 (maize); Hooykaas-Van Slogteren et al. (1984) Nature (London) 311:763-764; Bowen et al., U.S. Pat. No. 5,736,369 (cereals); Bytebier et al. (1987) Proc. Natl. Acad. Sci. USA 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505 (electroporation); Li et al. (1993) Plant Cell Reports 12:250-255 and Christou and Ford (1995) Annals of Botany 75:407-413 (rice); Osjoda et al. (1996) Nature Biotechnology 14:745-750 (maize via Agrobacterium tumefaciens); all of which are herein incorporated by reference.

The nucleotide constructs of the invention may also be introduced into plants by contacting plants with a virus or viral nucleic acids. Generally, such methods involve incorporating a nucleotide construct of the invention within a viral DNA or RNA molecule. It is recognized that a HGGT and/or gamma-tocopherol methyltransferase of the invention may be initially synthesized as part of a viral polyprotein, which later may be processed by proteolysis in vivo or in vitro to produce the desired recombinant polypeptide. Further, it is recognized that promoters of the invention also encompass promoters utilized for transcription by viral RNA polymerases. Methods for introducing nucleotide constructs into plants and expressing a polypeptide encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

As used herein, "transformed plants" include those plants directly transformed as provided herein, as well as plants that have the directly transformed plants in their pedigree and retain the change in genotype, such as the inclusion of the expression cassette, created by the original transformation.

The present invention may be used for transformation of any plant species, including, but not limited to, maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, maize, alfalfa, sunflower, *Brassica*, soybean, cotton, safflower, peanut, sorghum, wheat, barley, rice, sorghum, rye, millet, tobacco, etc.), more preferably cereal plants, yet more preferably maize, wheat, barley, rice, sorghum, rye and millet plants.

In some embodiments, the activity of a gene of the invention is reduced or eliminated by transforming a plant cell with an expression cassette expressing a polynucleotide that inhibits the expression of a target gene. The polynucleotide may inhibit the expression of one or more target genes directly, by preventing translation of the target gene messenger RNA, or indirectly, by encoding a polypeptide that inhibits the transcription or translation of a gene encoding the target gene. Methods for inhibiting or eliminating the expression of a gene in a plant are well known in the art, and any such method may be used in the present invention to inhibit the expression of one or more plant genes, such as, HGGT and/or gamma-tocoperol methyltransferase.

In accordance with the present invention, the expression of a target gene protein is inhibited if the protein level of the target gene is statistically lower than the protein level of the same target gene in a plant that has not been genetically modified or mutagenized to inhibit the expression of that target gene. In particular embodiments of the invention, the protein level of the target gene in a modified plant according to the invention is less than 95%, less than 90%, less than 85%, less than 80%, less than 75%, less than 70%, less than 65%, less than 60%, less than 50%, less than 40%, less than 30%, less than 20%, less than 10%, or less than 5% of the protein level of the same target gene in a plant that is not a mutant or that has not been genetically modified to inhibit the expression of that target gene. The expression level of the target gene may be measured directly, for example, by assaying for the level of target gene expressed in the maize cell or plant, or indirectly, for example, by measuring the activity of the target gene enzyme in the maize cell or plant. The activity of a target gene protein is "eliminated" according to the invention when it is not detectable by at least one assay method described elsewhere herein.

Many methods may be used to reduce or eliminate the activity of a target gene. More than one method may be used to reduce the activity of a single target gene. In addition, combinations of methods may be employed to reduce or eliminate the activity of two or more different target genes. Non-limiting examples of methods of reducing or eliminating the expression of a plant target are given below.

Many techniques for gene silencing are well known to one of skill in the art, including but not limited to knock-outs, such as, by insertion of a transposable element such as mu (Vicki Chandler, *The Maize Handbook* ch. 118 (Springer-Verlag 1994)), other genetic elements such as a FRT, Lox or other site specific integration site, alteration of the target gene by homologous recombination (Bolon, B. Basic Clin. Pharmacol. Toxicol. 95:4, 12, 154-61 (2004); Matsuda and Alba, A., Methods Mol. Bio. 259:379-90 (2004); Forlino, et. al., J. Biol. Chem. 274:53, 37923-30 (1999), antisense technology (see, e.g., Sheehy et al. (1988) *PNAS* USA 85:8805-8809; and U.S. Pat. Nos. 5,107,065; 5,453,566; and 5,759,829; U.S. Patent Publication No. 20020048814); sense suppression (e.g., U.S. Pat. No. 5,942,657; Flavell et al. (1994) *Proc. Natl. Acad. Sci. USA* 91: 3490-3496; Jorgensen et al. (1996) *Plant Mol. Biol.* 31: 957-973; Johansen and Carrington (2001) *Plant Physiol.* 126: 930-938; Broin et al. (2002) *Plant Cell* 14: 1417-1432; Stoutjesdijk et al (2002) *Plant Physiol.* 129: 1723-1731; Yu et al. (2003) *Phytochemistry* 63: 753-763; and U.S. Pat. Nos. 5,034,323, 5,283,184, and 5,942,657; U.S. Patent Publication No. 20020048814); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *PNAS* USA 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591, U.S. Pat. No. 4,987,071); hairpin structures (Smith et al. (2000) *Nature* 407:319-320; Waterhouse et al. (1998) *Proc. Natl. Acad. Sci. USA* 95: 13959-13964, Liu et al. (2002) *Plant Physiol.* 129: 1732-1743, Waterhouse and Helliwell (2003) *Nat. Rev. Genet.* 4:29-38; Chuang and Meyerowitz (2000) *Proc. Natl. Acad. Sci. USA* 97: 4985-4990; Stoutjesdijk et al. (2002) *Plant Physiol.* 129: 1723-1731; Panstruga et al. (2003) *Mol. Biol. Rep.* 30: 135-140; Smith et al. (2000) *Nature* 407: 319-320; Smith et al. (2000) *Nature* 407:319-320; Wesley et al. (2001) *Plant J.* 27: 581-590; Wang and Waterhouse (2001) *Curr. Opin. Plant Biol.* 5: 146-150; Waterhouse and Helliwell (2003) *Nat. Rev. Genet.* 4: 29-38; Helliwell and Waterhouse (2003) *Methods* 30: 289-295; Pandolfini et al. *BMC Biotechnology* 3: 7; U.S. Patent Publication No. 20030180945; U.S. Patent Publication No. 20030175965; WO 99/49029; WO 99/53050; WO 99/61631; and WO 00/49035); transcriptional gene silencing (TGS) (Aufsatz et al. (2002) *Proc. Nat'l. Acad. Sci.* 99 (Suppl. 4):16499-16506; Mette et al. (2000) *EMBO J.* 19(19):5194-5201; microRNA (Aukerman & Sakai (2003) Plant Cell 15:2730-2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); methods of using amplicons (Angell and Baulcombe (1997) *EMBO J.* 16: 3675-3684, Angell and Baulcombe (1999) *Plant J.* 20: 357-362, and U.S. Pat. No. 6,646, 805); polynucleotides that encode an antibody that binds to protein of interest (Conrad and Sonnewald (2003) *Nature Biotech.* 21: 35-36); transposon tagging (Maes et al. (1999) *Trends Plant Sci.* 4: 90-96; Dharmapuri and Sonti (1999) *FEMS Microbiol. Lett.* 179: 53-59; Meissner et al. (2000) *Plant J.* 22: 265-274; Phogat et al. (2000) *J. Biosci.* 25: 57-63; Walbot (2000) *Curr. Opin. Plant Biol.* 2: 103-107; Gai et al. (2000) *Nucleic Acids Res.* 28: 94-96; Fitzmaurice et al. (1999) *Genetics* 153: 1919-1928; the TUSC process for selecting Mu insertions in selected genes (Bensen et al. (1995) *Plant Cell* 7: 75-84; Mena et al. (1996) *Science* 274: 1537-1540; and U.S. Pat. No. 5,962,764); other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted (Ohshima et al. (1998) *Virology* 243: 472-481; Okubara et al. (1994) *Genetics* 137: 867-874; and Quesada et al. (2000) *Genetics* 154: 421-436; TILLING (Targeting Induced Local Lesions In Genomes) (McCallum et al. (2000) *Nat. Biotechnol.* 18: 455-457) and other methods or combinations of the above methods known to those of skill in the art. Each reference is herein incorporated by reference An expression cassette is designed to reduce activity of the target gene may express an RNA molecule corresponding to all or part of a messenger RNA encoding a target gene in the sense or antisense orientation or a combination of both sense and antisense. Overexpression of the RNA molecule can result in reduced expression of the native gene. Accordingly, multiple plant lines transformed with the sense suppression expression cassette are screened to identify those that show the greatest inhibition of the target gene's expression.

The polynucleotide used for target gene suppression may correspond to all or part of the sequence encoding the target gene, all or part of the 5' and/or 3' untranslated region of a target gene transcript, or all or part of both the coding region and the untranslated regions of a transcript encoding of the target gene or all or part of the promoter sequence responsible for expression of the target gene. A polynucleotide used for sense suppression or other gene silencing methods may share 99%, 98%, 97%, 96%, 95%, 94%, 93%, 92%, 91%, 90%, 89%, 88%, 87%, 85%, 80%, or less sequence identity with the target sequence. When portions of the polynucleotides are used to disrupt the expression of the target gene, generally, sequences of at least 15, 16, 17, 18, 19, 20, 21, 22, 23, 24, 25, 26, 27, 28, 29, 30, 35, 40, 45, 50, 60, 70, 80, 90, 100, 200, 300, 400, 450, 500, 550, 600, 650, 700, 750, 800, or 900 nucleotides or 1 kb or greater may be used.

The following examples are presented by way of illustration, not by way of limitation.

EXPERIMENTAL

The present invention is further defined in the following Examples, in which parts and percentages are by weight and degrees are Celsius, unless otherwise stated. It should be understood that these Examples, while indicating preferred embodiments of the invention, are given by way of illustration, not by way of limitation. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Alpha- and Beta-Tocotrienol Production in *Arabidopsis thaliana* by Transgenic Expression of Barley HGGT and Soybean Gamma-Tocopherol Methyltransferase The cDNA for barley homogentisate geranylgeranyl transferase (HGGT) (bdl2c.pk006.o2; SEQ ID NO:2) and soybean gamma-tocopherol methyltransferase (sah1c.pk004.g2; SEQ ID NO:12) were expressed in *Arabidopsis thaliana* to demonstrate the feasability of these cDNA for alpha and beta-tocotrienol production in transgenic plants.

A transformation vector was constructed using standard molecular tools that expressed the barley HGGT gene under the control of the β-conglycinin promoter of soybean (Beachy et al., *EMBO J.* 4:3047-3053 (1985)) and the soybean gamma-tocopherol methyltransferase gene under the control of the Kti promoter (Kunitz Trypsin Inhibitor, Jofuku et. al., (1989) Plant Cell 1:1079-1093).

The 1.1 kb DNA fragment containing the soybean gamma-tocopherol methyltransferase gene was excised from SC1 (see Example 3) using the restriction enzyme NotI, and ligated, in the sense orientation behind the Kti promoter, to DNA of KS126 (PCT Publication No. WO 04/071467) linearized with the restriction enzyme NotI to give KS308 (SEQ ID NO:41).

The 3.1 kb DNA fragment containing β-conglycinin promoter, HGGT gene, and phaseolin terminator was excised from SC38 (see Example 3) using the restriction enzyme Ascl, the ends were blunted with the large fragment of DNA polymerase I, and ligated to DNA of KS178 (construction described below) to give KS270 (SEQ ID NO:42). KS178 had previously been linearized with the restriction enzyme PacI followed by filling in of 3' overhangs with the large fragment of DNA polymerase I.

KS178 was constructed as follows. The 4.0 kb DNA fragment containing the SAMS/ALS/ALS3' cassette, was excised from pZSL13LeuB (PCT Publication No. WO 04/071467) using the restriction enzymes PstI and SmaI, the ends were blunted with the large fragment of DNA polymerase I, and ligated to DNA of KS102 (PCT Publication No. WO 04/071467) linearized with the restriction enzyme BamHI, to give KS178. Prior to ligation the ends of the linearized KS102 vector were blunted with the large fragment of DNA polymerase I.

The 3.4 kb DNA fragment containing the gamma-tocopherol methyltransferase expression cassette was excised from KS308 using the restriction enzyme Ascl, the ends were blunted with the large fragment of DNA polymerase I, and ligated to DNA of pBluescript II KS-(Stratagene) linearized with the restriction enzyme SmaI. The resulting vector was linearized with the restriction enzyme SnaBI, and ligated to the 3.0 kb DNA fragment containing the HGGT expression cassette removed from KS270 using the restriction enzymes PacI and BamHI to give KS318. Prior to ligation the ends of this fragment were blunted with the large fragment of DNA polymerase I. The 6.4 kb DNA fragment containing the HGGT and gamma-tocopherol methyltransferase expression cassettes was excised from KS318 using the restriction enzyme SalI, and ligated to DNA of the *Agrobacterium tumefaciens* binary vector pZBL120, linearized with SalI, to give KS319. The T-DNA of the plant transformation vector KS319 is set forth as SEQ ID NO:43.

Applicants note that the binary vector pZBL120 is identical to the pZBL1 binary vector (American Type Culture Collection Accession No. 209128) described in U.S. Pat. No. 5,968,793, except the NOS promoter was replaced with a 963 bp 35S promoter (NCBI Accession No. V00141; also known as NCBI General Indentifier No. 58821) from nucleotide 6494 to 7456 in the Nos/P-nptII-OCS 3' gene. The new 35S promoter-nptII-OCS 3' gene serves as a kanamycin (Kan) resistance plant selection marker in pZBL120.

Generation and Analysis of Transgenic Arabidospis Lines:

Plasmid DNA of KS319 was introduced into *Agrobacterium tumefaciens* NTL4 (Luo et al, *Molecular Plant-Microbe Interactions* (2001) 14(1):98-103) by electroporation. Briefly, 1 µg plasmid DNA was mixed with 100 µL of electrocompetent cells on ice. The cell suspension was transferred to a 100 µL electro oration curette (1 mm gap width) and electro orated using a BIORAD electro orator set to 1 kV, 400Ω and 25 µF. Cells were transferred to 1 mL LB medium and incubated for 2 h at 30° C. Cells were plated onto LB medium containing 50 µg/mL kanamycin. Plates were incubated at 30° C. for 60 h. Recombinant *agrobacterium* cultures (500 mL LB, 50 µg/mL kanamycin) were inoculated from single colonies of transformed *agrobacterium* cells and grown at 30° C. for 60 h. Cells were harvested by centrifugation (5000×g, 10 min) and resuspended in 1 L of 5% (WN) sucrose containing 0.05% (V/V) Silwet. *Arabidopsis* plants were grown in soil at a density of 30 plants per 100 cm² pot in metromix 360 soil mixture for 4 weeks (22° C., 16 h light/8 h dark, 100 µE m$^{-2}$s$^{-1}$). Plants were repeatedly dipped into the *agrobacterium* suspension harboring the binary vector KS319 and kept in a dark, high humidity environment for 24 h. Plants were grown for three to four weeks under standard plant growth conditions described above and plant material was harvested and dried for one week at ambient temperatures in paper bags. Seeds were harvested using a 0.425 mm mesh brass sieve.

Cleaned *Arabidopsis* seeds (2 grams, corresponding to about 100,000 seeds) were sterilized by washes in 45 mL of 80% ethanol, 0.01% triton X-100, followed by 45 mL of 30% (V/V) household bleach in water, 0.01% triton X-100 and finally by repeated rinsing in sterile water. Aliquots of 20,000 seeds were transferred to square plates (20×20 cm) containing 150 mL of sterile plant growth medium comprised of 0.5×MS salts, 1.0% (W/V) sucrose, 0.05 MES/KOH (pH 5.8), 200 µg/mL timentin, and 50 µg/mL kanamycin solidified with 10 g/L agar. Homogeneous dispersion of the seed on the medium was facilitated by mixing the aqueous seed suspension with an equal volume of melted plant growth medium. Plates were incubated under standard growth conditions for ten days. Kanamycin-resistant seedlings were transferred to plant growth medium without selective agent and grown to maturity.

A total of 137 transgenic lines were generated and subjected to HPLC analysis: 5 mg crushed seed were extracted at ambient temperature in 200 µL of heptane. Tocopherols and tocotrienols were quantitated by HPLC as described in Example 3. The highest total tocotrienol content was 2,800 ppm. The highest alpha-tocotrienol content was 400 ppm. In these events, 25% of all tocopherols and tocotrienols comprised of alpha-tocotrienol.

Two events, #58 and #135 were advanced to transgene homozygousity by repeated selfing. T2 seed of both events contained 25% of kanamycin-sensitive seed indicating that both events contained transgene insertion at a single genetic locus. Bulk seed were produced from T3 seed that no longer segregated kanamycin-sensitive progeny. 50 mg of T4 seed material was extracted in 1 mL of heptane. Tocopherol and tocotrienol were quantitated by HPLC and these results are found in Table 3. As discussed below, event #58 expressed HGGT and gamma-tocopherol methyltransferase genes. Event #135 expressed only HGGT.

TABLE 3

Tocol Composition (% of total tocols) of Homozygous T4 Seed Material of Transgenic *Arabidopsis* Lines

| line | | alpha-tocopherol | beta-tocopherol | gamma-tocopherol | delta-tocopherol | tocopherol |
|---|---|---|---|---|---|---|
| wild-type | ppm | 6 | 0 | 396 | 9 | 411 |
| | % | 2 | 0 | 96 | 2 | |
| #135 | ppm | 25 | 4 | 326 | 104 | 455 |
| | % | 1 | 0 | 12 | 4 | |
| #58 | ppm | 308 | 58 | 98 | 30 | 495 |
| | % | 15 | 3 | 5 | 1 | |

| | | alpha-tocotrienol | beta-tocotrienol | gamma-tocotrienol | delta-tocotrienol | tocotrienol |
|---|---|---|---|---|---|---|
| wild-type | ppm | 0 | 0 | 0 | 0 | 0 |
| | % | 0 | 0 | 0 | 0 | |
| #135 | ppm | 13 | 0 | 1754 | 590 | 2358 |
| | % | 0 | 0 | 62 | 21 | |
| #58 | ppm | 419 | 47 | 876 | 273 | 1615 |
| | % | 20 | 2 | 42 | 13 | |

Table 3 indicates that event #135 apparently only expresses the barley HGGT gene. The seed tocotrienol profile of event #135 resembles that of leaves of transgenic *Arabidopsis* plants over-expressing the barley HGGT gene. The leaf profile is dominated by gamma-tocotrienol with alpha-tocotrienol comprising less than 3% of the total tocotrienol fraction (see PCT Publication No. WO 03/082899; U.S. Application No. 2004/0034886; Cahoon et al. (2003) *Nat. Biotechnol.* 21:1082-1087). Applicants note that in line #135 only trace levels of alpha-tocotrienol are detected. Hence, there is very little endogenous enzyme activity present in *Arabidopsis* seed that can convert gamma-tocotrienol to alpha-tocotrienol.

In contrast to the above, the co-expression of the soybean gamma-tocopherol methyltransferase gene with the HGGT gene in event #58 leads to significant accumulation of alpha-tocotrienol with levels of 419 ppm. The oil content of heptane extracts was measured using sodium methoxide derivatization followed by GC analysis (see below). Using this analysis, it was determined that the seed oil of event #58 contained 1,200 ppm alpha-tocotrienol. The alpha-tocotrienol of event #58 makes up about 20% of the total tocopherols and tocotrienols. About 30% of gamma-tocotrienol is converted to alpha-tocotrienol. Applicants note that expression of the gamma-tocopherol methyltransferase gene may be low, because a heterologous promoter was used. Even higher levels of alpha-tocotrienol will very likely be observed if the gamma-tocopherol methyltransferase gene is expressed under control of an endogenous seed-preferred promoter. Nevertheless, the *Arabidopsis* data has demonstrated that the soybean gamma-tocopherol methyltransferase gene is an efficient enzyme catalyst for methylation of tocotrienols for the production of alpha- and beta-tocotrienol.

One skilled in the art understands that the homogentisate geranylgeranyl transferases (HGGT) and gamma-tocopherol methyltransferases found in Table 1 and Table 2, respectively, may also be expressed in *Arabidopsis thaliana* to demonstrate the feasability of using these cDNA to increase alpha and beta-tocotrienol production in transgenic plants.

GC/MS Analysis to Confirm Identity of Tocopherols and Tocotrienols:

Total tocol analysis was performed on an Agilent 6890 gas chromatograph in conjunction with Agilent 5973 Mass Selective Detector (MSD). Four µL samples of heptane extracts of *Arabidopsis* seeds of lines #58 and #135 were injected into a split/splitless injector (2:1 split ratio) held at 300° C. Chromatographic separation was performed on a 30 m×250 µm (ID)×0.25 µm (film thickness) Agilent DB5MS column using helium gas as the carrier (39 cm/sec linear velocity). The oven temperature profile was as follows: 260° C., hold 4 min; 2° C. ramp to 340° C., hold for 12 min. Compounds eluting from the column were directed into the MSD though a heated (325° C.) transfer line and ionized (70 eV). The MSD was tuned using the standard tune protocol and was run in Scan mode (10-500 mass range). Data was analyzed using ChemStation (Agilent) and AMDIS version 2.1 (National Institute of Standards and Technology; NIST).

Compound identity was confirmed by comparing compound elution times with those of authentic samples and by mass spectral comparisons with an electronic database (version 2.0, NIST). The database contained entries for alpha-, beta-, gamma- and delta-tocopherols, as well as the internal standard (alpha-tocopherol acetate). Library entries were not available for any of the tocotrienols. The identity of these compounds was therefore confirmed by comparison of the chromatographic elution and by visual comparison of the mass-spectrum with those of authentic standards run under the same chromatographic conditions.

Example 2

Production of Tocotrienols in Transgenic Soybean Lines

Molecular Stack of Barley HGGT and Soybean Gamma-Tocopherol Methyltransferase

To demonstrate the ability to produce increased levels of alpha- and beta-tocotrienols in transgenic soybean lines, the barley HGGT cDNA (bdl2c.pk006.o2; SEQ ID NO:2) and soybean gamma-tocopherol methyltransferase (sah1c.pk004.g2; SEQ ID NO:12) were used in a molecular stack (progeny with both transgene-related traits).

Transgenic soybean lines were generated with plasmid DNA of KS270 and KS308, see Example 1, using particle bombardment of embryogenic callus.

KS270 provides the barley HGGT gene under control of 617 bp of the soybean β-conglycinin promoter. The polyadenylation signal for the HGGT transcript is derived from the terminator of the phaseolin gene (from the bean *Phaseolus vulgaris*; Doyle et al. (1986) *J. Biol. Chem.* 261:9228-9238). The plasmid also contains the cDNA of a sulfonylurea-resistant variant of the soybean ALS gene that is under control of 1217 bp of the SAMS promoter. The polyadenylation signal for the HGGT transcript is derived from the terminator of the soybean ALS gene.

KS308 provides the gamma-tocopherol methyltransferase gene from soybean under the control of 2090 bp of the soybean Kti promoter. The polyadeylation signal for the gamma-tocopherol methyltransferase transcript is derived from the terminator of the Kti gene. KS308 also provides a hygromycin B phosphotransferase (HPT) resistance gene (Gritz et al. (1983) *Gene* 25:179-188) that is under control of 1408 bp of the 35S promoter from Cauliflower Mosaic Virus (Odell et al. (1985) *Nature* 313:810-812). The polyadenylation signal for the hygromycin resistance gene is derived from the terminator of nopaline synthase gene from the T-DNA of the Ti plasmid of *Agrobacterium tumefaciens*.

Soybean embryogenic suspension cultures were transformed with DNA plasmids KS270 in conjunction with KS308 by the method of particle gun bombardment (Klein et al. (1987) *Nature* (London) 327:70-73, U.S. Pat. No. 4,945,050) using a BIORAD Biolistic PDS1000/He instrument. The following stock solutions and media were used for transformation and regeneration of soybean plants:

Stock Solutions:
Sulfate 100× Stock: 37.0 g $MgSO_4.7H_2O$, 1.69 g $MnSO_4.H_2O$, 0.86 g $ZnSO_4.7H_2O$, 0.0025 g $CuSO_4.5H_2O$
Halides 100× Stock: 30.0 g $CaCl_2.2H_2O$, 0.083 g KI, 0.0025 g $CoCl_2.6H_2O$
P, B, Mo 100× Stock: 18.5 g $KH_2PO_4$, 0.62 g $H_3BO_3$, 0.025 g $Na_2MoO_4.2H_2O$
Fe EDTA 100× Stock: 3.724 g $Na_2EDTA$, 2.784 g $FeSO_4.7H_2O$
2,4-D Stock: 10 mg/mL
Vitamin B5 1000× Stock: 10.0 g myo-inositol, 0.10 g nicotinic acid, 0.10 g pyridoxine HCl, 1 g thiamine.

Media (per Liter):
SB196: 10 mL of each of the above stock solutions, 1 mL B5 Vitamin stock, 0.463 g $(NH_4)_2 SO_4$, 2.83 g $KNO_3$, 1 mL 2,4-D stock, 1 g asparagine, 10 g Sucrose, pH 5.7
SB103: 1 pk. Murashige & Skoog salts mixture, 1 mL B5 Vitamin stock, 750 mg $MgCl_2$ hexahydrate, 60 g maltose, 2 g gelrite, pH 5.7.
SB166: SB103 supplemented with 5 g per liter activated charcoal.
SB71-4: Gamborg's B5 salts, 1 mL B5 vitamin stock, 30 g sucrose, 5 g TC agar, pH 5.7.

To prepare tissue for transformation, soybean embryogenic suspension cultures were maintained in 35 mL liquid medium (SB196) on a rotary shaker (150 rpm) at 28° C. with fluorescent lights providing a 16 hour day/8 hour night cycle. Cultures were subcultured every 2 weeks by inoculating approximately 35 mg of tissue into 35 mL of fresh liquid media.

In particle gun bombardment procedures it is possible to use purified 1) entire plasmid DNA or, 2) DNA fragments containing only the recombinant DNA expression cassette(s) of interest. For every seventeen bombardment transformations, 85 µL of suspension is prepared containing 1 to 90 picograms (pg) of plasmid DNA per base pair of each DNA plasmid. Both recombinant DNA plasmids were co-precipitated onto gold particles as follows. The DNAs in suspension were added to 50 µL of a 20-60 mg/mL 0.6 µm gold particle suspension and then combined with 50 µL $CaCl_2$ (2.5 M) and 20 µL spermidine (0.1 M). The mixture was vortexed for 5 seconds, spun in a microfuge for 5 seconds, and the supernatant removed. The DNA-coated particles were then washed once with 150 µL of 100% ethanol, vortexed and spun in a microfuge again, then resuspended in 85 µL of anhydrous ethanol. Five µL of the DNA-coated gold particles were then loaded on each macrocarrier disk.

Approximately 150 to 250 mg of two-week-old suspension culture was placed in an empty 60 mm×15 mm petri plate and the residual liquid removed from the tissue using a pipette. The tissue was placed about 3.5 inches away from the retaining screen and each plate of tissue was bombarded once. Membrane rupture pressure was set at 650 psi and the chamber was evacuated to −28 inches of Hg. Three plates were bombarded, and, following bombardment, the tissue from each plate was divided between two flasks, placed back into liquid media, and cultured as described above.

Seven days after bombardment, the liquid medium was exchanged with fresh SB196 medium supplemented with 30-50 mg/L hygromycin. The selective medium was subsequently refreshed weekly or biweekly. Seven weeks post-bombardment, bright green, transformed tissue was observed growing from untransformed, chlorotic or necrotic embryogenic clusters. Isolated green tissue was removed and inoculated into individual wells in six-well culture dishes to generate new, clonally-propagated, transformed embryogenic suspension cultures. Thus, each new line was treated as independent transformation event in an individual well. These suspensions can then be maintained as suspensions of embryos clustered in an immature developmental stage through subculture or they can be regenerated into whole plants by maturation and germination of individual somatic embryos.

After two weeks in individual cell wells, transformed embryogenic clusters were removed from liquid culture and placed on solidified medium (SB166) containing no hormones or antibiotics for one week. Embryos were cultured for at 26° C. with mixed fluorescent and incandescent lights on a 16 hour day/8 hour night schedule. After one week, the cultures were then transferred to SB103 medium and maintained in the same growth conditions for 3 additional weeks.

Somatic embryos became suitable for germination after 4 weeks and were then removed from the maturation medium and dried in empty petri dishes for 1 to days. The dried embryos were then planted in SB71-4 medium where they were allowed to germinate under the same light and temperature conditions as described above. Germinated embryos were transferred to sterile soil and grown to maturity for seed production.

A total of fourteen events were created by co-transformation with KS270 and KS308 plasmids. Tocol composition of T1 seed was assayed as follows. A seed chip (approximately 5-15 mg of tissue) was obtained from the cotyledon tissue of the seed. The chip was extracted with 100 µL of heptane for 2 hours. Tocopherol and tocotrienol was quantitated by HPLC analysis as described in Example 3.

A total of 14 events were generated and analyzed. Seed from five events contained significant levels of tocotrienol. Three of these also contained significant levels (>150 ppm) of alpha- and beta-tocotrienol. One event did not show conversion of gamma- to alpha-tocotrienol and one event did only exhibit low levels of gamma-tocopherol methyltransferase activity (20-150 ppm alpha-tocotrienol). One event 4060.2.5.1 was selected for further work. For event 4060.2.5.1, seven out of ten T1 seed showed the transgenic trait, indicating that these events likely had a single or multiple transgenic insertion at a single genetic locus. Positive-positive T1 seed were planted and T2 seed were selected from individual plants. A total of forty-eight T2 seed was analyzed by HPLC and the results can be found in Table 4.

TABLE 4

Tocol Composition (% of total tocopherols (tocph.) and tocotrienols (toct.)) for T2 Progeny of Event 4060.2.5.1

| No. | alpha-tocph. | beta-tocph. | gamma-tocph. | delta-tocph. | alpha-toct. | beta-toct. | gamma-toct. | delta-toct. | tocph. (ppm) | toct. (ppm) |
|---|---|---|---|---|---|---|---|---|---|---|
| 1 | 8 | 4 | 0 | 0 | 31 | 24 | 12 | 20 | 406 | 2786 |
| 2 | 9 | 5 | 0 | 0 | 31 | 22 | 15 | 19 | 474 | 3100 |

TABLE 4-continued

Tocol Composition (% of total tocopherols (tocph.) and tocotrienols (toct.)) for T2 Progeny of Event 4060.2.5.1

| No. | alpha-tocph. | beta-tocph. | gamma-tocph. | delta-tocph. | alpha-toct. | beta-toct. | gamma-toct. | delta-toct. | tocph. (ppm) | toct. (ppm) |
|---|---|---|---|---|---|---|---|---|---|---|
| 3 | 8 | 4 | 0 | 0 | 30 | 24 | 13 | 21 | 453 | 3172 |
| 4 | 9 | 4 | 0 | 0 | 30 | 23 | 14 | 20 | 471 | 2922 |
| 5 | 7 | 4 | 0 | 0 | 30 | 24 | 13 | 21 | 389 | 3059 |
| 6 | 9 | 5 | 0 | 0 | 29 | 22 | 13 | 22 | 479 | 3046 |
| 7 | 9 | 5 | 0 | 0 | 29 | 23 | 12 | 22 | 434 | 2596 |
| 8 | 9 | 5 | 0 | 0 | 29 | 22 | 13 | 22 | 454 | 2693 |
| 9 | 9 | 5 | 0 | 0 | 28 | 22 | 13 | 22 | 442 | 2595 |
| 10 | 10 | 5 | 0 | 0 | 28 | 22 | 13 | 22 | 487 | 2686 |
| 11 | 8 | 5 | 0 | 0 | 28 | 22 | 15 | 21 | 292 | 1846 |
| 12 | 10 | 5 | 0 | 0 | 27 | 22 | 12 | 23 | 401 | 2120 |
| 13 | 10 | 5 | 0 | 0 | 27 | 23 | 12 | 23 | 384 | 2164 |
| 14 | 10 | 5 | 0 | 0 | 27 | 19 | 17 | 23 | 424 | 2481 |
| 15 | 8 | 3 | 0 | 0 | 26 | 14 | 26 | 22 | 382 | 2912 |
| 16 | 8 | 5 | 0 | 0 | 26 | 22 | 14 | 26 | 468 | 3128 |
| 17 | 8 | 5 | 0 | 0 | 26 | 22 | 14 | 26 | 399 | 2692 |
| 18 | 9 | 5 | 0 | 0 | 25 | 21 | 14 | 25 | 477 | 2906 |
| 19 | 7 | 5 | 0 | 0 | 25 | 23 | 13 | 26 | 365 | 2580 |
| 20 | 7 | 5 | 0 | 0 | 25 | 21 | 14 | 27 | 405 | 2826 |
| 21 | 7 | 5 | 0 | 0 | 25 | 22 | 14 | 27 | 442 | 3138 |
| 22 | 11 | 5 | 0 | 0 | 24 | 16 | 19 | 24 | 408 | 2084 |
| 23 | 8 | 6 | 0 | 0 | 24 | 22 | 14 | 27 | 435 | 2818 |
| 24 | 7 | 5 | 0 | 0 | 24 | 20 | 15 | 29 | 411 | 2947 |
| 25 | 9 | 6 | 0 | 0 | 24 | 21 | 13 | 27 | 412 | 2340 |
| 26 | 9 | 6 | 0 | 0 | 24 | 20 | 15 | 27 | 453 | 2624 |
| 27 | 9 | 6 | 0 | 0 | 23 | 21 | 14 | 27 | 392 | 2315 |
| 28 | 9 | 6 | 0 | 0 | 23 | 20 | 14 | 28 | 443 | 2415 |
| 29 | 8 | 2 | 1 | 0 | 22 | 10 | 36 | 21 | 460 | 3873 |
| 30 | 7 | 5 | 0 | 0 | 22 | 21 | 14 | 30 | 386 | 2723 |
| 31 | 9 | 5 | 0 | 0 | 22 | 18 | 17 | 30 | 435 | 2718 |
| 32 | 16 | 1 | 73 | 10 | 0 | 0 | 0 | 0 | 383 | 0 |
| 33 | 51 | 2 | 45 | 2 | 0 | 0 | 0 | 0 | 368 | 0 |
| 34 | 35 | 2 | 59 | 4 | 0 | 0 | 0 | 0 | 362 | 0 |
| 35 | 20 | 1 | 69 | 10 | 0 | 0 | 0 | 0 | 353 | 0 |
| 36 | 36 | 2 | 56 | 5 | 0 | 0 | 0 | 0 | 325 | 0 |
| 37 | 18 | 2 | 71 | 10 | 0 | 0 | 0 | 0 | 357 | 0 |
| 38 | 35 | 3 | 58 | 5 | 0 | 0 | 0 | 0 | 307 | 0 |
| 39 | 13 | 2 | 74 | 11 | 0 | 0 | 0 | 0 | 302 | 0 |
| 40 | 25 | 2 | 64 | 9 | 0 | 0 | 0 | 0 | 353 | 0 |
| 41 | 18 | 1 | 71 | 10 | 0 | 0 | 0 | 0 | 328 | 0 |
| 42 | 25 | 2 | 64 | 9 | 0 | 0 | 0 | 0 | 353 | 0 |
| 43 | 17 | 2 | 70 | 11 | 0 | 0 | 0 | 0 | 384 | 0 |
| 44 | 14 | 1 | 73 | 12 | 0 | 0 | 0 | 0 | 337 | 0 |
| 45 | 20 | 1 | 70 | 8 | 0 | 0 | 0 | 0 | 344 | 0 |
| 46 | 16 | 1 | 73 | 10 | 0 | 0 | 0 | 0 | 335 | 0 |
| 47 | 16 | 1 | 74 | 10 | 0 | 0 | 0 | 0 | 328 | 0 |
| 48 | 18 | 1 | 71 | 8 | 0 | 0 | 0 | 2 | 354 | 0 |

The T2 seed were generated through selfing of a transgenic line that was heterzogous for a single dominant transgenic trait. Accordingly, one would expect to detect 25% (12/48) non-transgenic segregants. Applicants observed 35% (17/48) non-transgenic segregants (see numbers 32-48). Seeds numbers 1 to 31 are transgenic segregants.

T2 progeny with both transgene-related traits were found to contain at least 590 ppm and as much as 1,099 ppm alpha-tocotrienol and at least 401 ppm and as much as 868 ppm beta-tocotrienol. In these T2 lines, alpha-tocotrienol constituted at least 22% and up to 31%, and integers in between, of the total tocopherol and tocotrienol fraction. Oil content of the heptane extracts was determined by derivatization with sodium methoxide followed by GC analysis. Oil could be calculated from that tocotrienol concentrations expressed as ppm. T2 progeny with both transgene-related traits contained an oil with at least 2,618 ppm and as much as 4,891 alpha-tocotrienol and at least 1,732 ppm and as much as 3,804 ppm beta-tocotrienol. Applicants also tested for a possible negative effect of the high alpha- and beta-tocotrienol content on seed weight. To this end, seed weight of the forty-eight T2 seed was plotted against alpha-tocotrienol content. No correlation between seed weight and alpha-tocotrienol content could be detected. Moreover, no unusual seed phenotypes related to seed shape, coloration or germination behaviour were observed in seed with the high alpha- and beta-tocotrienol trait.

One skilled in the art understands that the homogentisate geranylgeranyl transferases (HGGT) and gamma-tocopherol methyltransferases found in Table 1 and Table 2, respectively, may also be expressed in soybean to demonstrate the feasability of these cDNA for alpha- and beta-tocotrienol production in transgenic plants.

In summary, gamma-tocopherol methyltransferase enzyme from soybean can efficiently use tocotrienol substrates, for example, by the foregoing method to generate a seed or an extracted oil with high levels of alpha- and beta-tocotrienol. The alpha-tocotrienol content of soybeans overexpressing barley HGGT and the soybean gamma-tocopherol methyltransferase gene exceeds that of any non-transgenic seed or oil described previously by at least one order of magnitude (Packer et al. (2001) *J. Nutr.* 131:369 S-373S;

Bertoli et al. (1998) *JAOCS* 75:1037-1040; PCT Publication No. WO 00/072862). These results further demonstrate the ability to produce alpha- and beta-tocotrienols in a crop plant that does not normally accumulate these antioxidant molecules through the transgenic expression of nucleic acid fragments encoding HGGT and gamma-tocopherol methyltransferase polypeptides.

Example 3

Production of Tocotrienols in Somatic Soybean Embryos and Transgenic Soybean Lines Genetic Crossing of Barly HGGT and Soybean Gamma-Tocopherol Methyltransferase To demonstrate the ability to produce increased levels of alpha- and beta-tocotrienols in somatic soybean embryos and transgenic soybean lines, the barley HGGT cDNA (bdl2c.pk006.o2; SEQ ID NO:2) and soybean gamma-tocopherol methyltransferase (sah1c.pk004.g2; SEQ ID NO:12) were used in a genetic stack (progeny with both transgene-related traits produced by crossing).

Somatic soybean embryos have been used as model for the prediction of transgenic phenotypes in soybean seeds (Kinney, A. J. (1996) *J. Food Lipids* 3:273-292). Somatic soybean embryos and seeds are enriched in tocopherols, but contain little or no tocotrienols (Coughlan, unpublished result; The Lipid Handbook, 2nd Edition, Gunstone, F. D., et al., Eds., Chapman and Hall, London, 1994, pp. 129-131).

Plasmid DNA from clone sah1c.pk004.g2 was used as a template to prepare a NotI PCR fragment encoding the entire deduced open reading frame using the following PCR primers: forward primer 5'-AGCGCGGCCGCATGGCCAC-CGTGGTGAGGATCCCA-3' (SEQ ID NO:44), AND reverse primer 5'-AGCGCGGCCGCTTATTCAGGTTTTC-GACATGTAATGATG-3'(SEQ ID NO:45).

PCR amplification was achieved using Pfu polymerase, and DNA of EST sah1c.pk004.g2 was used as the template. The product of this PCR reaction was purified by agarose gel electrophoresis and subcloned into pCR-Script-AMP (Stratagene) as described in the manufacturer's protocol. The amplified open-reading frame of the soybean gamma-tocopherol methyltransferase gene was then released as a NotI fragment and cloned into the corresponding site of soybean expression vector pKS67 to generate plasmid pSC1 (SEQ ID NO:50). The plasmid pKS67 was prepared by replacing in pRB20 (described in U.S. Pat. No. 5,846,784, incorporated herein by reference) the 800 bp Nos 3' fragment, with the 285 bp Nos 3' fragment containing the polyadenylation signal sequence and described in Depicker et al. (1982) *J. Mol. Appl. Genet.* 1:561-573. Ligation products were transformed into *E. coli* and recombinant clones were selected using hygromycin B selection.

Restriction digestion of plasmid DNA was used to identify cultures harboring plasmid DNA in which the start codon of the soybean gamma-tocopherol methyltransferase cDNA was in close proximity to the transcription start site of the soybean β-conglycinin promoter. In this plasmid construct, henceforth referred to as SC1, the soybean gamma-tocopherol methyltransferase cDNA is under the control of a 617 bp fragment of the soybean β-conglycinin promoter. The polyadenylation signal for the HGGT transcript is derived from the terminator of the phaseolin gene. Plasmid SC1 (SEQ ID NO:50) contains hygromycin B phosphotransferase gene under control of the cauliflower mosaic 35S promoter, which allows for selection of transformed plant cells by resistance to the antibiotic hygromycin B. Plasmid DNA of SC1 was used to generate transgenic somatic embryos of soybean as described below.

Transformation of Soybean Somatic Embryo Cultures:

The following stock solutions and media were used for transformation and propagation of soybean somatic embryos:

| Stock Solutions | (g/L) |
|---|---|
| MS Sulfate 100x stock | |
| $MgSO_4 \cdot 7H_2O$ | 37.0 |
| $MnSO_4 \cdot H_2O$ | 1.69 |
| $ZnSO_4 \cdot 7H_2O$ | 0.86 |
| $CuSO_4 \cdot 5H_2O$ | 0.0025 |
| MS Halides 100x stock | |
| $CaCl_2 \cdot 2H_2O$ | 44.0 |
| KI | 0.083 |
| $CoCl_2 \cdot 6H_2O$ | 0.00125 |
| $KH_2PO_4$ | 17.0 |
| $H_3BO_3$ | 0.62 |
| $Na_2MoO_4 \cdot 2H_2O$ | 0.025 |
| $Na_2EDTA$ | 3.724 |
| $FeSO_4 \cdot 7H_2O$ | 2.784 |
| B5 Vitamin stock | |
| myo-inositol | 100.0 |
| nicotinic acid | 1.0 |
| pyridoxine HCl | 1.0 |
| thiamine | 10.0 |
| Media | |
| SB55 (per Liter) | |
| 10 mL of each MS stock | |
| 1 mL of B5 Vitamin stock | |
| 0.8 g $NH_4NO_3$ | |
| 3.033 g $KNO_3$ | |
| 1 mL 2,4-D (10 mg/mL stock) | |
| 0.667 g asparagine | |
| pH 5.7 | |
| SB103 (per Liter) | |
| 1 pk. Murashige & Skoog salt mixture* | |
| 60 g maltose | |
| 2 g gelrite | |
| pH 5.7 | |
| SB148 (per Liter) | |
| 1 pk. Murashige & Skoog salt mixture* | |
| 60 g maltose | |
| 1 mL B5 vitamin stock | |
| 7 g agarose | |
| pH 5.7 | |

*(Gibco BRL)

Soybean embryonic suspension cultures were maintained in 35 mL liquid media (SB55) on a rotary shaker (150 rpm) at 28° C. with a mix of fluorescent and incandescent lights providing a 16 hour day/8 hour night cycle. Cultures were subcultured every 2 to 3 weeks by inoculating approximately 35 mg of tissue into 35 mL of fresh liquid media.

Soybean embryonic suspension cultures were transformed with the plasmid containing the gamma-tocopherol methyltransferase sequence by the method of particle gun bombardment (see Klein et al. (1987) *Nature* 327:70-73) using a DuPont Biolistic PDS1000/He instrument. Five μL of pKS93s plastid DNA (1 mg/L), 50 μL $CaI_2$ (2.5 M), and 20 μL spermdine (0.1 M) were added to 50 μL of a 60 mg/mol 1 mm gold particle suspension. The particle preparation was agitated for 3 minutes, spun on a microphage for 10 seconds and the supernatant removed. The DNA-coated particles were then washed once with 400 μL of 70% ethanol and resuspended in 40 μL of anhydrous ethanol. The DNA/particle suspension was sonicated three times for 1 second each. Five μL of the DNA-coated gold particles were then loaded on each macro carrier disk.

Approximately 300 to 400 mg of two-week-old suspension culture was placed in an empty 60 mm×15 mm petri dish and the residual liquid removed from the tissue using a pipette. The tissue was placed about 3.5 inches away from the retaining screen and bombarded twice. Membrane rupture pressure was set at 1100 psi and the chamber was evacuated to −28 inches of Hg. Two plates were bombarded, and following bombardment, the tissue was divided in half, placed back into liquid media, and cultured as described above.

Fifteen days after bombardment, the liquid media was exchanged with fresh SB55 containing 50 mg/mL hygromycin. The selective media was refreshed weekly. Six weeks after bombardment, green, transformed tissue was isolated and inoculated into flasks to generate new transformed embryonic suspension cultures.

Transformed embryonic clusters were removed from liquid culture media and placed on a solid agar media, SB103, containing 0.5% charcoal to begin maturation. After one week, embryos were transferred to SB103 media minus charcoal. After five weeks on SB103 media, maturing embryos were separated and placed onto SB148 media. During maturation embryos were kept at 26° C. with a mix of fluorescent and incandescent lights providing a 16 hour day/8 hour night cycle. After three weeks on SB148 media, embryos were analyzed for the expression of the tocopherols. Each embryonic cluster gave rise to 5 to 20 somatic embryos.

Non-transformed somatic embryos were cultured by the same method as used for the transformed somatic embryos. Analysis of Transformed Somatic Embryos:

At the end of the sixth week on SB148 medium, somatic embryos were harvested from 25 independently transformed lines. Somatic embryos were collected in pools of five and weighed for fresh weight. Excess embryos were stored in 96-well plates at −80° C. The pooled somatic embryos were lyophilized for 18 hours and the dry weight measured. The lyophilized somatic embryos were briefly pulverized with a hand held Potter homogeniser and then 600 μL of heptane added and the samples incubated for 24 hours in the dark at room temperature to extract oils and tocopherols. The heptane was decanted and a further 300 μL added to the samples. The extracts were combined and centrifuged (5 minutes, 12000 g). The supernatant was stored in amber hulk auto sampler vials at −20° C. prior to analysis.

HPLC analysis of the extracts was carried out using an HP1100 system (Agilent Technologies) 25 μL of the heptane sample was applied to a Lichrosphere Si 60 column (5 micron, 4×12.5 mm). The column was eluted with heptane/isopropanol (98:2 v/v) at a flow rate of 1 mL/min. After six minutes all four tocopherol isomers were eluted, as detected by a HP1100 fluorescence detector (Excitation wavelength 295 nm, emission wavelength 330 nm). Individual tocopherol standards (Matreya) were diluted with HPLC grade heptane to levels between 1 and 200 ng/μL to construct a 6-point external standard curve. Tocopherols in each oil were quantified using a standard curve run on the same day as the samples. The sum of tocopherol peak areas of samples from a non-transformed control line were compared with those of 25 independent gamma-tocopherol methyltransferase-transformed, hygromycin resistant lines.

Several events were identified that showed over-expression of the soybean gamma-tocopherol methyltransferase gene. In many of the lines 80% of the total tocol fraction was comprised of alpha-tocopherol in contrast to untransformed soybean embryos where gamma-tocopherol constitutes the dominant tocol molecule. Soybean plants were generated from clonal tissue derived from ten independent transgenic soybean events with high levels of alpha-tocopherol. Several plants were generated for each of the ten events. Five T1 seed from each transgenic event were subjected to HPLC analysis to determine the composition of the tocopherol fraction. Briefly, individual dry beans were homogenized using a tissue pulverizer (Genogrinder). Approximately 30 mg of tissue powder were extracted with 600 μL for 2 hours at ambient temperature. The heptane extract was cleared by brief centrifugation. Tocol composition of the heptane extracts was analyzed by HPLC as described previously. Percent alpha-tocopherol of T1 seed is summarized in Table 5.

TABLE 5

Percent alpha-Tocopherol of T1 Seed

| Event | Seed # 1 | Seed # 2 | Seed # 3 | Seed # 4 | Seed # 5 |
|---|---|---|---|---|---|
| 719/1/1/A | 5.8 | 4.9 | 4.2 | 6.9 | 6.7 |
| 719/1/1/B | 8.4 | 5.6 | 7.0 | 8.8 | 7.6 |
| 719/1/1/C | 6.3 | 2.8 | 2.5 | 4.8 | 5.7 |
| 719/1/2/A | 52.4 | 56.5 | 53.0 | 47.0 | 51.1 |
| 719/1/2/B | 56.7 | 5.0 | 43.9 | 11.4 | 5.4 |
| 719/1/2/C | 41.9 | 44.4 | 2.9 | 42.7 | 5.9 |
| 719/1/3/A | 18.4 | 14.8 | 22.5 | 6.5 | 16.7 |
| 719/1/4/A | 7.0 | 5.3 | 11.7 | 5.6 | 10.6 |
| 719/1/4/B | 2.5 | 4.9 | 2.0 | 5.3 | 1.0 |
| 719/1/5/A | 34.1 | 52.9 | 31.2 | 37.6 | 9.2 |
| 719/1/5/B | 7.7 | 10.4 | 61.7 | 60.9 | 57.8 |
| 719/1/8/A | 30.7 | 15.2 | 33.9 | 42.4 | 53.1 |
| 719/1/10/A | 8.2 | 75.0 | 86.0 | 79.4 | 80.5 |
| 719/1/10/B | 85.3 | 81.2 | 8.0 | 7.4 | 80.1 |
| 719/1/10/C | 80.4 | 79.0 | 80.0 | 83.8 | 86.8 |
| 719/1/13/A | 14.6 | 9.1 | 7.3 | 10.2 | 9.2 |
| 719/1/13/B | 4.5 | 83.0 | 6.0 | 81.3 | 7.2 |
| 719/1/13/C | 78.1 | 9.5 | 9.7 | 9.2 | 10.7 |
| 719/1/13/D | 12.8 | 11.4 | 11.5 | 7.6 | 10.8 |
| 719/1/13/E | 8.5 | 11.5 | 14.2 | 14.0 | 10.9 |
| 720/4/1/A | 16.4 | 6.1 | 7.1 | 5.1 | 8.9 |
| 720/4/2/A | 7.2 | 79.6 | 73.1 | 50.9 | 34.7 |
| 720/4/2/B | 58.3 | 54.6 | 52.9 | 51.7 | 62.6 |
| 720/4/2/C | 7.0 | 53.7 | 59.8 | 79.1 | 42.7 |
| 721/7/1/A | 8.4 | 6.6 | 7.2 | 6.4 | 8.7 |

Event 719.1.10 was selected for advancement. The segregation of the high alpha-tocopherol trait in T1 seed indicated that this event has a single locus insertion of the over-expressed gamma-tocopherol methyltransferase gene. T1 plants were allowed to self and T2 seed selections from individual plants were subjected to HPLC analysis of individual seed. T2 seed selections were identified that no longer segregated seed with the low alpha-tocopherol content (alpha-tocopherol <10% of total tocol). Seed from these selections were planted and bulk seed that were homozygous of the transgene were harvested from these T2 plants.

Quantitative analysis of tocopherols of T3 seed was conducted as follows. Soybeans were ground in a FOSS tecator sample mill (FOSS, USA) using a 1 mm screen. 200 mg of tissue were extracted in 5 mL of heptane for two hours; alpha-tocopherol acetate was added as internal standard at a final concentration of 38 μg mL$^{-1}$. 10 μL of filtered heptane extract was subjected to HPLC using a Lichrospher column (250-4 HPLC cartridge, Si60, 5 μM particle size) using heptane containing 0.75% isopropanol as mobile phase at a flow rate of 1 mL min$^{-1}$. External standards of all four tocopherols and tocotrienols (2.5 μg mL$^{-1}$) separated under identical conditions were used for tocol quantitation. Tocols were detected using a fluorescence detector using excitation and emission wavelengths of 295 nm, 330 nm, respectively. Table 6 indicates that EMSP 719.1.10 expresses high level of gamma-tocopherol methyltransferase activity indicated by the nearly quantitative conversion of gamma- and delta- to alpha- and beta-tocopherol, respectively. Applicants note that no tocotrienols could be detected.

TABLE 6

Tocol Composition of Homozygous T3 Seed of Event EMSP 719.1.10

|     | alpha-tocopherol | beta-tocopherol | gamma-tocopherol | delta-tocopherol | tocopherol |
|-----|------------------|-----------------|------------------|------------------|------------|
| ppm | 148              | 29              | 5                | 3                | 183        |
| %   | 77               | 15              | 2                | 1                |            |

Generation of a Transgenic Soybean Line with Seed-Preferred Expression of the Barley HGGT Gene:

A DNA fragment was generated by PCR. The new DNA fragment contains the complete open reading frame (1224 bp; SEQ ID NO:46) of the barley HGGT cDNA flanked at 5' and 3' position by DNA sequences recognized by the restriction enzyme NotI. Briefly, the modified HGGT cDNA was amplified from a barley developing seed cDNA library (see PCT Publication No. WO 03/082899) using oligonucleotide primers that include NotI sites that start four nucleotides upstream of the start codon and two nucleotides downstream of the stop codon of the HGGT cDNA sequence, respectively. The sequences of the sense and antisense oligonucleotide primers used in this reaction were as follows:

(SEQ ID NO: 47)
5'-ttgcggccgcAGGATGCAAGCCGTCACGGCGGCAGCCG-3'
and (SEQ ID NO: 48)
5'-ttgcggccgcTTCACATCTGCTGGCCCTTGTAC-3'.

(Note: The lower case, underlined nucleotide sequences correspond to added NotI restriction sites.) PCR amplification was achieved using Pfu polymerase, and an aliquot of the barley developing seed cDNA library described in PCT Publication No. WO 03/082899 was used as the template. The product of this PCR reaction was purified by agarose gel electrophoresis and subcloned into pCR-Script-AMP (Stratagene) as described in the manufacturer's protocol.

The amplified open-reading frame of the barley HGGT was then released as a NotI fragment and cloned into the corresponding site of soybean expression vector pKS123 (construction described below) to generate plasmid pSC38 (SEQ ID NO:49).

The construction of vector pKS123 was previously described in PCT Publication No. WO 02/008269 (the contents of which are hereby incorporated by reference). Briefly, plasmid pKS123 contains the hygromycin B phosphotransferase gene (HPT) (Gritz, L. and Davies, J. (1983) *Gene* 25:179-188), flanked by the T7 promoter and transcription terminator (T7prom/hpt/T7term cassette), and a bacterial origin of replication (ori) for selection and replication in bacteria (e.g., *E. coli*). In addition, pKS123 also contains the hygromycin B phosphotransferase gene, flanked by the 35S promoter (Odell et al. *Nature* (1985) 313:810-812) and NOS 3' transcription terminator (Depicker et al. *J. Mol. Appl. Genet.* (1982) 1:561:570) (35S/hpt/NOS3' cassette) for selection in plants such as soybean. pKS123 also contains a NotI restriction site, flanked by the promoter for the α' subunit of β-conglycinin (Beachy et al. *EMBO J.* (1985) 4:3047-3053) and the 3' transcription termination region of the phaseolin gene (Doyle, J. J. et al. *J. Biol. Chem.* (1986) 261:9228-9238) thus allowing for strong tissue-preferred expression in the seeds of soybean of genes cloned into the NotI site.

Ligation products were transformed into *E. coli* and recombinant clones were selected using hygromycin B selection. Restriction digestion of plasmid DNA was used to identify cultures harboring plasmid DNA in which the start codon of the HGGT cDNA was in close proximity to the transcription start site of the soybean β-conglycinin promoter. In this plasmid construct henceforth referred to as SC38, the barley HGGT cDNA is under the control of a 617 bp fragment of the β-conglycinin promoter. The polyadenylation signal for the HGGT transcript is derived from the terminator of the phaseolin gene. Plasmid SC38 contains hygromycin B phosphotransferase gene under control of the cauliflower mosaic 35S promoter, which allows for selection of transformed plant cells by resistance to the antibiotic hygromycin B. Plasmid DNA of SC38 was used to generate transgenic somatic embryos of soybean as described above.

A total of 31 independent events were created. Analysis of tocopherols and tocotrienols was performed by HPLC analysis as described above. Eight events could be identified that contained detectable levels of tocotrienols indicating that in these transgenic events the barley HGGT enzyme was expressed. Tocotrienol levels are below detection limits of fluorescence detection in unmodified leaf and seed tissue of soybean. Transgenic soybeans plants were generated from somatic embryo tissue of one event (1052.5.2). A total of eight T1 seed were subjected analysis of tocopherols and tocotrienols by HPLC of these six seed contained detectable levels of tocotrienols. The segregation of the tocotrienol trait in T1 seed indicated that this event contains a single locus insertion of the β-conglycinin::HGGT expression cassette.

Nineteen randomly selected T1 seed were grown and T2 seed were selected from individual plants. Initially, eight seed from each T2 progeny were subjected to HPLC analysis. This analysis allowed Applicants to identify five T2 progeny that did not produce seed lacking tocotrienols. The non-segregating nature of these progeny was further confirmed through analysis of another eight seed by HPLC. One of the homozygous T2 seed selections was used to produce bulked T3 seed. This seed material was used for quantitative tocol analysis and these results are found in Table 7. Table 7 shows that soybeans over-expressing the HGGT gene from barley accumulate only gamma- and delta-tocotrienol. No alpha- or beta-tocotrienol could be detected in these transgenic lines.

TABLE 7

Tocol Composition of Homozygous T3 Seed of Event EMSP 1052.5.2

|     | alpha-tocopherol | beta-tocopherol | gamma-tocopherol | delta-tocopherol | tocopherol |
|-----|------------------|-----------------|------------------|------------------|------------|
| ppm | 12               | 7               | 94               | 82               | 196        |
| %   | 0                | 0               | 3                | 3                |            |

|     | alpha-tocotrienol | beta-tocotrienol | gamma-tocotrienol | delta-tocotrienol | tocotrienol |
|-----|-------------------|------------------|-------------------|-------------------|-------------|
| ppm | 0                 | 0                | 1329              | 1212              | 2540        |
| %   | 0                 | 0                | 49                | 44                |             |

The tocotrienol profile of soybeans expressing the HGGT protein from barley indicate that there is no detectable activity converting gamma- and delta-tocotrienols to alpha- and beta-tocotrienols, respectively. Although not to be limited by theory, two possible scenarios could explain the lack of conversion of gamma- and delta-tocotrienol to alpha- and beta-tocotrienols in HGGT-expressing seed of dicotyledoneous plants such as soybean. First, gamma-tocopherol methyltransferase enzymes from plants that do not synthesize tocotrienols may not accept tocotrienol substrates. According to this scenario, gamma-tocopherol methyltransferase enzymes from monocotyledoneous plants have evolved into catalysts for tocotrienol methylation and their co-expression with HGGT would be required for biosynthesis of high levels of alpha- and beta-tocotrienols in dicots. Second, gamma-tocopherol methyltransferase enzymes from dicots may be effective enzymes for synthesis of alpha- and beta-tocotrienols, but their endogenous expression level is too low to achieve conversion of tocotrienol substrates (i.e., the gamma-tocopherol methyltransferase enzymes may be saturated with tocopherol substrates from the over-expression of HGGT).

Combination of Traits for Over-Expression of HGGT and Gamma-Tocopherol Methyltransferase by Genetic Crossing:

EMSP 719.1.10 was crossed to EMSP 1052.5.2 to test the feasability of the soybean gamma-tocopherol methyltransferase enzyme for biosynthesis of alpha- and beta-tocotrienol. A total of 20 F1 seed was generated. Quantitative analysis of tocol composition of F1 seed was conducted on a total of four F1 seed and the results are found in Table 8.

TABLE 8

Tocol Composition of F1 Seed Containing Transgenes for Seed-preferred Over-expression of the HGGT Gene from Barley and the gamma-Tocopherol Methyltransferase Gene from Soybean

|  |  | alpha-tocopherol | beta-tocopherol | gamma-tocopherol | delta-tocopherol | tocopherol |
|---|---|---|---|---|---|---|
| EMSP 1052.5.2 | ppm | 11 | 5 | 93 | 74 | 184 |
|  | % | 0.8 | 0.4 | 6 | 5 |  |
| EMSP 1052.5.2; | ppm | 143 | 81 | 0 | 2 | 226 |
| EMSP 719.1.10 | % | 14 | 8 | 0 | 0 |  |

|  |  | alpha-tocotrienol | beta-tocotrienol | gamma-tocotrienol | delta-tocotrienol | tocotrienol |
|---|---|---|---|---|---|---|
| EMSP 1052.5.2 | ppm | 0 | 0 | 581 | 681 | 1261 |
|  | % | 0 | 0 | 40 | 47 |  |
| EMSP 1052.5.2; | ppm | 274 | 289 | 54 | 146 | 763 |
| EMSP 719.1.10 | % | 28 | 29 | 5 | 15 |  |

Comparison of the tocol profile of EMSP 1052.5.2 to that of F1 beans of a cross of EMSP 1052.5.2 to EMSP 719.1.10 reveals dramatic differences. Whereas alpha-tocotrienol is not detectable in the 1052.5.2 parent, it constitutes the second most abundant tocotrienol species in the crossed material. Applicants note that gamma-tocotrienol is almost completely converted to alpha-tocotrienol. The soybean gamma-tocopherol methyltransferase enzyme evidently also converts delta- to beta-tocotrienol. The lower total tocotrienol concentration of the F1 beans (763 ppm compared to 1,261 ppm in the 1052.5.2 parent) may be attributed to the heterozygous state of the HGGT transgene in the F1 seed or could indicate that the two β-conglycinin promoter-driven transcripts are subject to transcriptional or post-transcriptional gene silencing due to identical promoter and/or 5'UTR sequences. F1 seed were germinated in soil and allow to self. A total of forty-eight F2 seed was analyzed by HPLC and the results are found in Table 9.

TABLE 9

Tocol Composition (percent of total tocopherols (tocph.) and tocotrienols (toct.))
for F2 Progeny of a Cross of EMSP 1052.5.2 to EMSP 719.1.10

| No. | alpha-tocph. | beta-tocph. | gamma-tocph. | delta-tocph. | alpha-toct. | beta-toct. | gamma-toct | delta-toct. | tocph. (ppm) | toct. (ppm) |
|---|---|---|---|---|---|---|---|---|---|---|
| 1 | 10 | 7 | 0 | 0 | 31 | 37 | 5 | 10 | 217 | 1128 |
| 2 | 10 | 7 | 0 | 0 | 31 | 38 | 5 | 9 | 248 | 1220 |
| 3 | 10 | 6 | 0 | 0 | 30 | 36 | 9 | 10 | 196 | 1067 |
| 4 | 13 | 7 | 0 | 0 | 30 | 37 | 5 | 8 | 279 | 1124 |
| 5 | 9 | 6 | 0 | 0 | 30 | 33 | 9 | 13 | 239 | 1366 |
| 6 | 8 | 6 | 0 | 0 | 30 | 39 | 6 | 11 | 229 | 1408 |
| 7 | 12 | 7 | 0 | 0 | 30 | 33 | 8 | 10 | 271 | 1098 |
| 8 | 11 | 7 | 0 | 0 | 30 | 34 | 9 | 9 | 258 | 1158 |
| 9 | 10 | 6 | 0 | 0 | 29 | 34 | 7 | 13 | 227 | 1177 |
| 10 | 15 | 7 | 0 | 0 | 29 | 31 | 8 | 9 | 265 | 903 |
| 11 | 10 | 7 | 0 | 0 | 28 | 29 | 12 | 14 | 199 | 1005 |
| 12 | 8 | 6 | 0 | 0 | 28 | 36 | 8 | 14 | 227 | 1449 |
| 13 | 12 | 6 | 0 | 0 | 28 | 32 | 12 | 10 | 255 | 1144 |
| 14 | 9 | 7 | 0 | 0 | 28 | 35 | 8 | 13 | 227 | 1190 |
| 15 | 10 | 7 | 0 | 0 | 27 | 37 | 7 | 12 | 240 | 1196 |
| 16 | 13 | 8 | 0 | 0 | 27 | 31 | 7 | 14 | 263 | 996 |
| 17 | 11 | 7 | 0 | 0 | 27 | 34 | 8 | 13 | 228 | 1017 |
| 18 | 11 | 8 | 0 | 0 | 27 | 33 | 7 | 14 | 261 | 1095 |
| 19 | 10 | 7 | 0 | 0 | 27 | 36 | 7 | 12 | 256 | 1207 |
| 20 | 13 | 7 | 0 | 0 | 27 | 31 | 10 | 12 | 210 | 822 |
| 21 | 11 | 7 | 0 | 0 | 26 | 39 | 6 | 10 | 250 | 1108 |
| 22 | 8 | 7 | 0 | 0 | 26 | 40 | 7 | 12 | 228 | 1260 |
| 23 | 8 | 6 | 0 | 0 | 26 | 35 | 8 | 17 | 230 | 1409 |
| 24 | 12 | 7 | 0 | 0 | 26 | 28 | 14 | 14 | 193 | 818 |
| 25 | 10 | 8 | 0 | 0 | 26 | 37 | 6 | 13 | 265 | 1155 |
| 26 | 7 | 7 | 0 | 0 | 25 | 41 | 7 | 13 | 237 | 1472 |
| 27 | 8 | 7 | 0 | 0 | 24 | 38 | 7 | 15 | 224 | 1262 |
| 28 | 10 | 7 | 0 | 0 | 24 | 32 | 9 | 17 | 282 | 1385 |
| 29 | 7 | 6 | 0 | 0 | 24 | 37 | 8 | 18 | 176 | 1171 |
| 30 | 9 | 7 | 0 | 0 | 21 | 29 | 13 | 21 | 219 | 1111 |
| 31 | 2 | 1 | 7 | 4 | 1 | 0 | 46 | 40 | 238 | 1554 |
| 32 | 1 | 0 | 4 | 3 | 0 | 0 | 45 | 45 | 232 | 2284 |
| 33 | 1 | 1 | 5 | 3 | 0 | 0 | 47 | 43 | 190 | 1740 |
| 34 | 1 | 1 | 6 | 4 | 0 | 0 | 44 | 44 | 231 | 1784 |
| 35 | 2 | 0 | 6 | 3 | 0 | 0 | 51 | 37 | 225 | 1788 |
| 36 | 2 | 1 | 5 | 4 | 0 | 0 | 41 | 46 | 204 | 1499 |
| 37 | 86 | 14 | 0 | 0 | 0 | 0 | 0 | 0 | 244 | 0 |
| 38 | 84 | 16 | 0 | 0 | 0 | 0 | 0 | 0 | 253 | 0 |
| 39 | 83 | 17 | 0 | 0 | 0 | 0 | 0 | 0 | 183 | 0 |
| 40 | 82 | 18 | 0 | 0 | 0 | 0 | 0 | 0 | 216 | 0 |
| 41 | 81 | 17 | 1 | 1 | 0 | 0 | 0 | 0 | 317 | 0 |
| 42 | 80 | 19 | 1 | 0 | 0 | 0 | 0 | 0 | 221 | 0 |
| 43 | 78 | 19 | 2 | 1 | 0 | 0 | 0 | 0 | 226 | 0 |
| 44 | 34 | 3 | 56 | 7 | 0 | 0 | 0 | 0 | 225 | 0 |
| 45 | 26 | 3 | 59 | 11 | 0 | 0 | 0 | 0 | 337 | 0 |
| 46 | 23 | 2 | 64 | 10 | 0 | 0 | 0 | 0 | 213 | 0 |
| 47 | 13 | 2 | 69 | 17 | 0 | 0 | 0 | 0 | 261 | 0 |
| 48 | 12 | 2 | 70 | 16 | 0 | 0 | 0 | 0 | 216 | 0 |

Tocol analysis of forty-eight F2 seed revealed 30 F2 seed that expressed both transgene-related traits (see numbers 1-30), six and seven seed with only HGGT or gamma-tocopherol methyltransferase traits, (see numbers 31-36 and 37-43, respectively), and five wild-type seed (see numbers 44-48). These findings are very close to the expected segregation of two unlinked, dominant traits in the F2 generation of a cross of two parents that were homozygous for one of each of the dominant traits. The expected frequency of F2s with both transgenic traits is 62.5% (30/48). The expected frequency of F2s with a single transgenic trait or no transgenic trait is 12.5% (6/48).

F2 progeny with both transgene-related traits were found to contain at least 258 ppm and as much as 487 ppm alpha-tocotrienol and at least 278 ppm and as much as 701 ppm beta-tocotrienol. The oil content of the heptane extracts was determined by derivatization with sodium methoxide followed by GC analysis. Oil was calculated from the tocotrienol concentrations expressed as ppm. F2 progeny with both transgene-related traits contained an oil with at least 1,670 ppm and as much as 2,940 alpha-tocotrienol and at least 1,800 ppm and as much as 4,080 ppm beta-tocotrienol. Applicants also tested for a possible negative effect of the high alpha- and beta-tocotrienol content on seed weight. To this end, seed weight of the forty-eight F2 seed was plotted against alpha-tocotrienol content. No correlation between seed weight and alpha-tocotrienol content could be detected.

In summary, gamma-tocopherol methyltransferase enzyme from soybean can efficiently use tocotrienol substrates, and the foregoing is a method to generate a seed or an extracted oil with high levels of alpha- and beta-tocotrienol. The alpha-tocotrienol content of soybeans over-expressing barley HGGT and the soybean gamma-tocopherol methyltransferase gene exceeds that of any non-transgenic seed or oil described previously by at least one order of magnitude (Packer et al. (2001) *J. Nutr.* 131:369 S-373S; Bertoli et al. (1998) *JAOCS* 75:1037-1040; PCT Publication No. WO 00/072862). These results further demonstrate the ability to produce alpha- and beta-tocotrienols in a crop plant that does not normally accumulate these antioxidant molecules through the transgenic expression of nucleic acid fragments encoding HGGT and gamma-tocopherol methyltransferase polypeptides.

Example 4

Production of Alpha- and Beta-Tocotrienols in Maize (*Zea mays*) Seed

Maize oil, which is derived primarily from the embryo of maize seeds, is typically enriched in tocopherols but contains little or no tocotrienols (The Lipid Handbook, 2nd Edition, Gunstone, F. D., et al., Eds., Chapman and Hall, London, 1994, pp. 129-131). Embryo-preferred expression of the barley HGGT gene in maize leads to accumulation of high levels of tococtrienols. 70-80% of the tocotrienols accumulate in the form of gamma-tocotrienol and only 5-10% of the total tocotrienol fraction is represented by alpha-tocotrienol (see PCT Publication No. WO 03/082899; U.S. Application No. 2004/0034886, Cahoon et al. (2003) *Nat. Biotechnol.* 21:1082-1087.

Based on results disclosed in Examples 1, 2 and 3 of the instant application, the barley HGGT cDNA (bdl2c.pk006.o2; SEQ ID NO:2) and soybean gamma-tocopherol methyltransferase (sah1c.pk004.g2; SEQ ID NO:12) can be expressed in seed embryo of maize to increase the tocol antioxidant content of this tissue and the extracted oil to produce a novel tocol composition that is dominated by alpha- and beta-tocotrienols. As described below, this result can be achieved by transforming maize with an expression cassette comprising the soybean gamma-tocopherol methyltransferase open reading frame operably linked on its 5' end to an embryo preferred promoter, such as the promoter for the maize 16 kDa oleosin gene (Lee, K. and Huang, A. H. (1994) *Plant Mol. Biol.* 26:1981-1987) and the barley HGGT open reading frame operably linked to the maize embryo abundant (EAP1) promoter and terminator.

An expression cassette comprising the promoter from the maize 16 kDa oleosin gene (OLE PRO), the coding sequence of soybean gamma-tocopherol methyltransferase (SEQ ID NO:14) derived from cDNA clone sah1c.pk001.k8:fis (SEQ ID NO:13) (PCT Publication No. WO 00/032757) and the polyadenylation signal sequence/terminator from the nopaline synthase (NOS) gene of *Agrobacterium tumefaciens* is constructed using methods and technologies known in the art. A second expression cassette comprises the barley HGGT coding sequence (PCT Publication No. WO 03/082899; U.S. Application No. 2004/0034886) under the transcriptional control of the maize embryo abundant protein (EAP1) promoter and terminator, with the maize ADH1 INTRON1 inserted between the promoter and coding sequence for enhanced expression. The two expression cassettes are linked, together with a gene encoding a selectable marker, in a binary vector suitable for *Agrobacterium*-mediated transformation of maize.

Similarly, a vector may be created as described above, with the maize gamma-tocopherol methyltransferase (SEQ ID NO:16) derived from cDNA clone p0060.coran49r:fis (SEQ ID NO:15) (PCT Publication No. WO 00/032757) used in place of the soybean gamma-tocopherol methyltransferase, using the same promoter/terminator elements and HGGT expression cassette already described. Furthermore, one skilled in the art understands that the homogentisate geranylgeranyl transferases (HGGT) and gamma-tocopherol methyltransferases found in Table 1 and Table 2, respectively, may also be expressed in maize to demonstrate the feasability of these cDNA for alpha and beta-tocotrienol production in transgenic plants.

An *Agrobacterium*-based protocol can be used for the transformation of maize (see below). The resulting binary vector is introduced into *Agrobacterium* LBA4404 (PHP10523) cells, preferably by electroporation. An in vivo recombination generates a cointegrate plasmid between the introduced binary vector and the vir plasmid (PHP10523) resident in the *Agrobacterium* cells. The resulting *Agrobacterium* cells are used to transform maize.

Transformation of Maize Mediated by *Agrobacterium*:

Freshly isolated immature embryos of maize, about ten days after pollination (DAP), can be incubated with the *Agrobacterium*. The preferred genotype for transformation is the highly transformable genotype Hi-II (Armstrong (1991) Maize *Gen. Coop. Newsletter* 65:92-93). An F1 hybrid created by crossing a Hi-II with an elite inbred may also be used. After *Agrobacterium* treatment of immature embryos, the embryos can be cultured on medium containing toxic levels of herbicide. Only those cells that receive the herbicide resistance gene, and the linked gene(s), grow on selective medium. Transgenic events so selected can be propagated and regenerated to whole plants, produce seed, and transmit transgenes to progeny.

Preparation of *Agrobacterium*:

The engineered *Agrobacterium tumefaciens* LBA4404 can be constructed to contain plasmids for seed-preferred expression of HGGT and gamma-tocopherol methyltransferase genes, as disclosed in U.S. Pat. No. 5,591,616 (the contents of which are hereby incorporated by reference). To use the engineered construct in plant transformation, a master plate of a single bacterial colony transformed with plasmids for seed-preferred expression of HGGT and gamma-tocopherol methyltransferase genes can be prepared by inoculating the bacteria on minimal AB medium and allowing incubation at 28° C. for approximately three days. (The composition and preparation of minimal AB medium has been previously described in PCT Publication No. WO 02/009040 (the contents of which are hereby incorporated by reference). A working plate can then be prepared by streaking the transformed *Agrobacterium* on YP medium (0.5% (w/v) yeast extract, 1% (w/v) peptone, 0.5% (w/v) sodium chloride, 1.5% (w/v) agar) that contains 50 µg/mL of spectinomycin.

The transformed *Agrobacterium* for plant transfection and co-cultivation can then be prepared one day prior to maize transformation. Into 30 mL of minimal A medium (prepared as described in PCT Publication No. WO 02/009040) in a flask was placed 50 µg/mL spectinomycin, 100 µM acetosyringone, and about a 1/8 loopful of *Agrobacterium* from a one to two-day-old working plate. The *Agrobacterium* can then be grown at 28° C. with shaking at 200 rpm for approximately fourteen hours. At mid-log phase, the *Agrobacterium* can be harvested and resuspended at a density of 3 to 5×10⁸ CFU/mL in 561Q medium that contains 100 µM acetosyringone using standard microbial techniques. The composition and preparation of 561Q medium was described in PCT Publication No. WO 02/009040.

Immature Embryo Preparation:

Nine to ten days after controlled pollination of a maize plant, developing immature embryos are opaque and 1-1.5 mm long. This length is the optimal size for infection with the PHP18749-transformed *Agrobacterium*. The husked ears can be sterilized in 50% commercial bleach and one drop Tween-20 for thirty minutes, and then rinsed twice with sterile water. The immature embryos can then be aseptically removed from the caryopsis and placed into 2 mL of sterile holding solution consisting of medium 561Q that contains 100 µM of acetosyringone.

Agrobacterium Infection and Co-Cultivation of Embryos:

The holding solution can be decanted from the excised immature embryos and replaced with transformed *Agrobacterium*. Following gentle mixing and incubation for about five minutes, the *Agrobacterium* can be decanted from the immature embryos. Immature embryos were then moved to a plate of 562P medium, the composition of which has been previously described in PCT Publication No. WO 02/009040. The immature embryos can be placed on this media scutellum surface pointed upwards and then incubated at 20° C. for three days in darkness. This can be followed by incubation at 28° C. for three days in darkness on medium 562P that contains 100 µg/mL carbenecillin as described in U.S. Pat. No. 5,981,840.

Selection of Transgenic Events:

Following incubation, the immature embryos can be transferred to 5630 medium, which can be prepared as described in PCT Publication No. WO 02/009040. This medium contains Bialaphos for selection of transgenic plant cells as conferred by the BAR gene that is linked to barley HGGT expression cassette. At ten to fourteen-day intervals, embryos were transferred to 5630 medium. Actively growing putative transgenic embryogenic tissue can be after six to eight weeks of incubation on the 5630 medium.

Regeneration of $T_0$ Plants:

Transgenic embryogenic tissue is transferred to 288 W medium and incubated at 28° C. in darkness until somatic embryos matured, or about ten to eighteen days. Individual matured somatic embryos with well-defined scutellum and coleoptile are transferred to 272 embryo germination medium and incubated at 28° C. in the light. After shoots and roots emerge, individual plants are potted in soil and hardened-off using typical horticultural methods.

288 W medium contains the following ingredients: 950 mL of deionized water; 4.3 g of MS Salts (Gibco); 0.1 g of myo-inositol; 5 mL of MS Vitamins Stock Solution (Gibco); 1 mL of zeatin (5 mg/mL solution); 60 g sucrose; 8 g of agar (Sigma A-7049, Purified), 2 mL of indole acetic acid (0.5 mg/mL solution*); 1 mL of 0.1 mM ABA*; 3 mL of Bialaphos (1 mg/mL solution*); and 2 mL of carbenicillin (50 mg/mL solution). The pH of this solution is adjusted to pH 5.6. The solution is autoclaved and ingredients marked with an asterisk (*) are added after the media has cooled to 60° C. Medium 272 contains the following ingredients: 950 mL of deionized water; 4.3 g of MS salts (Gibco); 0.1 g of myo-inositol; 5 mL of MS vitamins stock solution (Gibco); 40 g of Sucrose; and 1.5 g of Gelrite. This solution is adjusted to pH 5.6 and then autoclaved.

Example 5

Expression of Chimeric Genes in Microbial Cells

The cDNAs encoding the instant HGGT and gamma-tocopherol methyltransferase polypeptides can be used to produce alpha- and beta-tocotrienols in microbes such as algal and cyanobacterial cells that contain an operable tocopherol biosynthetic pathway. Expression of cDNAs encoding the instant HGGT polypeptides in these cells are expected to result in the condensation of geranylgeranyl pyrophosphate and homogentisate. The product of the HGGT reaction 2-methyl-6-geranylgeranylbenzoquinol can then be converted to alpha- and beta-tocotrienols by tocopherol biosynthetic enzymes native to the host microbial cell and the instant gamma-tocopherol methyltransferase polypeptides. Tocotrienols can be produced in microbes by linking the cDNAs encoding the instant HGGT and gamma-tocopherol methyltransferase polypeptides with promoter elements that are suitable to direct gene expression in the selected host cell. The resulting chimeric genes can be introduced into the host microbial cell using techniques such as homologous recombination (Williams, J. G. K. (1988) *Methods Enzymol.* 167: 766-778; Legarde, D. et al. (2000) *App. Environ. Microbiol.* 66:64-72). Host cells transformed with cDNAs for the instant HGGT and gamma-tocopherol methyltransferase polypeptides operably linked to functional promoters can then be analyzed for tocotrienol production using techniques described in Example 1.

Example 6

Production of Alpha- and Beta-Tocotrienol in Plant Cells

The cDNAs encoding the instant HGGT and gamma-tocopherol methyltransferase polypeptides can be used to produce alpha- and beta-tocotrienols in plant cells. Even higher levels of alpha- and beta-tocotrienol production may be achieved when genes encoding the instant HGGT and gamma-tocopherol methyltransferase polypeptides are co-expressed with genes that encode enzymes that participate either in the conversion of plastidic chorismate pools to homogentisate or in the conversion of 2-methyl-6-prenylbenzoquinol to 2,3-methyl-6-prenylbenzoquinol. To this end, transgenic plants are generated with DNA constructs that provide constitutive- or seed-specific expression of bifunctional chorismate mutase-prephenate dehydratase genes (TYRA) of bacterial or fungal origin and p-hydroxyphenylpyruvate dioxygenase genes (HPPD) and 2-methyl-6-prenylbenzoquinol methyltransferase genes (VTE3) from plants or photosynthetic bacteria. The TRYA gene products are targeted to the chloroplast by way of being fused to suitable chloroplast target peptides.

Plant transformations are performed as described above in Examples 1-3. Transgenic lines expressing high levels TYRA, HPPD and VTE3 are identified by measuring tocochromanol content as described above in Examples 1-3. The events with high levels of tocochromanols are crossed to events generated with constructs expressing the instant HGGT and gamma-tocopherol methyltransferase polypeptides. Suitable constructs to generate the latter events are KS319 (Example 1), SC1 and SC38 (Example 2), KS270 and KS308 (Example 3). Alternatively, new DNA constructs are generated using standard methods of molecular biology that provide seed-specific or constitutive expression of five genes comprised of TYRA, HPPD, VTE3 and HGGT and gamma-tocopherol methyltransferase genes of instant invention. Plant transformations are performed as described in Examples 1-3. Transgenic lines expressing high levels of all five gene products are identified by measuring tocochromanol content of plant tissue as described in Examples 1-3.

Example 7

Production of Tocotrienols in Transgenic Soybean Lines

Molecular Stack of Barley HGGT and Maize Gamma-Tocopherol Methyltransferase

To demonstrate the ability to produce increased levels of alpha- and beta-tocotrienols in transgenic soybean lines, the barley HGGT cDNA (bdl2c.pk006.o2; SEQ ID NO:2) and maize gamma-tocopherol methyltransferase (p0060.coran49r:fis; SEQ ID NO:15) (PCT Publication No. WO 00/032757) were used in a molecular stack (progeny with both transgene-related traits).

A construct for seed specific expression of maize gamma-tocopherol methyltransferase in soybean was generated as follows. DNA of KS126 (see Example 1) was linearized with NotI. 5' overhangs were completely filled in with T4 polynucleotid kinase and dephosphorylated using calf intestinal phosphatase. A restriction fragment containing the complete ORF of the maize GTMT cDNA was excised from the EST clone using restriction enzymes DraI and SnaBI and ligated to the KS126 vector. Ligation products were introduced into *E. coli*. Plasmid DNA was isolated form recombinant clones and subjected to restriction digests with BamHI. Plasmid clones which produced a DNA fragment of 2.8 kb when digested with BamHI contain the maize GTMT gene in an orientation in which the 5' end of the transcript is in proximity to the 3' end of the KTI promoter (sense orientation). This plasmid was named KS325. Its sequence is set forth as SEQ ID NO:51.

Transgenic soybean lines were generated with plasmid DNA of KS270 (see Example 1) and KS325 using particle bombardment of embryogenic callus.

KS270 provides the barley HGGT gene under control of 617 bp of the soybean β-conglycinin promoter. The polyadenylation signal for the HGGT transcript is derived from the terminator of the phaseolin gene (from the bean *Phaseolus vulgaris*; Doyle et al. (1986) *J. Biol. Chem.* 261:9228-9238). The plasmid also contains the cDNA of a sulfonylurea-resistant variant of the soybean ALS gene that is under control of 1217 bp of the SAMS promoter. The polyadenylation signal for the HGGT transcript is derived from the terminator of the soybean ALS gene.

KS325 provides the gamma-tocopherol methyltransferase gene from maize under the control of 2090 bp of the soybean Kti promoter. The polyadeylation signal for the gamma-tocopherol methyltransferase transcript is derived from the terminator of the Kti gene. KS325 also provides a hygromycin B phosphotransferase (HPT) resistance gene (Gritz et al. (1983) *Gene* 25:179-188) that is under control of 1408 bp of the 35S promoter from Cauliflower Mosaic Virus (Odell et al. (1985) *Nature* 313:810-812). The polyadenylation signal for the hygromycin resistance gene is derived from the terminator of nopaline synthase gene from the T-DNA of the Ti plasmid of *Agrobacterium tumefaciens*.

Soybean embryogenic suspension cultures were transformed with DNA plasmids KS270 in conjunction with KS325 by the method of particle gun bombardment (Klein et al. (1987) *Nature* (London) 327:70-73; U.S. Pat. No. 4,945,050) using a BIORAD Biolistic PDS1000/He instrument. The following stock solutions and media were used for transformation and regeneration of soybean plants:

Stock Solutions:
Sulfate 100× Stock: 37.0 g MgSO$_4$.7H$_2$O, 1.69 g MnSO$_4$.H$_2$O, 0.86 g ZnSO$_4$.7H$_2$O, 0.0025 g CuSO$_4$.5H$_2$O
Halides 100× Stock: 30.0 g CaCl$_2$.2H$_2$O, 0.083 g KI, 0.0025 g CoCl$_2$.6H$_2$O
P, B, Mo 100× Stock: 18.5 g KH$_2$PO$_4$, 0.62 g H$_3$BO$_3$, 0.025 g Na$_2$MoO$_4$.2H$_2$O
Fe EDTA 100× Stock: 3.724 g Na$_2$EDTA, 2.784 g FeSO$_4$.7H$_2$O 2,4-D Stock: 10 mg/mL
Vitamin B5 1000× Stock: 10.0 g myo-inositol, 0.10 g nicotinic acid, 0.10 g pyridoxine HCl, 1 g thiamine.

Media (per Liter):
SB196: 10 mL of each of the above stock solutions, 1 mL B5 Vitamin stock, 0.463 g (NH$_4$)$_2$ SO$_4$, 2.83 g KNO$_3$, 1 mL 2,4-D stock, 1 g asparagine, 10 g Sucrose, pH 5.7
SB103: 1 pk. Murashige & Skoog salts mixture, 1 mL B5 Vitamin stock, 750 mg MgCl$_2$ hexahydrate, 60 g maltose, 2 g gelrite, pH 5.7.
SB166: SB103 supplemented with 5 g per liter activated charcoal.
SB71-4: Gamborg's B5 salts, 1 mL B5 vitamin stock, 30 g sucrose, 5 g TC agar, pH 5.7.

To prepare tissue for transformation, soybean embryogenic suspension cultures were maintained in 35 mL liquid medium (SB196) on a rotary shaker (150 rpm) at 28° C. with fluorescent lights providing a 16 hour day/8 hour night cycle. Cultures were subcultured every two weeks by inoculating approximately 35 mg of tissue into 35 mL of fresh liquid media.

In particle gun bombardment procedures it is possible to use purified 1) entire plasmid DNA; or 2) DNA fragments containing only the recombinant DNA expression cassette(s) of interest. For every seventeen bombardment transformations, 85 µL of suspension is prepared containing 1 to 90 picograms (pg) of plasmid DNA per base pair of each DNA plasmid. Both recombinant DNA plasmids were co-precipitated onto gold particles as follows. The DNAs in suspension were added to 50 µL of a 20-60 mg/mL 0.6 µm gold particle suspension and then combined with 50 µL CaCl$_2$ (2.5 M) and 20 µL spermidine (0.1 M). The mixture was vortexed for 5 seconds, spun in a microfuge for 5 seconds, and the supernatant removed. The DNA-coated particles were then washed once with 150 µL of 100% ethanol, vortexed and spun in a microfuge again, then resuspended in 85 µL of anhydrous ethanol. Five µL of the DNA-coated gold particles were then loaded on each macrocarrier disk.

Approximately 150 to 250 mg of two-week-old suspension culture was placed in an empty 60 mm×15 mm petri plate and the residual liquid removed from the tissue using a pipette. The tissue was placed about 3.5 inches away from the retaining screen and each plate of tissue was bombarded once. Membrane rupture pressure was set at 650 psi and the chamber was evacuated to −28 inches of Hg. Three plates were bombarded, and, following bombardment, the tissue from each plate was divided between two flasks, placed back into liquid media, and cultured as described above.

Seven days after bombardment, the liquid medium was exchanged with fresh SB196 medium supplemented with 30-50 mg/L hygromycin. The selective medium was subsequently refreshed weekly or biweekly. Seven weeks post-bombardment, bright green, transformed tissue was observed growing from untransformed, chlorotic or necrotic embryogenic clusters. Isolated green tissue was removed and inoculated into individual wells in six-well culture dishes to generate new, clonally-propagated, transformed embryogenic suspension cultures. Thus, each new line was treated as independent transformation event in an individual well. These suspensions can then be maintained as suspensions of embryos clustered in an immature developmental stage through subculture or they can be regenerated into whole plants by maturation and germination of individual somatic embryos.

After two weeks in individual cell wells, transformed embryogenic clusters were removed from liquid culture and placed on solidified medium (SB166) containing no hormones or antibiotics for one week. Embryos were cultured for at 26° C. with mixed fluorescent and incandescent lights on a 16 hour day/8 hour night schedule. After one week, the cultures were then transferred to SB103 medium and maintained in the same growth conditions for 3 additional weeks.

Somatic embryos became suitable for germination after four weeks and were then removed from the maturation medium and dried in empty petri dishes for 1 to five days. The dried embryos were then planted in SB71-4 medium where they were allowed to germinate under the same light and temperature conditions as described above. Germinated embryos were transferred to sterile soil and grown to maturity for seed production.

A total of eighteen events were created by co-transformation with KS270 and KS325 plasmids. Tocol composition of five T1 seed was assayed for each events as follows. A seed chip (approximately 5-15 mg of tissue) was obtained from the cotyledon tissue of the seed. The chip was extracted with 100 μL of heptane for 2 hours. Tocopherol and tocotrienol was quantitated by HPLC analysis as described in Example 3.

A total of eighteen events were generated and analyzed (see Table 10).

TABLE 10

Tocol Composition (percent of total tocopherols (tocph.) and tocotrienols (toct.)) for T1 Seed Chips of Events Generated with KS270 and KS325

| Event ID | alpha-tocph. | beta-tocph. | gamma-tocph. | delta-tocph. | alpha-toct. | beta-toct. | gamma-toct | delta-toct. | tocph. (ppm) | toct. (ppm) |
|---|---|---|---|---|---|---|---|---|---|---|
| 4652.1.10.1A | 1 | 1 | 2 | 3 | 2 | 1 | 44 | 46 | 167 | 2175 |
| 4652.1.10.1B | 17 | 2 | 80 | 0 | 0 | 0 | 0 | 0 | 240 | 0 |
| 4652.1.10.1C | 2 | 1 | 3 | 0 | 2 | 1 | 44 | 47 | 279 | 4711 |
| 4652.1.10.1D | 11 | 1 | 88 | 0 | 0 | 0 | 0 | 0 | 310 | 0 |
| 4652.1.10.1E | 2 | 1 | 4 | 0 | 4 | 2 | 42 | 46 | 317 | 4070 |
| 4652.1.11.1A | 1 | 0 | 3 | 0 | 0 | 0 | 44 | 51 | 156 | 3463 |
| 4652.1.11.1B | 1 | 1 | 4 | 0 | 0 | 0 | 47 | 47 | 127 | 2133 |
| 4652.1.11.1C | 1 | 0 | 4 | 0 | 0 | 0 | 50 | 46 | 96 | 1900 |
| 4652.1.11.1D | 20 | 2 | 78 | 0 | 0 | 0 | 0 | 0 | 270 | 0 |
| 4652.1.11.1E | 1 | 0 | 5 | 0 | 0 | 0 | 53 | 39 | 201 | 2600 |
| 4652.1.2.1A | 1 | 0 | 3 | 0 | 1 | 0 | 42 | 52 | 101 | 2204 |
| 4652.1.2.1B | 1 | 0 | 3 | 0 | 1 | 0 | 46 | 50 | 149 | 3923 |
| 4652.1.2.1C | 11 | 1 | 88 | 0 | 0 | 0 | 0 | 0 | 192 | 0 |
| 4652.1.2.1D | 1 | 0 | 3 | 0 | 1 | 0 | 44 | 51 | 153 | 3310 |
| 4652.1.2.1E | 0 | 0 | 3 | 0 | 1 | 0 | 41 | 54 | 109 | 2831 |
| 4652.1.7.1A | 6 | 4 | 0 | 0 | 38 | 41 | 4 | 7 | 240 | 2051 |
| 4652.1.7.1B | 6 | 4 | 0 | 0 | 42 | 40 | 3 | 5 | 169 | 1597 |
| 4652.1.7.1C | 22 | 2 | 76 | 0 | 0 | 0 | 0 | 0 | 273 | 0 |
| 4652.1.7.1D | 6 | 5 | 0 | 0 | 35 | 45 | 3 | 6 | 214 | 1756 |
| 4652.1.7.1E | 5 | 5 | 0 | 0 | 32 | 52 | 2 | 5 | 400 | 3670 |
| 4652.1.8.1A | 16 | 2 | 83 | 0 | 0 | 0 | 0 | 0 | 175 | 0 |
| 4652.1.8.1B | 0 | 0 | 4 | 0 | 0 | 0 | 47 | 48 | 115 | 2429 |
| 4652.1.8.1C | 17 | 2 | 82 | 0 | 0 | 0 | 0 | 0 | 160 | 0 |
| 4652.1.8.1D | 1 | 0 | 4 | 0 | 0 | 0 | 45 | 50 | 114 | 2277 |
| 4652.1.8.1E | 1 | 0 | 4 | 0 | 0 | 0 | 51 | 44 | 100 | 1962 |
| 4652.2.10.1A | 0 | 0 | 4 | 0 | 0 | 0 | 42 | 53 | 124 | 2292 |
| 4652.2.10.1B | 0 | 0 | 4 | 0 | 0 | 0 | 47 | 47 | 147 | 2767 |
| 4652.2.10.1C | 1 | 0 | 5 | 0 | 0 | 0 | 48 | 46 | 223 | 3502 |
| 4652.2.10.1D | 9 | 1 | 90 | 0 | 0 | 0 | 0 | 0 | 254 | 0 |
| 4652.2.10.1E | 11 | 2 | 87 | 0 | 0 | 0 | 0 | 0 | 267 | 0 |
| 4652.2.11.1A | 11 | 1 | 87 | 0 | 0 | 0 | 0 | 0 | 164 | 0 |
| 4652.2.11.1B | 6 | 5 | 0 | 0 | 37 | 50 | 0 | 1 | 197 | 1604 |
| 4652.2.11.1C | 7 | 6 | 0 | 0 | 36 | 50 | 0 | 0 | 466 | 2950 |
| 4652.2.11.1D | 12 | 1 | 86 | 0 | 0 | 0 | 0 | 0 | 209 | 0 |
| 4652.2.11.1E | 6 | 7 | 0 | 0 | 32 | 55 | 0 | 0 | 440 | 2973 |
| 4652.2.13.1A | 10 | 1 | 88 | 0 | 0 | 0 | 0 | 0 | 243 | 0 |
| 4652.2.13.1B | 10 | 1 | 88 | 0 | 0 | 0 | 0 | 0 | 230 | 0 |
| 4652.2.13.1C | 15 | 2 | 82 | 0 | 0 | 0 | 0 | 0 | 155 | 0 |
| 4652.2.13.1D | 11 | 1 | 88 | 0 | 0 | 0 | 0 | 0 | 284 | 0 |
| 4652.2.13.1E | 11 | 1 | 88 | 0 | 0 | 0 | 0 | 0 | 229 | 0 |
| 4652.2.14.1A | 85 | 14 | 1 | 0 | 0 | 0 | 5 | 0 | 360 | 0 |
| 4652.2.14.1B | 4 | 4 | 0 | 0 | 31 | 43 | 5 | 12 | 267 | 2796 |
| 4652.2.14.1C | 9 | 6 | 0 | 0 | 40 | 44 | 0 | 1 | 342 | 1855 |
| 4652.2.14.1D | 86 | 13 | 0 | 0 | 0 | 0 | 0 | 0 | 254 | 1 |
| 4652.2.14.1E | 5 | 4 | 0 | 0 | 32 | 58 | 0 | 1 | 262 | 2495 |
| 4652.2.6.1A | 6 | 8 | 0 | 0 | 32 | 54 | 0 | 0 | 353 | 2192 |
| 4652.2.6.1B | 65 | 14 | 0 | 0 | 15 | 6 | 0 | 0 | 378 | 102 |
| 4652.2.6.1C | 8 | 7 | 0 | 0 | 33 | 52 | 0 | 0 | 488 | 2762 |
| 4652.2.6.1D | 6 | 6 | 0 | 0 | 33 | 53 | 0 | 1 | 399 | 2905 |
| 4652.2.6.1E | 63 | 16 | 0 | 0 | 15 | 6 | 0 | 0 | 358 | 95 |
| 4652.2.7.1A | 2 | 1 | 4 | 0 | 1 | 1 | 42 | 49 | 205 | 2779 |
| 4652.2.7.1B | 2 | 1 | 4 | 0 | 2 | 1 | 43 | 48 | 176 | 2660 |
| 4652.2.7.1C | 1 | 1 | 3 | 0 | 2 | 1 | 45 | 48 | 110 | 2192 |
| 4652.2.7.1D | 1 | 0 | 4 | 0 | 2 | 1 | 42 | 50 | 170 | 2679 |
| 4652.2.7.1E | 3 | 1 | 6 | 0 | 2 | 1 | 48 | 40 | 199 | 1889 |
| 4652.2.9.1A | 5 | 4 | 0 | 0 | 28 | 31 | 11 | 22 | 252 | 2495 |
| 4652.2.9.1B | 6 | 5 | 0 | 0 | 33 | 40 | 5 | 11 | 214 | 1614 |
| 4652.2.9.1C | 4 | 2 | 3 | 0 | 17 | 8 | 37 | 29 | 212 | 2148 |

TABLE 10-continued

Tocol Composition (percent of total tocopherols (tocph.) and tocotrienols (toct.))
for T1 Seed Chips of Events Generated with KS270 and KS325

| Event ID | alpha-tocph. | beta-tocph. | gamma-tocph. | delta-tocph. | alpha-toct. | beta-toct. | gamma-toct | delta-toct. | tocph. (ppm) | toct. (ppm) |
|---|---|---|---|---|---|---|---|---|---|---|
| 4652.2.9.1D | 5 | 4 | 0 | 0 | 30 | 33 | 10 | 19 | 245 | 2521 |
| 4652.2.9.1E | 4 | 2 | 1 | 0 | 19 | 14 | 24 | 36 | 194 | 2212 |
| 4652.3.15.1A | 85 | 14 | 1 | 0 | 0 | 0 | 0 | 0 | 213 | 0 |
| 4652.3.15.1B | 76 | 23 | 0 | 0 | 0 | 0 | 0 | 0 | 379 | 0 |
| 4652.3.15.1C | 13 | 2 | 86 | 0 | 0 | 0 | 0 | 0 | 183 | 0 |
| 4652.3.15.1D | 77 | 22 | 0 | 0 | 0 | 0 | 0 | 1 | 167 | 1 |
| 4652.3.15.1E | 78 | 21 | 1 | 0 | 0 | 0 | 0 | 0 | 248 | 0 |
| 4652.3.17.1A | 8 | 7 | 0 | 0 | 36 | 47 | 1 | 1 | 361 | 2029 |
| 4652.3.17.1B | 8 | 5 | 0 | 0 | 42 | 44 | 1 | 1 | 362 | 2419 |
| 4652.3.17.1C | 18 | 10 | 0 | 0 | 34 | 37 | 0 | 1 | 471 | 1198 |
| 4652.3.17.1D | 8 | 6 | 0 | 0 | 38 | 45 | 1 | 1 | 334 | 1941 |
| 4652.3.17.1E | 9 | 7 | 0 | 0 | 38 | 45 | 0 | 1 | 276 | 1392 |
| 4652.3.3.1A | 4 | 4 | 0 | 0 | 37 | 41 | 5 | 9 | 272 | 2905 |
| 4652.3.3.1B | 5 | 4 | 0 | 0 | 37 | 45 | 3 | 6 | 282 | 2714 |
| 4652.3.3.1C | 8 | 6 | 0 | 0 | 36 | 48 | 1 | 2 | 416 | 2608 |
| 4652.3.3.1D | 4 | 4 | 0 | 0 | 36 | 53 | 1 | 2 | 233 | 2390 |
| 4652.3.3.1E | 5 | 5 | 0 | 0 | 31 | 43 | 5 | 12 | 344 | 3319 |
| 4652.3.5.1A | 18 | 2 | 80 | 0 | 0 | 0 | 0 | 0 | 161 | 0 |
| 4652.3.5.1B | 21 | 2 | 77 | 0 | 0 | 0 | 0 | 0 | 192 | 0 |
| 4652.3.5.1C | 4 | 4 | 0 | 0 | 22 | 28 | 13 | 29 | 203 | 2315 |
| 4652.3.5.1D | 18 | 2 | 80 | 0 | 0 | 0 | 0 | 0 | 191 | 0 |
| 4652.3.5.1E | 6 | 4 | 1 | 0 | 28 | 27 | 14 | 20 | 296 | 2450 |
| 4652.3.6.1A | 16 | 2 | 82 | 0 | 0 | 0 | 0 | 0 | 182 | 0 |
| 4652.3.6.1B | 7 | 5 | 0 | 0 | 43 | 43 | 1 | 1 | 328 | 2451 |
| 4652.3.6.1C | 7 | 5 | 0 | 0 | 41 | 44 | 1 | 1 | 292 | 2060 |
| 4652.3.6.1D | 9 | 6 | 0 | 0 | 41 | 42 | 1 | 1 | 288 | 1654 |
| 4652.3.6.1E | 15 | 2 | 84 | 0 | 0 | 0 | 0 | 0 | 244 | 0 |
| 4652.3.8.1A | 30 | 4 | 66 | 0 | 0 | 0 | 0 | 0 | 137 | 0 |
| 4652.3.8.1B | 24 | 3 | 73 | 0 | 0 | 0 | 0 | 0 | 180 | 0 |
| 4652.3.8.1C | 16 | 2 | 82 | 0 | 0 | 0 | 0 | 0 | 196 | 0 |
| 4652.3.8.1D | 30 | 3 | 68 | 0 | 0 | 0 | 0 | 0 | 205 | 0 |
| 4652.3.8.1E | 44 | 6 | 49 | 0 | 0 | 0 | 0 | 0 | 194 | 0 |

Seed chips from fifteen events contained significant levels of tocotrienol. Ten of these also contained significant levels (>150 ppm) of alpha- and beta-tocotrienol. Alpha-tocotrienol content in seed chips reached 1300 ppm in event 4652.1.7.1E (i.e, (400+3670)×0.32=1302). For several events greater than 40% of the total tocopherol and tocotrienol content was alpha-tocotrienol. Seed chips do not provide a comprehensive picture of the oil composition of the entire seed. Therefore, the entire T1 seed from selected events were subjected to tocol analysis as described in Example 2 (see Table 11).

The highest whole seed alpha-tocotrienol level (847 ppm) was reached in event 4652.1.7.1. For the six events subjected to whole seed tocol analysis at least 24% and up to 36% of the total tocopherol and tocotrienol content was derived from alpha-tocotrienol. In all six events gamma- and delta-tocotrienol levels are at very low levels compared to the best transgenic event generated in similar experiments performed with the soybean GTMT sequence (Example 2). The maize GTMT provides an excellent enzyme for methylation of gamma- and delta-tocotrienol in developing soybean seed.

TABLE 11

Tocol Composition (percent of total tocopherols (tocph.) and tocotrienols (toct.))
for T1 Seed of Events Generated with KS270 and KS325

| Event ID | alpha-tocph. | beta-tocph. | gamma-tocph. | delta-tocph. | alpha-toct. | beta-toct. | gamma-toct | delta-toct. | tocph. (ppm) | toct. (ppm) |
|---|---|---|---|---|---|---|---|---|---|---|
| 4652.1.7.1 A | 5 | 4 | 0 | 0 | 31 | 45 | 3 | 10 | 261 | 2355 |
| 4652.1.7.1 B | 5 | 4 | 0 | 0 | 36 | 44 | 3 | 8 | 214 | 2162 |
| 4652.2.11.1 B | 4 | 5 | 0 | 0 | 29 | 59 | 1 | 2 | 213 | 2028 |
| 4652.2.11.1 C | 6 | 7 | 0 | 0 | 24 | 62 | 0 | 0 | 224 | 1414 |
| 4652.2.14.1 C | 6 | 6 | 0 | 0 | 30 | 53 | 1 | 3 | 245 | 1694 |
| 4652.2.6.1 C | 7 | 9 | 0 | 0 | 25 | 57 | 0 | 2 | 320 | 1636 |
| 4652.2.6.1 D | 7 | 8 | 0 | 0 | 27 | 57 | 0 | 1 | 327 | 1986 |
| 4652.3.17.1 B | 5 | 6 | 0 | 0 | 28 | 54 | 2 | 6 | 210 | 1688 |
| 4652.3.17.1 D | 7 | 6 | 0 | 0 | 31 | 51 | 1 | 4 | 238 | 1612 |
| 4652.3.6.1 B | 5 | 4 | 0 | 0 | 36 | 51 | 1 | 2 | 227 | 2077 |
| 4652.3.6.1 C | 6 | 5 | 0 | 0 | 35 | 50 | 1 | 2 | 238 | 1802 |

Example 8

Alpha-Tocotrienol Production in *Arabidopsis thaliana* by Transgenic Expression of Barley HGGT and Maize Gamma-Tocopherol Methyltransferase A construct for co-expression of barley homogentisate geranylgeranyl transferase and maize gamma-tocopherol methyltransferase in *Arabidopsis thaliana* was generated as follows. The maize GTMT expression cassette comprised of Kti promoter GTMT gene and Kti terminator was excised from KS325 (see Example 7) as a 3.6 kb fragment by complete digestion with AscI. This DNA fragment was ligated to SC38 DNA that had previously been linearaized by partial digestion with AscI. Recombinant clones were recovered and plasmid DNA was isolated using standard techniques. This new plasmid is referred to KS325xSC38. A 6.7 kb DNA fragment containing expression cassettes for barley HGGT and maize GTMT genes was excised from this plasmid by partial digestion with SalI and ligated to pZBL120 (see Example 1) linearized with SalI to give pZBL120xKS325xSC38. The T-DNA of the plant transformation vector pZBL120xKS325xSC38 is set forth as SEQ ID NO:52. Transgenic *Arabidopsis* lines were generated using pZBL20xKS325xSC38 as described in Example 1. A total of 38 lines were generated and tocochromanol content of T2 seed was determined by HPLC analysis as described in Example 1 (see Table 12).

TABLE 12

Tocol Composition (percent of total tocopherols (tocph.) and tocotrienols (toct.))
of T2 Seed Material of Transgenic *Arabidopsis* Lines Expressing
Barley HGGT and Maize gamma-Tocopherol Methyltransferase Genes

| Event ID | alpha-tocph. | beta-tocph. | gamma-tocph. | delta-tocph. | alpha-toct. | beta-toct. | gamma-toct | delta-toct. | tocph. (ppm) | toct. (ppm) |
|---|---|---|---|---|---|---|---|---|---|---|
| 38 | 24 | 1 | 14 | 1 | 51 | 2 | 7 | 1 | 244 | 382 |
| 17 | 33 | 1 | 12 | 0 | 50 | 0 | 4 | 0 | 327 | 382 |
| 31 | 27 | 1 | 14 | 1 | 49 | 0 | 8 | 1 | 421 | 577 |
| 3 | 30 | 0 | 14 | 0 | 49 | 0 | 7 | 0 | 489 | 626 |
| 34 | 24 | 1 | 12 | 1 | 49 | 3 | 9 | 2 | 180 | 300 |
| 32 | 32 | 1 | 12 | 1 | 49 | 2 | 4 | 0 | 347 | 418 |
| 2 | 28 | 1 | 18 | 1 | 48 | 0 | 3 | 0 | 254 | 271 |
| 35 | 24 | 1 | 15 | 1 | 48 | 2 | 8 | 1 | 245 | 348 |
| 6 | 23 | 0 | 30 | 0 | 47 | 0 | 0 | 0 | 165 | 148 |
| 12 | 17 | 2 | 7 | 1 | 47 | 7 | 16 | 2 | 388 | 987 |
| 29 | 26 | 1 | 13 | 1 | 47 | 2 | 8 | 2 | 318 | 461 |
| 25 | 29 | 1 | 14 | 1 | 47 | 2 | 6 | 1 | 327 | 407 |
| 15 | 25 | 1 | 22 | 1 | 47 | 2 | 2 | 0 | 350 | 374 |
| 18 | 27 | 1 | 16 | 1 | 46 | 0 | 8 | 1 | 344 | 429 |
| 27 | 26 | 1 | 16 | 1 | 45 | 2 | 8 | 1 | 335 | 435 |
| 33 | 28 | 1 | 16 | 1 | 45 | 0 | 7 | 1 | 214 | 246 |
| 20 | 29 | 1 | 16 | 1 | 45 | 0 | 8 | 1 | 330 | 385 |
| 13 | 28 | 0 | 17 | 1 | 44 | 0 | 9 | 1 | 356 | 419 |
| 26 | 27 | 1 | 20 | 1 | 40 | 0 | 11 | 1 | 284 | 312 |
| 30 | 35 | 1 | 17 | 1 | 40 | 0 | 7 | 1 | 400 | 354 |
| 21 | 31 | 0 | 22 | 1 | 38 | 0 | 8 | 1 | 329 | 282 |
| 22 | 14 | 1 | 11 | 1 | 38 | 3 | 29 | 4 | 358 | 965 |
| 1 | 38 | 0 | 21 | 1 | 34 | 0 | 6 | 0 | 422 | 286 |
| 5 | 31 | 0 | 28 | 0 | 33 | 0 | 8 | 0 | 168 | 117 |
| 28 | 49 | 1 | 19 | 0 | 29 | 0 | 2 | 0 | 240 | 108 |
| 10 | 22 | 0 | 39 | 1 | 29 | 0 | 9 | 1 | 260 | 160 |
| 11 | 3 | 0 | 94 | 1 | 2 | 0 | 0 | 0 | 377 | 8 |
| 23 | 69 | 0 | 30 | 1 | 0 | 0 | 0 | 0 | 400 | 2 |
| 4 | 1 | 0 | 98 | 1 | 0 | 0 | 0 | 0 | 291 | 0 |
| 7 | 17 | 0 | 82 | 1 | 0 | 0 | 0 | 0 | 311 | 0 |
| 8 | 1 | 0 | 98 | 1 | 0 | 0 | 0 | 0 | 347 | 0 |
| 9 | 1 | 0 | 98 | 2 | 0 | 0 | 0 | 0 | 417 | 0 |
| 14 | 65 | 0 | 34 | 1 | 0 | 0 | 0 | 0 | 426 | 0 |
| 16 | 1 | 0 | 98 | 2 | 0 | 0 | 0 | 0 | 266 | 0 |
| 19 | 1 | 0 | 98 | 1 | 0 | 0 | 0 | 0 | 379 | 0 |
| 24 | 68 | 1 | 30 | 1 | 0 | 0 | 0 | 0 | 323 | 0 |
| 36 | 69 | 1 | 30 | 1 | 0 | 0 | 0 | 0 | 305 | 0 |
| 37 | 1 | 0 | 97 | 2 | 0 | 0 | 0 | 0 | 262 | 0 |
| wild-type | 1 | 0 | 98 | 1 | 0 | 0 | 0 | 0 | 173 | 0 |

Of the 38 events analyzed 26 showed greater than 100 ppm tocotrienols and reached levels as high as 990 ppm. In these 26 events alpha-tocotrienol represented at least 28% and as much as 51% of the total tocochromanol content. In T2 seed of the best event (Event ID 12) alpha-tocotrienol levels reached 640 ppm (i.e., (388+987)×0.47=646). The T2 material described so far still contains 25% of wild-type seed. Events 3, 12, 29, 31 and 32 were germinated on selective media. When grown on selective media T2 seed of all six events produced 25% of kanamycin-sensitive wild-type seed. For each event 15 kanamycin resistant seedlings were transferred to soil allowed to self-fertilize and grown to maturity. For each event three T3 seed selections were identified that no longer segregated kanamycin-sensitive seedlings. This seed material was subjected to tocochromanol quantitation as described above (see Table 13).

TABLE 13

Tocol Composition (percent of total tocopherols (tocph.) and tocotrienols (toct.))
of Homozygous T3 Seed Material of Transgenic *Arabidopsis* Lines Expressing
Barley HGGT and Maize gamma-Tocopherol Methyltransferase Genes

| Event ID | alpha-tocph. | beta-tocph. | gamma-tocph. | delta-tocph. | alpha-toct. | beta-toct. | gamma-toct | delta-toct. | tocph. (ppm) | toct. (ppm) |
|---|---|---|---|---|---|---|---|---|---|---|
| 3  | 29 | 1 | 2 | 1 | 61 | 2 | 3  | 1 | 229 | 464 |
| 3  | 33 | 1 | 2 | 1 | 58 | 2 | 3  | 0 | 493 | 849 |
| 3  | 32 | 1 | 2 | 1 | 58 | 2 | 4  | 1 | 307 | 545 |
| 12 | 24 | 2 | 2 | 1 | 59 | 7 | 4  | 1 | 407 | 971 |
| 12 | 19 | 5 | 1 | 1 | 55 | 14 | 4 | 2 | 361 | 1031 |
| 12 | 21 | 3 | 9 | 1 | 53 | 7 | 5  | 1 | 441 | 880 |
| 29 | 23 | 2 | 2 | 0 | 58 | 6 | 7  | 2 | 345 | 943 |
| 29 | 28 | 2 | 3 | 0 | 53 | 4 | 8  | 2 | 320 | 647 |
| 29 | 17 | 2 | 2 | 0 | 51 | 7 | 15 | 5 | 219 | 770 |
| 32 | 21 | 2 | 1 | 0 | 64 | 8 | 4  | 1 | 213 | 675 |
| 32 | 22 | 2 | 1 | 0 | 63 | 6 | 4  | 1 | 291 | 841 |
| 32 | 24 | 2 | 2 | 1 | 61 | 5 | 4  | 1 | 346 | 865 |
| 31 | 21 | 2 | 2 | 2 | 65 | 3 | 4  | 1 | 300 | 795 |
| 31 | 22 | 3 | 1 | 1 | 66 | 4 | 3  | 1 | 213 | 562 |
| 31 | 21 | 3 | 2 | 2 | 63 | 4 | 5  | 1 | 297 | 785 |

In the homozygous T3 seed material of the five events alpha-tocotrienol represented at least 51% and as much as 65% of the total tocochromanol content. In homozygous T3 seed of one event (Event ID 12) alpha-tocotrienol levels reached 810 ppm (i.e., (407+971)×0.59=813). In all five events gamma tocotrienol levels are at very low levels compared to the best transgenic event generated in similar experiments performed with the soybean GTMT sequence (Example 1). The maize GTMT provides an excellent enzyme for methylation of gamma-tocotrienol in developing *Arabidopsis* seed.

All publications and patent applications mentioned in the specification are indicative of the level of those skilled in the art to which this invention pertains. All publications and patent applications are herein incorporated by reference in their entirety to the same extent as if each individual publication or patent application was specifically and individually indicated to be incorporated by reference in its entirety.

Although the foregoing invention has been described in some detail by way of illustration and example for purposes of clarity of understanding, one of ordinary skill will recognize that certain changes and modifications may be practiced and are included within the scope of the foregoing invention and the appended claims.

What is claimed is:

1. A transformed microbial cell comprising:
   (a) a first recombinant nucleic acid molecule comprising at least one regulatory sequence operably linked to at least one nucleotide sequence selected from the group consisting of:
      (i) the nucleotide sequence set forth in SEQ ID NO: 15;
      (ii) a nucleotide sequence encoding the amino acid sequence set forth in SEQ ID NO:16; and
      (iii) a nucleotide sequence encoding a polypeptide having an amino acid sequence having at least 100% sequence identity to SEQ ID NO:16 wherein the polypeptide is a gamma-tocopherol methyltransferase; and
   (b) a second recombinant nucleic acid molecule comprising at least one regulatory sequence operably linked to at least one nucleotide sequence selected from the group consisting of:
      (iv) the nucleotide sequence set forth in SEQ ID NO:1;
      (v) a nucleotide sequence encoding the amino acid sequence set forth in SEQ ID NO:2; and (vi) a nucleotide sequence encoding a polypeptide having an amino acid sequence having at least 100% sequence identity to SEQ ID NO:2 wherein the polypeptide is a homogentisate geranylgeranyl transferase; and wherein the first recombinant nucleic acid molecule and the second recombinant nucleic acid molecule are stably incorporated into the transgenic microbial cell.

2. The transformed microbial cell of claim 1, wherein the microbial cell is an algal cell.

3. The transformed microbial cell of claim 1, wherein the at least one regulatory sequence of said first recombinant nucleic acid molecule is a promoter and wherein the at least one regulatory sequence of said second recombinant nucleic acid molecule is a promoter that is the same as or different from the promoter of the first recombinant nucleic acid molecule.

* * * * *